(12) United States Patent
Langlade Demoyen et al.

(10) Patent No.: US 12,064,474 B2
(45) Date of Patent: Aug. 20, 2024

(54) TELOMERASE ENCODING DNA VACCINE

(71) Applicant: INVECTYS, Paris (FR)

(72) Inventors: Pierre Langlade Demoyen, Neuilly sur Seine (FR); Simon Wain-Hobson, Montigny le Bretonneux (FR); Thierry Huet, Nogent sur Marne (FR); Christelle Liard, Chatillon (FR); Elodie Pliquet, Cachan (FR)

(73) Assignee: Invectys, Paris (FR)

( * ) Notice: Subject to any disclaimer, the term of this patent is extended or adjusted under 35 U.S.C. 154(b) by 1717 days.

(21) Appl. No.: 16/111,475

(22) Filed: Aug. 24, 2018

(65) Prior Publication Data
US 2019/0000946 A1 Jan. 3, 2019

Related U.S. Application Data

(63) Continuation of application No. 15/032,966, filed as application No. PCT/EP2014/073164 on Oct. 28, 2014, now Pat. No. 10,183,065.

(30) Foreign Application Priority Data

Oct. 28, 2013 (EP) .................................... 13190547

(51) Int. Cl.
*A61K 39/00* (2006.01)
*C12N 9/12* (2006.01)

(52) U.S. Cl.
CPC .... *A61K 39/001157* (2018.08); *C12N 9/1276* (2013.01); *A61K 2039/53* (2013.01);
(Continued)

(58) Field of Classification Search
CPC ........ A61K 39/001157; A61K 2039/53; A61K 39/0011; C12N 9/1276; C12N 15/52;
(Continued)

(56) References Cited

U.S. PATENT DOCUMENTS 5,539,084 A 7/1996 Geysen
5,840,839 A 11/1998 Wang et al.
(Continued)

FOREIGN PATENT DOCUMENTS

JP 2012-039877 A 3/2012
WO 1998014593 A2 4/1998
(Continued)

OTHER PUBLICATIONS

Yang (Yang et al. (2002) Experimental Cell Research, 277:201-209). (Year: 2002).*
NM_198253.2 (*Homo sapiens* telomerase reverse transcriptase (TERT), transcript variant 1, mRNA, priority to Oct. 27, 2012, 8 pages). (Year: 2012).*
(Continued)

*Primary Examiner* — Abigail Vanhorn
*Assistant Examiner* — Morgan T Lindgren Baltzell
(74) *Attorney, Agent, or Firm* — COOLEY LLP

(57) ABSTRACT

The invention provides a nucleic acid construct comprising a sequence that encodes a human telomerase reverse transcriptase (hTERT) protein which is devoid of telomerase catalytic activity and of a nucleolar localization signal. The construct is useful triggering an immune response in a subject, against cells that overexpress telomerase, preferably dysplasia cells or tumor cells.

6 Claims, 58 Drawing Sheets
(6 of 58 Drawing Sheet(s) Filed in Color)

Specification includes a Sequence Listing.

(52) U.S. Cl.
    CPC ...... C07K 2319/09 (2013.01); C07K 2319/35
               (2013.01); C12Y 207/07049 (2013.01)
(58) Field of Classification Search
    CPC ............... C12N 15/62; C07K 2319/09; C07K
               2319/35; C12Y 207/07049; A61P 35/00;
               A61P 37/04
    See application file for complete search history.

(56) References Cited

U.S. PATENT DOCUMENTS

| | | | |
|---|---|---|---|
| 8,003,773 | B2 | 8/2011 | Langlade-Demoyen et al. |
| 8,222,392 | B2 | 7/2012 | Cech et al. |
| 9,931,387 | B2 | 4/2018 | Langlade Demoyen et al. |
| 10,138,488 | B2 | 11/2018 | Langlade Demoyen et al. |
| 10,183,065 | B2 | 1/2019 | Demoyen et al. |
| 10,675,337 | B2 | 6/2020 | Langlade Demoyen et al. |
| 2003/0143228 | A1 | 7/2003 | Chen et al. |
| 2004/0106128 | A1 | 6/2004 | Majumdar et al. |
| 2008/0090778 | A1 | 4/2008 | Scarselli et al. |
| 2009/0162405 | A1 | 6/2009 | Qian |
| 2009/0175892 | A1* | 7/2009 | Langlade-Demoyen ............. C12N 9/1241 435/325 |
| 2009/0269739 | A1 | 10/2009 | Cech et al. |
| 2011/0318380 | A1 | 12/2011 | Brix et al. |
| 2016/0046950 | A1 | 2/2016 | Langlade Demoyen et al. |
| 2016/0051650 | A1 | 2/2016 | Langlade-Demoyen et al. |
| 2016/0347798 | A1 | 12/2016 | Poma et al. |

FOREIGN PATENT DOCUMENTS

| | | | | |
|---|---|---|---|---|
| WO | 2011073796 | A2 | 6/2001 | |
| WO | 2003038047 | A2 | 5/2003 | |
| WO | WO-2007014740 | A2 * | 2/2007 | ......... A61K 39/0011 |
| WO | 2008043760 | A1 | 4/2008 | |
| WO | WO-2008043760 | A1 * | 4/2008 | ........... C07K 14/245 |

OTHER PUBLICATIONS

Delogu G, Li A, Repique C, Collins F, Morris SL. DNA vaccine combinations expressing either tissue plasminogen activator signal sequence fusion proteins or ubiquitin-conjugated . . . Infect Immun. Jan. 2002;70(1):292-302 (Year: 2002).*
Sylviane (Sylviane, M. (1994) Manual of Biological Markers of Disease, B2.3:1-11) (Year: 1994).*
GenBank databases, NCBI. Accession No. AAD30037, May 11, 1999, [online], searched on May 30, 2018, <URL: https://www.ncbi.nim.nih.gov/protein/4808973?sat=4&satkey=35386002>, 3 pages total.
Kimeno, K. et al., "Immune Therapy Against Tumors Based on the Ubiquitin-Proteasome Pathway" Fukuoka acta medica, Kyushu University Institutional Repository (2007) vol. 98, No. 8, pp. 312-319, <URL:https://catalog.lib.kyushu-u.ac.jp/opac_download_md/7962/fam98-8_p312.pdf>.
Clinical immunology & allergology (2012) vol. 58, No. 1, pp. 105-111; <URL:https://search.jamas.or.jp/link/ui/2012319115>.
Zhang, M. et al., "A Novel DNA Vaccine Based on Ubiquitin-Proteasome Pathway Targetting 'Self'-Antigens Expressed in Melanoma/Melanocyte" Gene Therapy (2005) vol. 12, No. 13, pp. 1049-1057.
Duan, X. et al., "The Ubiquitin-Proteasome System Plays Essential Roles in Presenting an 8-Mer CTL Epitope Expressed in APC to Corresponding CD8+ T Cells" International Immunology (2006) vol. 18, No. 5, pp. 679-687.
Chou, B. et al., "Antiangiogenic Tumor Therapy by DNA Vaccine Inducing Aquaporin-1-Specific CTL Based on Uniquitin-Proteasome System in Mice" Journal of Immunology (2012) vol. 189, No. 4, p. 1618-1626.

Eslami, N. S. et al., "Simultaneous Immunisation with a Wilms' Tumous 1 Epitope and its Ubiquitin Fusions Results in Enhanced Cell Mediated Immunity and Tumour Rejection In C57BL/6 Mice" Molecular Immunology (2012) vol. 51, No. 3-4, pp. 325-331.
Adotevi, O. et al. "Immunogenic HLA-B*0702-Restricted Epitopes Derived from Human Telomerase Reverse Transcriptase that Elicit Antitumor Cytotoxic T-Cell Responses" Clin Cancer Res (2006) vol. 12, No. 10, pp. 3158-3167.
Adotevi, O. et al. "Targeting human telomerase reverse transcriptase with recombinant lentivector is highly effective to stimulate antitumor CD8 T-cell immunity in vivo" Blood (2010) vol. 115, No. 15, pp. 3025-3032.
Andersson, H.A. et al., "Maximizing Antigen Targeting to the Proteasome for Gene-Based Vaccines" Molecular Therapy (2004) vol. 10, No. 3, pp. 432-446.
Armbruster, B.N. et al., "N-Terminal Domains of the Human Telomerase Catalytic Subunit Required for Enzyme Activity in Vivo" Molecular and Cellular Biology (2001) vol. 21, No. 22, pp. 7775-7786.
Artandi, S. E. et al., "Telomeres and telomerase in cancer" Carcinogenesis (2010) vol. 31, No. 1, pp. 9-18.
Bevan, M. J., "Helping the CD8+ T-Cell Response" Nature Reviews Immunology (2004) vol. 4, pp. 595-602.
Bolonaki, I. et al., "Vaccination of Patients with Advanced Non-Small-Cell Lung Cancer With an Optimized Cryptic Human Telomerase Reverse Transcriptase Peptide" Journal of Clinical Oncology: Official Journal of the American Society of Clinical Oncology (2007) vol. 25, No. 19, pp. 2727-2734.
Cadile, C.D. et al., "Telomerase activity as a marker for malignancy in feline tissues" American Journal of Veterinary Research (2001) vol. 62, No. 10, pp. 1578-1581.
Delogu, G. et al., "DNA Vaccine Combinations Expressing Either Tissue Plasminogen Activator Signal Sequence Fusion Proteins or Ubiquitin-Conjugated Antigens Induce Sustained Protective Immunity in a Mouse Model of Pulmonary Tuberculosis" Infection and Immunity (2002) vol. 70, No. 1, pp. 292-302.
Drosopoulos, W.C. et al., "The active site residue Valine 867 in human telomerase reverse transcriptase influences nucleotide incorporation and fidelity" Nucleic Acids Research (2007) vol. 35, No. 4, pp. 1155-1168.
English Translation of Japanese Office Action Issued in JP2016-504709, mailed Oct. 10, 2017, 5 pages.
English Translation of Japanese Office Action issued in JP2016-504710, mailed Oct. 10, 2017, 6 pages.
European Communication Pursuant to Article 94(3) EPC issued in EP14716530.2 and dated Jan. 17, 2017, 5 pages.
European Communication Pursuant to Article 94(3) EPC issued in EP14790592.1 and dated May 30, 2017, 4 pages.
European Communication Pursuant to Rule 114(2) EPC issued in EP14790592.1 and dated Jul. 6, 2018, 3 pages total.
European Search Report and Opinion dated Sep. 24, 2012, which issued during prosecution of European Application No. 12305319.1, 7 pages.
Godet, Y. et al. "Analysis of Spontaneous Tumor-Specific CD4 T-cell immunity in Lung Cancer Using Promiscuous HLA-DR Telomerase-Derived Epitopes: Potential Synergistic Effect with Chemotherapy Response" Clinical Cancer Research: An Official Journal of the American Association for Cancer Research (2012) vol. 18, No. 10, pp. 2943-2953.
Hanahan, D. et al., "Hallmarks of Cancer: The Next Generation" Cell (2014) vol. 144, pp. 646-674.
Huang, J.J. et al., "Ectopic Expression of a COOH-terminal Fragment of the Human Telomerase Reverse Transcriptase Leads to Telomere Dysfunction and Reduction of Growth and Tumorigenicity in Hela Cells" Cancer Research (2002) vol. 62, pp. 3226-3232.
Huo, L. et al., "Cancer Immunotherapy Targeting the Telomerase Reverse Transcriptase" Cellular and Molecular Immunology (2006) vol. 3, No. 1, pp. 1-9.

(56) References Cited

OTHER PUBLICATIONS

Impellizeri, J. A. et al., "Electro-gene-transfer as a new tool for cancer immunotherapy in animals" Veterinary and Comparative Oncology, Short Communication (2012) vol. 12, Issue 4, pp. 1-9, DOI: 10.1111/vco.12006.
International Preliminary Report on Patentability issued Sep. 29, 2015 during prosecution of International Patent Application No. PCT/EP2014/056381, 8 pages.
International Preliminary Report on Patentability Issued in International Application No. PCT/EP2013/054592 dated Sep. 16, 2014, 5 pages.
International Preliminary Report on Patentability Issued in International Application No. PCT/EP2014/073164 Issued May 3, 2016, 6 pages.
International Search Report and Written Opinion of the International Searching Authority dated Apr. 12, 2013, which issued during prosecution of International Application No. PCT/EP2013/054592, 13 pages.
International Search Report and Written Opinion of the International Searching Authority dated Feb. 4, 2015, which issued during prosecution of international Application No. PCT/EP2014/073164, 10 pages.
International Search Report and Written Opinion of the International Searching Authority dated Jul. 2, 2014, which issued during prosecution of International Application No. PCT/EP2014/056381, 13 pages.
International Search Report and Written Opinion of the International Searching Authority issued in PCT/EP2014/056380, mailed on Jul. 23, 2014, 14 pages.
Kiecker, F. et al., "Analysis of Antigen-Specific T-Cell Responses With Synthetic Peptides—What Kind of Peptide for Which Purpose?" Human Immunology (2004) vol. 65, pp. 523-536.
Klebanoff, C.A. et al., "Therapeutic cancer vaccines: are we there yet?" Immunology Reviews (2011) vol. 239, pp. 27-44.
Kyte, J.A. et al., "Telomerase Peptide Vaccination Combined with Temozolomide: A Clinical Trial in Stage IV Melanoma Patients" Clinical Cancer Research (2011) vol. 7, No. 13, pp. 4568-4580.
Martinez, Paula et al., "Telomeric and extra-telomeric roles for telomerase and the telomere-binding proteins" Reviews Cancer (2011) vol. 11, pp. 161-176.
Muller S., "Ubiquitin" Manual of Biological Markers of Disease (1994) B2, 3, pp. 1-11.
NCBI Reference Sequence NM_198253.2, *Homo sapiens* telomerase reverse transcriptase (TERT), transcript variant 1, mRNA, dated Oct. 27, 2012, 8 pages.
NCBI Reference Sequence XP_019669508.1, Predicted: Low Quality Protein: telomerase reverse transcriptase, partial [Felis catus], dated Dec. 29, 2016, 2 pages.
NCBI Reference Sequence AAC51724.1, Telomerase catalytic subunit [*Homo sapiens*], dated Aug. 28, 1997, 2 pages.
Ng, SSM et al., "A novel glioblastoma cancer gene therapy using AAV-mediated long-term expression of human TERT-terminal polypeptide" Cancer Gene Therapy (2007) vol. 14, pp. 561-572.
Osen, W. et al., "Screening of Human Tumor Antigens for CD4+ T Cell Epitopes by Combination of HLA-Transgenic Mice, Recombinant Adenovirus and Antigen Peptide Libraries" PLoS One (2010) vol. 5, Issue 11, p. e14137.
Peruzzi, D., et al., "Telomerase and HER-2/neu as targets of genetic cancer vaccines in dogs" Vaccine (2010) vol. No. 5, pp. 1201-1208.
Peruzzi, D. et al., "A Vaccine Targeting Telomerase Enhances Survival of Dogs Affected by B-cell Lymphoma" Therapy (2010) vol. 18, No. 8, pp. 1559-1567.
Reay, P. et al., "Use of Global Amino Replacements to Define the Requirements for MHC Binding and T Cell of Moth Cytochrome. c (93-103)" Journal of Immunology (1994) vol. 152, pp. 3946-3957.
Ruden, M. et al., "Novel anticancer therapeutics targeting telomerase" Cancer Treatment Reviews (2013) vol. 39, 5, pp. 444-456.
Scardino, A. et al., "HER-2/neu and hTERT Cryptic Epitopes as Novel Targets for Broad Spectrum Tumor Immunotherapy" The Journal of Immunology (2002) vol. 168, pp. 5900-5906.
Schlapbach, C. et al., "Telomerase-specific GV1001 peptide vaccination fails to induce objective tumor response in patients with cutaneous 1 cell lymphoma" Journal of Dermatological Science (2011) vol. 62. No. 2, pp. 75-83.
Schroers, R. et at., "Human Telomerase Reverse Transcriptase-Specific T-Helper Responses Induced by Promiscuous Major Histocornpatibility Complex Class it-Restricted Epitopes" Clinical Cancer Research: An Official Journal of the American Association for Cancer Research (2003) vol. 9, No. 13, pp. 4743-4755.
Schroers, R. et at. "Identification of HLA DR7-restricted Epitopes from Human Telomerase Reverse Transcriptase Recognized by CD4+ T-Helper Cells" Cancer Research, American Association for Cancer Research (2002) vol. 62, No. 9, pp. 2600-2605.
Velders, M. P. et al., "Defined Flanking Spacers and Enhanced Proteolysis Is Essential for Eradication of Established Tumors by an Epitope String DNA Vaccine" Journal Immunology (2001) vol. 166, pp. 5366-5373.
Wang, Q. et al., "Improved Cellular Immune Response Elicited by a Ubiquitin-Fused DNA Vaccine Against Mycobacterium tuberculosis" DNA and Cell Biology (2012) vol. 31, No. 4, pp. 489-495.
Yamano, T. et al., "Immunity Against Breast Cancer by Tert DNA Vaccine Primed with Chemokine CCL21" Cancer Gene Therapy (2007) vol. 14, pp. 451-459.
Yang, Y. et al., "Nucleolar Localization of hTERT Protein is Associated with Telomerase Function" Experimental Research (2002) vol. 277, No. 2, pp. 201-209.
Xu, W., et al., "Chaperone-dependent E3 ubiquitin ligase CHIP mediates a degradative pathway for c-ErbB2/Neu," Proceedings of the National Academy of Sciences, Oct. 1, 2002, 99(20):12847-12852.

* cited by examiner

FIG. 16A

```
         NotI    < eRNA11a RIGI agonist
    1 gctagcaccgttggtttccgtagtgtagtggttatcacgttcgcctaacacgcgaaaggt    60
                                              < dsRNA region
   61 cccccggttcgaaaccgggcactacaaaccaacaacgttaaaaaacaggtcctccccatac   120
  121 tctttcattgtacacaccgcaagctcgacaatcatcggattgaagcattgtcgcacacat   180
                   dsRNA region >
  181 cttccacacaggatcagtacctgcttcgcttttaaccaaggcttttctccaagggatat   240
  241 ttatagtctcaaaacacacaattactttacagttagggtgagtttccttttgtgctgttt   300
  301 tttaaaataataatttagtatttgtatctcttatagaaatccaagcctatcatgtaaaat   360
  361 gtagctagtattaaaaagaacagattatctgtcttttatcgcacattaagcctctatagt   420
  421 tactaggaaatattatatgcaattaaccggggcaggggagtagccgagcttctcccaca    480
                              eRNA11a RIGI agonist >    <trpA
  481 agtctgtgcgagggggccggcgcgggcctagagatggcgggtcggatcggccagcccgc   540
         Prokaryotic terminator >    < Adenovirus 5 VA RNAI
  541 ctaatgagcgggcttttttttcttaggggtgcaaaggagagcctgtaagcgggcactctt   600
  601 ccgtggtctggtggataaaattcgcaagggtatcatggcggacgaccggggttcgagccc   660
  661 gtatccggccgtccgccgtgatccatgcggttaccgcccgcgtgtcgaacccaggtgtgc   720
                      VA RNAI >          < PAS-BH
  721 gacgtcagacaacggggagtgctccttttggcttccttcccctaccggtctgcctcgcg   780
         Primosomal assembly site (PAS-BH) extended origin
  781 cgtttcggtgatgacggtgaaaacctctgacacatgcagctcccggagacggtcacagct   840
  841 tgtctgtaagcggatgccgggagcagacaagcccgtcagggcgcgtcagcgggtgttggc   900
  901 gggtgtcggggcgcagccatgacccagtcacgtagcgatagcggagtgtatactggctta   960
  961 actatgcggcatcagagcagattgtactgagagtgcaccatatgcggtgtgaaataccgc  1020
                              PAS-BH ><   pUC replication origin
 1021 acagatgcgtaaggagaaaataccgcatcaggcgctcttccgcttcctcgctcactgact  1080
 1081 cgctgcgctcggtcgttcggctgcggcgagcggtatcagctcactcaaaggcggtaatac  1140
 1141 ggttatccacagaatcaggggataacgcaggaaagaacatgtgagcaaaaggccagcaaa  1200
 1201 aggccaggaaccgtaaaaaggccgcgttgctggcgtttttccataggctccgcccccctg  1260
 1261 acgagcatcacaaaaatcgacgctcaagtcagaggtggcgaaacccgacaggactataaa  1320
 1321 gataccaggcgtttccccctggaagctccctcgtgcgctctcctgttccgaccctgccgc  1380
 1381 ttaccggatacctgtccgcctttctcccttcgggaagcgtggcgctttctcatagctcac  1440
 1441 gctgtaggtatctcagttcggtgtaggtcgttcgctccaagctgggctgtgtgcacgaac  1500
 1501 cccccgttcagcccgaccgctgcgccttatccggtaactatcgtcttgagtccaacccgg  1560
 1561 taagacacgacttatcgccactggcagcagccactggtaacaggattagcagagcgaggt  1620
 1621 atgtaggcggtgctacagagttcttgaagtggtggcctaactacggctacactagaagaa  1680
 1681 cagtatttggtatctgcgctctgctgaagccagttaccttcggaaaaagagttggtagct  1740
 1741 cttgatccggcaaacaaaccaccgctggtagcggtggtttttttgtttgcaagcagcaga  1800
 1801 ttacgcgcagaaaaaaaggatctcaagaagatcctttgatcttttctacgggtctgacg  1860
```

FIG. 16B

```
1861 ctcagtggaacgaaaactcacgttaagggattttggtcatgagattatcaaaaggatct 1920

1921 tcacctagatccttttaaattaaaaatgaagttttaaatcaatctaaagtatatatgagt 1980

1981 aaacttggtctgacagttaccaatgcttaatcagtgaggcacctatctcagcgatctgtc 2040
           pUC replication origin >        DraIII   <  RNA-OUT
2041 tatttcgttcatccatagttgcctgactcctgcaaac cacgttgtgg tagaattggtaaa 2100

2101 gagagtcgtgtaaaatatcgagttcgcacatcttgttgtctgattattgattttggcga 2160

2161 aaccatttgatcatatgacagatgtgtatctaccttaacttaatgattttgataaaaat 2220
       RNA-OUT  ><  SV40 enhancer block
2221 catta ggtaccc ctgatca ctgtggaatgtgtgtcagttagggtgtggaaagtccccagg 2280
            KpnI    BclI 2281 ctccccagcaggcagaagtatgcaaagcatgcatctcaattagtcagcaaccaggtgtgg 2340

2341 aaagtccccaggctccccagcaggcagaagtatgcaaagcatgcatctcaattagtcagc 2400
                                SV40 enhancer block   ><
2401 aaccatagtcccgcccctaactccgcccatcccgcccctaactccgccca gttacgggt 2460

Human CMV-IE enhancer promoter block
2461 cattagttcatagcccatatatggagttccgcgttacataacttacggtaaatggcccgc 2520

2521 ctggctgaccgcccaacgacccccgcccattgacgtcaataatgacgtatgttcccatag 2580

2581 taacgccaatagggactttccattgacgtcaatgggtggagtatttacggtaaactgccc 2640

2641 acttggcagtacatcaagtgtatcatatgccaagtacgccccctattgacgtcaatgacg 2700

2701 gtaaatggcccgcctggcattatgcccagtacatgaccttatgggactttcctacttggc 2760
                                                       NcoI
2761 agtacatctacgtattagtcatcgctatta ccatgg tgatgcggttttggcagtacatca 2820

2821 atgggcgtggatagcggtttgactcacggggatttccaagtctccaccccattgacgtca 2880

><       CMV promoter
2881 atgggagtttgttttg gcaccaaaatcaacgggactttccaaaatgtcgtaacaactccg 2940

2941 ccccattgacgcaaatgggcggtaggcgtgtacggtgggaggtctatataagcagagctc 3000
                            ><  untranslated leader (exon 1)
3001 gtttagtgaaccgtcaga tcgcctggagacgccatccacgctgttttgacctccatagaa 3060
                                  < HTLV-1 R region of LTR
3061 gacaccgggaccgatccagcctccgcgg ctcgcatctctccttcacgcgcccgccct 3120

3121 acctgaggccgccatccacgccggttgagtcgcgttctgccgcctcccgcctgtggtgcc 3180
        untranslated leader >
3181 tcctgaactgcgtccgccgtcta ggtaagtttaaagctcaggtcgagaccgggcctttgt 3240

3241 ccggcgctcccttggagcctacctagactcagccggctctccacgctttgcctgaccctg 3300
         HTLV-1 R   >       < 3' Rabbit beta-globin-based intron
3301 cttgctcaactcta gttctctcg ttaacttaatgagacagatagaaactggtcttgtaga 3360

3361 aacagagtagtcgcctgcttttctgccaggtgctgacttctctcccctgggcttttttct 3420
         ><  Exon 2 (SR-protein binding sites)         SalI>
3421 ttttctc aggttgaaaagaagaagacgaagaagacgaagaagacaaaccgt gtcgacaa 3480

HindIII     BglII
3481 gcttacc atgc agatct tcgtgaagaccctgaccggcaagaccatcactctcgaggtgga 3540
             M  Q  I  F  V  K  T  L  T  G  K  T  I  T  L  E  V  E
```

FIG. 16C

```
                 < Human ubiquitin 3541 gcccagtgacaccatcgaaaatgtgaaggccaagatccaagataaagaaggcatcccacc 3600
           P  S  D  T  I  E  N  V  K  A  K  I  Q  D  K  E  G  I  P  P 3601 cgaccagcagagagctcatctttgctggcaagcagctggaagatggccgcactctgtctga 3660
           D  Q  Q  R  L  I  F  A  G  K  Q  L  E  D  G  R  T  L  S  D SalI                                 NotI
     3661 ctacaacatccagaaagagtcgaccctgcacctggtcctgcgtctgagaggcggccgcgc 3720
           Y  N  I  Q  K  E  S  T  L  H  L  V  L  R  L  R  G  G  R  A
                                          Human ubiquitin   >< hTERT 3721 tctggtggcccagtgcctggtgtgcgtgcctgggacgcacggccaccccctgccgcacc 3780
           L  V  A  Q  C  L  V  C  V  P  W  D  A  R  P  P  P  A  A  P
           Human telomerase reverse transcriptase coding sequence (hTERT)

3781 ctcattccgccaagtgtcctgcctgaaggagctggtggcccgagtgctgcagaggctgtg 3840
           S  F  R  Q  V  S  C  L  K  E  L  V  A  R  V  L  Q  R  L  C 3841 cgagcgcggcgcgaagaacgtgctggccttcggcttcgcgctgctggacggggctcgcgg 3900
           E  R  G  A  K  N  V  L  A  F  G  F  A  L  L  D  G  A  R  G 3901 aggcccaccgaggccttcaccaccagcgtgcgcagctacctgcccaacacggtgaccga 3960
           G  P  P  E  A  F  T  T  S  V  R  S  Y  L  P  N  T  V  T  D 3961 cgcactgcggggagcggggcgtgggggctgctgttgcgccgcgtgggcgacgacgtgct 4020
           A  L  R  G  S  G  A  W  G  L  L  R  R  V  G  D  D  V  L 4021 ggttcacctgctggcacgctgcgcgctctttgtgctggtggctcccagctgcgcctacca 4080
           V  H  L  L  A  R  C  A  L  F  V  L  V  A  P  S  C  A  Y  Q 4081 ggtgtgcgggccgccgctgtaccagctcggggctgccactcaggcacggcctccacctca 4140
           V  C  G  P  P  L  Y  Q  L  G  A  A  T  Q  A  R  P  P  P  H 4141 cgctagtggaccccgaaggcgtctgggatgcgaacgggcctgaaccatagcgtcaggga 4200
           A  S  G  P  R  R  R  L  G  C  E  R  A  W  N  H  S  V  R  E 4201 ggccgggtccccctggcctgccagcccggggtgcgaggaggcgcgggggcagtgccag 4260
           A  G  V  P  L  G  L  P  A  P  G  A  R  R  R  G  G  S  A  S 4261 ccgaagtctgccgttgcccaagaggccaggcgtggcgctgcccctgagccggagcggac 4320
           R  S  L  P  L  P  K  R  P  R  R  G  A  A  P  E  P  E  R  T 4321 gcccgttgggcaggggtcctgggccacccgggcaggacgcgtggaccgagtgaccgtgg 4380
           P  V  G  Q  G  S  W  A  H  P  G  R  T  R  G  P  S  D  R  G 4381 tttctgtgtggtgtcacctgccagaccccgccgaagaagccacctctttggagggtgcgct 4440
           F  C  V  V  S  P  A  R  P  A  E  E  A  T  S  L  E  G  A  L 4441 ctctggcacgcgccactcccaccccatccgtgggccgccagcaccacgcgggccccccatc 4500
           S  G  T  R  H  S  H  P  S  V  G  R  Q  H  H  A  G  P  P  S 4501 cacatcgcggccaccacgtccctgggacacgccttgtccccggtgtacgccgagaccaa 4560
           T  S  R  P  P  R  P  W  D  T  P  C  P  P  V  Y  A  E  T  K 4561 gcacttcctctactcctcaggcgacaaggagcagctgcggccatccttcctgctgagctc 4620
           H  P  L  Y  S  S  G  D  K  E  Q  L  R  P  S  F  L  L  S  S 4621 tctgaggcccagcctgactggcgctcggaggctcgtggagaccatctttctggttccag 4680
           L  R  P  S  L  T  G  A  R  R  L  V  E  T  I  F  L  G  S  R 4681 gccctggatgccagggactcccgcaggttgccccgcctgccccagcgctactggcaaat 4740
           P  W  M  P  G  T  P  R  R  L  P  R  L  P  Q  R  Y  W  Q  M 4741 gcggccctgtttctggagctgcttgggaaccacgcgcagtgccctacggggtgctcct 4800
           R  P  L  F  L  E  L  L  G  N  H  A  Q  C  P  Y  G  V  L  L
```

FIG. 16D

```
4801 caagacgcactgcccgctgcgagctgcggtcaccccagcagccggtgtctgtgcccggga 4860
      K  T  H  C  P  L  R  A  A  V  T  P  A  A  G  V  C  A  R  E 4861 gaagccccagggctctgtggcggcccccgaggaggaggacacagacccccgtcgcctggt 4920
      K  P  Q  G  S  V  A  A  P  E  E  D  T  D  P  R  R  L  V 4921 gcagctgctccgccagcacagcagccctggcaggtgtacggcttcgtgcgggcctgcct 4980
      Q  L  L  R  Q  H  S  S  P  W  Q  V  Y  G  F  V  R  A  C  L 4981 gcgccggctggtgccccaggcctctgggctccaggcacaacgaacgccgcttcctcag 5040
      R  R  L  V  P  P  G  L  W  G  S  R  H  N  E  R  R  F  L  R 5041 gaacaccaagaagttcatctccctggggaagcatgccaagctctcgctgcaggagctgac 5100
      N  T  K  K  F  I  S  L  G  K  H  A  K  L  S  L  Q  E  L  T 5101 gtggaagatgagcgtgcggggctgcgcttggctgcgcaggagcccaggggttggctgtgt 5160
      W  K  M  S  V  R  G  C  A  W  L  R  R  S  P  G  V  G  C  V 5161 tccggccgcagagcaccgtctgcgtgaggagatcctggccaagttcctgcactggctgat 5220
      P  A  A  E  H  R  L  R  E  E  I  L  A  K  F  L  H  W  L  M 5221 gagtgtgtacgtcgtcgagctgctcaggtcattctttacgtgacggagaccacgtttca 5280
      S  V  Y  V  V  E  L  L  R  S  F  F  Y  V  T  E  T  T  F  Q 5281 aaagaacaggctgttttctaccggaagagtgtctggagcaagttgcaaagcattggaat 5340
      K  N  R  L  F  F  Y  R  K  S  V  W  S  K  L  Q  S  I  G  I 5341 cagacagcacttgaagagggtgcagctgcgggagctgtcggaagcagaggtcaggcagca 5400
      R  Q  H  L  K  R  V  Q  L  R  E  L  S  E  A  E  V  R  Q  H 5401 tcgggaagccaggcccgcctgctgacgtccagactccgcttcatccccaagcctgacgg 5460
      R  E  A  R  P  A  L  L  T  S  R  L  R  F  I  P  K  P  D  G 5461 gctgcggccgattgtgaacatggactacgtcgtgggagccagaacgttccgcagagaaaa 5520
      L  R  P  I  V  N  M  D  Y  V  V  G  A  R  T  F  R  R  E  K 5521 gagggccgagcgtctcacctcacgggtgaaggcactgttcagcgtgctcaactacgagcg 5580
      R  A  E  R  L  T  S  R  V  K  A  L  F  S  V  L  N  Y  E  R 5581 ggctcggcgccctggcctcctgggcgcctctgtgctgggctggacgatatccacagggc 5640
      A  R  R  P  G  L  L  G  A  S  V  L  G  L  D  D  I  H  R  A 5641 ctggcgcaccttcgtgctgcgtgtgcgggcccaggacccgccgcctgagctgtactttgt 5700
      W  R  T  F  V  L  R  V  R  A  Q  D  P  P  P  E  L  Y  F  V 5701 caaggtggatgtgacgggcgcgtacgacaccatcccccaggacaggctcacggaggtcat 5760
      K  V  D  V  T  G  A  Y  D  T  I  P  Q  D  R  L  T  E  V  I 5761 cgccagcatcatcaaaccccagaacacgtactgcgtgcgtcggtatgccgtggtccagaa 5820
      A  S  I  I  K  P  Q  N  T  Y  C  V  R  R  Y  A  V  V  Q  K
                                                          NcoI
5821 ggccgcccatggcacgtccgcaaggccttcaagagccacgtctctaccttgacagacct 5880
      A  A  H  G  H  V  R  K  A  F  K  S  H  V  S  T  L  T  D  L 5881 ccagccgtacatgcgacagttcgtggctcacctgcaggagaccagcccgctgagggatgc 5940
      Q  P  Y  M  R  Q  F  V  A  H  L  Q  E  T  S  P  L  R  D  A 5941 cgtcgtcatcgagcagagctcctccctgaatgaggccagcagtggcctcttcgacgtctt 6000
      V  V  I  E  Q  S  S  S  L  N  E  A  S  S  G  L  F  D  V  F
                                DraIII
6001 cctacgcttcatgtgccaccacgccgtgcgcatcagggcaagtcctacgtccagtgcca 6060
      L  R  F  M  C  H  H  A  V  R  I  R  G  K  S  Y  V  Q  C  Q 6061 gggatcccgcagggctccatcctctccacgctgctctgcagctgtgctacggcgacat 6120
      G  I  P  Q  G  S  I  L  S  T  L  L  C  S  L  C  Y  G  D  M
```

FIG. 16E

```
6121 ggagaacaagctgtttgcggggattcggcgggacggctgctcctgcgtttgttcttgtt 6180
      E  N  K  L  F  A  G  I  R  R  D  G  L  L  L  R  L  F  L  L
                                                         *
6181 ggtgacacctcacctcacccacgcgaaaaccttcctcaggaccctggtccgaggtgtcc 6240
      V  T  P  H  L  T  H  A  K  T  F  L  R  T  L  V  R  G  V  P 6241 tgagtatggctgcgtggtgaacttgcggaagacagtggtgaacttcctgtagaagacga 6300
      E  Y  G  C  V  V  N  L  R  K  T  V  V  N  F  P  V  E  D  E 6301 ggccctgggtggcacggcttttgttcagatgccggcccacggcctattccctggtgcgg 6360
      A  L  G  G  T  A  F  V  Q  M  P  A  H  G  L  F  P  W  C  G 6361 cctgctgctggatacccggaccctggaggtgcagagcgactactccagctatgcccgga c 6420
      L  L  L  D  T  R  T  L  E  V  Q  S  D  Y  S  S  Y  A  R  T 6421 ctccatcagagccagtctcaccttcaaccgcggcttcaaggctggga ggaacatgcgtcg 6480
      S  I  R  A  S  L  T  F  N  R  G  F  K  A  G  R  N  M  R  R 6481 caaactctttggggtcttgcggctgaagtgtcacagcctgtttctggatttgcaggtgaa 6540
      K  L  F  G  V  L  R  L  K  C  H  S  L  F  L  D  L  Q  V  N 6541 cagcctccagacggtgtgcaccaacatctacaagatcctcctgctgcaggcgtacaggtt 6600
      S  L  Q  T  V  C  T  N  I  Y  K  I  L  L  Q  A  Y  R  F 6601 tcacgcatgtgtgctgcagctcccatttcatcagcaagtttggaagaaccccacattttt 6660
      H  A  C  V  L  Q  L  P  F  H  Q  Q  V  W  K  N  P  T  F 6661 cctgcgcgtcatctctgacacggctccctctgctactccatcctgaaagccaagaacgc 6720
      L  R  V  I  S  D  T  A  S  L  C  Y  S  I  L  K  A  K  N  A 6721 aggatgtcgctgggggccaagggcgcgccggccctctgccctccgaggccgtgcagtg 6780
      G  M  S  L  G  A  K  G  A  A  G  P  L  P  S  E  A  V  Q  W 6781 gctgtgccaccaagcattcctgctcaagctgactcgacaccgtgtcacctacgtgccact 6840
      L  C  H  Q  A  F  L  L  K  L  T  R  H  R  V  T  Y  V  P  L 6841 cctgggtcactcaggacagcccagacgcagctgagtcggaagctcccggggacgacgct 6900
      L  G  S  L  R  T  A  Q  T  Q  L  S  R  K  L  P  G  T  T  L human TERT orf end
6901 gactgccctggaggccgcagccaaccggcactgccctcagacttcaagaccatcctgga 6960
      T  A  L  E  A  A  A  N  P  A  L  P  S  D  F  K  T  I  L  D >    >XbaI BglII < Eukaryotic terminator
6961 ctaataatctagaagatcttttccctctgccaaaaattatgggacatcatgaagcccc 7020
     ▯  ▯
                       polyA signal sequence
7021 ttgagcatctgacttctggctaataaaggaaatttatttcattgcaatagtgtgttgga 7080

Eukaryotic terminator > NotI
7081 attttttgtgtctctcactcggaaggacataagggcggcc 7120
```

FIG. 17A

```
         < Human ubiquitin
    ----------|----------|----------|----------|----------|
  1 atgcagattttcgtcaaaacattgacaggaaagaccatcacactggaagt  50
  1  M  Q  I  F  V  K  T  L  T  G  K  T  I  T  L  E  V   17

----------|----------|----------|----------|----------|
 51 ggagccaagcgacactattgagaacgtcaaagccaagattcaggacaagg 100
 18  E  P  S  D  T  I  E  N  V  K  A  K  I  Q  D  K  E   34

----------|----------|----------|----------|----------|
101 agggcatcccaccagaccagcagaggctgattttttgccggaaagcagctg 150
 35   G  I  P  P  D  Q  Q  R  L  I  F  A  G  K  Q  L    50

----------|----------|----------|----------|----------|
151 gaggacggacgcacactcagtgactacaatatccagaaggaaagtactct  200
 51  E  D  G  R  T  L  S  D  Y  N  I  Q  K  E  S  T  L   67
           Human ubiquitin ><hTERT
    ----------|----------|----------|----------|----------|
201 gcatctggtccttcgcctgcgcggcggactggccaccttcgtgcggcgcc 250
 68  H  L  V  L  R  L  R  G  G  L  A  T  F  V  R  R  L   84

----------|----------|----------|----------|----------|
251 tgggacccagggctggcggctggtgcagcgcggggaccctgctgcttc   300
 85   G  P  Q  G  W  R  L  V  Q  R  G  D  P  A  A  F   100

----------|----------|----------|----------|----------|
301 agagctctcgtcgcccagtgtctggtctgcgttccttgggacgcacggcc  350
101  R  A  L  V  A  Q  C  L  V  C  V  P  W  D  A  R  P  117

----------|----------|----------|----------|----------|
351 cccaccgccgcccccagtttccggcaggtgagttgtctcaaagagttgg  400
118  P  P  A  A  P  S  F  R  Q  V  S  C  L  K  E  L  V  134

----------|----------|----------|----------|----------|
401 ttgctcgggtgttgcagcggctttgtgaaaggggagcaaagaacgtcctt  450
135   A  R  V  L  Q  R  L  C  E  R  G  A  K  N  V  L   150

----------|----------|----------|----------|----------|
451 gcctttggcttcgctttgctcgatggagcacgcggagggcctcctgaggc  500
151  A  F  G  F  A  L  L  D  G  A  R  G  G  P  P  E  A  167

----------|----------|----------|----------|----------|
501 attcactactagcgtccggtcctacctgcccaacacagtgaccgacgctc  550
168  F  T  T  S  V  R  S  Y  L  P  N  T  V  T  D  A  L  184

----------|----------|----------|----------|----------|
551 tgagaggttcaggtgcctggggtctgctgctgcgggagggtgggtgatgat  600
185   R  G  S  G  A  W  G  L  L  L  R  R  V  G  D  D   200

----------|----------|----------|----------|----------|
601 gttctggttcacctcctgccccggtgtgccctgttcgtgctggtggctcc  650
201  V  L  V  H  L  L  A  R  C  A  L  F  V  L  V  A  P  217

----------|----------|----------|----------|----------|
651 ctcctgcgcataccaggtctgcggaccccactttatcagctcggcgctg  700
218   S  C  A  Y  Q  V  C  G  P  P  L  Y  Q  L  G  A  A 234

----------|----------|----------|----------|----------|
701 ctactcaggccgccaccaccacacgctcaggtccaagacgccggctg    750
235   T  Q  A  R  P  P  P  H  A  S  G  P  R  R  R  L    250

----------|----------|----------|----------|----------|
751 ggctgcgaacgggcatggaatcatagcgtgcgggaggcaggtgtgcctct  800
251  G  C  E  R  A  W  N  H  S  V  R  E  A  G  V  P  L  267
```

FIG. 17B

```
           ----------|----------|----------|----------|----------|
       801 cggcctgccagccccggagcaaggagacgcggtggatccgccagtcgct 850
       268  G  L  P  A  F  G  A  R  R  R  G  G  S  A  S  R  S  284

----------|----------|----------|----------|----------|
       851 cactcccttgcctaagaggccaagaagaggagccgccctgaaccgag 900
       285  L  P  L  P  K  R  F  R  R  G  A  A  F  E  E  300

----------|----------|----------|----------|----------|
       901 agaacacctgtcggccagggctcctgggctcacccggaaggaccagggg 950
       301  R  T  P  V  G  Q  G  S  W  A  H  P  G  R  T  R  G  317

----------|----------|----------|----------|----------|
       951 cccaagcgatagggcttctgtgttgtgtcaccagccaggcctgccgaag 1000
       318  P  S  D  R  G  F  C  V  V  S  P  A  R  P  A  E  334

----------|----------|----------|----------|----------|
      1001 aggctacctccttggaaggagccctcagtggcaccaggcattctcatcca 1050
       335  A  T  S  L  E  G  A  L  S  G  T  R  H  S  H  P  350

----------|----------|----------|----------|----------|
      1051 tctgtgggtaggcagcatcatgcggccccctctacaagcagacctcc 1100
       351  S  V  G  R  Q  H  H  A  G  P  P  S  T  S  R  P  P  367

----------|----------|----------|----------|----------|
      1101 cagaccttggacacacctgcccaccagtgtatgccgagaccaagcact 1150
       368  R  P  W  D  T  P  C  P  P  V  Y  A  E  T  K  H  F  384

----------|----------|----------|----------|----------|
      1151 ttttgtattccagtggcgataaagagcagctccggcctctttctgctc 1200
       385  L  Y  S  S  G  D  K  E  Q  L  R  P  S  F  L  L  400

----------|----------|----------|----------|----------|
      1201 tcaagcctccgccctctctgaccggagctcgcaggctggtggagaccat 1250
       401  S  S  L  R  P  S  L  T  G  A  R  R  L  V  E  T  I  417

----------|----------|----------|----------|----------|
      1251 ctttctgggctcaagaccatggatgccaggcaccccccgcagactgcca 1300
       418  F  L  G  S  R  P  W  M  P  G  T  P  R  R  L  P  434

----------|----------|----------|----------|----------|
      1301 ggctccccagcggtactggcagatgcgccctctctttctggaacttctg 1350
       435  L  P  Q  R  Y  W  Q  M  R  P  L  F  L  E  L  L  450

----------|----------|----------|----------|----------|
      1351 ggtaaccacgccagtgcccatatggcgtcctgctgaagacccactgtcc 1400
       451  G  N  H  A  Q  C  P  Y  G  V  L  L  K  T  H  C  P  467

----------|----------|----------|----------|----------|
      1401 tctgagggccgccgtgacccagccgccggtgtgtgtgctagagaaaaac 1450
       468  L  R  A  A  V  T  P  A  A  G  V  C  A  R  E  K  484

----------|----------|----------|----------|----------|
      1451 cccagggctcagtggctgcacctgaagaggaggacactgaccctcgcgc 1500
       485  Q  G  S  V  A  A  P  E  E  D  T  D  P  R  R  500

----------|----------|----------|----------|----------|
      1501 cttgtccagttgctcaggcagcattcatcaccatggcaggtgtacggctt 1550
       501  L  V  Q  L  L  R  Q  H  S  S  F  W  Q  V  Y  G  F  517

----------|----------|----------|----------|----------|
      1551 cgtgagggcttgcctgcggagactggtccccccggattgtggggatctc 1600
       518  V  R  A  C  L  R  R  L  V  P  P  G  L  W  G  S  R  534

----------|----------|----------|----------|----------|
      1601 ggcacaacgaacggcgctttctgaggaatacaaagaagtttatctccctg 1650
       535  H  N  E  R  R  F  L  R  N  T  K  K  F  I  S  L  550
```

FIG. 17C

```
            ----------|----------|----------|----------|----------|
       1651 ggcaagcatgcaaagctcagcttgcaggagctgacatggaagatgagcgt 1700
        551  G  K  H  A  K  L  S  L  Q  E  L  T  W  K  M  S  V  567

----------|----------|----------|----------|----------|
       1701 tagaggatgcgcatggctcaggcggtcacctggagttggatgcgttccag 1750
        568  R  G  C  A  W  L  R  R  S  P  G  V  G  C  V  P  A  584

----------|----------|----------|----------|----------|
       1751 cagcagagcacaggctgcgcgaagagattctcgcaaagttcctgcactgg 1800
        585  A  E  H  R  L  R  E  E  I  L  A  K  F  L  H  W  600

----------|----------|----------|----------|----------|
       1801 cttatgagcgtctacgtggtcgaactgctgcgggtctttcttctacgtgac 1850
        601  L  M  S  V  Y  V  V  E  L  L  R  S  F  F  Y  V  T  617

----------|----------|----------|----------|----------|
       1851 agagaccacttttcagaagaacagactgttcttctacaggaagtccgtct 1900
        618  E  T  T  F  Q  K  N  R  L  F  F  Y  R  K  S  V  W  634

----------|----------|----------|----------|----------|
       1901 ggagcaagctccagagtattggtattagacagcaccttaagagagttcag 1950
        635  S  K  L  Q  S  I  G  I  R  Q  H  L  K  R  V  Q  650

----------|----------|----------|----------|----------|
       1951 cttagagagctgtccgaagctgaagtccgccagcaccgcgaagctcgcc 2000
        651  L  R  E  L  S  E  A  E  V  R  Q  H  R  E  A  R  P  667

----------|----------|----------|----------|----------|
       2001 cgccctcctgacctctcggctgcggtttattcccaaacccgatggcctta 2050
        668  A  L  L  T  S  R  L  R  F  I  P  K  P  D  G  L  R  684

----------|----------|----------|----------|----------|
       2051 gacctatcgtgaatatggattacgtcgtgggtgcccgcacttcagaagg 2100
        685  P  I  V  N  M  D  Y  V  V  G  A  R  T  F  R  R  700

----------|----------|----------|----------|----------|
       2101 gagaagcgcgccgagagactgacatctcgcgtgaaggcacttttttctgt 2150
        701  E  K  R  A  E  R  L  T  S  R  V  K  A  L  F  S  V  717

----------|----------|----------|----------|----------|
       2151 gcttaattatgaaagagcccgcagacctggtcttctcggagccagcgtgc 2200
        718  L  N  Y  E  R  A  R  R  P  G  L  L  G  A  S  V  L  734

----------|----------|----------|----------|----------|
       2201 tcggcctggatgatatccatgggcttggcgcacctttgtgcttcgggtg 2250
        735  G  L  D  D  I  H  R  A  W  R  T  F  V  L  R  V  750

----------|----------|----------|----------|----------|
       2251 agggcacaggatcctcctcctgagctttattttgtgaaagttgatgttac 2300
        751  R  A  Q  D  P  P  P  E  L  Y  F  V  K  V  D  V  T  767

----------|----------|----------|----------|----------|
       2301 tggtgcttacgatacaatccctcaggaccggctcaccgaggtgatcgcct 2350
        769  G  A  Y  D  T  I  P  Q  D  R  L  T  E  V  I  A  S  784

----------|----------|----------|----------|----------|
       2351 ctattatcaaaccccagaacacctactgcgtgagaaggtacgccgtcgtt 2400
        785  I  I  K  P  Q  N  T  Y  C  V  R  R  Y  A  V  V  800

----------|----------|----------|----------|----------|
       2401 cagaaagccgcacacggacacgtgcgcaaagctttcaaatcccacgtgtc 2450
        801  Q  K  A  A  H  G  H  V  R  K  A  F  K  S  H  V  S  817

----------|----------|----------|----------|----------|
       2451 taccttgacagaccctccagcttatatgcggcagtttgtcgcacacctgc 2500
        818  T  L  T  D  L  Q  P  Y  M  R  Q  F  V  A  H  L  Q  834
```

FIG. 17D

```
     ----------|----------|----------|----------|----------|
2501 aggagactagcccttgagggacgctgtggtcatcgaacagtccagctct 2550
 835   E  T  S  P  L  R  D  A  V  V  I  E  Q  S  S    850

----------|----------|----------|----------|----------|
2551 ctcaatgaggcatcctcaggcctgtttgatgtgttcctgcgctttatgtg 2600
 851 L  N  E  A  S  S  G  L  F  D  V  F  L  R  F  M  C 867

----------|----------|----------|----------|----------|
2601 ccaccacgccgtgcggattaggggcaagtcttacgtgcagtgccagggca 2650
 868 H  H  A  V  R  I  R  G  K  S  Y  V  Q  C  Q  G  I 884

----------|----------|----------|----------|----------|
2651 tccacagggtagcatcctgagcacactgctgtgtagcctgtgctatggc 2700
 885 P  Q  G  S  I  L  S  T  L  L  C  S  L  C  Y  G   900

----------|----------|----------|----------|----------|
2701 gatatggagaataaattgttcgccggtatcagaagattcctgctggttac 2750
 901 D  M  E  N  K  L  F  A  G  I  R  R  F  L  L  V  T 917
                                        *

----------|----------|----------|----------|----------|
2751 ccccatctgactcatgccaaaacatttttgcggactctggttaggggcg 2800
 918 P  H  L  T  H  A  K  T  F  L  R  T  L  V  R  G  V 934

----------|----------|----------|----------|----------|
2801 tgccagagtatggctgtgttgtgaatttgcggaaaactgtggttaatttc 2850
 935 P  E  Y  G  C  V  V  N  L  R  K  T  V  V  N  F   950

----------|----------|----------|----------|----------|
2851 ccagtggaggacgaagctctcggaggcacagcttttgttcagatgcctgc 2900
 951 P  V  E  D  E  A  L  G  G  T  A  F  V  Q  M  P  A 967

----------|----------|----------|----------|----------|
2901 ccacggcctgttccatggtgcggactgctgctcgataccggacctcg 2950
 968 H  G  L  F  P  W  C  G  L  L  L  D  T  R  T  L  E 984

----------|----------|----------|----------|----------|
2951 aggtgcagtccgattatagttcctatgcaagaacatcaattcgggctagc 3000
 985 V  Q  S  D  Y  S  S  Y  A  R  T  S  I  R  A  S   1000

----------|----------|----------|----------|----------|
3001 ctgactttcaacagggggcttcaaggccggccggaatatgagaaggaaact 3050
1001 L  T  F  N  R  G  F  K  A  G  R  N  M  R  R  K  L 1017

----------|----------|----------|----------|----------|
3051 gttcggagtgttgagacttaagtgtcatagtctttttttggacttgcagg 3100
1018 F  G  V  L  R  L  K  C  H  S  L  F  L  D  L  Q  V 1034

----------|----------|----------|----------|----------|
3101 tcaattctctccagacagtgtgtaccaacatttataaaatcctcttgctg 3150
1035   N  S  L  Q  T  V  C  T  N  I  Y  K  I  L  L  L 1050

----------|----------|----------|----------|----------|
3151 caggcttacagattccatgcctgcgtcctgcagctgcctttccaccagca 3200
1051 Q  A  Y  R  F  H  A  C  V  L  Q  L  P  F  H  Q  Q 1067

----------|----------|----------|----------|----------|
3201 ggtgtggaaaaaccctaccttcttcctgcgggtgattagcgacaccgcca 3250
1068 V  W  K  N  P  T  F  F  L  R  V  I  S  D  T  A  S 1084

----------|----------|----------|----------|----------|
3251 gtctttgctactccatcttgaaagcaaaaaacgctggcatgagcttggga 3300
1085 L  C  Y  S  I  L  K  A  K  N  A  G  M  S  L  G   1100

----------|----------|----------|----------|----------|
3301 gctaagggcgccgctggacctctgccagtgaagcagtccagtggctgtg 3350
1101 A  K  G  A  A  G  P  L  P  S  E  A  V  Q  W  L  C 1117
```

FIG. 17E

```
          ----------|----------|----------|----------|----------|
     3351 tcatcaggctttcctccttaaactgacacgccaccgcgtgacttacgtcc 3400
     1118  H  Q  A  F  L  L  K  L  T  R  H  R  V  T  Y  V  P 1134

----------|----------|----------|----------|----------|
     3401 cactcctgggctccctgagaactgctcagacccagctttcccggaagctt 3450
     1135  L  L  G  S  L  R  T  A  Q  T  Q  L  S  R  K  L  1150

----------|----------|----------|----------|----------|
     3451 ccaggcactacccttaccgcactcgaagcagccgccaaccctgccctgcc 3500
     1151  P  G  T  T  L  T  A  L  E  A  A  A  N  P  A  L  P 1167
                                          hTERT>< tag V5
          ----------|----------|----------|----------|----------|
     3501 ctccgactttaagactatcctggacggcaagccaattcctaatccattgc 3550
     1168  S  D  F  K  T  I  L  D  G  K  P  I  P  N  P  L  L 1184
                                >STOP
          ----------|----------|
     3551 tgggcctggactcaacttga 3570
     1185  G  L  D  S  T  □   1189
```

FIG. 18A

```
    < Human ubiquitin
    ---------|---------|---------|---------|---------|
  1 atgcagatttcgtcaaaacattgacaggaaagaccatcacactggaagt  50
  1  M  Q  I  F  V  K  T  L  T  G  K  T  I  T  L  E  V   17

---------|---------|---------|---------|---------|
 51 ggagccaagcgacactattgagaacgtcaaagccaagattcaggacaagg 100
 18  E  P  S  D  T  I  E  N  V  R  A  K  I  Q  D  K  E   34

---------|---------|---------|---------|---------|
101 agggcatcccaccagaccagcagaggctgatttttgccggaaagcagctg 150
 35   G  I  P  P  D  Q  Q  R  L  I  F  A  G  K  Q  L    50

---------|---------|---------|---------|---------|
151 gaggacggacgcacactcagtgactacaatatccagaaggaaagtactct 200
 51  E  D  G  R  T  L  S  D  Y  N  I  Q  K  E  S  T  L   67
             Human ubiquitin   ><    hTERT
    ---------|---------|---------|---------|---------|
201 gcatctggtccttcgcctgcgcggcggactggccaccttgtgcggcgcc 250
 68  H  L  V  R  L  R  G  G  L  A  T  F  V  R  L       84

---------|---------|---------|---------|---------|
251 tgggaccccagggctggcggctggtgcagcgcggggaccctgctgctttc 300
 85   G  P  Q  G  W  R  L  V  Q  R  G  D  P  A  A  F    100

---------|---------|---------|---------|---------|
301 agagctctcgtcgccagtgtctggtctgcgttccttgggacgcacggcc 350
101  R  A  L  V  A  Q  C  L  V  C  V  P  W  D  A  R  P  117

---------|---------|---------|---------|---------|
351 cccacccgcgccccagtttcggcaggtgagttgtctcaaagagttgg 400
118   P  A  A  P  S  F  R  Q  V  S  C  L  K  E  L  V    134

---------|---------|---------|---------|---------|
401 ttgctcgggtgttgcagcggctttgtgaaaggggagcaaagaacgtcctt 450
135    A  R  V  L  Q  R  L  C  E  R  G  A  K  N  V  L   150

---------|---------|---------|---------|---------|
451 gcctttggcttcgctttgctcgatggagcacgcggaggccctcctgaggc 500
151 A  F  G  F  A  L  L  D  G  A  R  G  G  P  P  E  A   167

---------|---------|---------|---------|---------|
501 attcactactagcgtccggtcctacctgcccaacacagtgacgacgctc 550
168  F  T  T  S  V  R  S  Y  L  P  N  T  V  T  D  A  L  184

---------|---------|---------|---------|---------|
551 tgagaggttcaggtgcctgggtctgctgctgcgggaggtgggtgatgat  600
185    R  G  S  G  A  W  G  L  L  L  R  V  G  D  D      200

---------|---------|---------|---------|---------|
601 gttctggttcacctcctggcccggtgtgccctgttcgtgctggtggctcc 650
201  V  L  V  H  L  L  A  R  C  A  L  F  V  L  V  A  P  217

---------|---------|---------|---------|---------|
651 ctcctgcgcataccaggtctgcggaccccactttatcagctcggcgctg  700
218   S  C  A  Y  Q  V  C  G  P  P  L  Y  Q  L  G  A  A 234

---------|---------|---------|---------|---------|
701 ctactcaggccgcccaccaccacacgcctcaggtccaagacgcggctg  750
235    T  Q  A  R  P  P  P  H  A  S  G  P  R  R  L      250

---------|---------|---------|---------|---------|
751 ggctgcgaacgggcatggaatcatagcgtgcgggaggcaggtgtgcctct 800
251  G  C  E  R  A  W  N  H  S  V  R  E  A  G  V  P  L  267
```

FIG. 18B

```
         ----------|----------|----------|----------|----------|
    801  cggcctgccagccccggagcaaggagacgcggtggatccgccagtcgct  850
    268   G  L  P  A  P  G  A  R  R  R  G  G  S  A  S  R  S   284

----------|----------|----------|----------|----------|
    851  cactcccttgcctaagaggccaagaagaggagccgccctgaacccgag  900
    285   L  P  L  P  K  R  P  R  R  G  A  A  P  E  P  E      300

----------|----------|----------|----------|----------|
    901  agaacacctgtcggccagggctcctgggctcaccccggaaggaccagggg  950
    301   R  T  P  V  G  Q  G  S  W  A  H  P  G  R  T  R  G   317

----------|----------|----------|----------|----------|
    951  cccaagcgatagggcttctgtgttgtgtcaccagccaggcctgccgaag  1000
    318   P  S  D  R  G  F  C  V  V  S  P  A  R  P  A  E  E   334

----------|----------|----------|----------|----------|
   1001  aggctacctccttggaaggagccctcagtggcaccaggcattctcatcca  1050
    335   A  T  S  L  E  G  A  L  S  G  T  R  H  S  H  P      350

----------|----------|----------|----------|----------|
   1051  tctgtgggtaggcagcatcatgccggcccccctctacaagcagacctcc  1100
    351   S  V  G  R  Q  H  H  A  G  P  P  S  T  S  R  P  P   367

----------|----------|----------|----------|----------|
   1101  cagacttgggacacaccctgccaccagtgtatgccgagaccaagcact  1150
    368   R  P  W  D  T  P  C  P  P  V  Y  A  E  T  K  H  F   384

----------|----------|----------|----------|----------|
   1151  ttttgtattccagtggcgataaagagcagctccggccctcttttctgtc  1200
    385   L  Y  S  S  G  D  K  E  Q  L  R  P  S  F  L  L      400

----------|----------|----------|----------|----------|
   1201  tcaagcctccgcccctctctgaccggagctcgcaggctggtggagaccat  1250
    401   S  S  L  R  P  S  L  T  G  A  R  R  L  V  E  T  I   417

----------|----------|----------|----------|----------|
   1251  ctttctgggctcaagaccatggatgccaggcaccccccgcagactgccca  1300
    418   F  L  G  S  R  P  W  M  P  G  T  P  R  R  L  P  R   434

----------|----------|----------|----------|----------|
   1301  ggctcccccagcggtactggcagatgcgccctctctttctggaacttctg  1350
    435   L  P  Q  R  Y  W  Q  M  R  P  L  F  L  E  L  L      450

----------|----------|----------|----------|----------|
   1351  ggtaaccacgccagtgcccatatggcgtcctgctgaagacccactgtcc  1400
    451   G  N  H  A  Q  C  P  Y  G  V  L  L  K  T  H  C  P   467

----------|----------|----------|----------|----------|
   1401  tctgagggccgccgtgaccccagccgccggtgtgtgtgctagagaaaaac  1450
    468   L  R  A  A  V  T  P  A  A  G  V  C  A  R  E  K  P   484

----------|----------|----------|----------|----------|
   1451  cccagggctcagtggctgcacctgaagaggaggacactgaccctcgcgc  1500
    485   Q  G  S  V  A  A  P  E  E  D  T  D  P  R  R         500

----------|----------|----------|----------|----------|
   1501  cttgtccagttgctcaggcagcattcatcaccatggcaggtgtacggctt  1550
    501   L  V  Q  L  L  R  Q  H  S  S  P  W  Q  V  Y  G  F   517

----------|----------|----------|----------|----------|
   1551  cgtgagggcttgcctgcggagactggtccccccggattgtgggatctc  1600
    518   V  R  A  C  L  R  R  L  V  P  P  G  L  W  G  S  R   534

----------|----------|----------|----------|----------|
   1601  ggcacaacgaacgggctttctgaggaatacaaagaagtttatctccctg  1650
    535   H  N  E  R  R  F  L  R  N  T  K  K  F  I  S  L      550
```

FIG. 18C

```
         ----------|----------|----------|----------|----------|
    1651 ggcaagcatgcaaagctcagcttgcaggagctgacatggaagatgagcgt 1700
     551  G  K  H  A  K  L  S  L  Q  E  L  T  W  K  M  S  V   567

----------|----------|----------|----------|----------|
    1701 tagaggatgcgcatggctcaggcggtcacctggagttggatgcgttccag 1750
     568  R  G  C  A  W  L  R  R  S  P  G  V  G  C  V  P  A   584

----------|----------|----------|----------|----------|
    1751 cagcagagcacaggctgcgcgaagagattctcgcaaagttcctgcactgg 1800
     585  A  E  H  R  L  R  E  E  I  L  A  K  F  L  H  W   600

----------|----------|----------|----------|----------|
    1801 cttatgagcgtctacgtggtcgaactgctgcggtcttcttctacgtgac 1850
     601  L  M  S  V  Y  V  V  E  L  L  R  S  F  F  Y  V  T   617

----------|----------|----------|----------|----------|
    1851 agagaccactttcagaagaacagactgttcttctacaggaagtccgtct 1900
     618  E  T  T  F  Q  K  N  R  L  F  F  Y  R  K  S  V  W   634

----------|----------|----------|----------|----------|
    1901 ggagcaagctccagagtattggtattagacagcaccttaagagagttcag 1950
     635  S  K  L  Q  S  I  G  I  R  Q  H  L  K  R  V  Q   650

----------|----------|----------|----------|----------|
    1951 cttagagagctgtccgaagctgaagtccgccagcaccgcgaagctcgcc 2000
     651  L  R  E  L  S  E  A  E  V  R  Q  H  R  E  A  R  P   667

----------|----------|----------|----------|----------|
    2001 cgccctcctgacctctcggctgcggtttattcccaaacccgatggcctta 2050
     668  A  L  L  T  S  R  L  R  F  I  P  K  P  D  G  L  R   684

----------|----------|----------|----------|----------|
    2051 gacctatcgtgaatatggattacgtcgtgggtgcccgcactttcagaagg 2100
     685  P  I  V  N  M  D  Y  V  V  G  A  R  T  F  R  R   700

----------|----------|----------|----------|----------|
    2101 gagaagcgcgccgagagactgacatctcgcgtgaaggcacttttttctgt 2150
     701  E  K  R  A  E  R  L  T  S  R  V  K  A  L  F  S  V   717

----------|----------|----------|----------|----------|
    2151 gcttaattatgaaagagcccgcagacctggtcttctcggagccagcgtgc 2200
     718  L  N  Y  E  R  A  R  R  P  G  L  L  G  A  S  V  L   734

----------|----------|----------|----------|----------|
    2201 tcggcctggatgatatccatcgggcttggcgcacctttgtgcttcgggtg 2250
     735  G  L  D  D  I  H  R  A  W  R  T  F  V  L  R  V   750

----------|----------|----------|----------|----------|
    2251 agggcacaggatcctcctcctgagctttatttgtgaaagttgatgttac 2300
     751  R  A  Q  D  P  P  P  E  L  Y  F  V  K  V  D  V  T   767

----------|----------|----------|----------|----------|
    2301 tggtgcttacgatacaatccctcaggacgggctcaccgaggtgatcgcct 2350
     768  G  A  Y  D  T  I  P  Q  D  R  L  T  E  V  I  A  S   784

----------|----------|----------|----------|----------|
    2351 ctattatcaaacccagaacacctactgcgtgagaaggtacgccgtcgtt 2400
     785  I  I  K  P  Q  N  T  Y  C  V  R  R  Y  A  V  V   800

----------|----------|----------|----------|----------|
    2401 cagaaagccgcacacggacacgtgcgcaaagctttcaaatcccacgtgtc 2450
     801  Q  K  A  A  H  G  H  V  R  K  A  F  K  S  H  V  S   817

----------|----------|----------|----------|----------|
    2451 taccttgacagacctccagccttatatgcggcagtttgtcgcacacctgc 2500
     818  T  L  T  D  L  Q  P  Y  M  R  Q  F  V  A  H  L  Q   834
```

FIG. 18D

```
          ----------|----------|----------|----------|----------|
     2501 aggagactagcccttgagggacgctgtggtcatcgaacagtccagctct 2550
      835  E  T  S  P  L  R  D  A  V  V  I  E  Q  S  S  S     850

----------|----------|----------|----------|----------|
     2551 ctcaatgaggcatcctcaggctgtttgatgtgttcctgcgctttatgtg 2600
      851  L  N  E  A  S  S  G  L  F  D  V  F  L  R  F  M  C  867

----------|----------|----------|----------|----------|
     2601 ccaccacgccgtgcggattaggggcaagtcttacgtgcagtgccagggca 2650
      868  H  H  A  V  R  I  R  G  K  S  Y  V  Q  C  Q  G  I  884

----------|----------|----------|----------|----------|
     2651 tcccacagggtagcatcctgagcacactgctgtgtagcctgtgctatggc 2700
      885  P  Q  G  S  I  L  S  T  L  L  C  S  L  C  Y  G     900

----------|----------|----------|----------|----------|
     2701 gatatggagaataaattgttcgccggtatcagaagagacggtttgctcct 2750
      901  D  M  E  N  K  L  F  A  G  I  R  R  D  G  L  L     917

----------|----------|----------|----------|----------|
     2751 gaggctgctgactcatgccaaaacattttgcggactctggttaggggcg 2800
      918  R  L  L  T  H  A  K  T  F  L  R  T  L  V  R  G  V  934
              *

----------|----------|----------|----------|----------|
     2801 tgccagagtatggctgtgttgtgaatttgcggaaaactgtggttaatttc 2850
      935  P  E  Y  G  C  V  V  N  L  R  K  T  V  V  N  F     950

----------|----------|----------|----------|----------|
     2851 ccagtggaggacgaagctctcggaggcacagcttttgttcagatgcctgc 2900
      951  P  V  E  D  E  A  L  G  G  T  A  F  V  Q  M  P  A  967

----------|----------|----------|----------|----------|
     2901 ccacggctgttcccatggtgcggactgctgctcgataccggaccctcg 2950
      968  H  G  L  F  P  W  C  G  L  L  L  D  T  R  T  L  E  984

----------|----------|----------|----------|----------|
     2951 aggtgcagtccgattatagttcctatgcaagaacatcaattcgggctagc 3000
      985  V  Q  S  D  Y  S  S  Y  A  R  T  S  I  R  A  S    1000

----------|----------|----------|----------|----------|
     3001 ctgactttcaacagggggcttcaaggccggccggaatatgagaaggaaact 3050
     1001  L  T  F  N  R  G  F  K  A  G  R  N  M  R  R  K  L 1017

----------|----------|----------|----------|----------|
     3051 gttcggagtgttgagacttaagtgtcatagtctttttttggacttgcagg 3100
     1018  F  G  V  L  R  L  K  C  H  S  L  F  L  D  L  Q  V 1034

----------|----------|----------|----------|----------|
     3101 tcaattctctccagacagtgtgtaccaacatttataaaatcctcttgctg 3150
     1035  N  S  L  Q  T  V  C  T  N  I  Y  K  I  L  L  L    1050

----------|----------|----------|----------|----------|
     3151 caggcttacagattccatgcctgcgtcctgcagctgcctttccaccagca 3200
     1051  Q  A  Y  R  F  H  A  C  V  L  Q  L  P  F  H  Q  Q 1067

----------|----------|----------|----------|----------|
     3201 ggtgtggaaaaaccctaccttcttcctgcgggtgattagcgacaccgca 3250
     1068  V  W  K  N  P  T  F  F  L  R  V  I  S  D  T  A  S 1084

----------|----------|----------|----------|----------|
     3251 gtctttgctactccatcttgaaagcaaaaaacgctggcatgagcttggga 3300
     1085  L  C  Y  S  I  L  K  A  K  N  A  G  M  S  L  G   1100

----------|----------|----------|----------|----------|
     3301 gctaagggcgccgctggacctctgcccagtgaagcagtccagtggctgtg 3350
     1101  A  K  G  A  A  G  P  L  P  S  E  A  V  Q  W  L  C 1117
```

FIG. 18E

```
       ----------|----------|----------|----------|----------|
3351   tcatcaggctttcctccttaaactgacacgccaccgcgtgacttacgtcc 3400
1118    H  Q  A  F  L  L  K  L  T  R  H  R  V  T  Y  V  P  1134

----------|----------|----------|----------|----------|
3401   cactcctgggctccctgagaactgctcagacccagctttcccggaagctt 3450
1135    L  L  G  S  L  R  T  A  Q  T  Q  L  S  R  K  L     1150

----------|----------|----------|----------|----------|
3451   ccaggcactacccttaccgcactcgaagcagccgccaaccctgccctgcc 3500
1151    P  G  T  T  L  T  A  L  E  A  A  A  N  P  A  L  P  1167
                              hTERT>< tag V5
       ----------|----------|----------|----------|----------|
3501   ctccgactttaagactatcctggacggcaagccaattcctaatccattgc 3550
1168    S  D  F  K  T  I  L  D  G  K  P  I  P  N  P  L  1184
                              >STOP
       ----------|----------|
3551   tgggcctggactcaacttga 3570
1185    G  L  D  S  T  □  1139
```

FIG. 19A

```
            < Human ubiquitin
         ----------|----------|----------|----------|----------|
   1  atgcagatttttcgtcaaaacattgacaggaaagaccatcacactggaagt  50
   1   M  Q  I  F  V  K  T  L  T  G  K  T  I  T  L  E  V  17

----------|----------|----------|----------|----------|
  51  ggagccaagcgacactattgagaacgtcaaagccaagattcaggacaagg  100
  18   E  P  S  D  T  I  E  N  V  K  A  K  I  Q  D  K  E  34

----------|----------|----------|----------|----------|
 101  agggcatcccaccagaccagcagaggctgatttttgccggaaagcagctg  150
  35   G  I  P  P  D  Q  Q  R  L  I  F  A  G  K  Q  L     50

----------|----------|----------|----------|----------|
 151  gaggacggacgcacactcagtgactacaatatccagaaggaaagtactct  200
  51   E  D  G  R  T  L  S  D  Y  N  I  Q  K  E  S  T  L  67
                  Human ubiquitin  ><      hTERT
         ----------|----------|----------|----------|----------|
 201  gcatctggtccttcgcctgcgcggcggactggccaccttcgtgcggcgcc  250
  68   H  L  V  L  R  L  R  G  G  L  A  T  F  V  R  R  L  84

----------|----------|----------|----------|----------|
 251  tgggacccccagggctggcggctggtgcagcgcggggaccctgctgcttc  300
  85   G  P  Q  G  W  R  L  V  Q  R  G  D  P  A  A  F    100

----------|----------|----------|----------|----------|
 301  agagctctcgtcgcccagtgtctggtctgcgttccttgggacgcacggcc  350
 101   R  A  L  V  A  Q  C  L  V  C  V  P  W  D  A  R  P 117

----------|----------|----------|----------|----------|
 351  cccaccccgccgcccccagtttccggcaggtgagttgtctcaaagagttgg  400
 118   P  P  A  A  P  S  F  R  Q  V  S  C  L  K  E  L  V 134

----------|----------|----------|----------|----------|
 401  ttgctcgggtgttgcagcggctttgtgaaaggggagcaaagaacgtcctt  450
 135   A  R  V  L  Q  R  L  C  E  R  G  A  K  N  V  L    150

----------|----------|----------|----------|----------|
 451  gcctttggcttcgctttgctcgatggagcacgcggaggccctcctgaggc  500
 151   A  F  G  F  A  L  L  D  G  A  R  G  G  P  P  E  A 167

----------|----------|----------|----------|----------|
 501  attcactactagcgtcggtcctacctgcccaacacagtgaccgacgctc  550
 168   F  T  T  S  V  R  S  Y  L  P  N  T  V  T  D  A  L 184

----------|----------|----------|----------|----------|
 551  tgagaggttcaggtgcctggggtctgctgctgcggagggtgggtgatgat  600
 185   R  G  S  G  A  W  G  L  L  L  R  R  V  G  D  D    200

----------|----------|----------|----------|----------|
 601  gttctggttcacctcctggcccggtgtgccctgttcgtgctggtggctcc  650
 201   V  L  V  H  L  L  A  R  C  A  L  F  V  L  V  A  P 217

----------|----------|----------|----------|----------|
 651  ctcctgcgcataccaggtctgcggaccccactttatcagctcggcgctg  700
 218   S  C  A  Y  Q  V  C  G  P  P  L  Y  Q  L  G  A  A 234

----------|----------|----------|----------|----------|
 701  ctactcaggcccgccaccaccacacgcctcaggtccaagacgccggctg  750
 235   T  Q  A  R  P  P  P  H  A  S  G  P  R  R  R  L    250

----------|----------|----------|----------|----------|
 751  ggctgcgaacggcatggaatcatagcgtgcgggaggcaggtgtgcctct  800
 251   G  C  E  R  A  W  N  H  S  V  R  E  A  G  V  P  L 267
```

FIG. 19B

```
         ----------|----------|----------|----------|----------|
    801  cggcctgccagccccggagcaaggagacgcggtggatccgccagtcgct  850
    268   G  L  P  A  P  G  A  R  R  R  G  G  S  A  S  R  S  284

----------|----------|----------|----------|----------|
    851  cactccccttgcctaagaggccaagaagaggagccgcccctgaacccgag  900
    285   L  P  L  F  K  R  P  R  R  G  A  A  P  E  P  E   300

----------|----------|----------|----------|----------|
    901  agaacacctgtcggccagggctcctgggctcacccggaaggaccagggg   950
    301   R  T  P  V  G  Q  G  S  W  A  H  P  G  R  T  R  G  317

----------|----------|----------|----------|----------|
    951  cccaagcgatagggctcctgtgttgtgtcaccagccaggcctgccgaag  1000
    318   P  S  D  R  G  F  C  V  V  S  P  A  R  P  A  E   334

----------|----------|----------|----------|----------|
   1001  aggctacctccttggaaggagccctcagtggcaccaggcattctcatcca  1050
    335   A  T  S  L  E  G  A  L  S  G  T  R  H  S  H  P   350

----------|----------|----------|----------|----------|
   1051  tctgtgggtaggcagcatcatgccggcccccctctacaagcagacctcc  1100
    351   S  V  G  R  Q  H  H  A  G  P  P  S  T  S  R  P  P  367

----------|----------|----------|----------|----------|
   1101  cagaccttgggacacacctgcccaccagtgtatgccgagaccaagcact  1150
    368   R  P  W  D  T  P  C  P  P  V  Y  A  E  T  K  H  F  384

----------|----------|----------|----------|----------|
   1151  ttttgtattccagtggcgataaagagcagctccggcccctcttttctgctc  1200
    385   L  Y  S  S  G  D  K  E  Q  L  R  P  S  F  L  L   400

----------|----------|----------|----------|----------|
   1201  tcaagcctccgccctctctgaccggagctgcaggctggtggagaccat  1250
    401   S  S  L  R  P  S  L  T  G  A  R  R  L  V  E  T  I  417

----------|----------|----------|----------|----------|
   1251  ctttctgggctcaagaccatggatgccaggcaccccgcagactgcca  1300
    418   F  L  G  S  R  P  W  M  P  G  T  P  R  R  L  P  R  434

----------|----------|----------|----------|----------|
   1301  ggctccccagcggtactggcagatgcgccctctctttctggaacttctg  1350
    435   L  P  Q  R  Y  W  Q  M  R  P  L  F  L  E  L  L   450

----------|----------|----------|----------|----------|
   1351  ggtaaccacgcccagtgcccatatggggtcctgctgaagacccactgtcc  1400
    451   G  N  H  A  Q  C  P  Y  G  V  L  L  K  T  H  C  P  467

----------|----------|----------|----------|----------|
   1401  tctgagggccgccgtgaccccagccgccggtgtgtgtgctagagaaaaac  1450
    468   L  R  A  A  V  T  P  A  A  G  V  C  A  R  E  K  P  484

----------|----------|----------|----------|----------|
   1451  cccaggctcagtggctgcacctgaagaggaggacactgaccctcgccgc  1500
    485   Q  G  S  V  A  A  P  E  E  D  T  D  P  R  R   500

----------|----------|----------|----------|----------|
   1501  cttgtccagttgctcaggcagcattcatcaccatggcaggtgtacggctt  1550
    501   L  V  Q  L  L  R  Q  H  S  S  P  W  Q  V  Y  G  F  517

----------|----------|----------|----------|----------|
   1551  cgtgagggcttgcctgcgggagactggtccccccggattgtggggatctc  1600
    518   V  R  A  C  L  R  R  L  V  P  P  G  L  W  G  S  R  534

----------|----------|----------|----------|----------|
   1601  ggcacaacgaacggcgctttctgaggaatacaaagaagtttatctccctg  1650
    535   H  N  E  R  R  F  L  R  N  T  K  K  F  I  S  L   550
```

FIG. 19C

```
        ----------|----------|----------|----------|----------|
   1651 ggcaagcatgcaaagctcagcttgcaggagctgacatggaagatgagcgt 1700
    551  G  K  H  A  K  L  S  L  Q  E  L  T  W  K  M  S  V  567

----------|----------|----------|----------|----------|
   1701 tagaggatgcgcatggctcaggcggtcacctggagttggatgcgttccag 1750
    568  R  G  C  A  W  L  R  R  S  P  G  V  G  C  V  P  A  584

----------|----------|----------|----------|----------|
   1751 cagcagagcacaggctgcgcgaagagattctcgcaaagttcctgcactgg 1800
    585  A  E  H  R  L  R  E  E  I  L  A  K  F  L  H  W     600

----------|----------|----------|----------|----------|
   1801 cttatgagcgtctacgtggtcgaactgctgcggtcttttcttctacgtgac 1850
    601  L  M  S  V  Y  V  V  E  L  L  R  S  F  F  Y  V  T  617

----------|----------|----------|----------|----------|
   1851 agagaccacttttcagaagaacagactgttcttctacaggaagtccgtct 1900
    618  E  T  T  F  Q  K  N  R  L  F  F  Y  R  K  S  V  W  634

----------|----------|----------|----------|----------|
   1901 ggagcaagctccagagtattggtattagacagcaccttaagagagttcag 1950
    635  S  K  L  Q  S  I  G  I  R  Q  H  L  K  R  V  Q     650

----------|----------|----------|----------|----------|
   1951 cttagagagctgtccgaagctgaagtccgccagcaccgcgaagctcgccc 2000
    651  L  R  E  L  S  E  A  E  V  R  Q  H  R  E  A  R  P  667

----------|----------|----------|----------|----------|
   2001 cgccctcctgacctctcggctgcggtttattccaaaccgatggcctta   2050
    668  A  L  L  T  S  R  L  R  F  I  P  K  P  D  G  L  R  684

----------|----------|----------|----------|----------|
   2051 gacctatcgtgaatatggattacgtcgtgggtgcccgcacttcagaagg 2100
    685     P  I  V  N  M  D  Y  V  V  G  A  R  T  F  R  R  700

----------|----------|----------|----------|----------|
   2101 gagaagcgcgccgagagactgacatctcgcgtgaaggcacttttttctgt 2150
    701  E  K  R  A  E  R  L  T  S  R  V  K  A  L  F  S  V  717

----------|----------|----------|----------|----------|
   2151 gcttaattatgaaagagcccgcagacctggtcttctcggagccagctgc 2200
    718  L  N  Y  E  R  A  R  R  P  G  L  L  G  A  S  V  L  734

----------|----------|----------|----------|----------|
   2201 tcggctggatgatatccatcggcttggcgcacctttgtgcttcgggtg   2250
    735     G  L  D  D  I  H  R  A  W  R  T  F  V  L  R  V  750

----------|----------|----------|----------|----------|
   2251 agggcacaggatcctcctcctgagcttatttttgtgaaagttgatgttac 2300
    751  R  A  Q  D  P  P  P  E  L  Y  F  V  K  V  D  V  T  767

----------|----------|----------|----------|----------|
   2301 tggtgcttacgatacaatccctcaggaccggctcaccgaggtgatcgcct 2350
    768  G  A  Y  D  T  I  P  Q  D  R  L  T  E  V  I  A  S  784

----------|----------|----------|----------|----------|
   2351 ctattatcaaacccagaacacctactgcgtgagaaggtacgccgtcgtt 2400
    785     I  I  K  P  Q  N  T  Y  C  V  R  R  Y  A  V  V  800

----------|----------|----------|----------|----------|
   2401 cagaaagcgcacacggacacgtgcgcaaagctttcaaatcccacgtgtc 2450
    801  Q  K  A  A  H  G  H  V  R  K  A  F  K  S  H  V  S  817

----------|----------|----------|----------|----------|
   2451 taccttgacagacctccagccttatatgcggcagtttgtcgcacacctgc 2500
    818  T  L  T  D  L  Q  P  Y  M  R  Q  F  V  A  H  L  Q  834
```

FIG. 19D

```
           ----------|----------|----------|----------|----------|
     2501  aggagactagcccttgagggacgctgtggtcatcgaacagtccagctct  2550
      835    E  T  S  P  L  R  D  A  V  V  I  E  Q  S  S       850

----------|----------|----------|----------|----------|
     2551  ctcaatgaggcatcctcaggcctgtttgatgtgttcctgcgctttatgtg  2600
      851    L  N  E  A  S  S  G  L  F  D  V  F  L  R  F  M  C  867

----------|----------|----------|----------|----------|
     2601  ccaccacgccgtgcggattaggggcaagtcttacgtgcagtgccagggca  2650
      868    H  H  A  V  R  I  R  G  K  S  Y  V  Q  C  Q  G  I  884

----------|----------|----------|----------|----------|
     2651  tcccacagggtagcatcctgagcacactgctgtgtagcctgtgctatggc  2700
      885    P  Q  G  S  I  L  S  T  L  L  C  S  L  C  Y  G     900

----------|----------|----------|----------|----------|
     2701  gatatggagaataaattgttcgccggtgccaaaacattttttgcggactct  2750
      901    D  M  E  N  K  L  F  A  G  A  K  T  F  L  R  T  L  917
                                          *

----------|----------|----------|----------|----------|
     2751  ggttagggcgtgccagagtatggctgtgttgtgaatttgcggaaaactg   2800
      918    V  R  G  V  P  E  Y  G  C  V  V  N  L  R  K  T  V  934

----------|----------|----------|----------|----------|
     2801  tggttaatttccagtggaggacgaagctctcggaggcacagcttttgtt   2850
      935    V  N  F  P  V  E  D  E  A  L  G  G  T  A  F  V     950

----------|----------|----------|----------|----------|
     2851  cagatgcctgcccacggcctgttcccatggtgcggactgctgctcgatac  2900
      951    Q  M  P  A  H  G  L  F  P  W  C  G  L  L  D  T     967

----------|----------|----------|----------|----------|
     2901  ccggacctcgaggtgcagtccgattatagttcctatgcaagaacatcaa   2950
      968    R  T  L  E  V  Q  S  D  Y  S  S  Y  A  R  T  S  I  984

----------|----------|----------|----------|----------|
     2951  ttcgggctagcctgactttcaacaggggcttcaaggccggccggaatatg  3000
      985    R  A  S  L  T  F  N  R  G  F  K  A  G  R  N  M    1000

----------|----------|----------|----------|----------|
     3001  agaaggaaactgttcggagtgttgagacttaagtgtcatagtcttttttt  3050
     1001    R  R  K  L  F  G  V  L  R  L  K  C  H  S  L  F  L 1017

----------|----------|----------|----------|----------|
     3051  ggacttgcaggtcaattctctccagacagtgtgtaccaacatttataaaa  3100
     1018    D  L  Q  V  N  S  L  Q  T  V  C  T  N  I  Y  K  I 1034

----------|----------|----------|----------|----------|
     3101  tcctcttgctgcaggcttacagattccatgcctgcgtcctgcagctgcct  3150
     1035    L  L  Q  A  Y  R  F  H  A  C  V  L  Q  L  P       1050

----------|----------|----------|----------|----------|
     3151  ttccaccagcaggtgtggaaaaaccctaccttcttcctgcgggtgattag  3200
     1051    F  H  Q  Q  V  W  K  N  P  T  F  F  L  R  V  I  S 1067

----------|----------|----------|----------|----------|
     3201  cgacaccgccagtctttgctactccatcttgaaagcaaaaaacgctgga   3250
     1068    D  T  A  S  L  C  Y  S  I  L  K  A  K  N  A  G  M 1084

----------|----------|----------|----------|----------|
     3251  tgagcttgggagctaagggcgccgctggacctctgcccagtgaagcagtc  3300
     1085    S  L  G  A  K  G  A  A  G  P  L  P  S  E  A  V    1100

----------|----------|----------|----------|----------|
     3301  cagtggctgtgtcatcaggctttcctccttaaactgacacgccacgcgt   3350
     1101    Q  W  L  C  H  Q  A  F  L  L  K  L  T  R  H  R  V 1117
```

FIG. 19E

```
          ----------|----------|----------|----------|----------|
     3351 gacttacgtcccactcctgggctccctgagaactgctcagacccagcttt 3400
     1118  T  Y  V  P  L  L  G  S  L  R  T  A  Q  T  Q  L  S  1134

----------|----------|----------|----------|----------|
     3401 cccggaagcttccaggcactacccttaccgcactcgaagcagccgccaac 3450
     1135  P  K  L  P  G  T  T  L  T  A  L  E  A  A  A  N      1150
                                              hTERT><tag V5
          ----------|----------|----------|----------|----------|
     3451 cctgccctgccctccgactttaagactatcctggacggcaagccaattcc 3500
     1151  P  A  L  P  S  D  F  K  T  I  L  D  G  K  P  I  P  1167

>STOP
          ----------|----------|----------|-
     3501 taatccattgctgggcctggactcaacttga 3531
     1168  N  P  L  L  G  L  D  S  T  □  1176
```

FIG. 27A

```
     <  Human ubiquitin
     ----------|----------|----------|----------|----------|----------|
1    atgcagatttt cgtcaaaaca ttgacaggaa agaccatcac actggaagtg gagccaagc   60
1     M  Q  I  F  V  K  T  L  T  G  K  T  I  T  L  E  V  E  P  S        20

----------|----------|----------|----------|----------|----------|
61   gacactattg agaacgtcaa agccaagatt caggacaagg agggcatccc accagaccag  120
21    D  T  I  E  N  V  K  A  K  I  Q  D  K  E  G  I  P  P  D  Q       40

----------|----------|----------|----------|----------|----------|
121  cagaggctga ttttttgccg gaaagcagct ggaggacgga cgcacactca gtgactacaat 180
41    Q  R  L  I  F  A  G  K  Q  L  E  D  G  R  T  L  S  D  Y  N       60

Human ubiquitin >< hTERT Fragment 1
     ----------|----------|----------|----------|----------|----------|
181  atccagaagg aaagtactct gcatctggtc cttcgcctgc gcggcggact ggccaccttc  240
61    I  Q  K  E  S  T  L  H  L  V  L  R  L  R  G  G  L  A  T  F       80

----------|----------|----------|----------|----------|----------|
241  gtgcgacgcg cctgggaccc caggggctgg cggctggtgc agcgcgggga ccctgctgtt tc 300
81    V  R  R  L  G  P  Q  G  W  R  L  V  Q  R  G  D  P  A  A  F      100

----------|----------|----------|----------|----------|----------|
301  agagctctcg tcgcccagtg tctggtctgc gttccttggg gacgcacgg ccccacccgcc  360
101   R  A  L  V  A  Q  C  L  V  C  V  P  W  D  A  R  P  P  P  A      120

----------|----------|----------|----------|----------|----------|
361  gcccccagtt tccggcagg tgagttgat ctcaaagagt tggtgctcgg gtgttgcagcgg  420
121   A  P  S  F  R  Q  V  S  C  L  K  E  L  V  A  R  V  L  Q  R      140 hTERT
     ----------|----------|----------|----------|----------|----------|
421  cttgtgaaag gggagcaaag aacgtccttg cctttggctc gctttgctg atggagca    480
141   C  E  R  G  A  K  N  V  L  A  F  G  F  A  L  L  D  G  A         160

Fragment 1 >              <  hTERT Fragment 2
     ----------|----------|----------|----------|----------|----------|
481  cgcggaggcc ctcctgagc attcactact agcgtcggt cctactgccc aacacagtg    540
161   R  G  G  P  P  E  A  F  T  T  S  V  R  S  Y  L  P  N  T  V      180

----------|----------|----------|----------|----------|----------|
541  accgacgctc tgagaggt caggtgctg gggctgctg cgagaggtg gggatgat       600
181   T  D  A  L  R  G  S  G  A  W  G  L  L  L  R  R  V  G  D  D      200

----------|----------|----------|----------|----------|----------|
601  gtctggtcc acctcctgg ccggtgccc tgttgtgc ggtggtcc tcctgcgc         660
201   V  L  V  H  L  L  A  R  C  A  L  F  V  L  V  A  P  S  C  A      220
```

FIG. 27B

```
                              hTERT Fragment 2 >
         ----------|----------|----------|----------|----------|----------|
 661     taccaggtctgtgggaccccactttatcagctcggcgctgctactcaggcccgccacca       720
 221      Y  Q  V  C  G  P  P  L  Y  Q  L  G  A  A  T  Q  A  R  P  P      240

<  hTERT Fragment 3
         ----------|----------|----------|----------|----------|----------|
 721     ccacacgcctcaggtccaagacgccggctgggctgcgaacgggcatggaatcatagcgtg       780
 241      P  H  A  S  G  P  R  R  R  L  G  C  E  R  A  W  N  H  S  V      260

----------|----------|----------|----------|----------|----------|
 781     cgggaggcaagtgtgcctctcggcctgccagcccccggagcaaggagacgcggtgatcc       840
 261      R  G  Q  V  C  L  S  G  L  P  A  P  G  A  R  R  R  G  G  S      280 hTERT Fragment 3 >
         ----------|----------|----------|----------|----------|----------|
 841     gccagtcgctgactccccttgcctaagaggccaagaagaggagccgcccctgaaccgag       900
 281      A  S  R  S  L  P  L  P  K  R  P  R  R  G  A  A  P  E  P  E      300

<  hTERT Fragment 4
         ----------|----------|----------|----------|----------|----------|
 901     agaacacctgtcggccagggctcctgggctcaccccggaaggaccagggagcccaagcgat       960
 301      R  T  P  V  G  Q  G  S  W  A  H  P  G  R  T  R  G  P  S  D      320

----------|----------|----------|----------|----------|----------|
 961     agggggcttctgtgttgtgtcaccagccaggcctgcgaagagctacctccttggaagga      1020
 321      R  G  F  C  V  V  S  P  A  R  P  A  E  E  A  T  S  L  E  G      340 hTERT Fragment 4 >
         ----------|----------|----------|----------|----------|----------|
1021     gccctcagtggcaccaggcattctcatccatctgtgggtaggcagcatcatgccggccc      1080
 341      A  L  S  G  T  R  H  S  H  P  S  V  G  R  Q  H  H  A  G  P      360

<  hTERT Fragment 5
         ----------|----------|----------|----------|----------|----------|
1081     ccctctacaagcagacctcccagaccttgggacacaccctgccccaccagtgtatgccgag     1140
 361      P  S  T  S  R  P  P  R  P  W  D  T  P  C  P  P  V  Y  A  E      380

----------|----------|----------|----------|----------|----------|
1141     accaagcactttttgtattccagtggcgataaagagcagctccggccctctttctgtc      1200
 381      T  K  H  F  L  Y  S  S  G  D  K  E  Q  L  R  P  S  F  L  L      400

----------|----------|----------|----------|----------|----------|
1201     tcaaggctccggccctctctgaccggagctgcaggctggtggagaccatcttctgggg      1260
 401      S  S  L  R  P  S  L  T  G  A  R  R  L  V  E  T  I  F  L  G      420

----------|----------|----------|----------|----------|----------|
1261     ccaagaccatggatgccaggcacccccgcagactgcccaggctccccagcggtactgg     1320
 421      S  R  P  W  M  P  G  T  P  R  R  L  P  R  L  P  Q  R  Y  W      440

----------|----------|----------|----------|----------|----------|
1321     cagatgcgcccctcctttctggaacttctgggtaaccacgcccagtgcccatatggcgt     1380
 441      Q  M  R  P  L  F  L  E  L  L  G  N  H  A  Q  C  P  Y  G  V      460
```

FIG. 27C

```
                        hTERT Fragment 5  >       <  hTERT Fragment 6
         ----------|----------|----------|----------|----------|----------|
1381     atgctgaagacccactgtcctctgagggccgccgtgacccagccgccggtgtgtgtgct      1440
461       L  L  K  T  H  C  P  L  R  A  A  V  T  P  A  A  G  V  C  A      480

----------|----------|----------|----------|----------|----------|
1441     agagaaaaacccagggctcagtggttgcacctgaagaggaggacactgacccctgccgc      1500
481       R  E  K  P  Q  G  S  V  A  P  E  E  E  D  T  D  P  R  R        500

----------|----------|----------|----------|----------|----------|
1501     cttgtccagttgctcaggcagcattcatcaccatggcaggtgtacggcttcgtgagggct      1560
501       L  V  Q  L  L  R  Q  H  S  S  P  W  Q  V  Y  G  F  V  R  A      520

----------|----------|----------|----------|----------|----------|
1561     tgcctgcggagactggtcccccccggatgtgtgggatctcggcacaacgaaggagattt      1620
521       C  L  R  R  L  V  P  P  G  L  W  G  S  R  H  N  E  R  R         540

----------|----------|----------|----------|----------|----------|
1621     ctgaggaatacaaagagtttatctcccctgggcaagcatgcaaagctcagcttgcaggag     1680
541       L  R  N  T  K  R  F  I  S  L  G  K  H  A  K  L  S  L  Q  E      560 hTERT Fragment 6    >
         ----------|----------|----------|----------|----------|----------|
1681     attgacatggaagatgaggtgttagaggatgcgcatggctcaggcggtcacctggagttgga   1740
561       I  T  W  K  M  S  V  R  G  C  A  W  L  R  S  P  G  V  G         580

<  hTERT Fragment 7
         ----------|----------|----------|----------|----------|----------|
1741     tgcgttccagcagcagagcacaggctgcgcgaagagattctgcaaagttcctgcactgg     1800
581       C  V  P  A  A  E  H  R  L  R  E  E  I  L  A  K  F  L  H  W      600

----------|----------|----------|----------|----------|----------|
1801     cttatgagcgtctacgtggtcgaactgctgcggtctttcttctacgtgacagagacact     1860
601       L  M  S  V  Y  V  V  E  L  L  R  S  F  F  Y  V  T  E  T  T      620

----------|----------|----------|----------|----------|----------|
1861     tttcagaagaacagactgttcttctacaggaagtccgtctggagcaagctccagagtatt     1920
621       F  Q  K  N  R  L  F  F  Y  R  K  S  V  W  S  K  L  Q  S  I      640 hTERT Fragment 7  >    <  hTERT Fragment 8
         ----------|----------|----------|----------|----------|----------|
1921     ggtattagacagcagcttaagagagttcagcttagagagctgtccgaagctgaagtccgc     1980
641       G  I  R  Q  Q  H  L  K  R  V  Q  L  R  E  L  S  E  A  E  V  R   660

----------|----------|----------|----------|----------|----------|
1981     cagcaccgcgaagctcgccccgcccctcctgacctctcggctgcagtttattcccaaccc     2040
661       Q  H  R  E  A  R  P  A  L  L  T  S  R  L  R  F  I  P  K        680

----------|----------|----------|----------|----------|----------|
2041     gatggccttagacctatcgtgaatatggattacgtcgtgggtgcccgcacattcagaagg     2100
681       D  G  L  R  P  I  V  N  M  D  Y  V  V  G  A  R  T  F  R  R      700
```

FIG. 27D

```
         ----------|----------|----------|----------|----------|----------|
    2101 gagaagcgcgccgagagactgacatctcgcgtgaaggcacttttttctgtgcttaattat   2160
     701  E  K  R  A  E  R  L  T  S  R  V  K  A  L  F  S  V  L  N  Y      720

----------|----------|----------|----------|----------|----------|
    2161 gaaagagccccgcagacctggtcttctcggagccagcgtgctcggcctgatgatatccat   2220
     721  E  R  A  P  Q  T  W  S  S  R  A  S  V  L  G  L  M  I  S  I      740

----------|----------|----------|----------|----------|----------|
    2221 cgggcttggcgcaccttgtgctccaggtgagggcacaggatcctcctcctgagcttat     2280
     741  R  A  W  R  T  L  C  S  R  V  R  A  Q  D  P  P  P  E  L  Y      760

----------|----------|----------|----------|----------|----------|
    2281 tttgtgaaagttgatgttactggtgcttacgatacaatccctcaggaccgcctcaccgag   2340
     761  F  V  K  V  D  V  T  G  A  Y  D  T  I  P  Q  D  R  L  T  E      780

----------|----------|----------|----------|----------|----------|
    2341 gtgatcgcctctattatcaaaccccagaacacctactgcgtgagaaggtacgccgtgtt    2400
     781  V  I  A  S  I  I  K  P  Q  N  T  Y  C  V  R  R  Y  A  V  V      800
                       hTERT Fragment 8  >    <  hTERT Fragment 9

----------|----------|----------|----------|----------|----------|
    2401 cagaaagccgcacaggacacgtgcgcaaagctttcaaatcccacgtgtctacctgaca    2460
     801  Q  K  A  A  H  G  H  V  R  K  A  F  K  S  H  V  S  T  L  T      820

----------|----------|----------|----------|----------|----------|
    2461 gacctccagccttatatgcggcaagtttgtcgcacacctgcaggagactagcccttgagg   2520
     821  D  L  Q  P  Y  M  R  Q  F  V  A  H  L  Q  E  T  S  P  L  R      840

----------|----------|----------|----------|----------|----------|
    2521 gacgctgtggtcatcgaacagtccagctctctcaatgaggcatcctcaggccgtttgat    2580
     841  D  A  V  V  I  E  Q  S  S  S  L  N  E  A  S  S  G  L  F  D      860

----------|----------|----------|----------|----------|----------|
    2581 gtgttcctgcgctttatgtgccaccacgccgtgcggattaggggaaagtcttacgtgcag   2640
     861  V  F  L  R  F  M  C  H  H  A  V  R  I  R  G  K  S  Y  V  Q      880

----------|----------|----------|----------|----------|----------|
    2641 tgccagggcatcccacagggtagcatcctgagcacactgctgtgtagcctgtgctatggc   2700
     881  C  Q  G  I  P  Q  G  S  I  L  S  T  L  L  C  S  L  C  Y  G      900

----------|----------|----------|----------|----------|----------|
    2701 gatatggagaataaattgttcgccggtatcagaagagatgggttgctcctgaggctgttc   2760
     901  D  M  E  N  K  L  F  A  G  I  R  R  D  G  L  L  L  R  L  F      920
                                                              *

----------|----------|----------|----------|----------|----------|
    2761 ctgctggttacccacatgactcatgccaaaacattttgcggaatctgattagggc      2820
     921  L  L  V  T  H  M  T  H  A  K  T  F  L  R  T  L  V  R  G       940

----------|----------|----------|----------|----------|----------|
    2821 gtgccagagtatgctgtgtgttgaatttgcggaaaactgtggttaattccagtggag     2880
     941  V  P  E  Y  A  V  C  V  N  L  R  K  T  V  V  N  F  P  V  E      960

----------|----------|----------|----------|----------|----------|
    2881 gacgaagctctcagaggcactgctttgttcagatgcctgcacggcctgttccatgg      2940
     961  D  E  A  L  G  G  T  A  F  V  Q  M  P  A  H  G  L  F  P  W      980
```

FIG. 27E

```
               |----------|----------|----------|----------|----------|
      2941  tgcggactgctgctcgataccggaccctcgaggtgcagtccgattatagttcctatgca  3000
       981   C  G  L  L  L  D  T  R  T  L  E  V  Q  S  D  Y  S  S  Y   A      1000 hTERT Fragment 9  >              <  hTERT Fragment 10
               |----------|----------|----------|----------|----------|
      3001  agaacatcaattcgggctagcctgactttcaacagggggcttcaaggccggcggaatatg  3060
      1001   R  T  S  I  R  A  S  L  T  F  N  R  G  F  K  A  G  R  N  M  1020

|----------|----------|----------|----------|----------|
      3061  agaaggaaactgttcggagtgttgagactaagtgtcatagtcttttttggactgcag    3120
      1021   R  K  L  F  G  V  L  R  L  K  C  H  S  L  F  L  D  L  Q     1040

|----------|----------|----------|----------|----------|
      3121  gtcaattctctccagacagtgtgtaccaacatttataaaatcctcttgctgcaggcttac  3180
      1041   V  N  S  L  Q  T  V  C  T  N  I  Y  K  I  L  L  L  Q  A  Y  1060

|----------|----------|----------|----------|----------|
      3181  agattccatgcctgcgtcctgcagctgccttttccaccagcagtgtggaaaaaccctacc  3240
      1061   R  F  H  A  C  V  L  Q  L  P  F  H  Q  Q  V  W  K  N  P  T  1080

|----------|----------|----------|----------|----------|
      3241  ttcttcctgcgggtgattagcgacacggccagtctttgctactccatcttgaaagcaaa   3300
      1081   F  F  L  R  V  I  S  D  T  A  S  L  C  Y  S  I  L  K  A  K  1100

|----------|----------|----------|----------|----------|
      3301  aacgctggcatgagtttggacagctaaaggcgccgctggaccattgccagtgaagcagtc  3360
      1101   N  A  G  M  S  L  G  A  K  G  A  A  G  P  L  P  S  E  A  V  1120

|----------|----------|----------|----------|----------|
      3361  cagtggctgtgtcatcaggcttttcctccttaaaactgacacgccaccgcgtgacttacgt  3420
      1121   Q  W  L  C  H  Q  A  F  L  L  K  L  T  R  H  R  V  T  Y  V  1140

|----------|----------|----------|----------|----------|
      3421  ccactcctggggatccctgagaaactgctgagacccagcttttcccggaagcttccaggcact  3480
      1141   P  L  L  G  S  L  R  T  A  Q  T  Q  L  S  R  K  L  P  G     1160 hTERT
               |----------|----------|----------|----------|----------|
      3481  acccttaccgcatcgaagcagccgccaaccctgccctgcctatggactttaagactatc  3540
      1161   T  L  T  A  L  E  A  A  A  N  P  A  L  P  S  D  F  K  T  I  1180

Fragment 10 >< V5 Tag                      V5 Tag  >
               |----------|----------|----------|----------|----------|-
      3541  ctggacggcaagccaattcctaatccattgctgggcctggactcaacttga   3591
      1181   L  D  G  K  P  I  P  N  P  L  L  G  L  D  S  T  *         1196
```

FIG. 28A

```
        < Human ubiquitin
        ----------|----------|----------|----------|----------|
      1 atgcagatttccgtcaaaacattgacaggaaagaccatcacactggaagt 50
      1 M  Q  I  F  V  K  T  L  T  G  K  T  I  T  L  E  V  17

----------|----------|----------|----------|----------|
     51 ggagccaagcgacactattgagaacgtcaaagccaagattcaggacaagg 100
     18 E  P  S  D  T  I  E  N  V  K  A  K  I  Q  D  K  E  34

----------|----------|----------|----------|----------|
    101 agggcatcccaccagaccagcagaggctgattttgccggaaagcagctg 150
     35 G  I  P  P  D  Q  Q  R  L  I  F  A  G  K  Q  L  50

----------|----------|----------|----------|----------|
    151 gaggacggacgcacactcagtgactacaatatccagaaggaaagtactct 200
     51 E  D  G  R  T  L  S  D  Y  N  I  Q  K  E  S  T  L  67

Human ubiquitin  ><  G linker  ><  hTERT
        ----------|----------|----------|----------|----------|
    201 gcatctggtccttcgcctgcgcggcggaGGTGGAGGTGGAtgcgttccag 250
     68 H  L  V  L  R  L  R  G  G  G  G  G  C  V  P  A  84

Fragment 7
        ----------|----------|----------|----------|----------|
    251 cagcagagcacaggctgcgcgaagagattctcgcaaagttcctgcactgg 300
     85 A  E  H  R  L  R  E  E  I  L  A  K  F  L  H  W  100

----------|----------|----------|----------|----------|
    301 cttatgagcgtctacgtggtcgaactgctgcggtctttcttctacgtgac 350
    101 L  M  S  V  Y  V  V  E  L  L  R  S  F  F  Y  V  T  117

----------|----------|----------|----------|----------|
    351 agagaccacttttcagaagaacagactgttcttctacaggaagtccgtct 400
    118 E  T  T  F  Q  K  N  R  L  F  F  Y  R  K  S  V  134 hTERT Fragment 7 >
        ----------|----------|----------|----------|----------|
    401 ggagcaagctccagagtattggtattagacagcaccttaagagagttcag 450
    135 S  K  L  Q  S  I  G  I  R  Q  H  L  K  R  V  Q  150

<    G linker    ><   hTERT Fragment 2
        ----------|----------|----------|----------|----------|
    451 GGAGGTGGTGGAGGTGGAttcactactagcgtccggtcctacctgcccaa 500
    151 G  G  G  G  G  F  T  T  S  V  R  S  Y  L  P  N  167

----------|----------|----------|----------|----------|
    501 cacagtgaccgacgctctgagaggttcaggtgcctggggtctgctgctgc 550
    168 T  V  T  D  A  L  R  G  S  G  A  W  G  L  L  L  R  184

----------|----------|----------|----------|----------|
    551 ggagggtgggtgatgatgttctggttcacctcctggcccggtgtgccctg 600
    185 R  V  G  D  D  V  L  V  H  L  L  A  R  C  A  L  200
```

FIG. 28B

```
         ----------|----------|----------|----------|----------|
     601 ttcgtgctggtggctccctcctgcgcataccaggtctgcgggaccccact 650
     201  F  V  L  V  A  P  S  C  A  Y  Q  V  C  G  P  P  L  217 hTERT Fragment 2 ><    G linker     ><   hTERT
         ----------|----------|----------|----------|----------|
     651 ttatcagctcggcgctgctGGTGGAGGTGGTGGAGGTgccggtgtgtgtg 700
     218  Y  Q  L  G  A  A  G  G  G  G  G  A  G  V  C  A  234

Fragment 6
         ----------|----------|----------|----------|----------|
     701 ctagagaaaaaccccagggctcagtggctgcacctgaagaggaggacact 750
     235  R  E  K  P  Q  G  S  V  A  A  P  E  E  D  T  250

----------|----------|----------|----------|----------|
     751 gacctcgccgccttgtccagttgctcaggcagcattcatcaccatggca 800
     251  D  P  R  R  L  V  Q  L  L  R  Q  H  S  S  P  W  Q  267

----------|----------|----------|----------|----------|
     801 ggtgtacggcttcgtgagggcttgcctgcggagactggtccccccggat 850
     268  V  Y  G  F  V  R  A  C  L  R  R  L  V  P  P  G  L  284

----------|----------|----------|----------|----------|
     851 tgtggggatctcggcacaacgaacggcgctttctgaggaatacaaagaag 900
     285  W  G  S  R  H  N  E  R  R  F  L  R  N  T  K  K  300

----------|----------|----------|----------|----------|
     901 tttatctccctgggcaagcatgcaaagctcagcttgcaggagctgacatg 950
     301  F  I  S  L  G  K  H  A  K  L  S  L  Q  E  L  T  W  317 hTERT Fragment 6 ><
         ----------|----------|----------|----------|----------|
     951 gaagatgagcgttagaggatgcgcatggctcaggcggtcacctggagttG 1000
     318  K  M  S  V  R  G  C  A  W  L  R  R  S  P  G  V  G  334

G linker        ><  hTERT Fragment 4
         ----------|----------|----------|----------|----------|
    1001 GAGGTGGAGGTGGAGGAtcctgggctcaccccggaaggaccaggggccca 1050
     335  G  G  G  G  S  W  A  H  P  G  R  T  G  P  350

----------|----------|----------|----------|----------|
    1051 agcgatagggcttctgtgttgtgtcaccagccaggcctgccgaagaggc 1100
     351  S  D  R  G  F  C  V  V  S  P  A  R  P  A  E  E  A  367 hTERT Fragment 4     ><    G linker
         ----------|----------|----------|----------|----------|
    1101 tacctccttggaaggagccctcagtggcaccaggGGTGGTGGAGGTGGAG 1150
     368  T  S  L  E  G  A  L  S  G  T  R  G  G  G  G  G  384

><   hTERT Fragment 9
         ----------|----------|----------|----------|----------|
    1151 GAaaatcccacgtgtctaccttgacagacctccagcctatatgcggcag 1200
     385  K  S  H  V  S  T  L  T  D  L  Q  P  Y  M  R  Q  400
```

FIG. 28C

```
     ------------|------------|------------|------------|------------|
1201 tttgtcgcacacctgcaggagactagccccttgagggacgctgtggtcat 1250
 401  F  V  A  H  L  Q  E  T  S  P  L  R  D  A  V  V  I  417

------------|------------|------------|------------|------------|
1251 cgaacagtccagctctctcaatgaggcatcctcaggcctgtttgatgtgt 1300
 418  E  Q  S  S  L  N  E  A  S  S  G  L  F  D  V  F  434

------------|------------|------------|------------|------------|
1301 tcctgcgctttatgtgccaccacgccgtgcggattagggggcaagtcttac 1350
 435  L  R  F  M  C  H  H  A  V  R  I  R  G  K  S  Y  450

------------|------------|------------|------------|------------|
1351 gtgcagtgccagggcatcccacagggtagcatcctgagcacactgctgtg 1400
 451  V  Q  C  Q  G  I  P  Q  G  S  I  L  S  T  L  L  C  467

------------|------------|------------|------------|------------|
1401 tagcctgtgctatggcgatatggagaataaattgttcgccggtatcagaa 1450
 468  S  L  C  Y  G  D  M  E  N  K  L  F  A  G  I  R  R  484

------------|------------|------------|------------|------------|
1451 gagacggtttgctcctgaggctgttcctgctggttaccccccatctgact 1500
 485  D  G  L  L  R  L  F  L  L  V  T  P  H  L  T  500
                        *

------------|------------|------------|------------|------------|
1501 catgccaaaacattttgcggactctggttaggggcgtgccagagtatgg 1550
 501  H  A  K  T  F  L  R  T  L  V  R  G  V  P  E  Y  G  517

------------|------------|------------|------------|------------|
1551 ctgtgttgtgaatttgcggaaaactgtggttaatttcccagtggaggacg 1600
 518  C  V  V  N  L  R  K  T  V  V  N  F  P  V  E  D  E  534

------------|------------|------------|------------|------------|
1601 aagctctcggaggcacagcttttgttcagatgcctgcccacggcctgttc 1650
 535  A  L  G  G  T  A  F  V  Q  M  P  A  H  G  L  F  550

------------|------------|------------|------------|------------|
1651 ccatggtgcgggactgctgctcgatacccggaccctcgaggtgcagtccga 1700
 551  P  W  C  G  L  L  L  D  T  R  T  L  E  V  Q  S  D  567
                hTERT Fragment 9  ><    G linker    ><  hTERT
     ------------|------------|------------|------------|------------|
1701 ttatagttcctatgcaagaacatcaattGGAGGAGGTGGTGGAGGTtgga 1750
 568  Y  S  S  Y  A  R  T  S  I  G  G  G  G  G  G  W  N  584
     Fragment 3
     ------------|------------|------------|------------|------------|
1751 atcatagcgtgcgggaggcaggtgtgcctctcggcctgccagccccgga 1800
 585  H  S  V  R  E  A  G  V  P  L  G  L  P  A  P  G  600

------------|------------|------------|------------|------------|
1801 gcaaggagacgcggtggatccgccagtcgctcactccccttgcctaagag 1850
 601  A  R  R  R  G  G  S  A  S  R  S  L  P  L  P  K  R  617
```

FIG. 28D

```
     hTERT Fragment 3  ><    G linker    ><  hTERT Fragment 1
          ----------|----------|----------|----------|----------|
1851 gccaagaagaggagccGGTGGAGGAGGTGGTGGActggccaccttcgtgc 1900
 618   P   R   R   G   A   G   G   G   G   G   L   A   T   F   V   R  634

----------|----------|----------|----------|----------|
1901 ggcgcctgggaccccagggctggcggctggtgcagcgcggggaccctgct 1950
 635   R   L   G   P   Q   G   W   R   L   V   Q   R   G   D   P   A  650

----------|----------|----------|----------|----------|
1951 gctttcagagctctcgtcgcccagtgtctggtctgcgttccttgggacgc 2000
 651   A   F   R   A   L   V   A   Q   C   L   V   C   V   P   W   D   A  667

----------|----------|----------|----------|----------|
2001 acggccccaccgccgccccagtttccggcaggtgagttgtctcaaag 2050
 668   R   P   P   P   A   A   P   S   F   R   Q   V   S   C   L   K   E  684

----------|----------|----------|----------|----------|
2051 agttggttgctcgggtgttgcagcggctttgtgaaaggggagcaaagaac 2100
 685   L   V   A   R   V   L   Q   R   L   C   E   R   G   A   K   N  700 hTERT Fragment 1  ><   G linker
          ----------|----------|----------|----------|----------|
2101 gtccttgcctttggcttcgctttgctcgatggagcacgcggaGGAGGTGG 2150
 701   V   L   A   F   G   F   A   L   L   D   G   A   R   G   G   G  717

><  hTERT Fragment 8
          ----------|----------|----------|----------|----------|
2151 TGGAGGTGGAagagagctgtccgaagctgaagtccgccagcaccgcgaag 2200
 718   G   G   G   R   E   L   S   E   A   E   V   R   Q   H   R   E   A 734

----------|----------|----------|----------|----------|
2201 ctcgccccgccctcctgacctctcggctgcggtttattcccaaacccgat 2250
 735   R   P   A   L   L   T   S   R   L   R   F   I   P   K   P   D  750

----------|----------|----------|----------|----------|
2251 ggcctagacctatcgtgaatatggattacgtcgtgggtgcccgcacttt 2300
 751   G   L   R   P   I   V   N   M   D   Y   V   V   G   A   R   T   F  767

----------|----------|----------|----------|----------|
2301 cagaagggagaagcgcgccgagagactgacatctcgcgtgaaggcacttt 2350
 768   R   R   E   K   R   A   E   R   L   T   S   R   V   K   A   L   F  784

----------|----------|----------|----------|----------|
2351 tttctgtgcttaattatgaaagagcccgcagacctggtctctcggagcc 2400
 785   S   V   L   N   Y   E   R   A   R   R   P   G   L   L   G   A  800

----------|----------|----------|----------|----------|
2401 agcgtgctcggcctggatgatatccatcgggcttggcgcacctttgtgct 2450
 801   S   V   L   G   L   D   D   I   H   R   A   W   R   T   F   V   L 817
```

FIG. 28E

```
          ----------|----------|----------|----------|----------|
     2451 tcgggtgagggcacaggatcctcctcctgagctttattttgtgaaagttg 2500
      818  R  V  R  A  Q  D  P  P  P  E  L  Y  F  V  K  V  D 834

----------|----------|----------|----------|----------|
     2501 atgttactggtgcttacgatacaatccctcaggaccggctcaccgaggtg 2550
      835  V  T  G  A  Y  D  T  I  P  Q  D  R  L  T  E  V 850

----------|----------|----------|----------|----------|
     2551 atcgcctctattatcaaacccagaacacctactgcgtgagaaggtacgc 2600
      851  I  A  S  I  I  K  P  Q  N  T  Y  C  V  R  R  Y  A 867 hTERT Fragment 8  ><   G linker
          ----------|----------|----------|----------|----------|
     2601 cgtcgttcagaaagccgcacacggacacgtgcgcaaaGGTGGAGGAGGTG 2650
      868  V  V  Q  K  A  A  H  G  H  V  R  K  G  G  G  G 884

><    hTERT Fragment 10
          ----------|----------|----------|----------|----------|
     2651 GTGGAaacaggggcttcaaggccggccggaatatgagaaggaaactgttc 2700
      885  G  N  R  G  F  K  A  G  R  N  M  R  R  K  L  F 900

----------|----------|----------|----------|----------|
     2701 ggagtgttgagacttaagtgtcatagtctttttttggacttgcaggtcaa 2750
      901  G  V  L  R  L  K  C  H  S  L  F  L  D  L  Q  V  N 917

----------|----------|----------|----------|----------|
     2751 ttctctccagacagtgtgtaccaacatttataaaatcctcttgctgcagg 2800
      918  S  L  Q  T  V  C  T  N  I  Y  K  I  L  L  Q  A 934

----------|----------|----------|----------|----------|
     2801 cttacagattccatgcctgcgtcctgcagctgcctttccaccagcaggtg 2850
      935  Y  R  F  H  A  C  V  L  Q  L  P  F  H  Q  Q  V 950

----------|----------|----------|----------|----------|
     2851 tggaaaaaccctaccttcttcctgcgggtgattagcgacaccgccagtct 2900
      951  W  K  N  P  T  F  F  L  R  V  I  S  D  T  A  S  L 967

----------|----------|----------|----------|----------|
     2901 ttgctactccatcttgaaagcaaaaaacgctggcatgagcttgggagcta 2950
      968  C  Y  S  I  L  K  A  K  N  A  G  M  S  L  G  A  K 984

----------|----------|----------|----------|----------|
     2951 agggcgccgctggacctctgcccagtgaagcagtccagtggctgtgtcat 3000
      985  G  A  A  G  P  L  P  S  E  A  V  Q  W  L  C  H 1000

----------|----------|----------|----------|----------|
     3001 caggctttcctccttaaactgacacgccaccgcgtgacttacgtcccact 3050
     1001  Q  A  F  L  L  K  L  T  R  H  R  V  T  Y  V  P  L 1017

----------|----------|----------|----------|----------|
     3051 cctggcctccctgagaactgctcagacccagctttcccggaaacttccag 3100
     1018  L  G  S  L  R  T  A  Q  T  Q  L  S  R  K  L  P  G 1034
```

FIG. 28F

```
              ----------|----------|----------|----------|----------|
         3101 gcactacccttaccgcactcgaagcagccgccaaccctgccctgccctcc 3150
         1035  T  T  L  T  A  L  E  A  A  A  N  P  A  L  P  S     1050 hTERT Fragment 10  ><    G linker    ><   hTERT
              ----------|----------|----------|----------|----------|
         3151 gactttaagactatcctggacGGAGGTGGAGGTGGAGGTcccgcccacc 3200
         1051  D  F  K  T  I  L  D  G  G  G  G  G  P  C  P  P     1067

Fragment 5
              ----------|----------|----------|----------|----------|
         3201 agtgtatgccgagaccaagcacttttgtattccagtggcgataaagagc 3250
         1068  V  Y  A  E  T  K  H  F  L  Y  S  S  G  D  K  E  Q  1084

----------|----------|----------|----------|----------|
         3251 agctccggccctctttctgctctcaagcctccgcccctctctgaccgga 3300
         1085  L  R  P  S  F  L  L  S  S  L  R  P  S  L  T  G     1100

----------|----------|----------|----------|----------|
         3301 gctcgcaggctggtggagaccatctttctgggctcaagaccatggatgcc 3350
         1101  A  R  R  L  V  E  T  I  F  L  G  S  R  P  W  M  P  1117

----------|----------|----------|----------|----------|
         3351 aggcaccccccgcagactgcccaggctcccccagcggtactggcagatgc 3400
         1118  G  T  P  R  R  L  P  R  L  P  Q  R  Y  W  Q  M  R  1134

----------|----------|----------|----------|----------|
         3401 gccctctctttctggaacttctgggtaaccacgcccagtgcccatatggc 3450
         1135  P  L  F  L  E  L  L  G  N  H  A  Q  C  P  Y  G     1150 hTERT fragment 5  ><  G linker
              ----------|----------|----------|----------|----------|
         3451 gtcctgctgaagacccactgtcctctgagggccgccgtgaccGGAGGTGG 3500
         1151  V  L  L  K  T  H  C  P  L  R  A  A  V  T  G  G     1167

><  V5 Tag
              ----------|----------|----------|----------|----------|
         3501 TGGAGGAGGTggcaagccaattcctaatccattgctgggcctggactcaa 3550
         1168  G  G  G  K  P  I  P  N  P  L  L  G  L  D  S  T     1184

V5 Tag ><
              ------
         3551 cttga 3555
                 □
```

FIG. 29A

```
         < Human ubiquitin
         ----------|----------|----------|----------|----------|
   1     atgcagattttcgtcaaaacattgacaggaaagaccatcacactggaagt  50
   1      M  Q  I  F  V  K  T  L  T  G  K  T  I  T  L  E  V   17

----------|----------|----------|----------|----------|
  51     ggagccaagcgacactattgagaacgtcaaagccaagattcaggacaagg  100
  18      E  P  S  D  T  I  E  N  V  K  A  K  I  Q  D  K  E   34

----------|----------|----------|----------|----------|
 101     agggcatcccaccagaccagcagaggctgattttttgccggaaagcagctg  150
  35      G  I  P  P  D  Q  Q  R  L  I  F  A  G  K  Q  L      50

----------|----------|----------|----------|----------|
 151     gaggacggacgcacactcagtgactacaatatccagaaggaaagtactct  200
  51      E  D  G  R  T  L  S  D  Y  N  I  Q  K  E  S  T  L   67

Human ubiquitin  >< G linker ><   hTERT
         ----------|----------|----------|----------|----------|
 201     gcatctggtccttcgcctgcgcggcggaGGTGGAGGTGGAaacaggggct  250
  68      H  L  V  L  R  L  R  G  G  G  G  G  N  R  G  F      84

Fragment 10
         ----------|----------|----------|----------|----------|
 251     tcaaggccggccggaatatgagaaggaaactgttcggagtgttgagactt  300
  85      K  A  G  R  N  M  R  R  K  L  F  G  V  L  R  L      100

----------|----------|----------|----------|----------|
 301     aagtgtcatagtctttttttggacttgcaggtcaattctctccagacagt  350
 101      K  C  H  S  L  F  L  D  L  Q  V  N  S  L  Q  T  V   117

----------|----------|----------|----------|----------|
 351     gtgtaccaacatttataaaatcctcttgctgcaggcttacagattccatg  400
 118      C  T  N  I  Y  K  I  L  L  L  Q  A  Y  R  F  H  A   134

----------|----------|----------|----------|----------|
 401     cctgcgtcctgcagctgcctttccaccagcaggtgtggaaaaacccacc  450
 135       C  V  L  Q  L  P  F  H  Q  Q  V  W  K  N  P  T     150

----------|----------|----------|----------|----------|
 451     ttcttcctgcgggtgattagcgacaccgccagtctttgctactccatctt  500
 151      F  F  L  R  V  I  S  D  T  A  S  L  C  Y  S  I  L   167

----------|----------|----------|----------|----------|
 501     gaaagcaaaaaacgctggcatgagcttgggagctaagggcgccgctggac  550
 168      K  A  K  N  A  G  M  S  L  G  A  K  G  A  A  G  P   184

----------|----------|----------|----------|----------|
 551     ctctgcccagtgaagcagtccagtggctgtgtcatcaggctttcctcctt  600
 185      L  P  S  E  A  V  Q  W  L  C  H  Q  A  F  L  L      200
```

FIG. 29B

```
           ----------|----------|----------|----------|----------|
      601  aaactgacacgccaccgcgtgacttacgtcccactcctgggctccctgag  650
      201  K  L  T  R  H  R  V  T  Y  V  P  L  L  G  S  L  R   217

----------|----------|----------|----------|----------|
      651  aactgctcagacccagctttcccggaaacttccaggcactacccttaccg  700
      218  T  A  Q  T  Q  L  S  R  K  L  P  G  T  T  L  T  A   234
                                                         hTERT
           ----------|----------|----------|----------|----------|
      701  cactcgaagcagccgccaaccctgccctgccctccgactttaagactatc  750
      235  L  E  A  A  A  N  P  A  L  P  S  D  F  K  T  I     250

Fragment 10 ><     G linker     ><   hTERT Fragment 9
           ----------|----------|----------|----------|----------|
      751  ctggacGGAGGTGGTGGAGGTGGAaaatcccacgtgtctaccttgacaga  800
      251  L  D  G  G  G  G  G  K  S  H  V  S  T  L  T  D     267

----------|----------|----------|----------|----------|
      801  cctccagccttatatgcggcagtttgtcgcacacctgcaggagactagcc  850
      268  L  Q  P  Y  M  R  Q  F  V  A  H  L  Q  E  T  S  P  284

----------|----------|----------|----------|----------|
      851  ccttgagggacgctgtggtcatcgaacagtccagctctctcaatgaggca  900
      285  L  R  D  A  V  V  I  E  Q  S  S  L  N  E  A        300

----------|----------|----------|----------|----------|
      901  tcctcaggcctgtttgatgtgttcctgcgctttatgtgccaccacgccgt  950
      301  S  S  G  L  F  D  V  F  L  R  F  M  C  H  H  A  V  317

----------|----------|----------|----------|----------|
      951  gcggattaggggcaagtcttacgtgcagtgccagggcatcccacagggta 1000
      318  R  I  R  G  K  S  Y  V  Q  C  Q  G  I  P  Q  G  S  334

----------|----------|----------|----------|----------|
     1001  gcatcctgagcacactgctgtgtagcctgtgctatggcgatatggagaat 1050
      335  I  L  S  T  L  L  C  S  L  C  Y  G  D  M  E  N     350

----------|----------|----------|----------|----------|
     1051  aaattgttcgccggtatcagaagagacggtttgctcctgaggctgttcct 1100
      351  K  L  F  A  G  I  R  R  D  G  L  L  L  R  L  F  L  367
                                                         *
           ----------|----------|----------|----------|----------|
     1101  gctggttacccccatctgactcatgccaaaacattttttgcggactctgg 1150
      368  L  V  T  P  H  L  T  H  A  K  T  F  L  R  T  L  V  384

----------|----------|----------|----------|----------|
     1151  ttaggggcgtgccagagtatggctgtgttgtgaatttgcggaaaactgtg 1200
      385  R  G  V  P  E  Y  G  C  V  V  N  L  R  K  T  V     400

----------|----------|----------|----------|----------|
     1201  gttaatttcccagtggaggacgaagctctcggaggcacagcttttgttca 1250
      401  V  N  F  P  V  E  D  E  A  L  G  G  T  A  F  V  Q  417
```

FIG. 29C

```
           ----------|----------|----------|----------|----------|
      1251 gatgcctgcccacggcctgttcccatggtgcggactgctgctcgatacgc 1300
       418  M  P  A  H  G  L  F  P  W  C  G  L  L  L  D  T  R  434
                                              hTERT Fragment 9  >
           ----------|----------|----------|----------|----------|
      1301 ggaccctcgaggtgcagtccgattatagttcctatgcaagaacatcaatt 1350
       435  T  L  E  V  Q  S  D  Y  S  S  Y  A  R  T  S  I     450
                <    G linker    ><    hTERT Fragment 8
           ----------|----------|----------|----------|----------|
      1351 GGTGGAGGTGGTGGAGGTagagagctgtccgaagctgaagtccgccagca 1400
       451  G  G  G  G  G  R  E  L  S  E  A  E  V  R  Q  H     467
           ----------|----------|----------|----------|----------|
      1401 ccgcgaagctcgccccgccctcctgacctctcggctgcggtttattccca 1450
       468  R  E  A  R  P  A  L  L  T  S  R  L  R  F  I  P  K  484
           ----------|----------|----------|----------|----------|
      1451 aacccgatggccttagacctatcgtgaatatggattacgtcgtgggtgcc 1500
       485     P  D  G  L  R  P  I  V  N  M  D  Y  V  V  G  A  500
           ----------|----------|----------|----------|----------|
      1501 cgcactttcagaaggagaagcgcgccgagagactgacatctcgcgtgaaa 1550
       501  R  T  F  R  R  E  K  R  A  E  R  L  T  S  R  V  K  517
           ----------|----------|----------|----------|----------|
      1551 ggcactttttctgtgcttaattatgaaagagcccgcagacctggtcttc  1600
       518  A  L  F  S  V  L  N  Y  E  R  A  R  R  P  G  L  L  534
           ----------|----------|----------|----------|----------|
      1601 tcggagccagcgtgctcggcctggatgatatccatcgggcttggcgcacc 1650
       535     G  A  S  V  L  G  L  D  D  I  H  R  A  W  R  T  550
           ----------|----------|----------|----------|----------|
      1651 tttgtgcttcgggtgagggcacaggatcctcctcctgagctttatttgt  1700
       551  F  V  L  R  V  R  A  Q  D  P  P  P  E  L  Y  F  V  567
           ----------|----------|----------|----------|----------|
      1701 gaaagttgatgttactggtgcttacgatacaatccctcaggaccggctca 1750
       568  K  V  D  V  T  G  A  Y  D  T  I  P  Q  D  R  L  T  584
           ----------|----------|----------|----------|----------|
      1751 ccgaggtgatcgcctctattatcaaaccccagaacacctactgcgtgaga 1800
       585     E  V  I  A  S  I  I  K  P  Q  N  T  Y  C  V  R  600
                                          hTERT Fragment 8   >< G
           ----------|----------|----------|----------|----------|
      1801 aggtacgccgtcgttcagaaagccgcacacggacacgtgcgcaaaGGAGG 1850
       601  R  Y  A  V  V  Q  K  A  A  H  G  H  V  R  K  G  G  617
                   linker    ><   hTERT Fragment 7
           ----------|----------|----------|----------|----------|
      1851 TGGAGGTGGAGGAtgcgttccagcagcagagcacaggctgcgcgaagaga 1900
       618  G  G  G  G  C  V  P  A  A  E  H  R  L  R  E  E  I  634
```

FIG. 29D

```
          ----------|----------|----------|----------|----------|
     1901 ttctcgcaaagttcctgcactggcttatgagcgtctacgtggtcgaactg 1950
      635    L  A  K  F  L  H  W  L  M  S  V  Y  V  V  E  L    650

----------|----------|----------|----------|----------|
     1951 ctgcggtctttcttctacgtgacagagaccacttttcagaagaacagact 2000
      651    L  R  S  F  F  Y  V  T  E  T  T  F  Q  K  N  R  L 667

----------|----------|----------|----------|----------|
     2001 gttcttctacaggaagtccgtctggagcaagctccagagtattggtatta 2050
      668    F  F  Y  R  K  S  V  W  S  K  L  Q  S  I  G  I  R 684 hTERT Fragment 7  ><      G linker    ><    hTERT
          ----------|----------|----------|----------|----------|
     2051 gacagcaccttaagagagtt cagGGTGGTGGAGGTGGAGGAgcc ggtgtg 2100
      685    Q  H  L  K  R  V  Q  G  G  G  G  G  G  A  G  V    700

Fragment 6
          ----------|----------|----------|----------|----------|
     2101 tgtgctagagaaaaaccccagggctcagtggctgcacctgaagaggagga 2150
      701    C  A  R  E  K  P  Q  G  S  V  A  A  P  E  E  D    717

----------|----------|----------|----------|----------|
     2151 cactgaccctcgccgccttgtccagttgctcaggcagcattcatcaccat 2200
      718    T  D  P  R  R  L  V  Q  L  L  R  Q  H  S  S  P  W 734

----------|----------|----------|----------|----------|
     2201 ggcaggtgtacggcttcgtgagggcttgcctgcggagactggtcccccc 2250
      735    Q  V  Y  G  F  V  R  A  C  L  R  R  L  V  P  P    750

----------|----------|----------|----------|----------|
     2251 ggattgtggggatctcggcacaacgaacggcgctttctgaggaatacaaa 2300
      751    G  L  W  G  S  R  H  N  E  R  R  F  L  R  N  T  K 767

----------|----------|----------|----------|----------|
     2301 gaagtttatctcccctgggcaagcatgcaaagctcagcttgcaggagctga 2350
      768    K  F  I  S  L  G  K  H  A  K  L  S  L  Q  E  L  T 784 hTERT
          ----------|----------|----------|----------|----------|
     2351 catggaagatgagcgttagagga tgcgcatggctcaggcggtcacctgga 2400
      785    W  K  M  S  V  R  G  C  A  W  L  R  R  S  P  G    800

Fragment 6 ><    G linker     ><    hTERT Fragment 5
          ----------|----------|----------|----------|----------|
     2401 gtt GGAGGAGGTGGTGGAGGT ccc tgccaccagtgtatgccgagaccaa 2450
      801    V  G  G  G  G  G  G  P  C  P  P  V  Y  A  E  T  K 817

----------|----------|----------|----------|----------|
     2451 gcacttttttgtattccagtggcgataaagagcagctccggccctcttttc 2500
      818    H  F  L  Y  S  S  G  D  K  E  Q  L  R  P  S  F  L 834
```

FIG. 29E

```
           ----------|----------|----------|----------|----------|
      2501 tgctctcaagcctccgcccctctctgaccggagctcgcaggctggtggag 2550
       835  L  S  S  L  R  P  S  L  T  G  A  R  R  L  V  E    850

----------|----------|----------|----------|----------|
      2551 accatctttctgggctcaagaccatggatgccaggcaccccccgcagact 2600
       851  T  I  F  L  G  S  R  P  W  M  P  G  T  P  R  R  L  867

----------|----------|----------|----------|----------|
      2601 gcccaggctccccagcggtactggcagatgcgccctctctttctggaac 2650
       868  P  R  L  P  Q  R  Y  W  Q  M  R  P  L  F  L  E  L  884

----------|----------|----------|----------|----------|
      2651 ttctgggtaaccacgcccagtgcccatatggcgtcctgctgaagaccac 2700
       885  L  G  N  H  A  Q  C  P  Y  G  V  L  L  K  T  H    900 hTERT Fragment 5  ><    G linker    ><   hTERT
           ----------|----------|----------|----------|----------|
      2701 tgtcctctgagggccgccgtgaccGGTGGAGGAGGTGGTGGAtcctgggc 2750
       901  C  P  L  R  A  A  V  T  G  G  G  G  G  S  W  A   917

Fragment 4
           ----------|----------|----------|----------|----------|
      2751 tcaccccggaaggaccaggggggccaagcgatagggggcttctgtgttgtgt 2800
       918  H  P  G  R  T  R  G  P  S  D  R  G  F  C  V  V  S 934

----------|----------|----------|----------|----------|
      2801 caccagccaggcctgccgaagaggctacctccttggaaggagccctcagt 2850
       935  P  A  R  P  A  E  E  A  T  S  L  E  G  A  L  S   950 hTERT Fragment 4 ><     G linker     ><   hTERT Fragment 3
           ----------|----------|----------|----------|----------|
      2851 ggcaccaggGGAGGTGGTGGAGGTGGAtggaatcatagcgtgcgggaggc 2900
       951  G  T  R  G  G  G  G  G  W  N  H  S  V  R  E  A   967

----------|----------|----------|----------|----------|
      2901 aggtgtgcctctcggcctgccagccccggagcaaggagacgcggtggat 2950
       968  G  V  P  L  G  L  P  A  P  G  A  R  R  R  G  G  S 984 hTERT Fragment 3 ><
           ----------|----------|----------|----------|----------|
      2951 ccgccagtcgctcactcccttgcctaagaggccaagaagaggagccGGT 3000
       985  A  S  R  S  L  P  L  P  K  R  P  R  R  G  A  G   1000

G linker     ><   hTERT Fragment 2
           ----------|----------|----------|----------|----------|
      3001 GGAGGAGGTGGTGGAttcactactagcgtccggtcctacctgcccaacac 3050
      1001  G  G  G  G  G  F  T  T  S  V  R  S  Y  L  P  N  T 1017

----------|----------|----------|----------|----------|
      3051 agtgaccgacgctctgagaggttcaggtgcctggggtctgctgctgcgga 3100
      1018  V  T  D  A  L  R  G  S  G  A  W  G  L  L  L  R  R 1034
```

FIG. 29F

```
          ----------|----------|----------|----------|----------|
     3101 gggtgggtgatgatgttctggttcacctcctggcccggtgtgccctgttc 3150
     1035   V  G  D  D  V  L  V  H  L  L  A  R  C  A  L  F    1050

----------|----------|----------|----------|----------|
     3151 gtgctggtggctccctcctgcgcataccaggtctgcggacccccacttta 3200
     1051 V  L  V  A  P  S  C  A  Y  Q  V  C  G  P  P  L  Y  1067 hTERT Fragment 2 ><     G linker     >< hTERT Fragment 1
          ----------|----------|----------|----------|----------|
     3201 tcagctcggcgctgctGGAGGTGGAGGTGGAGGTctggccaccttcgtgc 3250
     1068   Q  L  G  A  A  G  G  G  G  G  L  A  T  F  V  R   1084

----------|----------|----------|----------|----------|
     3251 ggcgctgggaccccagggctggcggctggtgcagcgcggggaccctgct 3300
     1085   R  L  G  P  Q  G  W  R  L  V  Q  R  G  D  P  A   1100

----------|----------|----------|----------|----------|
     3301 gctttcagagctctcgtcgcccagtgtctggtctgcgttccttgggacgc 3350
     1101 A  F  R  A  L  V  A  Q  C  L  V  C  V  P  W  D  A  1117

----------|----------|----------|----------|----------|
     3351 acggccccacccgccgcccccagtttccggcaggtgagttgtctcaaag 3400
     1118 R  P  P  P  A  A  P  S  F  R  Q  V  S  C  L  K  E  1134

----------|----------|----------|----------|----------|
     3401 agttggttgctcgggtgttgcagcggctttgtgaaaggggagcaaagaac 3450
     1135   L  V  A  R  V  L  Q  R  L  C  E  R  G  A  K  N   1150 hTERT Fragment 1 ><    G
          ----------|----------|----------|----------|----------|
     3451 gtccttgcctttggcttcgctttgctcgatggagcacgcggaGGAGGTGG 3500
     1151 V  L  A  F  G  F  A  L  L  D  G  A  R  G  G  G    1167 linker    >< V5 Tag
          ----------|----------|----------|----------|----------|
     3501 TGGAGGAGGTggcaagccaattcctaatccattgctgggcctggactcaa 3550
     1168   G  G  G  K  P  I  P  N  P  L  L  G  L  D  S  T   1184

V5 Tag ><
                 -----
     3551 cttga 3555
```

TELOMERASE ENCODING DNA VACCINE

CROSS-REFERENCE TO RELATED APPLICATIONS

This application is a Continuation of U.S. application Ser. No. 15/032,966, filed on Apr. 28, 2016 and issued as U.S. Pat. No. 10,183,065, which is a U.S. National Phase application under 35 U.S.C. § 371 of International Patent Application No. PCT/EP2014/073164, filed on Oct. 28, 2014, which claims priority to European Patent Application No. EP 13190547.3, filed on Oct. 28, 2013, all of which applications are incorporated herein by reference in their entireties.

SEQUENCE LISTING

The instant application contains a Sequence Listing which has been submitted electronically in ASCII format and is hereby incorporated by reference in its entirety. Said ASCII copy, created on Nov. 22, 2017, is named 246393_000006_SL.txt and is 352,752 bytes in size.

FIELD OF THE INVENTION

The present invention relates to the field of anti-tumor vaccination. The invention more particularly provides a nucleic acid construct that encodes for an inactive enzymatic form of human telomerase reverse transcriptase protein.

BACKGROUND OF THE INVENTION

The stimulation of tumor-specific T-cell responses with active immunotherapy has several theoretical advantages over other forms of cancer treatment. In order to obtain clinical benefits T cell-based immunotherapy must stimulate both CD8 and CD4 tumor-reactive T cell responses which recognize tumor specific antigens. Consequently increasing attention has focused on identifying MHC class I and II epitopes from multiple tumor associated antigens (TAAs) (Cheever, et al, 2009). However, heterogeneous expression of most of the characterized tumor antigens among the different types of cancer limits the broad applicability of cancer vaccines that target such antigens. During the past few years, human telomerase reverse transcriptase (hTERT) has emerged as the first bona fide common tumor antigen and is actively investigated as a universal target for cancer immunotherapy. Human telomerase reverse transcriptase (hTERT) is the catalytic subunit of the telomerase enzyme that synthesizes telomeric DNA at the chromosome ends. hTERT is overexpressed in most human tumors (>85%) and virtually all types of cancer. In addition, telomerase activation has become one of the most important tumor escape mechanisms to circumvent telomere-dependent pathways of cell death. It is well established that therapeutic strategies targeting antigens not involved in tumor growth can result in the selection of antigen-loss tumor mutants that are clinically progressive. Hence, down-regulation or loss of telomerase activity will severely impact the growth potential of the tumor cells. Moreover, telomerase is relatively specific of cancer cells as normal body cells express little or no telomerase for most of their lifespan and generally have longer telomeres than those in tumor cells. All these findings justify the clinical applications of hTERT for anticancer immunotherapy.

Broadly used in several anticancer vaccine trials, peptide vaccination is the most advanced strategy concerning hTERT antigen. However several factors could influence the optimal success of this peptide-based vaccine strategy, such as (1) the human leukocyte antigen (HLA) restriction, (2) the natural processing of peptides in tumor cells, (3) the loss of antigen presentation on tumor cells, (4) the functionality of antigen-specific T cells, and (5) the long term persistence of the immune responses in the host after vaccination.

The memory response obtained with peptide vaccines and especially with short peptides is very low and not persistent. These suboptimal results can be explained in part by the absence of CD4 T-cell help. In addition, the half-life of MHC/peptide vaccine complex on presenting cells is only a few hours, the peptides then disappear. The dendritic cells then no longer present peptides to lymphocytes, and hence become tolerogenic. This defect in peptide presentation can be deleterious in some cases (Rosenberg et al., 2004).

SUMMARY OF THE INVENTION

The inventors have now developed a DNA vaccine strategy which does not show the drawbacks of the peptide (even long peptide) vaccination, restricted to certain epitopes of hTERT. Particularly, DNA vaccination avoids expensive and complicated procedures for protein production and purification. Moreover a DNA vaccine encoding the hTERT protein makes it possible to induce both CTL and CD4 helper T-cells independently of the HLA-restriction of the patient, while being safe and inducing a better quantitative and qualitative immune response.

The invention provides a nucleic acid construct comprising a sequence that encodes a human telomerase reverse transcriptase (hTERT) protein which is devoid of telomerase catalytic activity and of a nucleolar localization signal.

In a preferred embodiment, the hTERT protein may be fused at N-terminus with a protein enhancing addressing of the hTERT protein to proteasome, such as ubiquitin.

The nucleic acid construct of the invention is useful in triggering an immune response in a subject, preferably a cellular immune response, against cells that overexpress telomerase, preferably dysplasia cells or tumor cells, as well as cells infected with an oncovirus.

It is herein described a method for preventing or treating a tumor in a patient, which method comprises administering said nucleic acid construct to a patient in need thereof.

Such treatment can be referred to as an active immunotherapy or a therapeutic vaccination, as it triggers an immune response against the tumor, especially a cytotoxic CD8 T-cell response, along with a specific CD4 T-cell response.

A broad cellular immune response is obtained because both CD4 and CD8 T-cell repertoires are stimulated by the epitopes available on hTERT. The number of CD4 and CD8 T-cells directed against many epitopes of hTERT is higher than in peptide vaccination. Production of interleukins is improved, further to the induction of CD4 T-cells, especially Th1 cytokines, allowing an optimal growth and differentiation of CD8 T-cells with the hallmark of anti-tumor cells.

In another aspect of the invention, it is provided nucleic acid constructs comprising sequences that derive from human telomerase reverse transcriptase (hTERT), wherein said sequences that derive from hTERT
i) encode all or substantially all epitopes of hTERT, in any order, and
ii) encode a protein that is devoid of telomerase catalytic activity and of a nucleolar localization signal.

Indeed the inventors evidenced that such nucleic acid constructs, herein also designated as "shuffled" telomerase constructs, also trigger a hTERT specific in vivo immune response, especially a cytotoxic CD8 T-cell response.

BRIEF DESCRIPTION OF FIGURES

The patent or application file contains at least one drawing executed in color. Copies of this patent or patent application publication with color drawing(s) will be provided by the Office upon request and payment of the necessary fee.

The Figures and Examples illustrate the invention without limiting its scope.

Figure 1A:
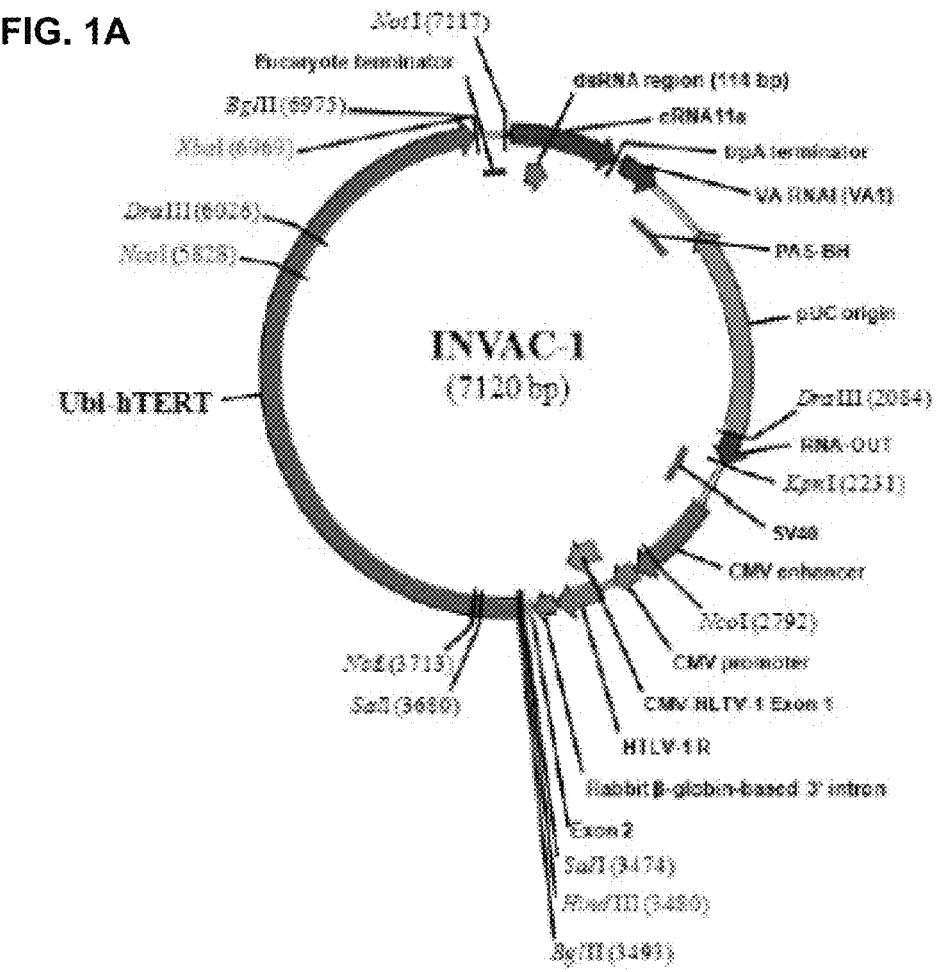

| FIG. 1A INVAC-1 plasmid map | | |
|---|---|---|
| Location (bases) | Sequence | Origin |
| 1-3478 | NTC8685-eRNA41H-HindIII-XbaI vector | NTC |
| 3479-3484 | HindIII cloning site: A.AGCTT | NTC/Invectys |
| 3485-6967 | Ubi-hTERT transgene | Invectys |
| 6968-6973 | XbaI cloning site: T.CTAGA | Invectys/NTC |
| 6974-7120 | NTC8685-eRNA41H-HindIII-XbaI vector | NTC |

Vector Features
  eRNA11a RIG-I agonist: 7-532
  trpA prokaryotic terminator: 535-564
  Adenovirus serotype 5 VA RNAI (VA1): 568-761
  Primosomal assembly site (PAS-BH) extended origin: 771-1055
  pUC replication origin: 1056-2070
  Sucrose selection marker (RNA-OUT): 2087-2231
  SV40 enhancer: 2232-2451
  CMV enhancer: 2452-2897
  CMV promoter: 2898-3017
  Untranslated leader (exon 1): 3018-3204
  HTLV-1 R: 3089-3314
  Synthetic Rabbit β-globin-based 3' intron: 3323-3429
  Exon 2 (SR-protein binding sites-Kozak): 3430-3478
  Ubi-hTERT transgene including HindIII-XbaI cloning sites—Invectys): 3479-6973
  Eukaryotic terminator: 6980-7114

Figure 1B:
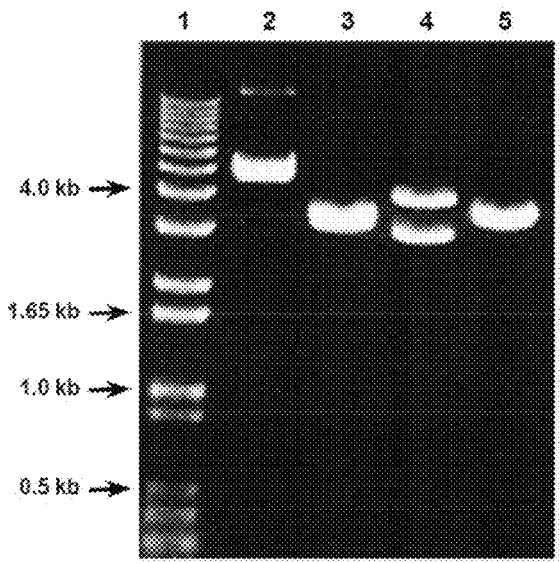

FIG. 1B Gel validation for INVAC-1

INVAC-1 expression vector was verified by restriction mapping. The pattern corresponds to expected restriction map.

Lane 1: 1 kb Ladder
Lane 2: Undigested INVAC-1
Lane 3: INVAC-1 digested with BglII/NotI (3496, 3262, 220, 142 bp bands)
Lane 4: INVAC-1 digested with NcoI (4084, 3036 bp bands)
Lane 5: INVAC-1 digested with HindIII/XbaI (3631, 3489 bp bands)

Figure 2A:
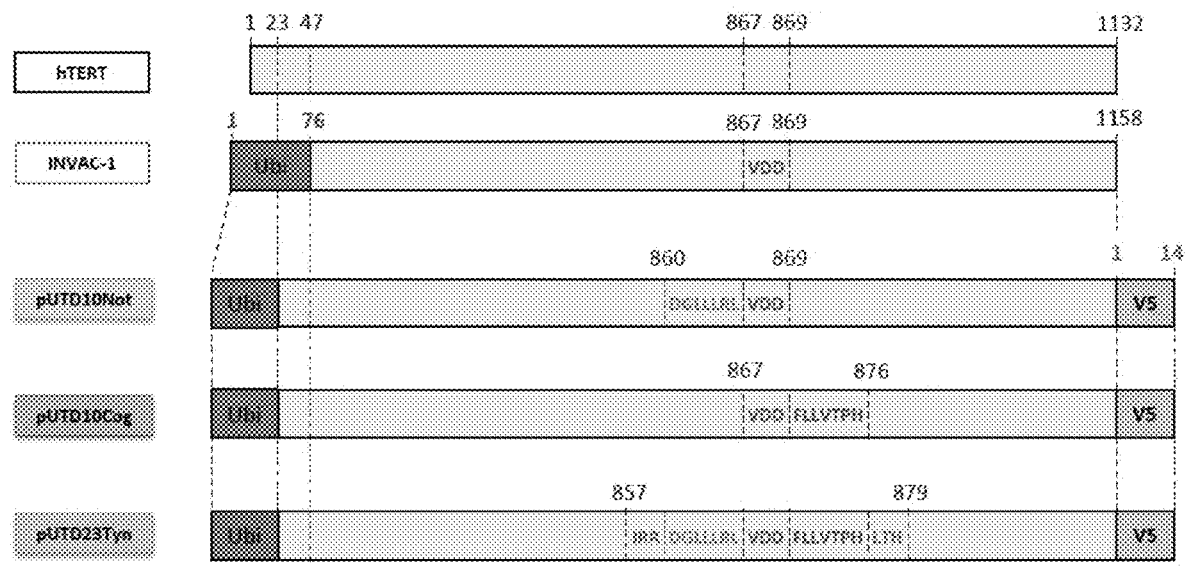

FIG. 2A hTERT, INVAC-1 and INVAC-1 derivatives.

Schematic alignment between wild-type hTERT and modified Ubi-hTERT proteins encoded by INVAC-1 and INVAC-1 derivatives: pUTD10Not (abbreviated as Δ10Not), pUTD10Cog (abbreviated as Δ10Cog) and pUTD23Tyn (abbreviated as Δ23).

Sequence Features:
  VDD: Deletion of amino acids 867-869 within the catalytic site
  DGLLLRL (SEQ ID NO: 19): Additional deletion of amino acids 860-867; upstream VDD deletion
  FLLVTPH (SEQ ID NO: 20): Additional deletion of amino acids 869-876; downstream VDD deletion
  IRR: Additional deletion of amino acids 857-859; upstream DGLLLRLVDD (SEQ ID NO: 21): deletion
  LTH: Additional deletion of amino acids 877-879; downstream VDDFLLVTPH (SEQ ID NO: 22): deletion
  Ubi: human ubiquitin sequence (1-76 amino acids)
  V5: C-terminal V5 tag for convenient protein detection
  (In FIG. 2A "IRRDGLLLRLVDDFLLVTPHLTH" is disclosed as SEQ ID NO: 101)

Figure 2B:
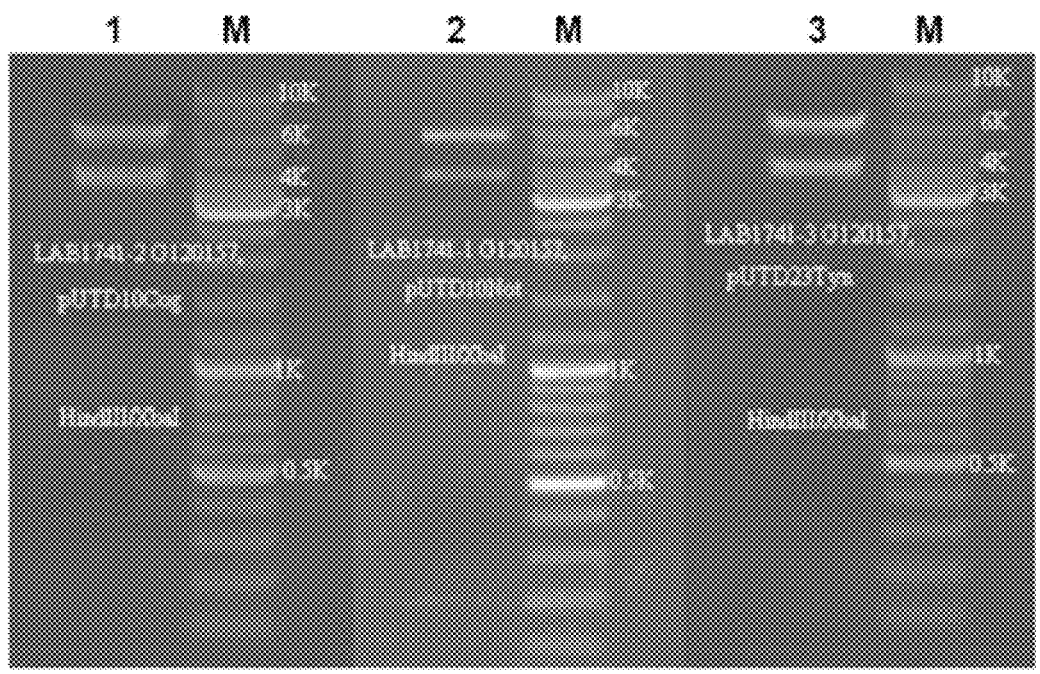

FIG. 2B Gel validation for INVAC-1 derivatives pUTD10Not, pUTD10Cog and pUTD23Tyn expression vectors (INVAC-1 derivatives) were verified by restriction mapping. The patterns correspond to expected restriction maps.

Lane M: 1 kb ladder
Lane 1: pUTD10Cog (5348, 3585 bp bands)
Lane 2: pUTD10Not (5348, 3585 bp bands)
Lane 3: pUTD23Tyn (5348, 3546 bp bands)

Figure 3A:
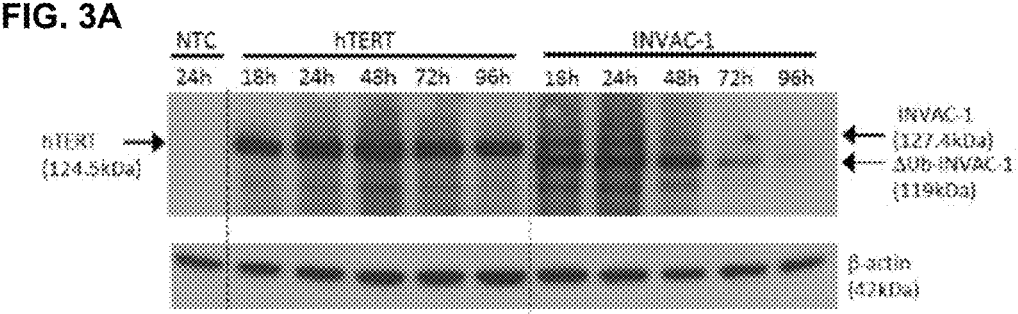
Figure 3B:
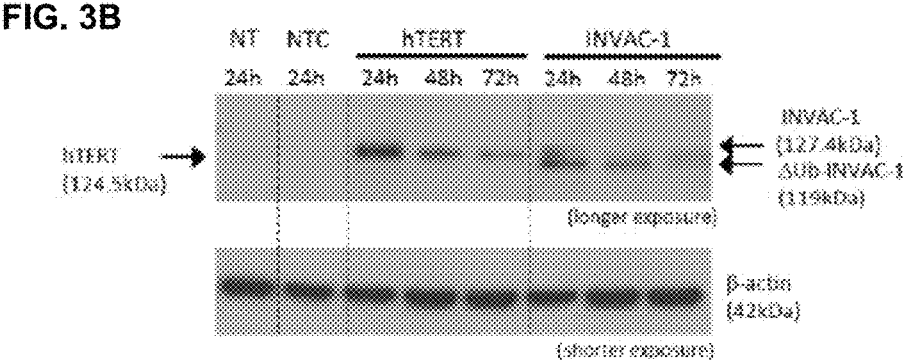
Figure 3C:
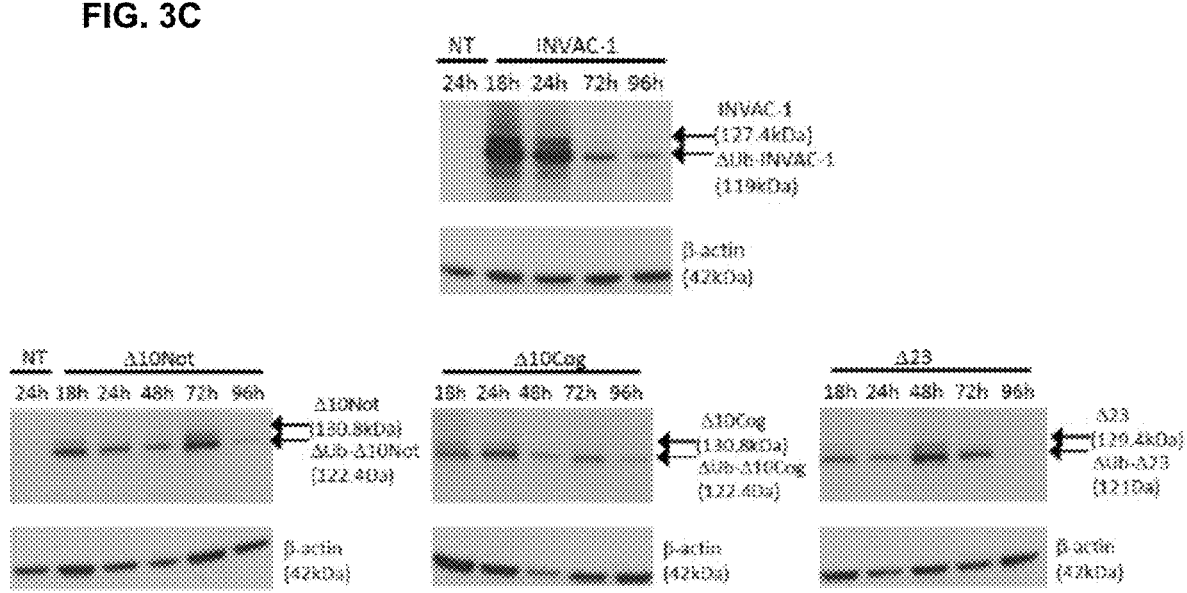

FIG. 3A-3C Expression of wild-type hTERT, INVAC-1 and INVAC-1 derivatives in vitro into different cell lines assessed by western blotting Wild-type hTERT (pTRIP-CMV-hTERT), empty vector (pNTC8685-eRNA41H, INVAC-1 backbone with no foreign coding sequence), INVAC-1 and INVAC-1 derivative constructs (pUTD10Not/Δ10Not, pUTD10Cog/Δ10Cog and pUTD23Tyn/Δ23) were transfected into HEK293T cells (FIG. 3A, FIG. 3C). Wild type hTERT, pNTC8685-eRNA41H empty vector and INVAC-1 constructs were transfected into CrFK cells (FIG. 3B).

Protein expression was monitored for 18-96 h post-transfection in HEK293T cells (FIG. 3A, FIG. 3C) and for 24-72 h in CrFK cells (FIG. 3B).

The time of cell harvesting is indicated on the top of each lane. Fifteen μg of total protein from cell lysates were loaded per lane for membranes FIG. 3A-C (hTERT, INVAC-1) and 20 μg of total protein lysates were loaded per lane for membranes FIG. 3C (Δ10Not, Δ10Cog, Δ 23). hTERT was detected with an anti-hTERT rabbit monoclonal antibody (hTERT, INVAC-1) or with an anti-tag V5 (Δ 10Not, Δ 10Cog, Δ 23). β-actin protein detection was used as a loading control and detected with an anti-β-actin mouse monoclonal antibody. Detection of hTERT proteins from CrFK cells (FIG. 3B) and INVAC-1 derivative proteins from HEK293T cells (FIG. 3C) required a longer exposure time.

FIG. 4A-4D Intracellular localization of hTERT and INVAC-1 constructs into different cell lines assessed by immunofluorescence Wild-type hTERT (pTRIP-CMV-hTERT), empty vector (pNTC8685-eRNA41H, INVAC-1 backbone with no foreign coding sequence) and INVAC-1 constructs were transfected into HEK293T (FIG. 4A) or CrFK cells (FIG. 4D) for 24 h, and into HeLa (FIG. 4B) or QT6 (FIG. 4C) cells for 24 h and 48 h.

The cells were processed to immunofluorescence staining with an anti-hTERT rabbit monoclonal antibody and a goat Alexa Fluor 488° anti-rabbit secondary antibody (green). The nuclei were stained with DAPI (blue). Untreated cells were stained with DAPI only. The cells were analyzed upon fluorescence microscopy (×63).

FIG. 5A-5D Telomerase activity of hTERT, INVAC-1 and INVAC-1 derivatives assessed by TRAP assay CrFK cells were transfected with wild-type hTERT (pTRIP-CMV-hTERT), INVAC-1 and INVAC-1 derivative constructs. Twenty-four hours later cells were collected, total cell proteins were extracted and telomerase (reverse transcriptase) activity was assessed by Telomeric Repeat Amplification Protocol (TRAP) assay. Absorbance measurements (OD450/690 nm) and Relative Telomerase Activity (RTA; sample/positive control ratio) of INVAC-1 (FIG. 5A, FIG. 5B) and INVAC-1 derivative constructs (FIG. 5C, FIG. 5D) compared to wild-type hTERT and untreated CrFK cells are displayed (n=3 for 2.1 µg of total protein concentration samples), \*\*: p=0.0016, \*\*\*: p<0,0001, unpaired t-test.

No telomerase activity was detected in CrFK cells transfected with INVAC-1 and INVAC-1 derivatives.

Figure 6:
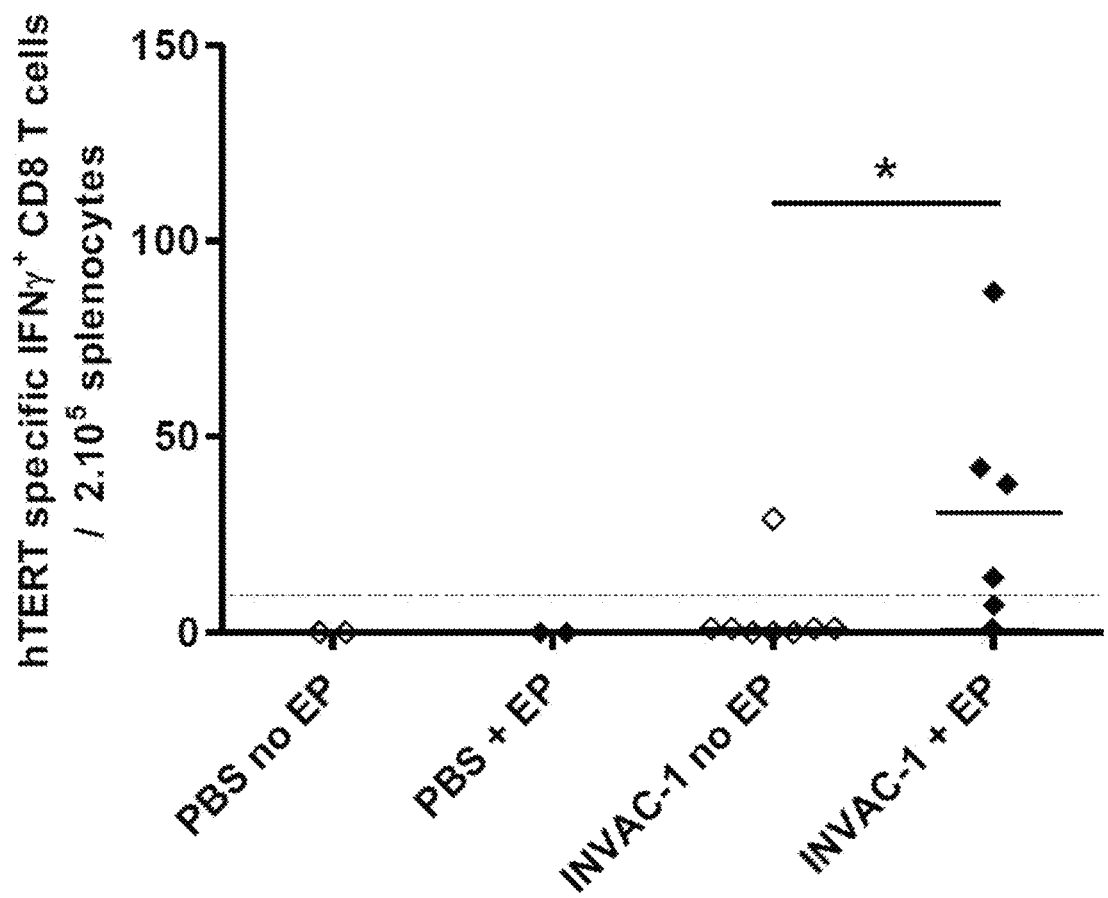

FIG. 6: Impact of electroporation to induce significant levels of hTERT specific CD8 T-cell secreting interferon-γ after ID administration of INVAC-1

Seven week-old C57BL/6 female mice were immunized ID (2-8 mice per group) with 100 µg of INVAC-1 or 1×PBS. For half of the animals an electroporation was performed at each vaccination site directly after immunization. Fourteen days after vaccination, spleens of all mice were harvested. Splenocytes were Ficoll purified and stimulated in an IFN-γ ELIspot assay in triplicates with a pool of 2 hTERT peptides restricted to the $H2^b$ MHC (p429, p660) for 19 hours. Spots were revealed with a biotin-conjugated detection antibody followed by streptavidin-AP and BCIP/NBT substrate solution. Results are the median frequency of hTERT specific CD8T cells secreting IFNγ/200,000 splenocytes. Kruskal-Wallis analysis with Dunn's multiple comparison test. \*: p-value<0.05. EP=electroporation.

Figure 7A:
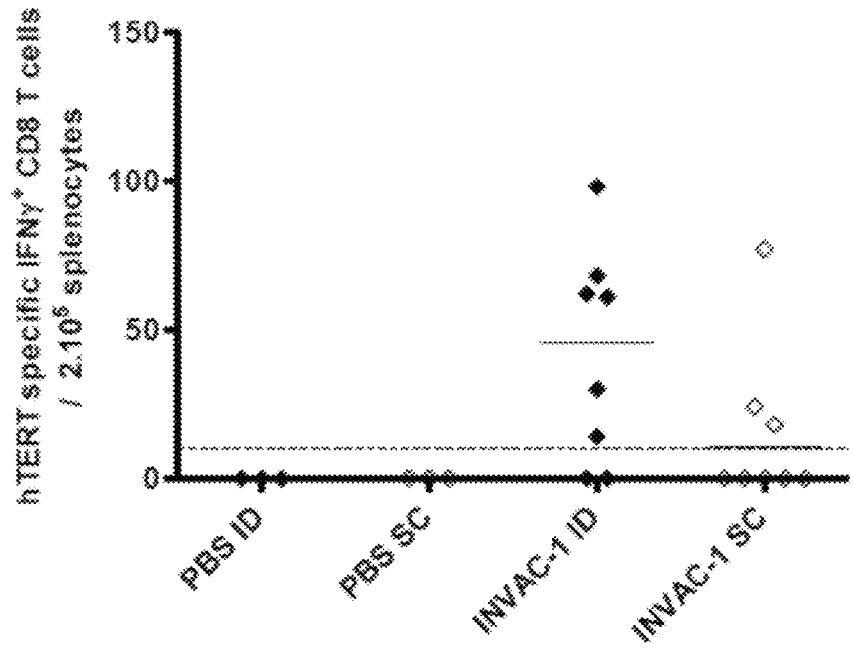
Figure 7B:
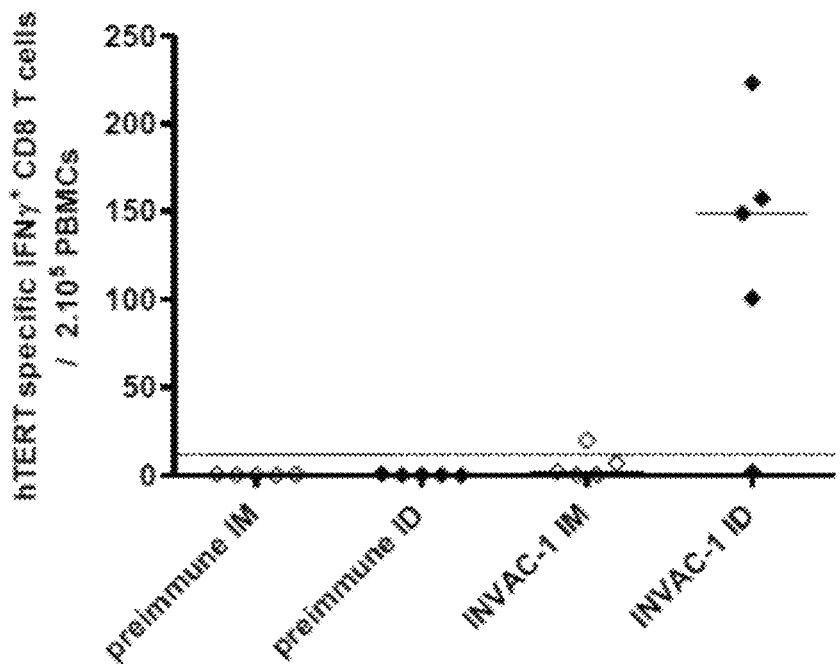

FIG. 7A-7B Evaluation of various administration routes for INVAC-1 vaccination followed by electroporation to induce hTERT specific CD8 T-cell secreting interferon-γ.

Seven to ten week-old transgenic HLA-B7 mice were immunized via FIG. 7A) the ID or SC route (3-8 mice per group) and FIG. 7B) via the ID or IM route (4-5 mice per group) with 25 µg of INVAC-1 or 1×PBS. All animals received an electroporation at each vaccination site directly after the immunization. Fourteen days after vaccination, spleens FIG. 7A) or peripheral blood FIG. 7B) of all mice were harvested. Splenocytes or PBMCs were Ficoll purified and stimulated in an IFN-γ ELIspot assay in triplicates with a pool of 3 hTERT specific peptides restricted to the HLA-B7 MHC (p351, p1123 and p277) for 19 hours. Spots were revealed with a biotin-conjugated detection antibody followed by streptavidin-AP and BCIP/NBT substrate solution. Results are the median frequency of hTERT specific CD8 T cells secreting IFNγ/200,000 splenocytes or PBMCs. Mann Whitney non parametric test, \*: p-value<0.05. A hatched line was voluntarily set at 10 hTERT specific CD8 T-cells secreting IFNγ/200,000 splenocytes as a cut-off threshold allowing the determination of responding animals.

Figure 8A:
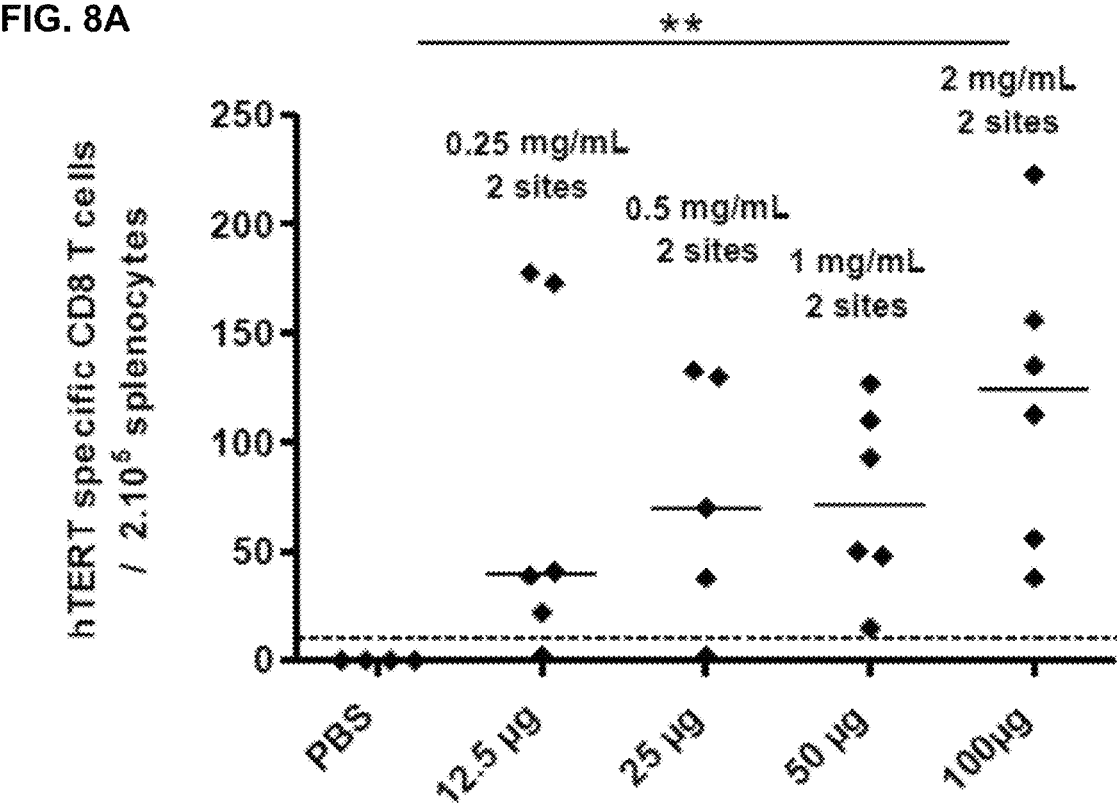
Figure 8B:
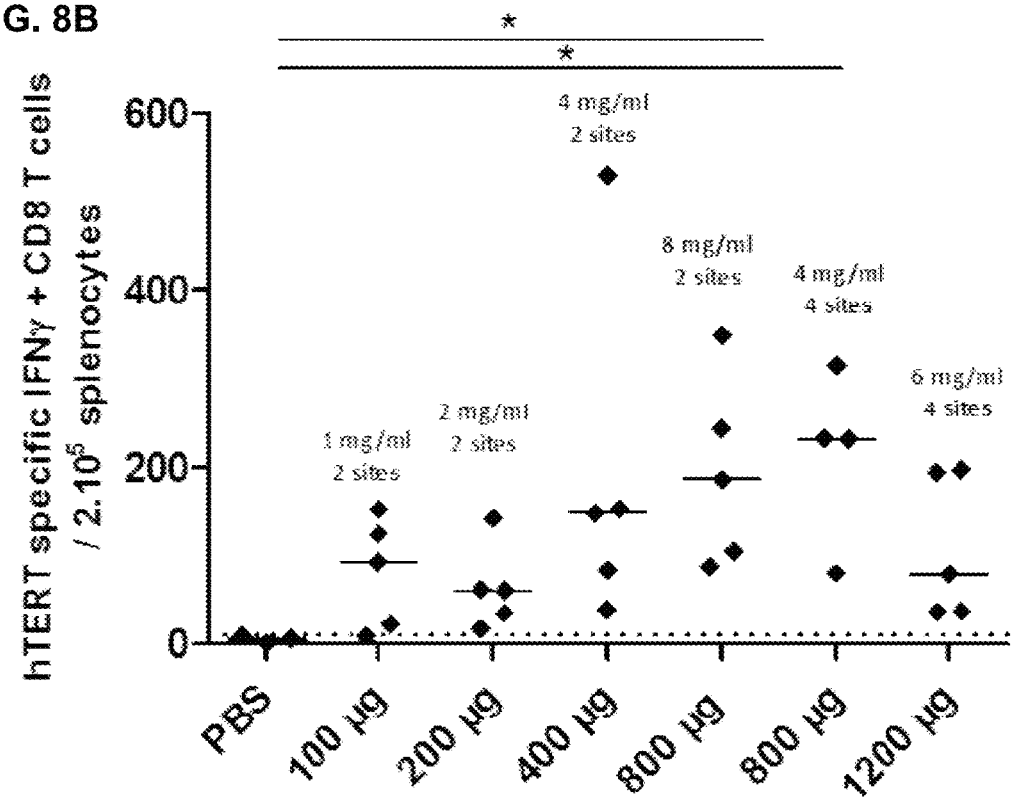

FIG. 8A-8B Impact of vaccine dose on hTERT specific CD8 T-cell response after a single ID immunization with INVAC-1 and electroporation Seven week-old C57BL/6 female mice were immunized ID FIG. 8A) with either 12.5, 25, 50 or 100 µg of INVAC-1 or 1×PBS (4-6 mice per group) and FIG. 8B) with either 100, 200, 400, 800 or 1200 µg of INVAC-1 or 1×PBS (3-5 mice per group). An electroporation was performed at each vaccination site directly after immunization. Fourteen days after vaccination, spleens of all mice were harvested. Splenocytes were Ficoll purified and stimulated in an IFN-γ ELIspot assay in triplicates with a pool of 2 hTERT peptides restricted to the H2b MHC (p429, p660) for 19 hours. Spots were revealed with a biotin-conjugated detection antibody followed by streptavidin-AP and BCIP/NBT substrate solution. Results are the median frequency of hTERT specific CD8 T-cells secreting IFNγ/200,000 splenocytes. Kruskal-Wallis analysis with Dunn's multiple comparison test. \*: p-value<0.05, \*\*: p-value<0.01. A hatched line was voluntarily set at 10 spots/200,000 splenocytes to allow determination of responding animals.

Figure 9:
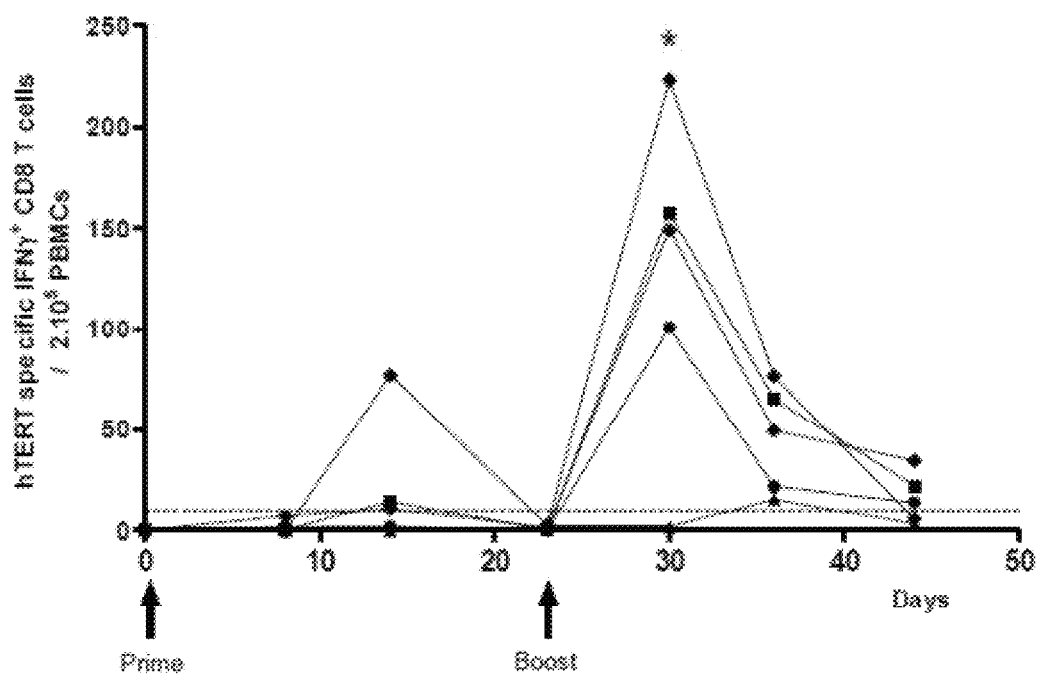

FIG. 9: Impact of a prime-boost vaccination regimen with INVAC-1 on hTERT specific CD8 T-cells secreting interferon-γ

Seven to ten week-old transgenic HLA-B7 mice were immunized via the ID route (5 mice per group) with 25 µg of INVAC-1. All animals received an electroporation at each vaccine site directly after the immunization. Twenty one days later mice received a boost injection using the same procedure. Peripheral blood was collected before the first immunization, at day 7, 15 and 21 post-priming and at day 9, 16 and 22 post-boost.

PBMCs were Ficoll purified and stimulated in an IFN-γ ELIspot assay in triplicates a pool of 3 hTERT specific peptides restricted to the HLA-B7 MHC (p351, p1123 and p277) for 19 hours. Spots were revealed with a biotin-conjugated detection antibody followed by streptavidin-AP and BCIP/NBT substrate solution. Results are the median frequency of hTERT specific CD8 T-cells secreting IFNγ/200,000 splenocytes. Mann-Whitney non parametric test, \*: p-value<0.05. A hatched line was voluntarily set at 10 spots/200,000 splenocytes to allow determination of responding animals.

Figure 10A:
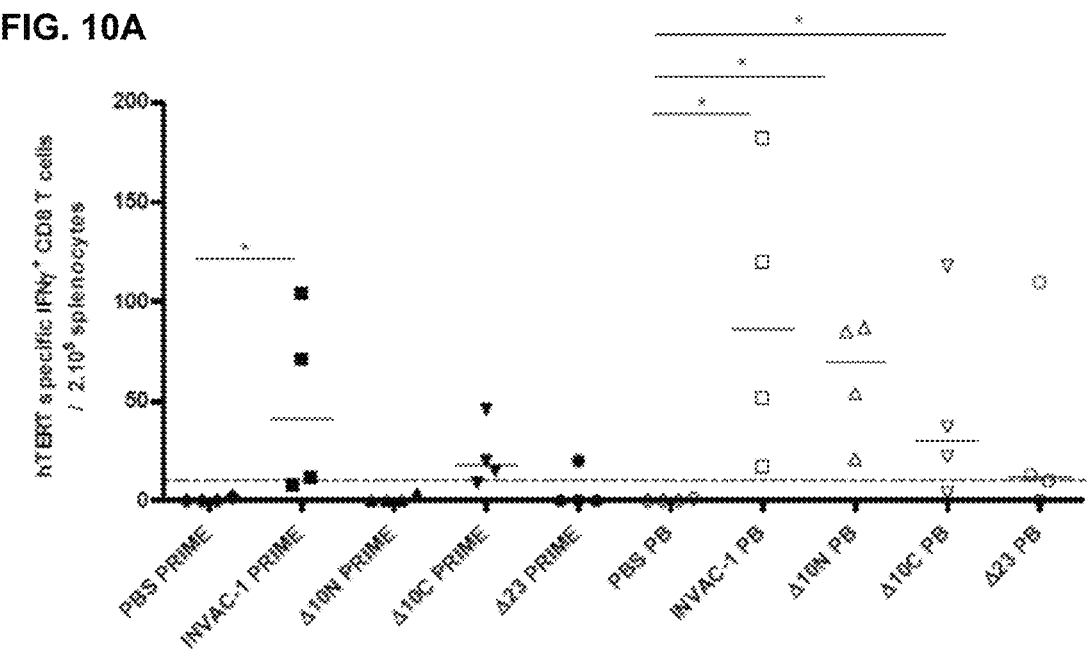
Figure 10B:
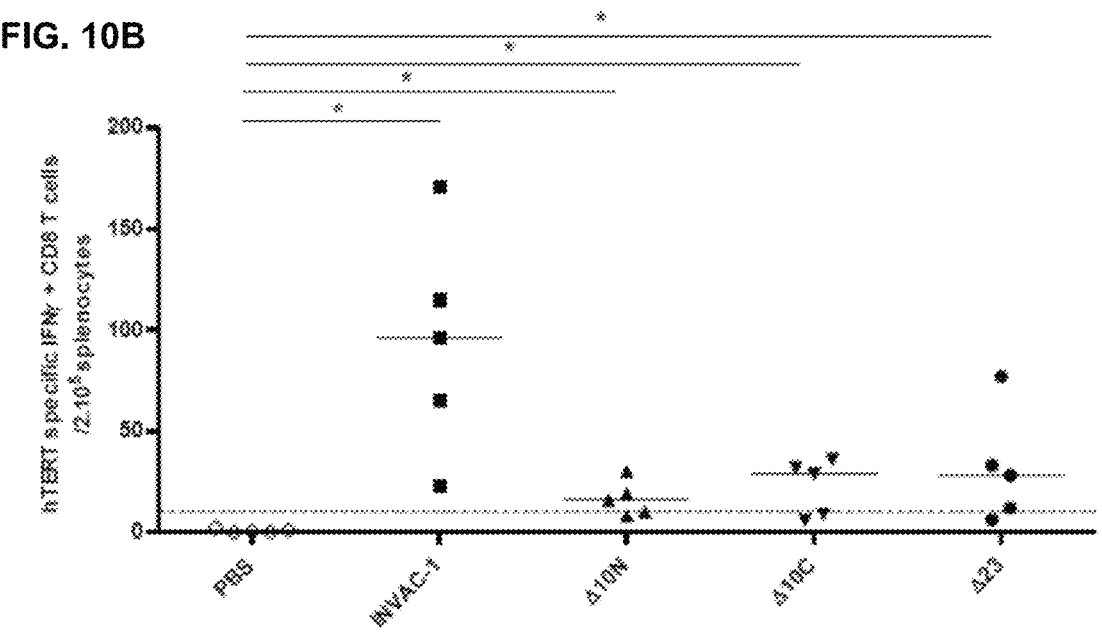

FIG. 10A-10B Evaluation of ID vaccination (single immunization vs. prime-boost regimen) with INVAC-1, Δ10Not, Δ10Cog or Δ23 followed by electroporation to induce hTERT specific CD8 T-cell secreting interferon-γ.

FIG. 10A) Seven-week-old C57BL/6 female mice were immunized ID (4 mice per group) with 100 µg of INVAC-1, Δ10Not, Δ10Cog or Δ23 or 1×PBS. An electroporation was performed at each vaccination site directly after immunization. Half of the animals received a boost injection twenty one days after the first vaccination using the same procedure. Mouse spleens were harvested 14 days or 10 days after the last immunization respectively for the animals which received a single or a priming and boost injections. Splenocytes were Ficoll purified and stimulated in an IFN-γ ELIspot assay in triplicates with a pool of 2 hTERT peptides restricted to the $H2^b$ MHC (p429, p660) for 19 hours. Spots were revealed with a biotin-conjugated detection antibody followed by streptavidin-AP and BCIP/NBT substrate solution. Results are the median frequency of hTERT specific CD8 T-cells secreting IFNγ/200,000 splenocytes for animals which received a single injection (PRIME, black dots) or a prime and boost injections (PB, white dots). Mann Whitney non parametric test, \*: p-value<0.05. A cut-off was voluntarily set at 10 hTERT specific CD8 T cells secreting IFNγ/200,000 splenocytes (hatched line) to allow the determination of responding animals. PB=post-boost.

FIG. 10B) Seven to ten week-old transgenic HLA-B7 mice were immunized via the ID route (5 mice per group) with 100 µg of INVAC-1, Δ10Not, Δ10Cog or Δ23 or 1×PBS. All animals received an electroporation at each vaccination site directly after the immunization. Twenty one days after the first vaccination, mice received a boost injection using the same procedure. Splenocytes were Ficoll purified and stimulated in an IFN-γ ELIspot assay in triplicates with a pool of 3 hTERT specific peptides restricted to the HLA-B7 MHC (p351, p1123 and p277) for 19 hours. Spots were revealed with a biotin-conjugated detection antibody followed by streptavidin-AP and BCIP/NBT substrate solution. Results are the median frequency of hTERT specific CD8 T-cells secreting IFNγ/200,000 splenocytes or PBLs. Mann Whitney non parametric test, \*: p-value<0.05. A cut-off was voluntarily set at 10 spots/200,000 splenocytes in order to determine the frequency of responding animals (hatched line).

Figure 11A:
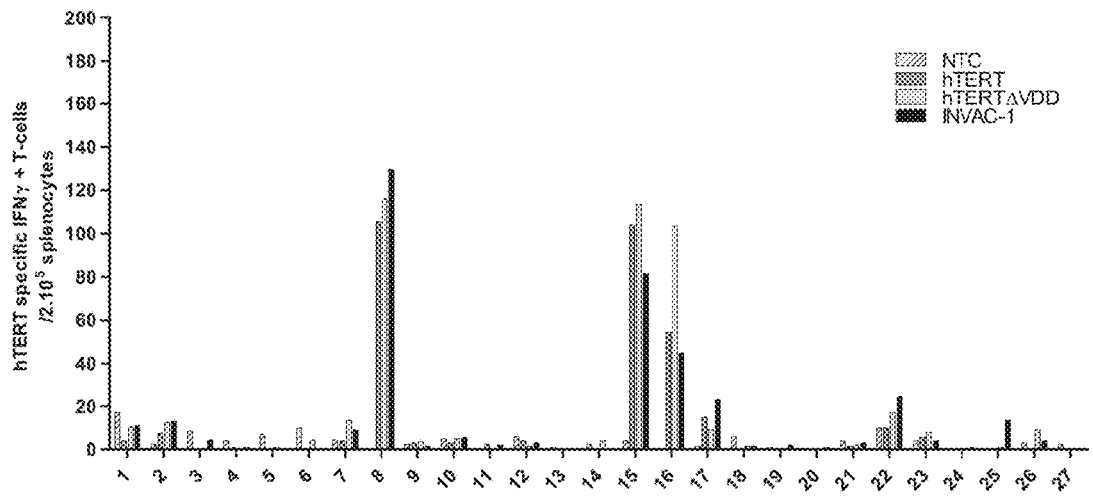
Figure 11B:
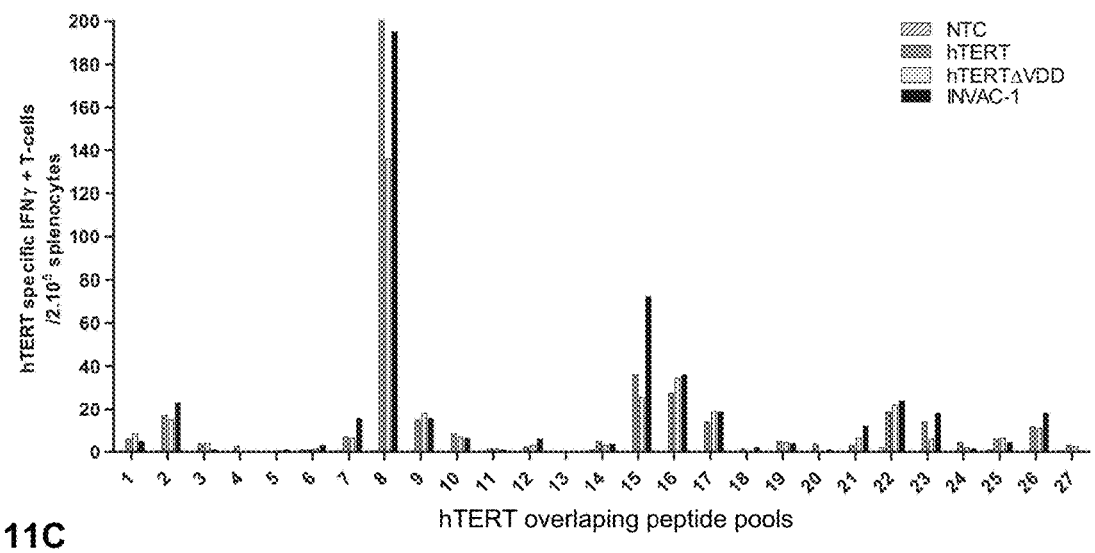
Figure 11C:
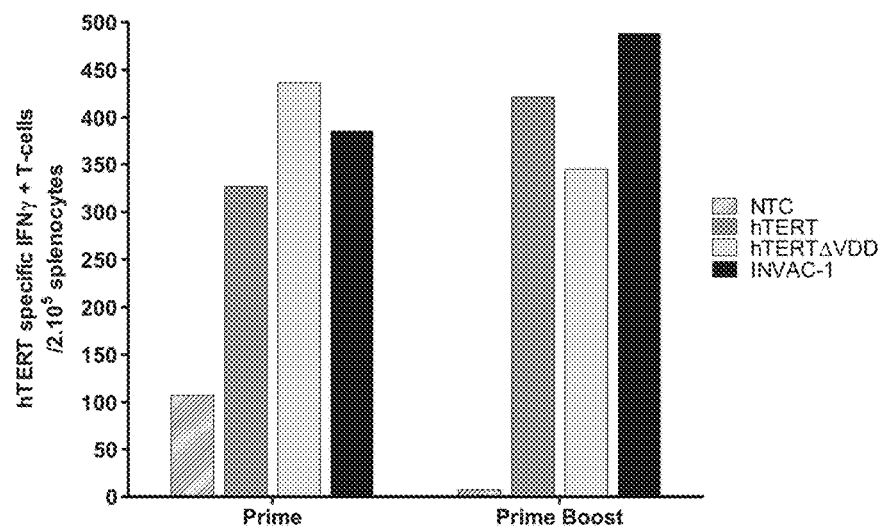

FIG. 11A-11C Breadth of hTERT specific T-cell response after ID immunization(s) followed by electroporation: Comparison between INVAC-1, pNTC-hTERT and pNTC-hTERT-ΔVDD contructs Seven to 13 week-old transgenic HLA-B7 mice were immunized via the ID route (6 mice per group) with 25 μg of INVAC-1, hTERTΔVDD (pNTC-hTERT-ΔVDD), hTERT (pNTC-hTERT) or empty vector NTC (pNTC8685-eRNA41H). Forty-eight animals received an electroporation at each vaccine site directly after the immunization. Half of the animals received a boost injection twenty one days after the first vaccination using the same procedure. Mice spleens were harvested 14 days or 10 days after the last immunization respectively for the animals which received a single or a priming and boost injections.

Splenocytes were Ficoll purified and stimulated in an IFN-γ ELIspot assay in triplicates, with a set of 269 purified peptides from hTERT (purity>70%, GenScript) divided into 27 pool of 9-10 hTERT overlapping peptides (15mer peptides overlapping by 11 amino acids), during an overnight stimulation (19 hours). Spots were revealed with a biotin-conjugated detection antibody followed by streptavidin-AP and BCIP/NBT substrate solution.

For each mouse, the median number of spots was calculated per triplicates and per stimulation condition (medium or peptides pool). The frequency (F) of hTERT specific T-cells was then calculated after subtraction of the median number of spots in medium stimulated wells from the median number of spots in peptides pool stimulated wells. Negative values were set to 0 for subsequent analyses.

This analysis was performed for the animals which received a single (FIG. 11A) or a prime-boost (FIG. 11B) vaccination. (FIG. 11A and FIG. 11B) For each vaccination group (INVAC-1, hTERTΔVDD, hTERT, NTC), a median (n=6) of frequency (F) of telomerase specific T-cells secreting IFN γ/200,000 splenocytes was calculated per stimulation condition to obtained one value for each of 27 pools.

(FIG. 11C) Sum of total median of frequency (F) of telomerase specific T-cell detected for the 27 pools (269 purified peptides) after vaccination by INVAC-1, hTERTΔVDD, hTERT or NTC. Statistical analyses were performed with Prism 5 software using a non-parametric Kruskal-Wallis test with Dunn's correction. p-value<0.05 was considered as statistically significant.

Figure 12A:
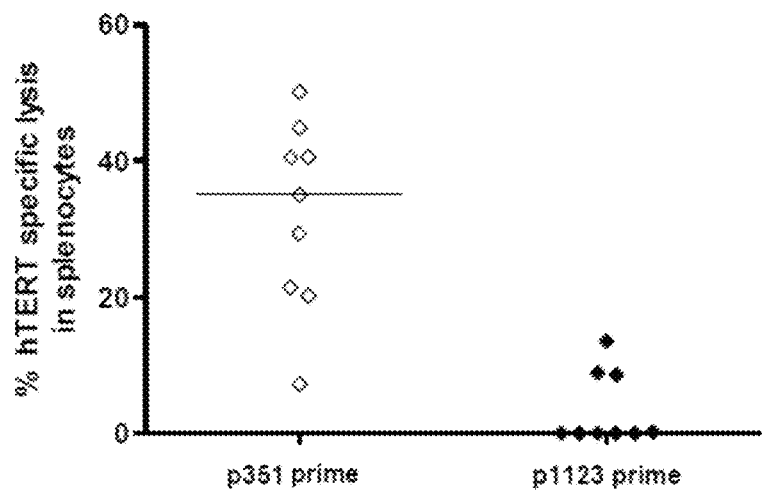
Figure 12B:
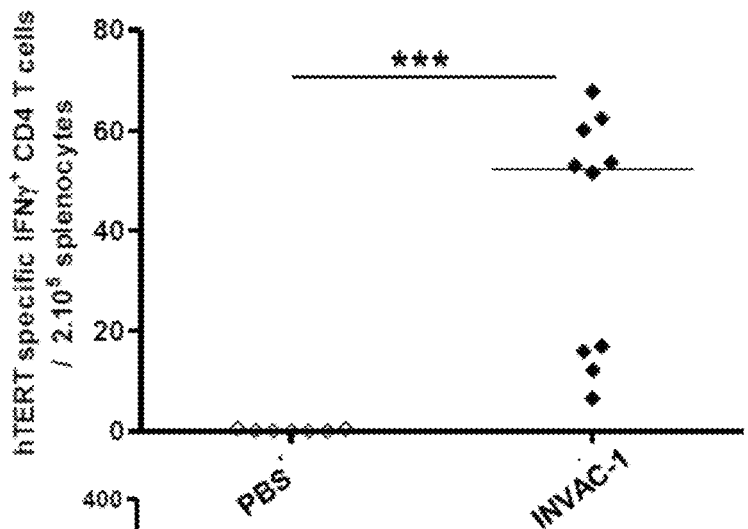
Figure 12C:
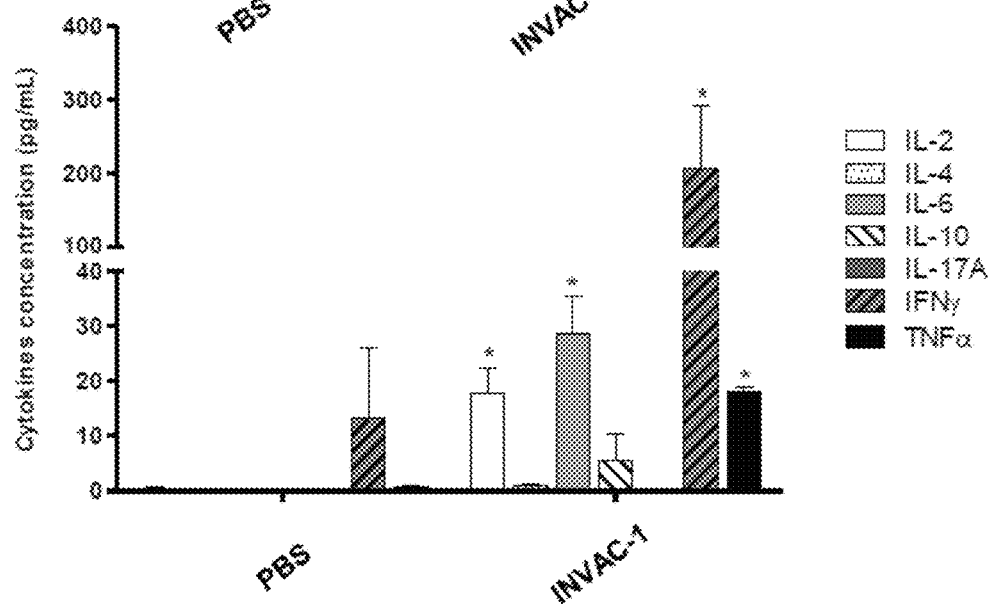

FIG. 12A-12C Potency of INVAC-1 ID vaccination and electroporation to generate specific cytotoxic CD8 T-cells and Th1-CD4 T-cells FIG. 12A) Seven to 10 week-old transgenic HLA-B7 mice were immunized via the ID route (5 mice per group) with 25 μg of INVAC-1 or 1×PBS. All animals received an electroporation at each vaccine site directly after the immunization. At day 14 post injection, syngeneic splenocytes, pulsed with individual hTERT peptides restricted to the HLA-B7 MHC (either p351 or p1123) or left unpulsed were labeled with carboxyfuorescein-diacetate succinimidyl ester (CFSE) at three different concentrations: high=1 μM (621), medium=0.5 μM (987) and low=0.1 μM (unpulsed). The same number of high, medium or low CFSE labeled cells was transferred IV to vaccinated mice. After 15-18 hours, the disappearance of peptide-pulsed cells was determined in the spleen by flow cytometry. The percentage of specific lysis was calculated by comparing the ratio of pulsed to unpulsed cells in vaccinated versus control mice. Data represent the percentage of specific lysis for each mouse against each individual peptide in the spleen after ID vaccination with INVAC-1. Horizontal bars show average percentage of lysis per peptide and per immunization route. Standard deviations are also plotted. (n=10 individual animals/group). Statistical analyses were performed with Prism 5 software using a non-parametric Kruskal-Wallis test with Dunn's correction. p-value<0.05 was considered as statistically significant.

FIG. 12B and FIG. 12C) Seven to ten week-old transgenic HLA-A2/DR1 mice were immunized via the ID route (7-10 mice per group) with 25 μg of INVAC-1 or 1×PBS. All animals received an electroporation at each vaccine site directly after the immunization. Fourteen days after vaccination, spleens of all mice were harvested. Splenocytes were Ficoll purified and FIG. 12B) half of them were stimulated in triplicates in an IFN-γ ELIspot assay with a pool of 3 hTERT specific peptides restricted to the HLA-DR1 MHC (p1029, p578 and p904) for 19 hours. Spots were revealed with a biotin-conjugated detection antibody followed by streptavidin-AP and BCIP/NBT substrate solution. Results are the median frequency of hTERT specific CD4 T-cells secreting IFNγ/200,000 splenocytes. Mann Whitney non parametric test, ***: p-value<0.001.

FIG. 12C) The second half of splenocytes was stimulated for 24 h with a pool of 3 hTERT specific peptides restricted to the HLA-DR1 MHC (p1029, p578 and p904). Supernatants from stimulated cells were recovered and tested in a CBA assay in order to evaluate the concentration of Th1/Th2 and Th17 cytokines secreted by hTERT specific CD4 T-cells. Results are the median cytokine concentrations in pg/mL. Kruskal-Wallis analysis with Dunn's multiple comparison test. *: p-value<0.05.

Figure 13A:
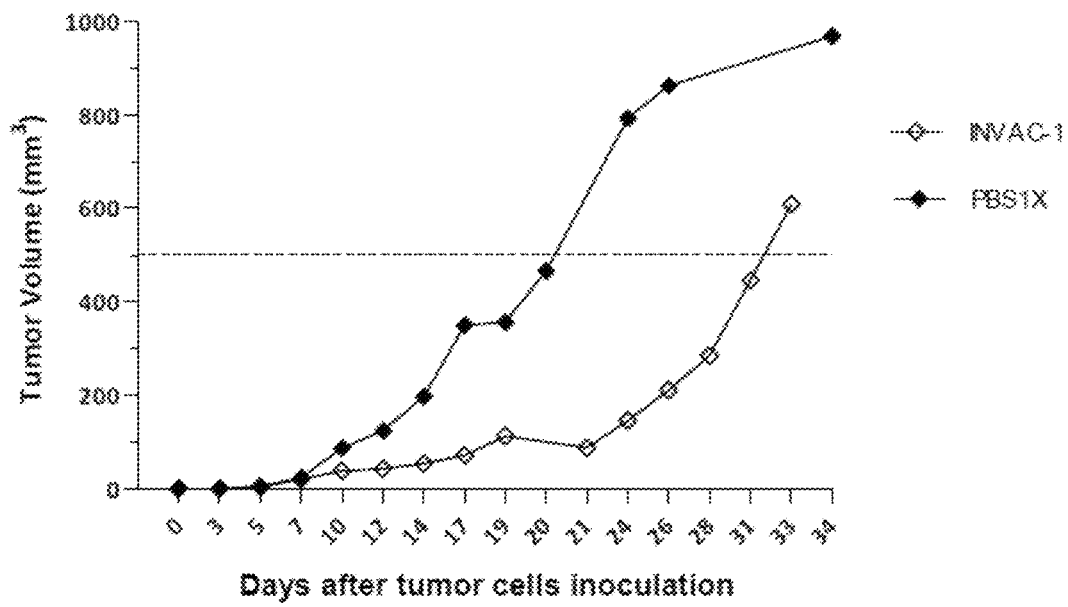
Figure 13B:
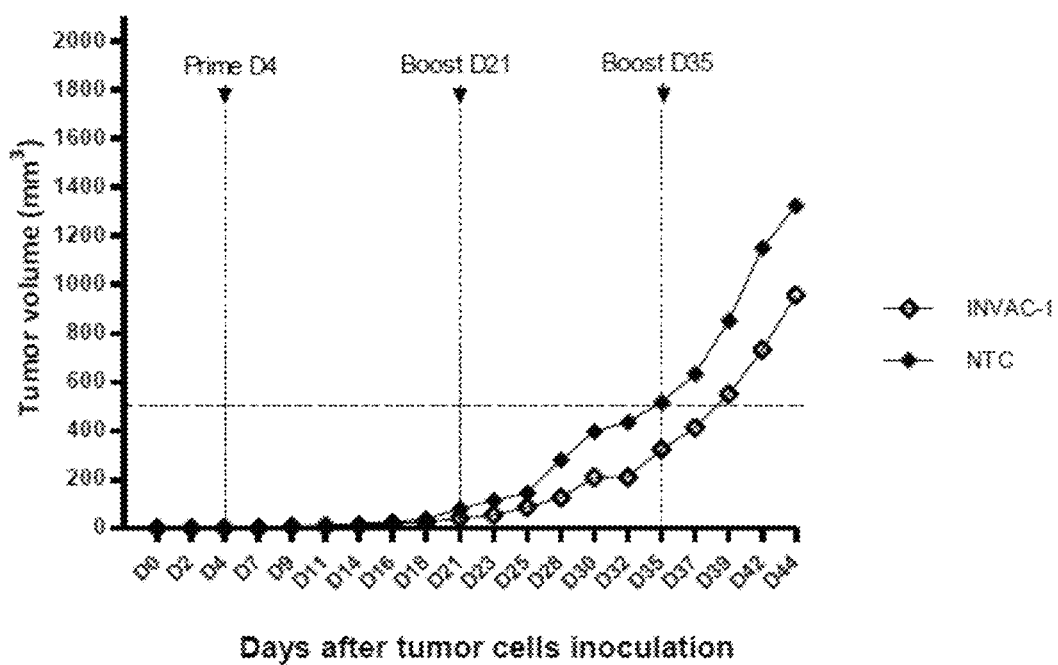

FIG. 13A-13B Impact of a therapeutic or preventive ID vaccination with INVAC-1 followed by electroporation in a syngeneic HLA-A2/DR1 transgenic mice tumor model.

FIG. 13A) Five to ten week-old transgenic HLA-A2/DR1 mice were immunized via the ID route (5 mice per group) with 100 μg of INVAC-1 or 1×PBS. All animals received an electroporation at each vaccine site directly after the immunization. Twenty one days after priming, mice received a boost injection following the same procedure. One month after boosting, mice were inoculated via the SC route with 50,000 Sarc-2 tumor cells (mouse fibrosarcoma). Median tumor volume in each vaccinated group is shown at different days after tumor cell engraftment. A hatched line was drawn at 500 mm$^3$ to allow calculation of the tumor growth delay.

FIG. 13B) Twenty four week-old transgenic HLA-A2/DR1 mice (10 mice per group) were inoculated via the SC route with 20,000 Sarc-2 tumor cells (mouse fibrosarcoma). Four days after tumor cells engraftment, animals were immunized via the ID route with 25 μg of INVAC-1 or an empty plasmid (NTC, INVAC-1 backbone with no antigen sequence). All animals received an electroporation at each vaccine site directly after the immunization. Twenty one and 35 days after priming, mice received boost injections using the same procedure. Median tumor volume in each vaccinated group is shown at different days after challenge. A hatched line was drawn at 500 mm$^3$ to allow calculation of the tumor growth delay.

Figure 14A:
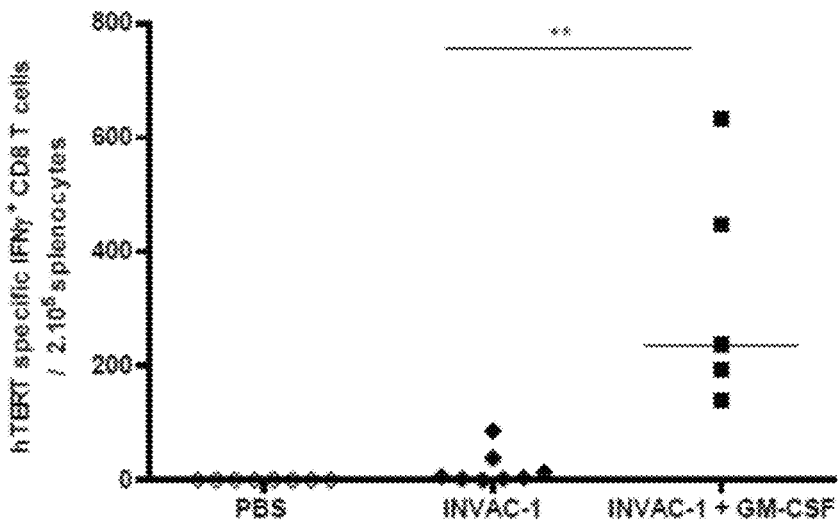
Figure 14B:
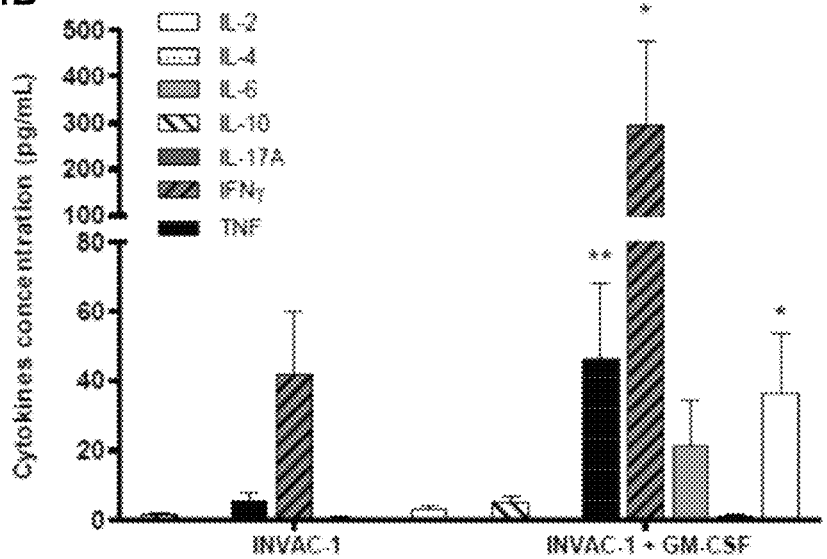
Figure 14C:
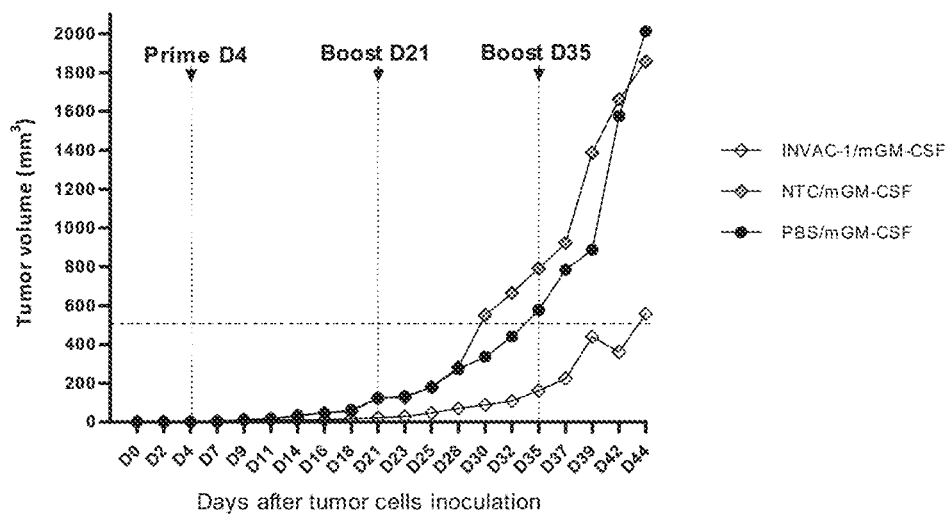

FIG. 14A-14C Potentialization of INVAC-1-induced cellular immune responses by GM-CSF and in vivo efficacy in a syngeneic HLA-A2/DR1 transgenic mouse tumor model FIG. 14A) Seven week-old C57BL/6 female mice were immunized ID (5 mice per group) with 25 μg of INVAC-1, 25 μg of INVAC-1 and 0.5 μg mGM-CSF or 1×PBS. Electroporation was performed at each vaccination site directly after INVAC-1 immunization. Fourteen days after vaccination, spleens from all mice were harvested. Splenocytes were Ficoll purified and stimulated in an IFN-γ ELIspot assay in triplicates with a pool of 2 hTERT peptides restricted to the H2$^b$ MHC (p429, p660) for 19 hours. Spots were revealed with a biotin-conjugated detection antibody followed by streptavidin-AP and BCIP/NBT substrate solution. Results are the median frequency of hTERT specific CD8 T-cells secreting IFNγ/200,000 splenocytes. Kruskal-Wallis analysis with Dunn's multiple comparison test. **: p-value<0.01.

FIG. 14B) Seven to ten week-old transgenic HLA-A2/DR1 mice were immunized via the ID route (5 mice per group) with 100 µg of INVAC-1, 100 µg of INVAC-1 and 5 µg mGM-CSF. All animals received an electroporation at each vaccine site directly after INVAC-1 immunization. Fourteen days after vaccination, spleens from all mice were harvested. Splenocytes were Ficoll purified and stimulated in triplicates with a pool of 3 hTERT specific peptides restricted to the HLA-DR1 MHC (p1029, p578 and p904) for 24 hours. Supernatants from stimulated cells were recovered and tested in a CBA assay in order to evaluate the concentration of Th1/Th2 and Th17 cytokines secreted by hTERT specific CD4 T-cells. Results are the median cytokine concentration in pg/mL. Kruskal-Wallis analysis with Dunn's multiple comparison test. *: p-value<0.05. **: p-value<0.01.

FIG. 14C) Seven to ten week-old transgenic HLA-A2/DR1 mice (10 mice per group) were inoculated via the SC route with 20,000 Sarc-2 tumor cells (mouse fibrosarcoma). Four days after tumor cells engraftment, animals were immunized via the ID route with 25 µg INVAC-1 and 0.5 µg mGM-CSF, an empty plasmid (NTC, INVAC-1 backbone with no antigen sequence) and 0.5 µg mGM-CSF or 1×PBS and 0.5 µg mGM-CSF. All animals received an electroporation at each vaccine site directly after INVAC-1 immunization. Twenty one and 35 days after priming, mice received boost injections with the same protocol. Median tumor volume in each vaccinated group is shown at different days after tumor cells engraftment.

A hatched line was drawn at 500 mm$^3$ to allow calculation of the tumor growth delay.

Figure 15:
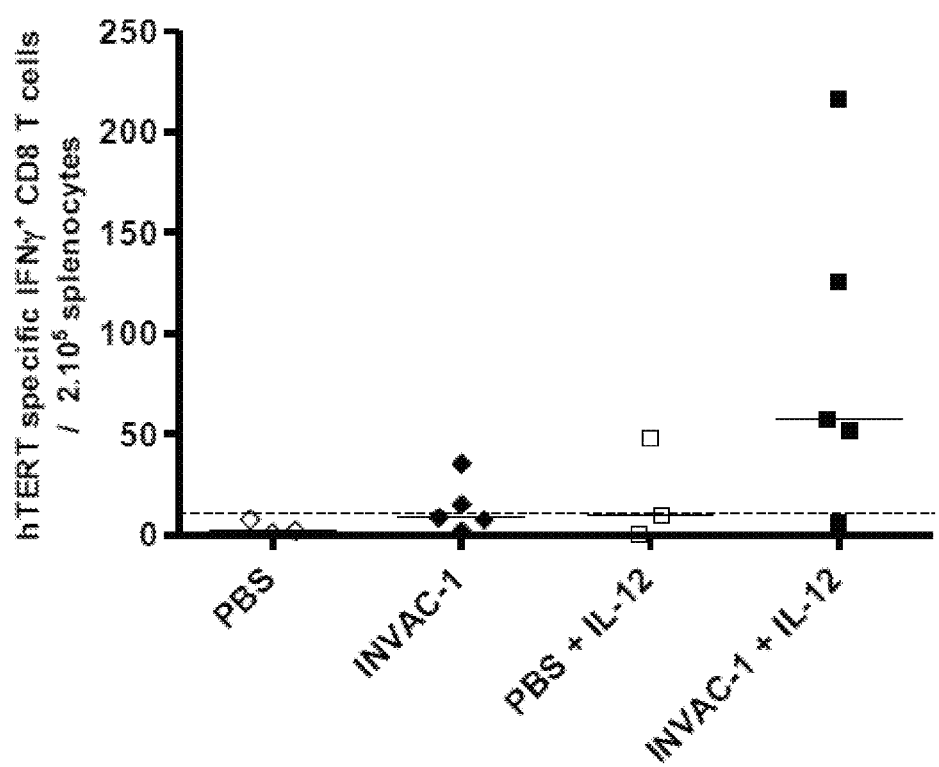

FIG. 15: Impact of IL-12 to potentiate INVAC-1 induced hTERT specific CD8 T-cell responses Seven to ten week-old transgenic HLA-A2/DR1 mice were immunized via the ID route (5 mice per group) with 100 µg of INVAC-1, 100 µg of INVAC-1 and 1 ng IL-12, 1×PBS or 1×PBS and 1 ng IL-12. All animals received an electroporation at each vaccine site directly after INVAC-1 immunization. Fourteen days after vaccination, spleens of all mice were harvested. Splenocytes were Ficoll purified and stimulated in triplicates in an IFN-γ ELIspot assay with a pool of 2 hTERT specific peptides restricted to the HLA-A2 (UCP4.1 and UCP2.1) for 19 hours. Spots were revealed with a biotin-conjugated detection antibody followed by streptavidin-AP and BCIP/NBT substrate solution. Results are the median frequency of hTERT specific CD8 T-cells secreting IFNγ/200,000 splenocytes. A hatched line was set at 10 spots/200,000 splenocytes to allow the determination of responding animals.

FIG. 16A-16E shows the complete nucleotide sequence of INVAC-1 plasmid expression vector (7120 bp). Vector features are detailed in FIG. 1A legend. INVAC-1-encoded hTERT fusion protein (1158 AA) starts at position 3488 (ATG coding for M amino-acid) and ends at 6961 (GAC coding for D amino-acid). INVAC-1/hTERT protein was deleted of the 47 first amino-acids (1-47 AA) which were replaced by an ubiquitin polypeptide (76 AA). The catalytic site was inactivated by a 9 bp deletion (between nucleotides 6172-6173) coding for VDD (* in the Sequence) and corresponding to AA 867-869 of wild-type human telomerase (hTERT; Accession number NM_198253). First line is the nucleotide sequence (SEQ ID NO: 11); Second line is the corresponding amino-acid sequence (SEQ ID NO: 12). Annotations (see also FIG. 1A) are given either above or below sequences. "☐": Stop codon.

FIG. 17A-17E shows the insert sequence encoding the D10Not human ubiquitin-telomerase fusion protein (Ubi-hTERT). hTERT was deleted of the 23 first amino acids (1-23 AA) which were replaced by an ubiquitin polypeptide (76 AA). An additional deletion was introduced between amino acids 912-913 (* see sequence), corresponding to AA 860-869 of wild-type human telomerase (hTERT; Accession number NM_198253). This 10 amino acids deletion includes the 3 AA deletion (ΔVDD) resulting in inactivation of human TERT enzymatic activity and the deletion of additional 7 AA upstream the VDD sequence. The 14 amino acids at the C-terminal sequence of the Ubi-hTERT code for the V5 epitope tag. First line is the nucleotide sequence (SEQ ID NO: 13); Second line is the corresponding amino acid sequence (SEQ ID NO: 14). Annotations are given either above or below sequences. "☐": Stop codon.

FIG. 18A-18E shows the insert sequence encoding the D10Cog human ubiquitin-telomerase fusion protein (Ubi-hTERT). hTERT was deleted of the 23 first amino acids (1-23 AA) which were replaced by an ubiquitin polypeptide (76 AA). An additional deletion was introduced between amino acids 919-920 (* see sequence), corresponding to AA 867-876 of wild-type human telomerase (hTERT; Accession number NM_198253). This 10 amino acids deletion includes the 3 AA deletion (ΔVDD) resulting in inactivation of human TERT enzymatic activity and the deletion of additional 7 AA downstream the VDD sequence. The 14 amino acids at the C-terminal sequence of the Ubi-hTERT code for the V5 epitope tag. First line is the nucleotide sequence (SEQ ID NO: 15); Second line is the corresponding amino acid sequence (SEQ ID NO: 16). Annotations are given either above or below sequences. "☐": Stop codon.

FIG. 19A-19E shows the insert sequence encoding the D23Tyn human ubiquitin-telomerase fusion protein (Ubi-hTERT). hTERT was deleted of the 23 first amino acids (1-23 AA) which were replaced by an ubiquitin polypeptide (76 AA). An additional deletion was introduced between amino acids 909-910 (* see sequence), corresponding to AA 857-879 of wild-type human telomerase (hTERT; Accession number NM_198253). This 23 amino acids deletion includes the 3 AA deletion (ΔVDD) resulting in inactivation of human TERT enzymatic activity and the deletion of additional 10 AA upstream and downstream the VDD sequence. The 14 amino acids at the C-terminal sequence of the Ubi-hTERT code for the V5 epitope tag. First line is the nucleotide sequence (SEQ ID NO: 17); Second line is the corresponding amino acid sequence (SEQ ID NO: 18). Annotations are given either above or below sequences. "☐": Stop codon.

| FIG. 20 INVAC-1 shuffled derivatives plasmid maps | | |
|---|---|---|
| Location (bases) | Sequence | Origin |
| 1-882 | pcDNA™3.1 (+) vector | Invitrogen commercial vector backbone used by GeneCust |
| 883-922 | Multiple cloning site (MCS) containing HindIII cloning site: A.AGCTT | Invitrogen |

FIG. 20 INVAC-1 shuffled derivatives plasmid maps

| Location (bases) | Sequence | Origin |
|---|---|---|
| 923-4474 | Ubi-hTERT shuffled transgenes | Invectys |
| 4475-4517 | Multiple cloning site (MCS) containing XbaI cloning site: T.CTAGA | Invitrogen |
| 4518-8918 | pcDNA ™3.1 (+) vector | Invitrogen commercial vector backbone used by GeneCust |

Figure 20A:
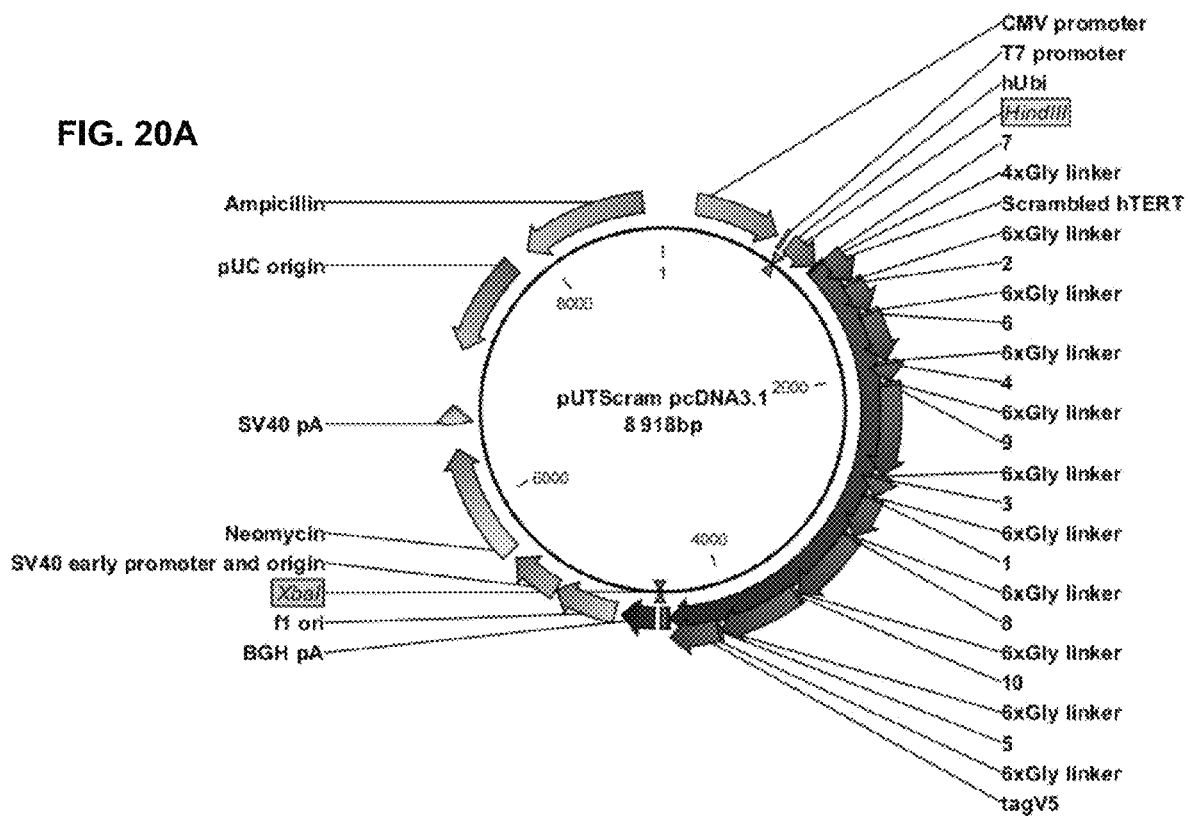

FIG. 20A pUTScram: Vector features

| Gene | Location (bases) |
|---|---|
| CMV promoter | 232-819 |
| T7 promoter | 863-882 |
| hUbi (human ubiquitin) | 923-1150 |
| 4xGly linker (SEQ ID NO: 98) | 1151-1162 |
| Scrambled hTERT (scrambled human TERT) | 1163-4414 |
| hTERT fragment 7 | 1163-1372 |
| 6xGly linker (SEQ ID NO: 99) | 1373-1390 |
| hTERT fragment 2 | 1391-1591 |
| 6xGly linker (SEQ ID NO: 99) | 1592-1609 |
| hTERT fragment 6 | 1610-1921 |
| 6xGly linker (SEQ ID NO: 99) | 1922-1939 |
| hTERT fragment 4 | 1940-2056 |
| 6xGly linker (SEQ ID NO: 99) | 2057-2074 |
| hTERT fragment 9 | 2075-2650 |
| 6xGly linker (SEQ ID NO: 99) | 2651-2668 |
| hTERT fragment 3 | 2669-2788 |
| 6xGly linker (SEQ ID NO: 99) | 2789-2806 |
| hTERT fragment 1 | 2807-3064 |
| 6xGly linker (SEQ ID NO: 99) | 3065-3082 |
| hTERT fragment 8 | 3083-3559 |
| 6xGly linker (SEQ ID NO: 99) | 3560-3577 |
| hTERT fragment 10 | 3578-4093 |
| 6xGly linker (SEQ ID NO: 99) | 4094-4111 |
| hTERT fragment 5 | 4112-4414 |
| 6xGly linker (SEQ ID NO: 99) | 4415-4432 |
| tag V5 | 4433-4474 |
| BGH polyadenylation sequence | 4518-4742 |
| f1 ori (f1 origin) | 4788-5216 |
| SV40 early promoter and origin | 5221-5564 |
| Neomycin gene | 5626-6420 |
| SV40 pA (SV40 early polyadenylation signal) | 6594-6724 |
| pUC origin (complementary strand) | 7107-7777 |
| Ampicillin gene (complementary strand) | 7922-8782 |

Figure 20B:
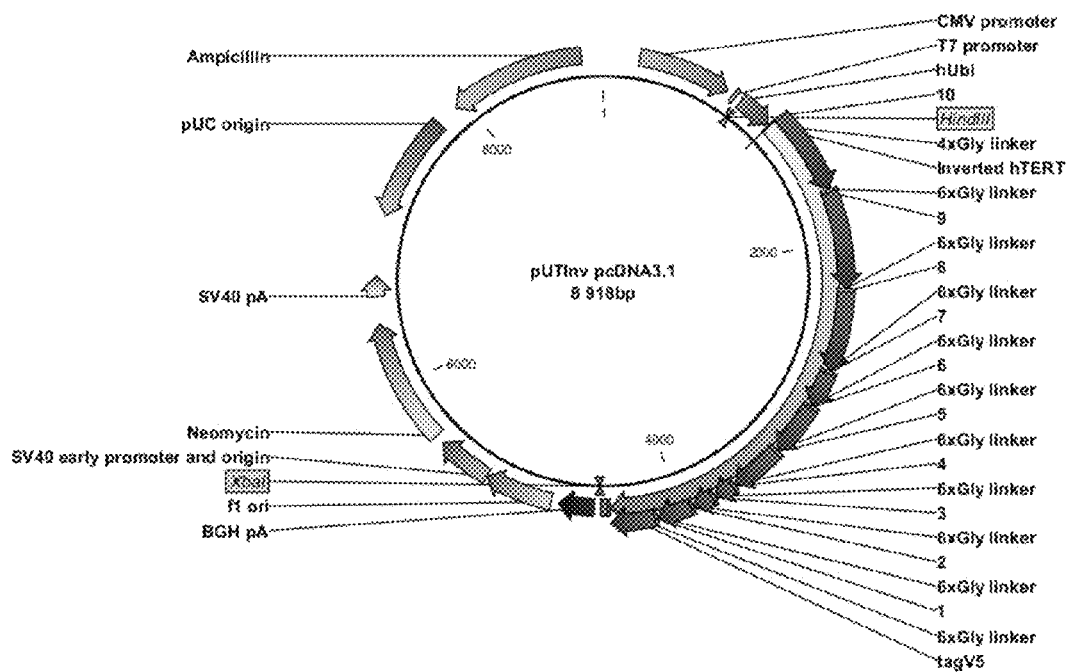

FIG. 20B pUTInv: Vector features

| Gene | Location (bases) |
|---|---|
| CMV promoter | 232-819 |
| T7 promoter | 863-882 |
| hUbi (human ubiquitin) | 923-1150 |
| 4xGly linker (SEQ ID NO: 98) | 1151-1162 |
| Inverted hTERT (inverted human TERT) | 1163-4414 |
| hTERT fragment 10 | 1163-1678 |
| 6xGly linker (SEQ ID NO: 99) | 1679-1696 |
| hTERT fragment 9 | 1697-2272 |
| 6xGly linker (SEQ ID NO: 99) | 2273-2290 |
| hTERT fragment 8 | 2291-2767 |
| 6xGly linker (SEQ ID NO: 99) | 2768-2785 |
| hTERT fragment 7 | 2786-2995 |
| 6xGly linker (SEQ ID NO: 99) | 2996-3013 |
| hTERT fragment 6 | 3014-3325 |
| 6xGly linker (SEQ ID NO: 99) | 3326-3343 |
| hTERT fragment 5 | 3344-3646 |
| 6xGly linker (SEQ ID NO: 99) | 3647-3664 |
| hTERT fragment 4 | 3665-3781 |
| 6xGly linker (SEQ ID NO: 99) | 3782-3799 |
| hTERT fragment 3 | 3800-3919 |
| 6xGly linker (SEQ ID NO: 99) | 3920-3937 |
| hTERT fragment 2 | 3938-4138 |
| 6xGly linker (SEQ ID NO: 99) | 4139-4156 |
| hTERT fragment 1 | 4157-4414 |
| 6xGly linker (SEQ ID NO: 99) | 4415-4432 |
| tag V5 | 4433-4474 |
| BGH polyadenylation sequence | 4518-4742 |
| f1 ori (f1 origin) | 4788-5216 |
| SV40 early promoter and origin | 5221-5564 |
| Neomycin gene | 5626-6420 |
| SV40 pA (SV40 early polyadenylation signal) | 6594-6724 |
| pUC origin (complementary strand) | 7107-7777 |
| Ampicillin gene (complementary strand) | 7922-8782 |

Figure 21A:
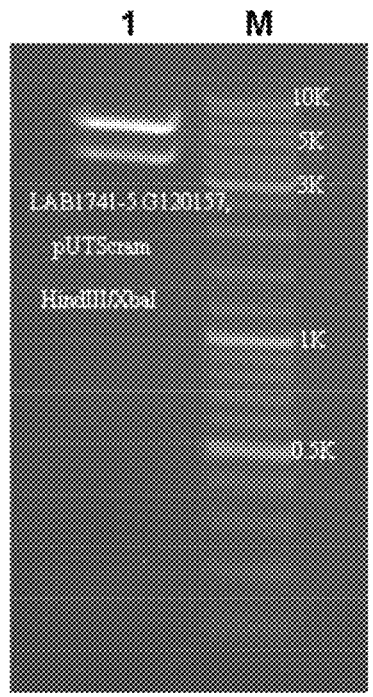

FIG. 21A Gel validation for pUTScram pUTScram expression vector was verified by restriction mapping. The pattern corresponds to expected restriction map.

Lane M: 1 kb Ladder

Lane 1: pUTScram digested with HindIII/XbaI (3576, 5342 bp bands)

Figure 21B:
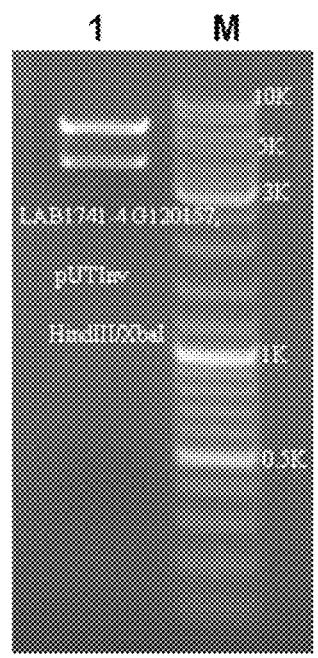

FIG. 21B Gel validation for pUTInv pUTInv expression vector was verified by restriction mapping. The pattern corresponds to expected restriction map.

Lane M: 1 kb Ladder

Lane 1: pUTInv digested with HindIII/XbaI (3576, 5342 bp bands)

Figure 22:
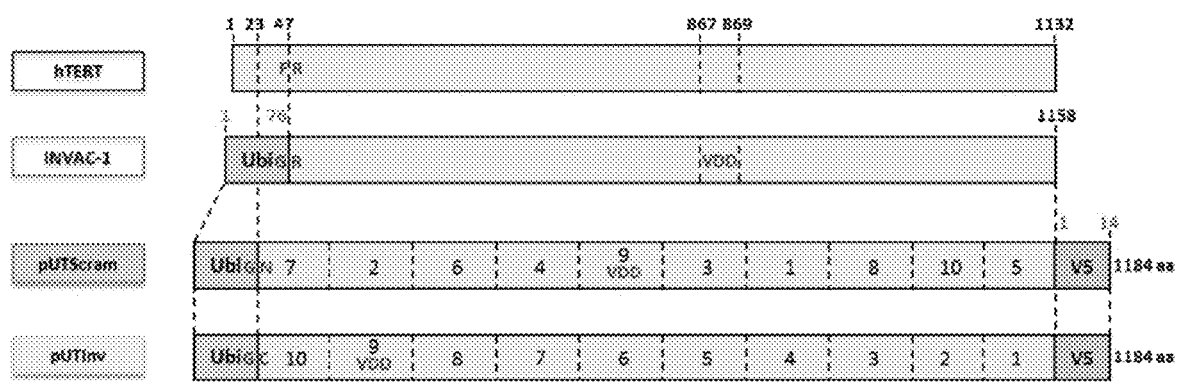

FIG. 22 hTERT, INVAC-1, pUTScram and pUTInv constructs

Schematic alignment between wild-type hTERT and modified Ubi-hTERT proteins encoded by INVAC-1 and INVAC-1 shuffled derivatives: pUTScram (Scrambled) and pUTInv (Inverted).

Modified hTERT sequence (ΔVDD) was divided into ten immunogenic fragments: fragment 1 (258 bp; Leu24-Gly109), fragment 2 (201 bp; Phe115-Ala181), fragment 3 (120 bp; Trp203-Ala242), fragment 4 (117 bp; Ser255-Arg293), fragment 5 (303 bp; Pro320-Thr420), fragment 6 (312 bp; Ala423-Val526), fragment 7 (210 bp; Cys528-Gln597), fragment 8 (477 bp; Arg599-Lys757), fragment 9 (576 bp; Lys760-Ile951), fragment 10 (516 bp; Asn958-Asp1129).

Sequence features:

VDD: Deletion of amino acids 867-869 within the catalytic site

Ubi: human ubiquitin sequence (1-76 amino acids)

F (Phe): Phenylalanine residue of hTERT (AA47)

G (Gly): C-terminal glycine residue of ubiquitin (AA76)

R (Arg): Arginine, first amino acid of INVAC-1 protein (AA 77)

N (Asn): Asparagine, first amino acid of artificial hTERT protein (Scrambled) encoded by pUTScram (AA 81)

C (Cys): Cysteine, first amino acid of artificial hTERT protein (Inverted) encoded by pUTInv (AA 81)

V5: C-terminal V5 tag for convenient protein detection

FIG. 23A-23D In vitro expression of wild-type hTERT, INVAC-1 and INVAC-1 shuffled derivatives assessed by western blotting Wild type hTERT, INVAC-1, pUTScram and pUTInv were transfected into HEK293T cells. Protein expression was monitored for 18-96 h post-transfection. (FIG. 23A and FIG. 23C) Wild-type hTERT and INVAC-1 samples for 18 h and 72 h were loaded at 15 µg of total protein concentration. These samples were used as positive controls of protein expressions. (FIG. 23A) Scrambled and (FIG. 23C) Inverted proteins were loaded at 20 µg of total protein from the cell lysates per lane. hTERT was detected with an anti-hTERT rabbit monoclonal antibody (hTERT, INVAC-1) or with an anti-tag V5 mouse monoclonal antibody (Scrambled, Inverted). Time of cells harvesting is indicated on the top of each lane. β-actin protein was used as a loading control and was detected with anti-β-actin mouse monoclonal antibody. Detection of INVAC-1 shuffled derivative products required a longer exposure time than wild-type hTERT and INVAC-1 proteins (10 sec to 30 min against less than 1 sec).

Shuffled protein signal intensities were normalized to β-actin signal on western blot (FIG. 23A and FIG. 23C) using ImageJ software. (FIG. 23B) Scrambled. (FIG. 23D) Inverted. Profile plots of loading control and protein bands were generated for each lane in order to obtain arbitrary numbers corresponding to the area under the curve profile. A ratio (relative density) is calculated by dividing the area value for each sample by the area value for the corresponding loading-control.

Figure 24A:
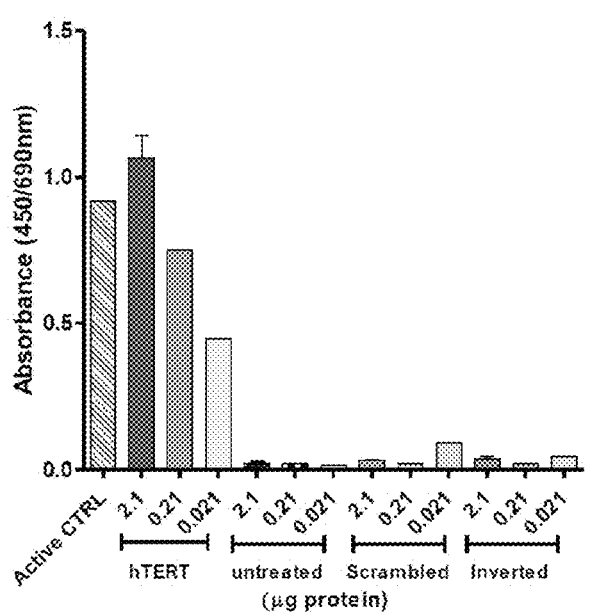
Figure 24B:
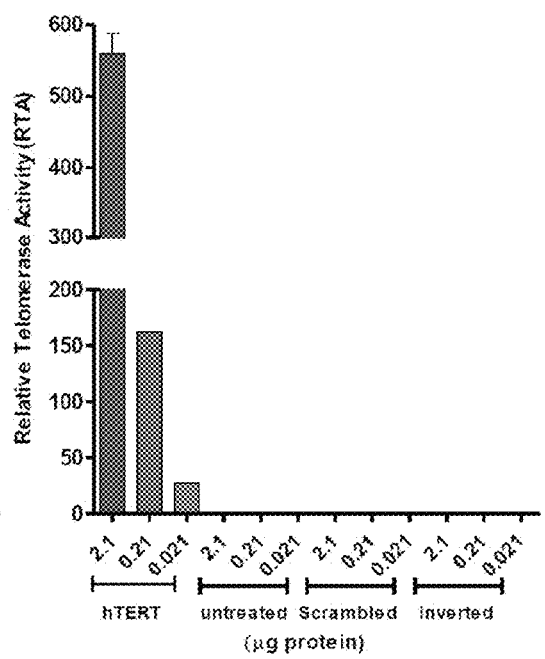

FIG. 24A-24B Telomerase activities of hTERT, INVAC-1 and INVAC-1 shuffled derivatives assessed by TRAP assay CrFK cells were transfected with wild-type hTERT (pTRIP-CMV-hTERT), pUTScram and pUTInv constructs. Twenty-four hours later cells were collected, total cell proteins were extracted and telomerase (reverse transcriptase) activity was assessed by Telomeric Repeat Amplification Protocol (TRAP) assay. Absorbance measurements (OD450/690 nm) and Relative Telomerase Activity (RTA; sample/positive control ratio) of shuffled constructs (FIG. 24A and FIG. 24B respectively) compared to wild-type hTERT and untreated CrFK cells are displayed (n=3 for 2.1 µg of total protein concentration samples), unpaired t-test was performed. No telomerase activity was detected in CrFK cells transfected with pUTScram and pUTInv constructs.

Figure 25:
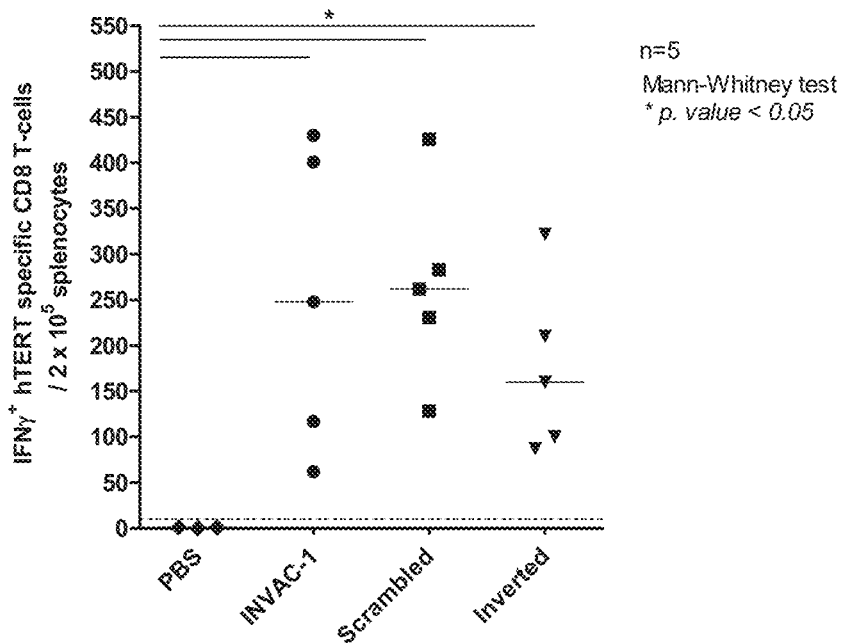

FIG. 25: Evaluation of ID vaccination with INVAC-1, pUTScram and pUTInv followed by electroporation to induce hTERT specific CD8 T-cell secreting interferon-γ.

Nine to fifteen week-old transgenic HLA-B7 mice were immunized via the ID route (3-5 mice per group) with 100 µg of INVAC-1, pUTScram, pUTInv or 1×PBS upon two immunization cycles (prime-boost regimen). An electroporation was performed at each vaccination site directly after each immunization. Mice spleens were harvested 10 days after the second immunization. Splenocytes were Ficoll purified and stimulated in an IFN-γ ELIspot assay in triplicates with a pool of 3 specific hTERT peptides restricted to the HLA-B7 MHC (p277, p351 and p1123) or free medium for 19 hours. Spots were revealed with a biotin-conjugated detection antibody followed by streptavidin-AP and BCIP/NBT substrate solution. Results are the median frequency of hTERT specific CD8 T-cells secreting IFNγ/200,000 splenocytes. Mann Whitney non parametric test was performed, *: p-value<0.05. A cut-off was voluntarily set at 10 spots/200,000 splenocytes in order to determine the frequency of responding animals (hatched line).

Figure 26:
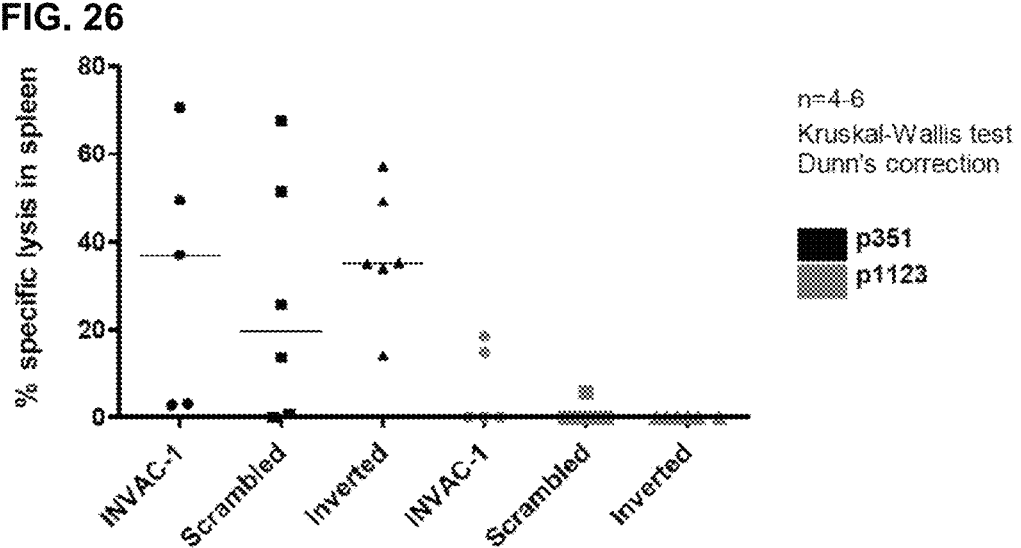

FIG. 26: Potency of pUTScram and pUTInv to generate hTERT specific cytotoxic CD8 T-cells after ID vaccination and electroporation Fifteen week-old transgenic HLA-B7 mice were immunized via the ID route (4-6 mice per group) with 100 µg of INVAC-1, pUTScram, pUTInv or 1×PBS. All animals received an electroporation at each vaccine site directly after the immunization. At day 14 post injection, syngeneic splenocytes, pulsed with individual hTERT peptides restricted to the HLA-B7 MHC (either p351 or p1123) or left unpulsed were labeled with carboxyfuorescein-diacetate succinimidyl ester (CFSE) at three different concentrations: high=5 µM (351), medium=2 µM (1123) and low=0.2 µM (unpulsed). A mix containing an equal number of CFSE labeled cells from each concentration was injected through the retro-orbital vein (IV) to vaccinated mice. After 15-18 hours, the disappearance of peptide-pulsed cells was determined in the spleen by flow cytometry. The percentage of specific lysis was calculated by comparing the ratio of pulsed to unpulsed cells in vaccinated versus control mice. Data represent the percentage of specific lysis for each mouse against each individual peptide in the spleen after ID vaccination. Horizontal bars show median percentage of lysis per peptide. Statistical analyses were performed with Prism 5 software using a non-parametric Kruskal-Wallis test with Dunn's correction. p-value<0.05 was considered as statistically significant.

FIG. 27A-27E shows the delineation of the immunogenic segments of Ubi-hTERT codon optimized sequence used for INVAC-1 shuffled derivative constructions. First line is the codon optimized nucleotide sequence of Ubi-hTERT (SEQ ID NO: 45) and second line is the corresponding amino acid sequence (SEQ ID NO: 46). Ubi-hTERT sequence was divided in ten fragments that include immunogenic sequences. These fragments are delineated by symbols (< ... >). Immunogenic sequences are highlighted in grey. Non-immunogenic inter-fragments hTERT sequences, which are not included in pUTScram and pUTInv constructs, are underlined. The 14 amino acids at the C-terminal sequence of the Ubi-hTERT code for the V5 epitope tag. Annotations are given either above or below sequences. (*) Indicates VDD sequence deletion. "☐": Stop codon.

FIG. 28A-28F shows the complete nucleotide sequence of pUTScram insert (3555 bp). Vector features are detailed in FIG. 20 legend. Ubi-hTERT shuffled insert (Scrambled, 1184 AA) starts at position 923 (ATG coding for M amino acid) and ends at position 4474 (ACT coding for T amino acid) of pUTScram. hTERT protein was deleted of the 23 first amino acids (1-23 AA) which were replaced by an ubiquitin polypeptide (76 AA). The catalytic site was inactivated by a 9 bp deletion coding for VDD (* in the sequence) and corresponding to AA 867-869 of wild-type human telomerase (hTERT; patent WO 2007/014740 and hTERT isoform 1 Accession number NM_198253). hTERT sequence was divided into ten immunogenic fragments and reassembled in the following specific order: fragment 7 (210 bp), fragment 2 (201 bp), fragment 6 (312 bp), fragment 4 (117 bp), fragment 9 (576 bp), fragment 3 (120 bp), fragment 1 (258 bp), fragment 8 (477 bp), fragment 10 (516 bp), fragment 5 (303 bp). These 10 fragments are bridged with 6×Gly linker (SEQ ID NO: 99) (G linker; 18 bp). The 14 amino acids at the C-terminal sequence of the Ubi-hTERT shuffled insert code for the V5 epitope tag. First line is the nucleotide sequence (SEQ ID NO:47); second line is the corresponding amino acid sequence (SEQ ID NO:48). Annotations (see also FIG. 20A) are given either above or below sequences. "☐": Stop codon.

FIG. 29A-29F shows the complete nucleotide sequence of pUTInv insert (3555 bp). Vector features are detailed in FIG. 20 legend. Ubi-hTERT shuffled insert (Inverted, 1184 AA) starts at position 923 (ATG coding for M amino acid) and ends at position 4474 (ACT coding for T amino-acid) of pUTInv. hTERT protein was deleted of the 23 first amino acids (1-23 AA) which were replaced by an ubiquitin polypeptide (76 AA). The catalytic site was inactivated by a 9 bp deletion coding for VDD (* in the sequence) and corresponding to AA 867-869 of wild-type human telomerase (hTERT; patent WO 2007/014740; Accession number NM_198253). hTERT sequence was divided into ten immunogenic fragments and reassembled in the following specific order: fragment 10 (516 bp), fragment 9 (576 bp), fragment 8 (477 bp), fragment 7 (210 bp), fragment 6 (312 bp), fragment 5 (303 bp), fragment 4 (117 bp), fragment 3 (120 bp), fragment 2 (201 bp), fragment 1 (258 bp). These 10 fragments were bridged with 6×Gly linker (SEQ ID NO: 99) (G linker; 18 bp). The 14 amino acids at the C-terminal sequence of the Ubi-hTERT shuffled insert code for the V5 epitope tag. First line is the nucleotide sequence (SEQ ID NO:49); second line is the corresponding amino acid sequence (SEQ ID NO:50). Annotations (see also FIG. 20B) are given either above or below sequences. "□": Stop codon.

DETAILED DESCRIPTION OF THE INVENTION

Definitions

The telomerase complex consists of an RNA template and protein components including a reverse transcriptase, designated "Telomerase Reverse Transcriptase" (TERT), which is the major determinant of telomerase activity. Unless otherwise specified, in the present specification, the term "telomerase" refers to TERT, including wild-type human telomerase, or variants thereof. Wild-type human telomerase (or hTERT) is known (GeneBank Accession number NM_198253), and has amino acid sequence SEQ ID NO: 2 (the cDNA is shown as SEQ ID NO: 1)

The "telomerase catalytic activity" refers to the activity of TERT as a telomerase reverse transcriptase. The term "devoid of telomerase catalytic activity" means that the nucleic acid sequence encodes a mutant TERT, which is inactive.

In the present invention, the term "variant" refers to allelic variants, splicing variants, natural or artificial mutants, which are homologous to the hTERT sequence of reference. Two amino acid sequences are "homologous", "substantially homologous" or "substantially similar" when one or more amino acid residue are replaced by a biologically similar residue or when greater than 80% of the amino acids are identical, or greater than about 90%, preferably greater than about 95%, are similar (functionally identical). Preferably, the similar or homologous sequences are identified by alignment using, for example, the GCG (Genetics Computer Group, Program Manual for the GCG Package, Version 7, Madison, Wisconsin) pileup program, or any of the programs known in the art (BLAST, FASTA, etc.).

By "substituted" or "modified" the present invention includes those amino acids that have been altered or modified from naturally occurring amino acids.

Variants include proteins having a sequence that differs from wild-type hTERT protein by one or several mutations (i.e. substitutions, deletions, insertions), still preferably one or several single point substitutions. The variant may comprise conservative substitutions.

The term "conservative substitution" as used herein denotes the replacement of an amino acid residue by another, without altering the overall conformation and function of the peptide, including, but not limited to, replacement of an amino acid with one having similar properties (such as, for example, polarity, hydrogen bonding potential, acidic, basic, shape, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Neutral hydrophilic amino acids, which can be substituted for one another, include asparagine, glutamine, serine and threonine.

The term "isolated polynucleotide" is defined as a polynucleotide removed from the environment in which it naturally occurs. For example, a naturally-occurring DNA molecule present in the genome of a living bacteria or as part of a gene bank is not isolated, but the same molecule separated from the remaining part of the bacterial genome, as a result of, e.g., a cloning event (amplification), is isolated. Typically, an isolated DNA molecule is free from DNA regions (e. g., coding regions) with which it is immediately contiguous at the 5' or 3' end, in the naturally occurring genome. Such isolated polynucleotides may be part of a vector or a composition and still be defined as isolated in that such a vector or composition is not part of the natural environment of such polynucleotide.

The term "immunogenic" means that the composition or construct to which it refers is capable of inducing an immune response upon administration. "Immune response" in a subject refers to the development of an innate and adaptative immune response, including a humoral immune response, a cellular immune response, or a humoral and a cellular immune response to an antigen. A "humoral immune response" refers to one that is mediated by antibodies. A "cellular immune response" is one mediated by T-lymphocytes. It includes the production of cytokines, chemokines and similar molecules produced by activated T-cells, white blood cells, or both. Immune responses can be determined using standard immunoassays and neutralization assays for detection of the humoral immune response, which are known in the art.

In the context of the invention, the immune response preferably encompasses stimulation or proliferation of cytotoxic CD8 T-cells and/or CD4 T-cells and can be determined using immunoassays such as the ELIspot assay, the in vivo cytotoxicity assay or the cytokine secretion binding assay.

As used herein, the term "treatment" or "therapy" or "immunotherapy" refers to any of the alleviation, amelioration and/or elimination, reduction and/or stabilization (e.g., failure to progress to more advanced stages) of a symptom, as well as delay in progression of the tumor or dysplasia, or of a symptom thereof. The term thus includes achievement of an efficient anti tumoral immune response observed in cancer patients.

As used herein, the term "prevention" or "preventing" refers to the alleviation, amelioration and/or elimination, reduction and/or stabilization (e.g., failure to progress to more advanced stages) of a prodrome, i.e. any alteration or early symptom (or set of symptoms) that might indicate the start of a disease before specific symptoms occur.

A cell that "overexpresses telomerase" refers to a cell in a subject, which either expresses telomerase, e.g. upon mutation or infection, especially infection by an oncovirus, whereas it does usually not, under normal conditions, or to a cell in a subject which expresses a higher level of telomerase (e.g. upon mutation or infection), when compared to normal conditions. Preferably the cell that overexpresses telomerase shows an increase of expression of at least 5%, at least 10%, at least 20%, 30%, 40%, 50%, 60%, 70%, 80%, or more.

The "patient" or "subject" is typically a mammal subject, preferably a human subject, of any age, sex, or severity of the condition.

Nucleic Acid Constructs

It is herein provided a nucleic acid construct that is designed to allow vaccination in patients. The nucleic acid construct encodes a telomerase that is devoid of telomerase catalytic activity (which abolishes its immortalizing activity) and devoid of a nucleolar localization signal (which prevents its transfer to the nucleolus).

The nucleic acid construct of the invention is in isolated form.

The nucleic acid may be DNA or RNA, but is preferably DNA, still preferably double stranded DNA.

The nucleic acid construct is not a naturally-occurring genomic nucleic acid, in particular it does not comprise introns.

As a first safety lock, the hTERT sequence is devoid of telomerase catalytic activity. In a preferred embodiment, the sequence that encodes hTERT contains mutations that provide inactivation of the catalytic activity of the hTERT protein. The term "mutation" includes a substitution of one or several amino acids, a deletion of one or several amino acids, and/or an insertion of one or several amino acids. In a particular embodiment, the hTERT protein is devoid of telomerase catalytic activity by deletion of at least one amino acid.

Preferably the sequence shows a deletion, preferably a deletion of amino acids VDD, as shown in FIG. 2A. Preferably the hTERT protein is devoid of telomerase catalytic activity by the sole deletion of amino acids 867-869 (VDD). In another particular embodiment, the hTERT protein is devoid of telomerase catalytic activity by a further deletion of 1 to 10, 11 or 12 amino acids upstream and/or downstream amino acids 867-869 (VDD).

As a second safety lock, the sequence encoding hTERT is further devoid of the nucleolar localization signal. This nucleolar localization signal is correlated with the subcellular localization of hTERT and thus its enzymatic activity. Preferably the hTERT protein is devoid of a nucleolar localization signal by deletion of at least amino acids 1-23, still preferably by deletion of amino acids 1-47.

In addition to the modifications that provide the first and second safety locks, the hTERT protein encoded by the nucleic acid construct of the invention may be a wild-type hTERT sequence, or a variant sequence.

In the sequence listing,
SEQ ID NO: 1 is the cDNA of the wild-type hTERT;
SEQ ID NO: 2 is the corresponding amino acid sequence;
SEQ ID NO: 3 is the cDNA of hTERT used in the INVAC-1 vector;
SEQ ID NO: 4 is the corresponding amino acid sequence;
SEQ ID NO: 5 is the cDNA of hTERT used in the pUTD10Not vector;
SEQ ID NO: 6 is the corresponding amino acid sequence;
SEQ ID NO: 7 is the cDNA of hTERT used in the pUTD10Cog vector;
SEQ ID NO: 8 is the corresponding amino acid sequence;
SEQ ID NO: 9 is the cDNA of hTERT used in the pUTD23Tyn vector;
SEQ ID NO: 10 is the corresponding amino acid sequence.

In a preferred embodiment, the invention employs a nucleic acid that encodes a protein of SEQ ID NO: 4.

Such nucleic acid may comprise sequence SEQ ID NO: 3.

In another embodiment, the nucleic acid construct encodes amino acid sequence SEQ ID NO: 6, 8 or 10, and preferably comprises SEQ ID NO: 5, 7 or 9.

In a preferred embodiment, the nucleic acid may further encode a protein which enhances the addressing of the hTERT protein to the proteasome (increasing class I presentation of the derived peptides). More particularly, the hTERT protein may be fused at the N-terminus with such protein enhancing addressing of the hTERT protein to the proteasome. Said protein may be preferably ubiquitin or it may be any chaperon protein, e.g. calreticulin.

In the sequence listing
SEQ ID NO: 11 is the full-length sequence of INVAC-1 plasmid including the cDNA of Ubi-hTERT encoded by INVAC-1;
SEQ ID NO: 12 is the corresponding amino acid sequence of Ubi-hTERT encoded by INVAC-1;
SEQ ID NO: 13 is the cDNA of the pUTD10Not insert;
SEQ ID NO: 14 is the corresponding amino acid sequence;
SEQ ID NO: 15 is the cDNA of the pUTD10Cog insert;
SEQ ID NO: 16 is the corresponding amino acid sequence;
SEQ ID NO: 17 is the cDNA of the pUTD23Tyn insert;
SEQ ID NO: 18 is the corresponding amino acid sequence.

In a particular embodiment, the nucleic acid construct encodes amino acid sequence SEQ ID NO: 12.

More particularly, the nucleic acid construct may comprise SEQ ID NO: 11, or nucleotides 3488 to 6961 of SEQ ID NO: 11.

In another embodiment, the nucleic acid construct encodes amino acid sequence SEQ ID NO: 14, 16, or 18, and preferably comprises SEQ ID NO: 13, 15, or 17.

In another embodiment, it is provided nucleic acid constructs comprising sequences that derive from human telomerase reverse transcriptase (hTERT), wherein said sequences that derive from hTERT
i) encode all or substantially all epitopes of hTERT, in any order, and
ii) encode a protein that is devoid of telomerase catalytic activity and of a nucleolar localization signal.

The nucleic acid construct of the invention is in isolated form.

The nucleic acid may be DNA or RNA, but is preferably DNA, still preferably double stranded DNA. The nucleic acid construct is not a naturally-occurring genomic nucleic acid, in particular it does not comprise introns.

These constructs are designated "shuffled constructs" or "polyepitope constructs" throughout the present description.

The term "epitope of hTERT" refers to any amino acid fragment of hTERT that is an antigenic determinant, i.e. it is recognized by cells of the immune system and is immunogenic, i.e. it can elicit an immune response. Preferably, it can be recognized, specifically by anti-hTERT T-cells. Several immunogenic epitope sequences of hTERT have been described. See e.g., international patent application WO07014740 for MHC class I restricted hTERT epitopes. Some others are described herein (see FIG. 27, and Table below).

These "shuffled constructs" are capable of eliciting a specific immune response against hTERT, i.e. that cytotoxic T lymphocytes (CTLs) recognize the wild type epitopes.

None of these "shuffled constructs" coincides with the coding sequence of the full length hTERT.

The term "substantially all epitopes" means that the nucleic acid construct encodes a protein that comprises at least 80%, still preferably at least 85%, still preferably at least 90%, or at least 95% of the epitopes of wild-type hTERT.

The polynucleotide units encoding the multiple epitopes can be rearranged in any order, consecutively, i.e., the 3' end of the first polynucleotide unit is directly linked to the 5' end of the second polynucleotide unit (and so on), resulting in a polynucleotide encoding a peptidic sequence exclusively composed of consecutive epitopes. The multiple epitopes can alternatively be separated by a one-amino acid spacer or a peptide spacer, i.e., meaning that the different polynucleotide units are separated by one or several codon(s) encoding respectively one or several amino acid(s). Typically, the immunogenic hTERT fragments can be separated by about four to six Gly amino acids (SEQ ID NO: 100).

The order in which the epitopes are rearranged can be determined by the man skilled in the art, according to the following criteria: some orders may facilitate either the transcription and/or the translation of the polynucleotide, may facilitate the transport of the resulting expressed polyepitope in the endoplasmic reticulum (ER), especially if the tridimensional conformation impacts the properties, and may facilitate the processing of the polyepitope in several epitopes or analogues and avoid the processing of overlapping epitopes.

In a preferred embodiment, all, or substantially all, immunogenic epitopes from amino acid 24 to amino acid 1132 of hTERT are encoded by the nucleic acid construct, although in any order.

The Table below shows immunogenic sequences that can be rearranged in a "Shuffle" construct:

| Immunogenic sequence | SEQ ID NO: |
|---|---|
| R R L G P Q G W R L V Q R G D P A A F R A L V A Q C L V C V P W D A R | 61 |
| V S C L K E L V A R V L Q R L | 62 |
| V L A F G F A L L | 63 |
| R S Y L P N T V T D A L R G S G A W G L L L R R V G D D V L V H L L A R C A L F V L V A P S C A Y Q V C G P P L Y | 64 |
| R E A G V P L G L | 65 |
| R R R G G S A S R S L P L P K R | 66 |
| G R T R G P S D R G F C V V S P A R P A E E A T S L E G A | 67 |
| Y A E T K H F L Y S S G D K E Q L R P S F L L S S L R P S L | 68 |
| A R R L V E T I F L G S R P | 69 |
| R R L P R L P Q R Y W Q M R P L F L E L L G N H A Q C P | 70 |
| V L L K T H C P L | 71 |
| R E K P Q G S V A | 72 |
| E E D T D P R R L V Q L L R | 73 |
| V Y G F V R A C L R R L V P P G L W G S | 74 |
| R R F L R N T K K | 75 |
| H A K L S L Q E L | 76 |
| S V R G C A W L R | 77 |
| E H R L R E E I L A K F L H W L M S V Y V V E L L R S F | 78 |
| E T T F Q K N R L | 79 |
| K S V W S K L Q S I G I R Q H | 80 |
| A E V R Q H R E A R P A L L T S R L R F I P K | 81 |
| D Y V V G A R T F R R E K R A E R L T S R V K A L | 82 |
| Y E R A R R P G L L G A S V L G L | 83 |
| H R A W R T F V L R V R A Q D P P P E L Y F V K V D V T G A Y D T I P Q D R L T E V I A S I I K P Q | 84 |
| T Y C V R R Y A V V Q K A A H | 85 |
| T L T D L Q P Y M R Q F V A H L | 86 |

| Immunogenic sequence | SEQ ID NO: |
|---|---|
| S P L R D A V V I E Q S S S L N E A S S G L F D V F L R | 87 |
| A V R I R G K S Y | 88 |
| I L S T L L C S L C Y G D M E N K L | 89 |
| I R R D G L L L R L F L L V T P H L T H A K T F L R T L V R G V P E Y G C V V N L R K T V V N F | 90 |
| D E A L G G T A F V Q M P A H G L F P W C G L L L D T R T L E V Q S D Y S S Y | 91 |
| A G R N M R R K L F G V L R L K C H S L F L D L Q V N S L Q T | 92 |
| I Y K I L L L Q A Y R F H A C V L Q L P F H Q Q V | 93 |
| N P T F F L R V I S D T A S L C Y S I L K A K N A G M S | 94 |
| G A K G A A G P L | 95 |
| W L C H Q A F L L K L T R H R V T Y V P L L G S L R T A Q T Q L S R K L P G T T L | 96 |
| L E A A A N P A L P S D F K T I L | 97 |

Accordingly, the invention provides a polyepitopic nucleic acid construct, comprising all or substantially all of the immunogenic sequences shown as SEQ ID NO: 61 to 97, in any order. The sequence is devoid of telomerase catalytic activity. In a preferred embodiment, the fragment that carries the hTERT catalytic activity contains mutations that provide inactivation of the catalytic activity. The term "mutation" includes a substitution of one or several amino acids, a deletion of one or several amino acids, and/or an insertion of one or several amino acids. In a particular embodiment, the protein is devoid of telomerase catalytic activity by deletion of at least one amino acid.

Preferably the sequence shows a deletion, preferably a deletion of amino acids VDD, as shown in FIG. 22. Preferably the hTERT protein is devoid of telomerase catalytic activity by the sole deletion of amino acids 867-869 (VDD). In another particular embodiment, the protein is devoid of telomerase catalytic activity by a further deletion of 1 to 10, 11 or 12 amino acids upstream and/or downstream amino acids 867-869 (VDD) of hTERT.

The sequence is further devoid of a nucleolar localization signal. This nucleolar localization signal is correlated with the subcellular localization of hTERT and thus its enzymatic activity. Preferably the protein is devoid of a nucleolar localization signal by deletion of at least amino acids 1-23, still preferably by deletion of amino acids 1-47 of hTERT.

In a preferred embodiment, the nucleic acid may further encode a protein which enhances the addressing of the protein to the proteasome (increasing class I presentation of the derived peptides). More particularly, the protein may be fused at the N-terminus with such protein enhancing addressing of the protein to the proteasome. Said protein may be preferably ubiquitin or it may be any chaperon protein, e.g. calreticulin.

ΔhTERT refers to hTERT deleted of VDD 867-869 amino acids.

A particular nucleic acid construct comprises, in any order, fragment 1 encoding Leu24 to Gly109 of ΔhTERT (SEQ ID NO:51), fragment 2 encoding Phe115 to Ala181 of ΔhTERT (SEQ ID NO:52), fragment 3 encoding Trp203 to Ala242 of ΔhTERT (SEQ ID NO:53), fragment 4 encoding Ser255 to Arg293 of ΔhTERT (SEQ ID NO:54), fragment 5 encoding Pro320 to Thr420 of ΔhTERT (SEQ ID NO:55), fragment 6 encoding Ala423 to Val526 of ΔhTERT (SEQ ID NO:56), fragment 7 encoding Cys528 to Gln597 of ΔhTERT (SEQ ID NO:57), fragment 8 encoding Arg599 to Lys757 of ΔhTERT (SEQ ID NO:58), fragment 9 encoding Lys760 to Ile951 of ΔhTERT (SEQ ID NO:59), fragment 10 encoding Asn958 to Asp1129 of ΔhTERT (SEQ ID NO:60).

A preferred construct encodes SEQ ID NO:48 (also herein called "Scrambled"), also shown on FIG. 28.

Another preferred construct encodes SEQ ID NO:50 (also herein called "Inverted"), also shown on FIG. 29.

Genetic Constructs, Immunogenic Compositions and Administration

Preferably, the nucleic acid is a genetic construct comprising a polynucleotide sequence as defined herein, and regulatory sequences (such as a suitable promoter(s), enhancer(s), terminator(s), etc.) allowing the expression (e.g. transcription and translation) of the protein product in the host cell or host organism.

The genetic constructs of the invention may be DNA or RNA, and are preferably double-stranded DNA. The genetic constructs of the invention may also be in a form suitable for transformation of the intended host cell or host organism, in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

In a preferred but non-limiting aspect, a genetic construct of the invention comprises i) at least one nucleic acid of the invention; operably connected to ii) one or more regulatory elements, such as a promoter and optionally a suitable terminator; and optionally also iii) one or more further elements of genetic constructs such as 3'- or 5'-UTR sequences, leader sequences, selection markers, expression markers/reporter genes, and/or elements that may facilitate or increase (the efficiency of) transformation or integration.

In a particular embodiment, the genetic construct can be prepared by digesting the nucleic acid polymer with a restriction endonuclease and cloning into a plasmid containing a promoter such as the SV40 promoter, the cytomegalovirus (CMV) promoter or the Rous sarcoma virus (RSV) promoter. In a preferred embodiment, the TERT nucleic acid sequences are inserted into a NTC8685-eRNA41H expression plasmid (see FIG. 1A).

Other vectors include retroviral vectors, lentivirus vectors, adenovirus vectors, vaccinia virus vectors, pox virus vectors, measles virus vectors and adenovirus-associated vectors.

Compositions can be prepared, comprising said nucleic acid or vector. The compositions are immunogenic. They can comprise a carrier or excipients that are suitable for administration in humans or mammals (i.e. non-toxic, and, if necessary, sterile). Such excipients include liquid, semisolid, or solid diluents that serve as pharmaceutical vehicles, isotonic agents, stabilizers, or any adjuvant. Diluents can include water, saline, dextrose, ethanol, glycerol, and the like. Isotonic agents can include sodium chloride, dextrose, mannitol, sorbitol, and lactose, among others. Stabilizers include albumin, among others. Any adjuvant known in the art may be used in the vaccine composition, including oil-based adjuvants such as Freund's Complete Adjuvant and Freund's Incomplete Adjuvant, mycolate-based adjuvants, bacterial lipopolysaccharide (LPS), peptidoglycans, proteoglycans, aluminum hydroxide, saponin, DEAE-dextran, neutral oils (such as miglyol), vegetable oils (such as *arachis* oil), Pluronic® polyols.

The nucleic acid or composition can be administered directly or they can be packaged in liposomes or coated onto colloidal gold particles prior to administration. Techniques for packaging DNA vaccines into liposomes are known in the art, for example from Murray, 1991. Similarly, techniques for coating naked DNA onto gold particles are taught in Yang, 1992, and techniques for expression of proteins using viral vectors are found in Adolph, 1996.

For genetic immunization, the vaccine compositions are preferably administered intradermally, subcutaneously, intramuscularly, into the tumors or in any types of lymphoid organs by injection or by gas driven particle bombardment, and are delivered in an amount effective to stimulate an immune response in the host organism. In a preferred embodiment of the present invention, administration comprises an electroporation step, also designated herein by the term "electrotransfer", in addition to the injection step (as described in Mir 2008, Sardesai and Weiner 2011).

The compositions may also be administered ex vivo to lymphoid or myeloid cells using liposomal transfection, particle bombardment or viral transduction (including co-cultivation techniques). The treated cells are then reintroduced back into the subject to be immunized.

While it will be understood that the amount of material needed will depend on the immunogenicity of each individual construct and cannot be predicted a priori, the process of determining the appropriate dosage for any given construct is straightforward. Specifically, a series of dosages of increasing size, starting at about 5 to 30 µg, or preferably 20-25 µg, up to about 500 µg to about 5 mg, preferably up to 500-1500 µg, 500-1200 µg, or 500-1000 µg, for instance, is administered to the corresponding species and the resulting immune response is observed, for example by detecting the cellular immune response by an IFNγ Elispot assay (as described in the experimental section), by detecting CTL responses using an in vivo lysis assay or a chromium release assay or detecting Th (helper T-cell) response using a cytokine release assay.

In a preferred embodiment, the vaccination regimen comprises one to three injections, preferably repeated three or four weeks later.

In a particular embodiment, the vaccination schedule can be composed of one or two injections followed three or four weeks later by at least one cycle of three to five injections.

In another embodiment, a primer dose consists of one to three injections, followed by at least a booster dose every year, or every two or years for instance.

These are examples only, and any other vaccination regimen is herein encompassed.

Prevention or Treatment of Tumors

The nucleic acid or immunogenic composition as described above is useful in a method for preventing or treating a tumor in a patient.

A method for preventing or treating a tumor in a patient is described, which method comprises administering an effective amount of said nucleic acid or immunogenic composition in a patient in need thereof. Said nucleic acid or immunogenic composition is administered in an amount sufficient to induce an immune response in the patient.

The tumor may be any undesired proliferation of cells, in particular a benign tumor or a malignant tumor, especially a cancer.

The cancer may be at any stage of development, including the metastatic stage. The cancer may be chronic or non-chronic (acute).

In a particular embodiment, tumor is a solid cancer or a carcinoma. Examples include melanoma, brain tumor such as glioblastoma, neuroblastoma and astrocytoma and carcinomas of the bladder, breast, cervix, colon, lung, especially non-small cell lung cancer (NSCLC), pancreas, prostate, head and neck cancer, or stomach cancer.

In another embodiment, the tumor may be a liquid tumor, e.g. a hematopoietic tumor or leukemia, such as a chronic or acute lymphocytic leukemia, chronic or acute myeloid leukemia, lymphoma including Hodgkin's disease, multiple myeloma, malignant myeloma.

In a particular embodiment, the treatment according to the invention may be combined with conventional therapy, including chemotherapy, radiotherapy or surgery. Combinations with adjuvant immunomodulating molecules such as GM-CSF or a cytokine like IL-2 or IL-12, could also be useful.

Example I

Abbreviations

AA: Amino Acid, APC: Antigen Presenting Cell, bp: Base-pair, CTL: Cytotoxic T-Lymphocyte, CMV: Cytomegalovirus, DNA: Deoxyribonucleic Acid, EP: Electroporation, HTLV-1: Human T-lymphotropic virus Type I, hTERT: human Telomerase Reverse Transcriptase, ID: Intradermal, IM: Intramuscular, IV: Intravenous, LTRs: Long Terminal Repeats, NoLS: Nucleolar Localization Sequence, PBMC: Peripheral Blood Mononuclear Cells, RIG-I: Retinoic acid-Inducible Gene 1, RNA: Ribonucleic Acid, RT: Room Temperature, RTA: Relative Telomerase Activity, SC: Subcutanous, TRAP: Telomeric Repeat Amplification Protocol, TERT: Telomerase Reverse Transcriptase, Ubi: Ubiquitin, VDD: Valine-Aspartic Acid-Aspartic Acid Materials and Methods Plasmid DNA Vectors
INVAC-1

INVAC-1 is a 7120 bp plasmid expression vector encoding a human ubiquitin-telomerase fusion construct of 1158 AA (Ubi-hTERT) corresponding to a protein of approximately 127.4 kDa (FIGS. 1A and 16). As INVAC-1 is intended to be used in human, the telomerase reverse transcriptase enzymatic activity has been inactivated for safety reasons. Indeed, the human TERT sequence encoded by INVAC-1 was modified in the catalytic site by a 9 bp deletion coding for three amino acid Valine-Aspartic Acid-Aspartic Acid (867-869 AA), abbreviated to VDD in the one letter code (FIG. 2A). In addition, the 47 AA of the N-terminal part of the protein, which include the nucleolar localization sequence (NoLS) required for telomerase subcellular localization (Yang, 2002), was replaced by the ubiquitin (Ubi) coding sequence (1-76 AA).

The Ubi-hTERT transgene is inserted into a NTC validated vector backbone (Nature Technology Corporation, Lincoln, Nebraska) combining carefully designed synthetic genes for high yield bacterial production, increased expression in mammalian cells and consequently effective immune responses.

Target gene expression is driven from an optimized chimeric promoter-intron (SV40-CMV-HTLV-1 R synthetic intron) composed of a CMV promoter and start of exon 1, a HTLV-I R sequence which contains the 5' splice acceptor site, a synthetic 3' acceptor site based on the rabbit β-globin intron, an exon 2 splicing enhancer comprising a serine-arginine rich (SR) protein binding site to improve RNA export (Lavigueur et al., 1993) and an exon 2 Kozak sequence upstream of the start codon for the gene of interest. DNA between the stop codon and the terminator is limited to reduce the possibility of cryptic peptide expression or unintended microRNA-mediated expression alteration.

To improve cellular immune responses the vector encodes an RNA polymerase III transcribed double stranded RNA agonist of the retinoic acid inducible gene-1 (RIG-I) innate immune response activator.

There is no known virulence feature associated with this vector. The plasmid does not replicate in eukaryotic target cells. The vector backbone itself does not contain protein coding sequences and no alternative protein encoding open reading frames have been identified in the vector backbone, hence there is no antibiotic resistance gene. Plasmid selection is performed by the mean of an antibiotic-free sucrose selectable marker (RNA-OUT).

Gene Synthesis and Cloning

The Ubi-hTERT gene was de novo synthesized through an overlapping 40-mer oligonucleotides assembly process (GeneCust, Luxembourg). Several conservative base changes were made to eliminate restriction sites and attenuate GC rich sequences. The insert was cloned into the expression vector pcDNA3.1(+) (Invitrogen, Carlsbad, USA) using HindIII-XbaI cloning sites and verified by sequencing.

Subcloning of the Ubi-hTERT Insert into the Cloning Vector NTC8685-eRNA41H-HindIII-XbaI The ubiquitin-telomerase insert was cloned into the NTC8685-eRNA41H-HindIII-XbaI expression vector designed by NTC. However, their best appropriate vector NTC8685-eRNA41H (ref. NTC-DV8685-41HLV) did not have restriction sites compatible with the Ubi-hTERT insert. Accordingly, this vector was digested with SalI and BglII and ligated to a synthetic double-stranded oligonucleotide which includes appropriate restriction sites for subcloning Ubi-hTERT, i.e., HindIII-XbaI:

(SEQ ID NO: 23)
SalI HindIII SmaI  XbaI BglII
GTCGACAAGCTTCCCGGGTCTAGAAGATCT

This new vector (NTC8685-eRNA41H-HindIII-XbaI) which now includes the above polylinker was verified by restriction digestion and sequencing using pVAC5' (GCTTTTCTGCCAGGTGCTGA SEQ ID NO: 24) and pVAC3' (GCCAGAAGTCAGATGCTCAA SEQ ID NO: 25) primers annealing to sequences upstream and downstream the polylinker site respectively.

The custom-made NTC8685-eRNA41H-HindIII-XbaI vector was digested with HindIII and XbaI and the 3631 bp vector was gel purified from the 12 bp linker. The pcDNA3.1-Ubi-hTERT construct was digested with HindIII and XbaI and the 3489 bp Ubi-hTERT insert transferred by ligating into NTC8685-eRNA41H-HindIII-XbaI acceptor to create NTC8685-eRNA41H-HindIII-XbaI-Ubi-hTERT (INVAC-1) (FIG. 1A). The ligation product was transformed into antibiotic free selection host NTC4862 (DH5α att$_\lambda$:: P$_{5/6\ 6/6}$-RNA-IN-SacB, catR) (ref. NTC-DVU-CC1). The resultant vector was verified by restriction digestion (FIG. 1B): BglII/NotI=3496, 3262, 220, 142 bp bands; NcoI=4084, 3036 bp bands; HindIII/XbaI=3631, 3489 bp bands, and the termini of the Ubi-hTERT insert verified by DNA sequencing with pVAC5' and pVAC3' primers. No nucleotide alteration was identified.

Plasmid Production

INVAC-1 was first produced by NTC under research grade quality conditions. Plasmid DNA was transformed into NTC4862 E. coli cells using electroporation. Cells were plated and propagated on 6% sucrose media as recommended by the manufacturer (NTC Instruction Manual, June 2011). After extraction, plasmid DNA was resuspended in endotoxin-free 1×PBS at a final concentration of 2 mg/ml.

INVAC-1 was subsequently manufactured by Eurogentec (Belgium) for GLP and GMP scale-up, and GMP production. Full-length sequencing of INVAC-1 plasmid was carried out at this point.

INVAC-1 Derivatives

All INVAC-1 derivative constructs are double stranded DNA plasmids of approximately 8.9 kb encoding human ubiquitin-telomerase fusion proteins which are enzymatically inactive (FIG. 2A). The Ubi-hTERT transgenes were inserted into Invitrogen pcDNA3.1(+) vector (5.4 kb) derived from pcDNA3.0 which was designed for high-level of stable and transient expressions in mammalian cells. This vector contains the human cytomegalovirus immediate-early (CMV-IE) promoter and the bovine growth hormone polyadenylation (BHG-polyA) signal as termination sequence.

pUTD10Not (Abbreviated as Δ10Not)

The hTERT coding sequence is located between the nucleotide 923 and 4492 bp of the pcDNA3.1 plasmid backbone. pUTD10Not encodes an 1189 AA human ubiquitin-telomerase fusion protein (Δ10Not) corresponding to approximately 130.8 kDa of molecular weight (FIG. 2A). The hTERT was deleted of the 23 first amino acids (1-23 AA) which were replaced by a ubiquitin polypeptide (76 AA). In the domain of the catalytic site, an additional deletion was introduced between amino acids 912-913 (* mark; FIG. 17), corresponding to AA 860-869 (DG- LLLRLVDD_SEQ ID NO: 21) of wild-type hTERT (Accession number NM_198253). This 10 amino acids deletion includes the 3 AA deletion (ΔVDD) resulting in inactivation of hTERT enzymatic activity and the deletion of additional 7 AA upstream the VDD sequence. Fourteen amino acids at the C-terminal sequence of the Ubi-hTERT code for the V5 epitope tag (FIG. 2A).

pUTD10Cog (Abbreviated as Δ10Cog)

The hTERT coding sequence is located between the nucleotide 923 and 4492 bp of the pcDNA3.1 plasmid backbone. pUTD10Cog encodes an 1189 AA human ubiquitin-telomerase fusion protein (Δ10Cog) corresponding to approximately 130.8 kDa of molecular weight (FIG. 2A). The hTERT was deleted of the 23 first amino acids (1-23 AA) which were replaced by an ubiquitin polypeptide (76 AA). In the domain of the catalytic site, an additional deletion was introduced between amino acids 919-920 (* mark; FIG. 18), corresponding to AA 867-876 (VDDFLL-VTPH_SEQ ID NO: 22) of wild-type hTERT (Accession number NM_198253). This 10 amino acids deletion includes the 3 AA deletion (ΔVDD) resulting in inactivation of hTERT enzymatic activity and the deletion of additional 7 AA downstream the VDD sequence. Fourteen amino acids at the C-terminal sequence of the Ubi-hTERT code for the V5 epitope tag (FIG. 2A).

pUTD23Tyn (Abbreviated as Δ23)

The hTERT coding sequence is located between the nucleotide 923 and 4453 bp of the pcDNA3.1 plasmid backbone. pUTD23Tyn encodes an 1176 AA human ubiquitin-telomerase fusion protein (Δ23) corresponding to approximately 129.4 kDa of molecular weight (FIG. 2A). The hTERT was deleted of the 23 first amino acids (1-23 AA) which were replaced by an ubiquitin polypeptide (76 AA). In the domain of the catalytic site, an additional deletion was introduced between amino acids 909-910 (* mark; FIG. 19), corresponding to AA 857-879 (IRRDG-LLLRLVDDFLLVTPHLTH_SEQ ID NO: 26) of wild-type hTERT (Accession number NM_198253). This 23 amino acids deletion includes the 3 AA deletion (ΔVDD) resulting in inactivation of hTERT enzymatic activity and the deletion of additional 10 AA upstream and 10 AA downstream the VDD sequence. Fourteen amino acids at the C-terminal sequence of the Ubi-hTERT code for the V5 epitope tag (FIG. 2A).

Genes Synthesis and Cloning

The genes were de novo synthesized as ubiquitin-telomerase fusion constructs through an overlapping 40-mer oligonucleotides assembly process (GeneCust, Luxembourg). Gene synthesis included unique flanking restriction sites HindIII/XbaI to allow subcloning of the gene into desired expression system. The synthesized genes were cloned between HindIII and XbaI restriction sites of the pcDNA3.1 (+) expression vector (Invitrogen, Carlsbad, USA). The sequences of the plasmids were verified by sequencing using PEGFP-N5' CGGTGGGAGGTCTATATAAG (SEQ ID NO: 27) and BGH CAGGGTCAAGGAAGGCAC (SEQ ID NO: 28) primers.

Plasmids Production

All INVAC-1 derivatives were transformed and produced in E. coli 5-alpha cells (fhuA2Δ(argF-lacZ)U169 phoA glnV44 Φ80 Δ(lacZ)M15 gyrA96 recA1 relA1 endA1 thi-1 hsdR17) (Lucigen Corporation, Middleton, USA, ref. 60602-2) by RD Biotech (Besançon, France). Concentrated endotoxin-free gigaprep plasmid stocks (2 mg/mL) resuspended in 1× sterile PBS were prepared. The vectors were verified by restriction mapping (HindIII-XbaI; FIG. 2B).

pTRIP-CMV-hTERT pTRIP-CMV-hTERT encodes the 1132 AA (corresponding to approximately 124.5 kDa) wild-type human TERT (hTERT) protein with catalytic activity. This plasmid was used as a positive control for in vitro assays. The construct was first described in patent application WO 2007/014740. The pTRIP-CMV-hTERT was constructed by first subcloning an EcoRI-SalI hTERT insert derived from the pBABE-hygro-hTERT plasmid (kindly provided by Dr. Robert Weinberg) into the pSP73 vector (Promega Life Science, Wisconsin, USA) to generate the pSPhTERT construct. A BglII-SalI fragment was then inserted into the pTRIP-CMV retroviral-derived vector cut with BamHI and XhoI to create pTRIP-CMV-hTERT. The hTERT expression is driven by the human cytomegalovirus (CMV) promoter.

The pTRIP-CMV-hTERT plasmid was transformed and produced in E. coli 5-alpha cells (fhuA2Δ(argF-lacZ)U169 phoA glnV44 Φ80 Δ(lacZ)M15 gyrA96 recA1 relA1 endA1 thi-1 hsdR17) (Lucigen Corporation, Middleton, USA, ref 60602-2) by RD Biotech (Besancon, France).

A 2 mg/ml concentrated endotoxin-free gigaprep plasmid stock resuspended in 1× sterile PBS was prepared. The produced vector was verified by restriction enzyme digestion (EcoRI+BamHI=10286+2720+886 bp bands).

pNTC-hTERT pNTC-hTERT encodes the 1132 AA wild-type human TERT (hTERT) protein with catalytic activity (SEQ. ID NO: 2). This plasmid was used to investigate the breadth of hTERT specific T-cell responses in vivo in comparison with INVAC-1 construct.

The wild-type hTERT insert was synthesized de novo with HindIII-XbaI cloning sites through an overlapping oligonucleotides assembly process (GenScript, USA). The synthetic construct (3417 bp) was cloned in pUC57 (2710 bp) by HindIII and XbaI sites and then verified by sequencing using M13/pUC (−20) and M13/pUC (−26) primers and restriction mapping (HindIII/XbaI). Consequently, the hTERT insert was subcloned by NTC into the cloning vector NTC8685-eRNA41H-HindIII-XbaI as described above (see INVAC-1 construct). The resultant vector pNTC-hTERT was verified by restriction digestion (XmaI=4375, 2041, 506, 120 bp bands; BamHI/XmnI=6887, 155 bp bands; HindIII/XbaI=3631, 3411 bp bands) and DNA sequencing using pVAC5', pVAC3' and hTERTseq (5' GGCAAGTCC-TACGTCCAGTG 3', SEQ ID NO: 44) primers.

pNTC-hTERT plasmid was produced by NTC under research grade quality conditions as described before for INVAC-1 plasmid.

pNTC-hTERT-ΔVDD pNTC-hTERT-ΔVDD encodes the 1129 AA human TERT (hTERT) sequence modified in the catalytic site by a 9 bp deletion coding for Valine-Aspartic Acid-Aspartic Acid (ΔVDD; 867-869 AA). This plasmid was used to investigate the breadth of hTERT specific T-cell responses in vivo in comparison with INVAC-1 construct.

hTERT-ΔVDD DNA sequence is identical to the wild-type hTERT except for a 3 amino acid deletion (ΔVDD). A 167 bp DNA insert including the 152 bp BamHI/XmnI fragment of hTERT, but with the ΔVDD deletion and additional EcoRV restriction sites was synthesized de novo by GenScript. This synthetic fragment was cloned in pUC57 vector (2710 bp) using EcoRV cloning sites. The synthesized gene was verified by sequencing using M13/pUC (−20) and M13/pUC (−26) primers and restriction digests (BamHI/NdeI). This vector was then digested using BamHI/XmnI sites and the ΔVDD-BamHI/XmnI fragment was cloned in the BamHI/XmnI predigested hTERT region of the pNTC-hTERT vector (6887, 155 bp bands). The resultant vector pNTC-hTERT-ΔVDD was verified by restriction digestion (XmaI=4375, 2032, 506, 120 bp bands; BamHI/XmnI=6887, 146 bp bands; HindIII/XbaI=3631, 3402 bp bands) and DNA sequencing using pVAC5', pVAC3' and hTERTseq (5' GGCAAGTCCTACGTCCAGTG 3' SEQ ID NO: 44) primers.

pNTC-hTERT-ΔVDD was produced by NTC as described before for INVAC-1 and pNTC-hTERT constructs.

Cell Cultures and Transient Transfections for Western Blot and TRAP Assays

CrFK (Crandell Rees feline kidney), HEK293T (Human embryonic kidney) and HeLa (Henrietta Lacks'—Human cervical adenocarcinoma) cell lines were cultured in Dulbecco's modified Eagle's medium (DMEM) supplemented with 10% heat-inactivated fetal calf serum (PAA, Velizy-Villacoublay, France) and 1% penicillin/streptomycin (Life Technologies, Saint-Aubin, France).

QT6 (Quail Japanese fibrosarcoma) cell line was cultured in Ham's F10 (Eurobio, Courtaboeuf, France) supplemented with 10% heat-inactivated fetal calf serum (PAA), 1% penicillin/streptomycin (Life Technologies), 1% chicken serum (PAA), 10 mM L-glutamine (Sigma-Aldrich, St. Louis, USA), 0.5% tryptose broth (Sigma-Aldrich, St. Louis, USA).

Cells were grown as monolayers in 75 cm$^2$ flasks at 37° C. in a humidified atmosphere containing 5% $CO_2$. The cells were grown until 70-80% confluence on the day of transfection. For western blot assays, 5×10$^5$ cells were seeded in six-well tissue culture plates and incubated for 24 h. For TRAP assays, 7×10$^5$ cells were seeded in six-well tissue culture plates and incubated for 24 h. INVAC-1 and INVAC-1 derivative constructs were transfected into target cells using jetPrime cationic polymer transfection reagent according to manufacturer's instructions (Polyplus-transfection Inc., France). Cells transfected with pTRIP-CMV-hTERT plasmid was used as positive control and non-transfected cells or pNTC8685-eRNA41H empty plasmid transfected cells as negative control. Transfection mediums were removed 4 hours later and replaced by 2 mL of DMEM culture medium. After appropriate time of transfection—18-96 hours for western blot assays and 24 hours for TRAP assays, cells were harvested and analyzed for telomerase expression and activity.

Western Blot

For western blot analyses, transfected CrFK and HEK293T cells were lysed on ice for 10-20 minutes in RIPA buffer (Sigma-Aldrich, St. Louis, USA) supplemented with a protease inhibitor cocktail (Roche Diagnostic, Indianapolis, USA). Lysates were cleared by centrifugation at 14,000 rpm for 15 minutes at 4° C. The supernatants were harvested and the protein concentration was measured using the Bradford colorimetric assay. Protein samples were denatured 5 minutes at 95° C., separated on Nu-PAGE® Novex 4-12% Bis-Tris gels (Invitrogen, Carlsbad, USA) and electroblotted onto PVDF membranes (iBlot® transfer stack, Invitrogen, Carlsbad, USA) using the iBlot® device (Invitrogen, Carlsbad, USA). Novex® Sharp Prestained Protein Ladder (Invitrogen, Carlsbad, USA) were used to determine molecular weight. The membranes were cut approximately at 60 kDa and blocked with 1×PBS, 0.05% Tween® 20, 3% milk. The upper part of the membrane was probed with an anti-hTERT rabbit monoclonal antibody (Abcam, Cambridge, UK) diluted at 1/2000 in blocking buffer or an anti-V5 mouse monoclonal antibody (Invitrogen, Carlsbad, USA) diluted at 1/5000. The lower part of the membrane was probed with an anti-β-actin mouse monoclonal antibody (Sigma Aldrich SARL, Saint-Quentin Fallavier, France) diluted at 1/5000.

Finally, the relevant proteins were visualized by staining with the appropriate secondary horseradish peroxidase (HRP) conjugated antibody for 1 h at room temperature—anti-mouse HRP linked antibody (GE Healthcare, Vélizy, France) diluted at 1/5000 or anti-rabbit HRP linked antibody (Cell Signaling, Danvers, USA) diluted at 1/1000 in blocking buffer. The immunoblot signals were detected by enhanced chemiluminescence assay using ECL HRP chemiluminescent substrate Reagent Kit. The films and the corresponding cassette were purchased from GE Healthcare (Buckinghamshire, UK).

TRAP Assay

Telomerase activity was assessed through Telomeric Repeat Amplification Protocol (TRAP) approach (Kim et al. 1994) using the TeloTAGGG Telomerase PCR ELISAPLUS kit (Roche Diagnostic GmbH Mannheim, Germany) according to the manufacturer's instructions. Twenty-four hours after transfection as described above, CrFK cells were harvested. Cells were washed with 1×PBS, followed by centrifugation at 1,600 rpm for 5 minutes at 4° C. Cells were resuspended in 0.2 ml of lysis buffer and incubated on ice for 30 minutes. Lysates were cleared by centrifugation at 14,000 rpm, 20 min at 4-8° C. The supernatants were harvested and the protein concentration was measured using the Bradford colorimetric assay. Supernatants were used for telomerase-mediated elongation of telomeric sequences and products were amplified by PCR using biotinylated primers. Each cellular supernatant was previously split into two aliquots before performing the assay: one was used to prepare a negative control by heat inactivation of telomerase for 10 min. at 85° C., the other one was used to evaluate the telomerase-mediated elongation of telomeric sequences. Furthermore, a 216 bp length internal standard, present in the reaction mixture, was simultaneously amplified to exclude false negative results due to Taq DNA-polymerase inhibitors that may be present in lysates. Lysis buffer was used as a negative control. All reaction mixtures were incubated 20 minutes at 25° C. and then 5 minutes at 94° C. Telomerase products were amplified in 30 PCR cycles: 94° C. for 30 seconds, 50° C. for 30 seconds, 72° C. for 90 seconds ended by 1 cycle at 72° C. for 10 minutes and held at 4° C. 2.5 μL of PCR amplification products were incubated for 10 minutes at RT with denaturation reagent provided in the kit. After incubation, 100 μL of hybridization buffer was added per well. Each solution was mixed and 100 μL was transferred to streptavidin pre-coated microplate and incubated for 2 hours at 37° C. under gentle agitation (300 rpm). Then, the wells were washed with a washing buffer and incubated with an anti-digoxigenin horseradish peroxidase (HRP) linked antibody (1/50) for 30 minutes at RT. HRP substrate (TMB) was then added for 15 minutes at RT for colorimetric measurement. The reaction was stopped with ELISA stop reagent. The level of telomerase activity in each sample was determined by comparing the signal from the sample to the signal obtained using a known amount of positive control template (template DNA with the same sequence as a telomerase product with eight telomeric repeats). Absorbance values were reported by $A_{450}$ reading against blank (reference wavelength $A_{690}$ nm). The relative telomerase activity (RTA) was obtained using the following formula:

$$RTA = [(A_S - A_{S0})]/A_{S,IS}]/[(A_{TS8} - A_{TS8,0})/A_{TS8,IS}] \times 100$$

where:
$A_S$ is the absorbance of sample,
$A_{S0}$, absorbance of heat-treated sample,
$A_{S,IS}$, absorbance of internal standard (IS) of the sample, $A_{TS8}$, absorbance of control template (TS8),
$A_{TS8,0}$, absorbance of lysis buffer,
$A_{TS8,IS}$, the absorbance of internal standard (IS) of the control template (TS8).

Immunofluorescence

CrFK, HEK293T, HeLa and QT6 cells were seeded on 8-well Lab-Tek® chamber slides (Sigma-Aldrich, St. Louis, USA) at $2 \times 10^4$ cells/well in 200 µL of culture medium and incubated overnight at 37° C., 5% $CO_2$. The next day, culture medium was discarded and 200 µL of fresh medium were added. Ten µL of a mix solution containing 0.2 µg of INVAC-1, pTRIP-CMV-hTERT or control empty plasmid pNTC8685-eRNA41H and 0.5 µL of Fugene HD (Promega France, Charbonnières-les-bains, France) in OptiMEM (Life Technologies, Saint-Aubin, France) were added to the corresponding chamber. $2 \times 10^4$ untreated cells per chamber were used as a negative control. Chamber slides were incubated for 24 and 48 hours at 37° C., 5% $CO_2$. Transfected cells were carefully washed with 1×PBS and 200 µL 2% PFA were added to each well for 10 minutes at 4° C. in order to fix and permeabilize the cells. Then, wells were washed twice with 1×PBS 0.05% Tween 20 and incubated 30 minutes at room temperature with 200 µl of blocking solution (0.5% Triton X100; Sigma-Aldrich, 3% BSA; Sigma-Aldrich, 10% Goat Serum; Invitrogen, in 1×PBS 0.05% Tween®20). Primary anti-hTERT rabbit monoclonal antibody (Abcam, Cambridge, UK) diluted at 1/100 in blocking buffer was applied on the cells for 1.5 hour at room temperature under agitation. After three washes in 1×PBS 0.05% Tween 20, a secondary goat anti-rabbit-Alexa Fluor 488® antibody (Life Technologies, Saint-Aubin, France) diluted in blocking solution (1/500) was applied for 45 minutes at room temperature under agitation. Wells were washed three times with 1×PBS 0.05% Tween®20 and mounted in VECTASHIELD® mounting medium containing DAPI (Vector laboratories, Cambridgeshire, UK). Cover slips were analyzed under fluorescence microscope (Axio observer Z1, Carl Zeiss MicroImaging GmbH, Jena, Germany) equipped with an image processing and analysis system (Axiovision, Carl Zeiss MicroImaging GmbH, Jena, Germany).

Mice

Female C57BL/6 mice (6-8 week old) were purchased from Janvier laboratories (Saint-Berthevin, France).

Two transgenic mouse strains were used: HLA-B*0702 and HLA-A2/DR1.

The HLA-B*0702 transgenic mice express the human HLA-B*0702 α1-α2 domains of the molecule and the murine α3 domain of the H2D molecule. These mice do not express the H2-D$^b$ and H2-K$^b$ molecules (Rohrlich et al., 2003).

The HLA-A2/DR1 transgenic mice express the human HLA-A*0201 α1-α2 domains, the murine α3 domain of the H2D molecule and the human β2-microglobulin. Moreover these transgenic mice express the human HLA-DRB1*0101 and HLA-DRA*0101 molecules. They are knock-out for murine H2-D$^b$, H2-K$^b$ and IA$^b$ genes (Pajot et al., 2004).

Both transgenic mouse strains were used between 6 and 10 weeks of age and were supplied by the Pasteur Institute of Paris. Animals were housed at the Specific Pathogen Free animal facility of the Pasteur Institute (Animal Facilities Lwoff n° 22, agreement number B 75 15-07). Prior to intradermal (ID), intramuscular (IM) or subcutaneous (SC) immunizations or intravenous (IV) injection, mice were anesthetized with a mix solution of 2% xylazine (Rompun, Bayer Santé, Loos, France) and 8% Ketamine (Imalgen 1000, Merial, Lyon, France) in 1× Phosphate Buffer Saline (1×PBS, Life Technologies, Saint-Aubin, France) through the intraperitoneal route (IP) according to individual animal weight and duration of anesthesia. All animals were handled in strict accordance with good animal practice and complied with local animal experimentation (Directive 2010/63/UE).

hTERT Peptides hTERT peptides restricted to HLA-B*0702, HLA-A*0201 or HLA-DR were previously described (see references in Table 1). hTERT peptides restricted to H2-D$^b$ and H2-K$^b$ were determined by in-silico epitope prediction in order to bind mouse MHC Class I molecules using four algorithms available online: Syfpeithi (www.syfpeithi.de/), Bimas (www-bimas.cit.nih.gov/), NetMHCpan and SMM (tools.immuneepitope.org/main/). All synthetic peptides were purchased lyophilized (>90% purity) from Proimmune (Oxford, United Kingdom). Lyophilized peptides were dissolved in sterile water at 2 mg/mL and stored at −20° C. prior use. Details of peptide sequences and MHC restriction are shown in Table 1.

TABLE 1 hTERT peptides and MHC restriction

| Peptide Code (reference) | Sequence | MHC Restriction | Mouse Strain |
|---|---|---|---|
| 277 (Adotevi et al., 2006) | RPAEEATSL (SEQ ID NO: 30) | HLA-B*0702 | Transgenic HLA-B7 |
| 351 (Adotevi et al., 2006) | RPSLTGARRL (SEQ ID NO: 29) | | |
| 1123 (Cortez-Gonzalez et al., 2006) | LPSDFKTIL (SEQ ID NO: 31) | | |
| 540 (Firat et al., 2002) | ILAKFLHWL (SEQ ID NO: 32) | HLA-A*0201 | Transgenic HLA-A2/DR1 |
| Y572 (Firat et al., 2002) | YLFFYRKSV (SEQ ID NO: 33) | | |
| Y988 (Firat et al., 2002) | YLQVNSLQTV (SEQ ID NO: 34) | | |
| UCP2.1 (Dosset et al., 2012) | SVWSKLQSI (SEQ ID NO: 35) | HLA-A*0201 | |
| UCP4.1 (Dosset et al., 2012) | SLCYSILKA (SEQ ID NO: 36) | HLA-A*0201 | |

TABLE 1-continued hTERT peptides and MHC restriction

| Peptide Code (reference) | Sequence | MHC Restriction | Mouse Strain |
|---|---|---|---|
| UCP2 (Godet et al., 2012) | KSVWSKLQSIGIRQH (SEQ ID NO: 37) | HLA-DR | Transgenic HLA-A2/DR1 |
| UCP3 (Godet et al., 2012) | GTAFVQMPAHGLFPW (SEQ ID NO: 38) | | |
| UCP4 (Godet et al., 2012) | SLCYSILKAKNAGMS (SEQ ID NO: 39) | | |
| 429 | RPIVNMDYV (SEQ ID NO: 40) | H2D$^b$ | C57/BL6J |
| 660 | HAQCPYGVL (SEQ ID NO: 41) | H2K$^b$ | C57/Bl6J |
| 1034 | QAYRFHACVL (SEQ ID NO: 42) | H2K$^b$ | C57/Bl6J |
| 1021 | QTVCTINIYKI (SEQ ID NO: 43) | H2D$^b$ | C57/Bl6J | hTERT Peptide Library

Lyophilized hTERT peptides (purity>70%) were purchased from GenScript (USA). This set is composed of 269 peptides of 15 AA overlapping of 11 AA and recovering the whole protein sequence of INVAC-1 hTERT. Each peptide was resuspended in distilled water at 2 mg/mL prior use according to supplier recommendations and kept frozen at −20° C. before use. Twenty-seven pools of 9-10 hTERT overlapping peptides (Table 2) were used to screen the breadth of hTERT specific T-cell response in an IFNγ ELISPOT assay.

TABLE 2

Pools of hTERT overlapping peptides

| P1 | P2 | P3 | P4 | P5 | P6 | P7 | P8 | P9 | P10 | P11 | P12 | P13 | P14 | P15 |
|---|---|---|---|---|---|---|---|---|---|---|---|---|---|---|
| 1 | 11 | 21 | 31 | 41 | 51 | 61 | 71 | 81 | 91 | 101 | 111 | 121 | 131 | 141 |
| 2 | 12 | 22 | 32 | 42 | 52 | 62 | 72 | 82 | 92 | 102 | 112 | 122 | 132 | 142 |
| 3 | 13 | 23 | 33 | 43 | 53 | 63 | 73 | 83 | 93 | 103 | 113 | 123 | 133 | 143 |
| 4 | 14 | 24 | 34 | 44 | 54 | 64 | 74 | 84 | 94 | 104 | 114 | 124 | 134 | 144 |
| 5 | 15 | 25 | 35 | 45 | 55 | 65 | 75 | 85 | 95 | 105 | 115 | 125 | 135 | 145 |
| 6 | 16 | 26 | 36 | 46 | 56 | 66 | 76 | 86 | 96 | 106 | 116 | 126 | 136 | 146 |
| 7 | 17 | 27 | 37 | 47 | 57 | 67 | 77 | 87 | 97 | 107 | 117 | 127 | 137 | 147 |
| 8 | 18 | 28 | 38 | 48 | 58 | 68 | 78 | 88 | 98 | 108 | 118 | 128 | 138 | 148 |
| 9 | 19 | 29 | 39 | 49 | 59 | 69 | 79 | 89 | 99 | 109 | 119 | 129 | 139 | 149 |
| 10 | 20 | 30 | 40 | 50 | 60 | 70 | 80 | 90 | 100 | 110 | 120 | 130 | 140 | 150 |

| P16 | P17 | P18 | P19 | P20 | P21 | P22 | P23 | P24 | P25 | P26 | P27 |
|---|---|---|---|---|---|---|---|---|---|---|---|
| 151 | 161 | 171 | 181 | 191 | 201 | 211 | 221 | 231 | 241 | 251 | 261 |
| 152 | 162 | 172 | 182 | 192 | 202 | 212 | 222 | 232 | 242 | 252 | 262 |
| 153 | 163 | 173 | 183 | 193 | 203 | 213 | 223 | 233 | 243 | 253 | 263 |
| 154 | 164 | 174 | 184 | 194 | 204 | 214 | 224 | 234 | 244 | 254 | 264 |
| 155 | 165 | 175 | 185 | 195 | 205 | 215 | 225 | 235 | 245 | 255 | 265 |
| 156 | 166 | 176 | 186 | 196 | 206 | 216 | 226 | 236 | 246 | 256 | 266 |
| 157 | 167 | 177 | 187 | 197 | 207 | 217 | 227 | 237 | 247 | 257 | 267 |
| 158 | 168 | 178 | 188 | 198 | 208 | 218 | 228 | 238 | 248 | 258 | 268 |
| 159 | 169 | 179 | 189 | 199 | 209 | 219 | 229 | 239 | 249 | 259 | 269 |
| 160 | 170 | 180 | 190 | 200 | 210 | 220 | 230 | 240 | 250 | 260 | |

Tumor Cell Line

The Sarc-2 tumor cell line used to assess the anti-tumor effect mediated by INVAC-1 was obtained from a spontaneous fibrosarcoma of a HLA-A2/DR3 mouse. The tumor mass was dissociated under sterile conditions and a primary cell suspension was generated. The cell line was shown to express the HLA-A*0201 molecule. Cells were cultured in RPMI glutamax medium (Life Technologies) supplemented with 10% FBS (Life Technologies) and 1% Penicillin/Streptomycin.

Mouse Immunization and In Vivo Electroporation Procedure

Intradermal (ID) immunization was performed on the lower part of the mouse flank with insulin syringes and specific needles (U-100, 29GX½"-0.33×12 mm, Terumo, Belgium) after shaving. No erythema was observed after shaving, during and after the immunization procedures. Intramuscular immunization (IM) was performed in the anterior *tibialis cranialis* muscle, also using insulin syringes and specific needles U-100. Subcutaneous immunization (SC) was performed at the base of the tail, also using insulin syringes and specific needles U-100. Each animal received a priming IM, ID or SC injection of plasmid (INVAC-1, NTC, pUTD10Not, pUTD10Cog or pUTD23Tyn) corresponding to either 12.5, 25, 50, 100, 200, 400, 800 or 1200 μg of DNA or 1×PBS, depending on the experiment. According to the vaccine regimen, mice could receive a similar second or third injection of DNA or 1×PBS.

In vivo DNA electroporation was performed using the CLINIPORATOR® 2 electroporation system and software (IGEA, Italy) equipped with plate electrodes (P-30-8G, IGEA). Directly after ID or SC vaccination, a skin fold was made at the injection site, entirely covered with conductive gel (Labo FH, blue contact gel, NM Medical, France) and placed between the plate electrodes. Two pulses of different voltages were applied (HV-LV): HV: 1250 V/cm, 1 Hz, 100 μs; 1 pulse, 1000 ms break; LV: 180 V/cm, 1 Hz, 400 ms, 1 pulse. Directly after IM injection, each muscle was entirely covered with conductive gel and placed between the plate electrodes. Two pulses of different voltages were applied (HV-LV): HV: 750 V/cm, 1 Hz, 100 μs; 1 pulse, 1000 ms break; LV: 100 V/cm, 1 Hz, 400 ms, 1 pulse.

In certain experiments, 18 hours before DNA vaccination or concomitantly to the administration of INVAC-1, mice were injected ID with 0.5 μg of murine GM-CSF or 1 ng of murine IL-12 in a final volume of 25 μl/flank. Both cytokines were purchased from Miltenyi (Germany).

ELispot Assay

Spleens from immunized mice were taken and mashed, and cell suspensions were filtered through a 70 mm nylon mesh (Cell Strainer, BD Biosciences, France) to isolate splenocytes. Blood from immunized mice was collected through retro-orbital puncture under anaesthesia in order to isolate peripheral mononuclear blood cells (PBMC). Splenocytes or PBMC were purified using Ficoll (Lymphocyte Separation Medium, Eurobio, France). Ficoll-purified lymphocytes from blood or spleen were numerated using the Cellometer® Auto T4 Plus counter (Ozyme, France).

ELISpot PVDF microplates (IFNγ Elispot kit, Diaclone, Abcyss, France, ref. 862.031.010P) were coated overnight with capture antibody (anti-mouse IFN-γ) and blocked with 1×PBS-2% milk. Cell suspensions were added to the plates in triplicates at $2\times10^5$ cells/well and stimulated with 5 μg/ml of HLA or H2 restricted hTERT derived peptides with serum free culture medium or with PMA-ionomycin (respectively 0.1 μM and 1 μM). After 19 hours, spots were revealed with the biotin-conjugated detection antibody followed by streptavidin-AP and BCIP/NBT substrate solution. Spots were counted using the Immunospot ELIspot counter and software (CTL, Germany). When analyzing ELIspot data, a vaccinated animal is considered as a responder if the frequency of spots, corresponding to hTERT specific CD8 or CD4 T-cells, is superior to the cut-off value of 10 spots.

In Vivo Cytotoxicity Assay

For target cell preparation, splenocytes from naive HLA-B7 mice were labeled by a 1×PBS solution containing high (5 medium (1 μM) or low (0.2 μM) concentrations of CFSE (Vybrant CFDA-SE cell-tracer kit; Life Technologies, Saint-Aubin, France). Naive splenocytes labeled with 5 and 1 μM CFSE were pulsed respectively with 2 different HLA-B7 peptides, 1123 and 351 at 5 μg/mL for 1.5 hour at room temperature. CFSE low labeled splenocytes were left unpulsed. Each mouse previously vaccinated with INVAC-1 or 1×PBS received, at day 14 post-prime or at day 10 post-boost injection, $10^7$ CFSE-labeled cells of a mix containing an equal number of cells from each fraction through the retro-orbital vein. After 15-18 hours, single-cell suspensions from spleens were analyzed by flow cytometry using MACSQUANT® flow cytometer (Miltenyi, Germany).

The disappearance of peptide-pulsed cells was determined by comparing the ratio of pulsed (high/medium CFSE fluorescence intensity) to unpulsed (low CFSE fluorescence intensity) populations in INVAC-1 immunized mice versus control (1×PBS) mice. The percentage of specific killing per test animal was established according to the following formula: $[1-[\text{mean } (CFSE^{low}PBS/CFSE^{high/medium}PBS)/(CFSE^{low}pDNA/CFSE^{high/medium}pDNA)]]\times 100$.

Cytokine Binding Assay (CBA)

Splenocytes ($6\times10^5$ cells) from vaccinated HLA-A2/DR1 mice were cultured 24 h at 37° C. with HLA-DR-restricted hTERT derived peptides (578, 904, and 1029) at 5 μg/mL. Cytokine culture supernatants were recovered and kept frozen at −20° C. until testing. A commercially available kit, the mouse Th1/Th2/Th17 Cytometric Beads Array (CBA, BD biosciences) kit was used to quantify respectively the concentration of IL-2, IFNγ, TNFα, IL-4, IL-6, IL-17a and IL-10. The CBA immunoassay was carried out according to the manufacturer's instructions. Flow cytometry acquisition was done using the FACScan LSRII flow cytometer (BD Biosciences); analyses were performed using the FCAP Array™ Software version 3.0 (BD Biosciences).

In Vivo Anti-Tumor Effect

For therapeutic vaccination experiments, 24 week-old HLA-A2/DR1 mice were subcutaneously engrafted with $2.10^4$ Sarc-2 cells on the right abdominal flank. Then, animals were immunized with DNA vaccines via the ID route followed by electroporation as described above at day 4, 21 and 35 post-engraftment. Every 2 to 3 days, tumor growth was monitored using a caliper. Mouse weight was also monitored every 2 to 3 days. Mice were euthanized when tumors reached 2000 mm³. The guidelines for the welfare and use of animals in cancer research were followed, especially for monitoring of clinical signs necessitating immediate intervention (Workman et al. 2010, BJC). Tumor volume was calculated using the following formula: $(L*1^2)/2$. Results are expressed in mm³ (L=length; 1=width).

For prophylactic vaccination, 5-10 week-old HLA-A2/DR1 mice were vaccinated twice (days 0 and 21) as described above. Thirty two days after the last immunization, animals were subcutaneously engrafted with $5.10^4$ Sarc-2 cells. Mice weight and tumor growth were monitored every 2 to 3 days as described before. Mice were euthanized when tumors reached 2000 mm³.

The tumor growth delay (TGD) criterion was used to assess vaccine efficacy. It compares the time to reach a defined tumor volume (500 mm³) in control and treated groups.

Statistical Analysis and Data Handling

Prism-5 software was used for data handling, analysis and graphic representations. Data are represented as the mean±standard deviation or as median. Statistical analyses of ELISpot assays were performed using a Mann Whitney non parametric and/or a Kruskal-Wallis analysis with Dunn's multiple comparison test. Significance was set at p-value<0.05.

Results

Characterization and Sequence Analysis of INVAC-1 Plasmid DNA

Ubi-hTERT transgene was successfully inserted into pNTC8685-eRNA41H-HindIII-XbaI as shown by restriction mapping using various restriction endonucleases (FIGS. 1A & 1B). The resulting pNTC8685-eRNA41H-HindIII-XbaI-Ubi-hTERT (INVAC-1) vector was also partially sequenced at junctions using pVAC5' and pVAC3' primers. Sequences confirmed that the cloning process was successfully achieved.

Full-length sequencing of INVAC-1 plasmid has been performed on the Master Cell Bank plasmid material (SEQ ID NO: 11 & FIG. 16). The result matched the expected sequence except for one base. Indeed, this full sequencing identified a silent mutation (G6064C; GGG glycine to GGC glycine) when compared to the human telomerase gene filed in databases (Accession number NM_198253). This silent mutation could be considered as an additional signature of INVAC-1 as this base change destroys a unique BamHI site (GGATCC to GCATCC) present in the wild-type telomerase gene.

Characterization and Sequence Analysis of INVAC-1 Derivative Constructs

Three INVAC-1 derivative DNA plasmids expressing different Ubi-hTERT fusion proteins were synthesized and cloned (FIG. 2A). All Ubi-hTERT transgenes were successfully ligated into pcDNA3.1(+) Invitrogen expression vector as shown by HindIII and XbaI digestion and electrophoresis (FIG. 2B). Inserts and junctions were sequenced using PEGFP-N5' and BGH primers matching the vector sequence flanking the DNA insert. Sequencing results confirmed that transgenes have been correctly cloned (SEQ ID NO: 13, 15, 17 & FIGS. 17 to 19).

INVAC-1 and INVAC-1 Derivative Proteins are Correctly Expressed In Vitro and Degraded by the Proteasome Pathway Western blot assay was performed to provide information about the global expression of wild-type hTERT, INVAC-1 and INVAC-1 derivative proteins after 18 h to 96 h of in vitro transient transfection into HEK293T and CrFK cell lines. The bands of wild-type hTERT protein corresponded to the size of unmodified hTERT at 124.5 kDa (FIGS. 3A and 3B, left part of the Figure). Wild-type hTERT protein expression appeared to be stable over the time, especially in HEK293T cells. By contrast, INVAC-1 (FIGS. 3A and 3B, right part of the Figure and FIG. 3C, upper part of the Figure) and INVAC-1 derivative proteins (FIG. 3C, lower part of the Figure) were rapidly degraded over the time.

In contrast to wild-type hTERT (pTRIP-CMV-hTERT), INVAC-1 construct produced two distinct bands: A weak upper band corresponding to the Ubi-hTERT fusion protein at the predicted size of 127.4 kDa and a lower band corresponding to INVAC-1-encoded hTERT protein lacking the ubiquitin polypeptide (119 kDa). These two forms of INVAC-1-encoded hTERT protein were detected in both cell lines, HEK293T and CrFK (FIGS. 3A and 3B). The same pattern was observed for INVAC-1 derivative constructs, Δ10Not, Δ10Cog and Δ23 (FIG. 3C). Taken together, the weaker expression of INVAC-1 and INVAC-1 derivatives proteins as compared to wild-type hTERT, their expression patterns and their kinetics of disappearance over time suggest that these proteins were rapidly degraded by the ubiquitin-dependent proteasome pathway in accordance with the proposed model for the degradation of ubiquitin fusion proteins (Bachmair, 1986). The rapid appearance of INVAC-1 band of 119 kDa indicates that the majority of the protein was cotranslationally cleaved or nearly so by ubiquitin-specific processing proteases at the Ubi-hTERT junction. Consequently, the protein entered into a rapid proteasome-dependent degradation pathway according to the so-called N-end rule for protein degradation (Tasaki, 2012; Varshavsky, 1996).

These results validate the in vitro expression pattern and identity of Ubi-hTERT fusion proteins encoded by INVAC-1 and INVAC-1 derivatives. The ubiquitin polypeptide fused to hTERT-derived proteins played its role by enhancing the degradation of the proteins in accordance with the N-end rule. According to this N-end rule, hTERT became an unstable protein rapidly degraded by the proteasome system involved in the production of peptides for antigen presentation by major histocompatibility complex (MHC) class I molecules (Cadima-Couto, 2009; Michalek et al, 1993). Thus, these data indicate that the Ubi-hTERT fusion constructs which undergo enhanced degradation in mammalian tissue culture cells, could also be rapidly degraded in vivo and can effectively induce higher CD8+ T-cell responses than wild-type hTERT.

INVAC-1 Protein has a Predominant Cytoplasmic Distribution and a Nucleolar Exclusion Pattern With the idea to delocalize INVAC-1-derived hTERT protein to enhance its degradation, the nucleolar localization signal (N-terminal part of hTERT) was removed. Therefore, the cellular localization of hTERT encoded by INVAC-1 was assessed by immunofluorescence analysis after transfection into CrFK, HEK293, HeLa, QT6 cell lines (FIG. 4).

Figure 4A:
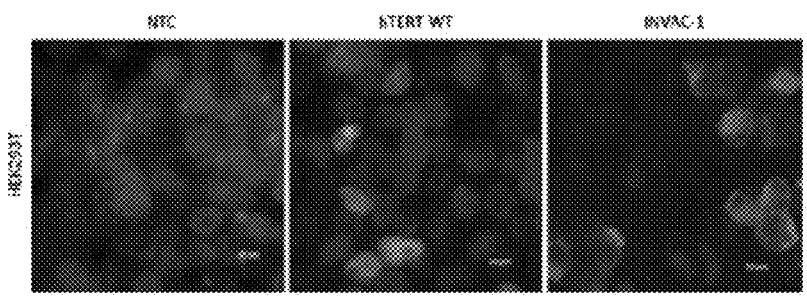
Figure 4B:
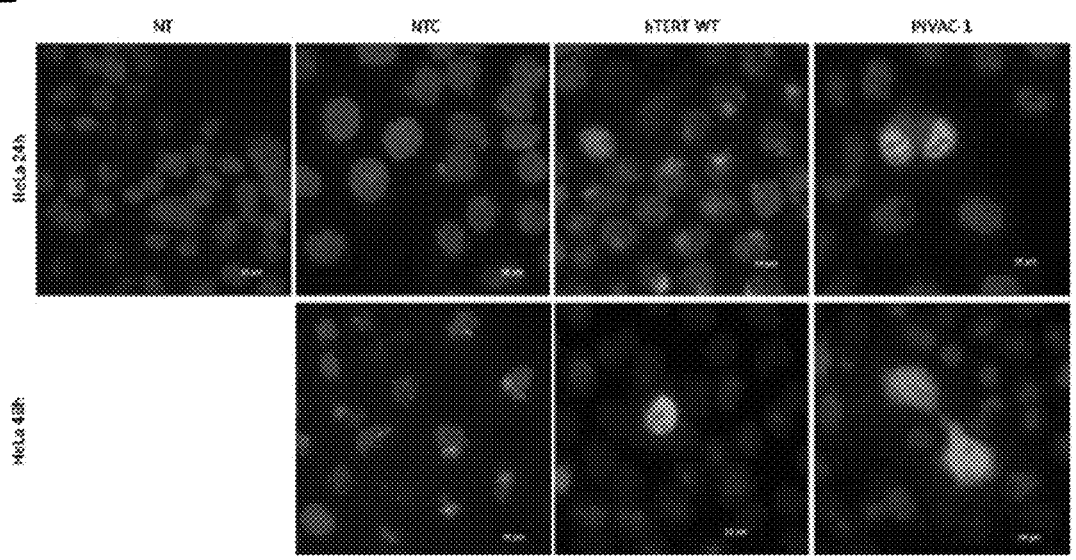

Wild-type hTERT (pTRIP-CMV-hTERT) was shown to predominantly localize into the nucleus and nucleolus in transfected HEK293T cells at 24 h (FIG. 4A). In contrast, INVAC-1 protein was distributed between nucleus and cytoplasm with, first and foremost, a clear nucleolar exclusion pattern (FIG. 4A). Transient transfection of wild-type hTERT (pTRIP-CMV-hTERT) and INVAC-1 plasmids into HeLa cells showed similar localization patterns at 24 and 48 hours post-transfection for both proteins (FIG. 4B).

The weak anti-hTERT fluorescence signal which could be observed in HEK293T and HeLa cells after transfection of pNTC8685-eRNA41H empty backbone vector was probably due to the cross reactivity with endogenous hTERT.

Figure 4C:
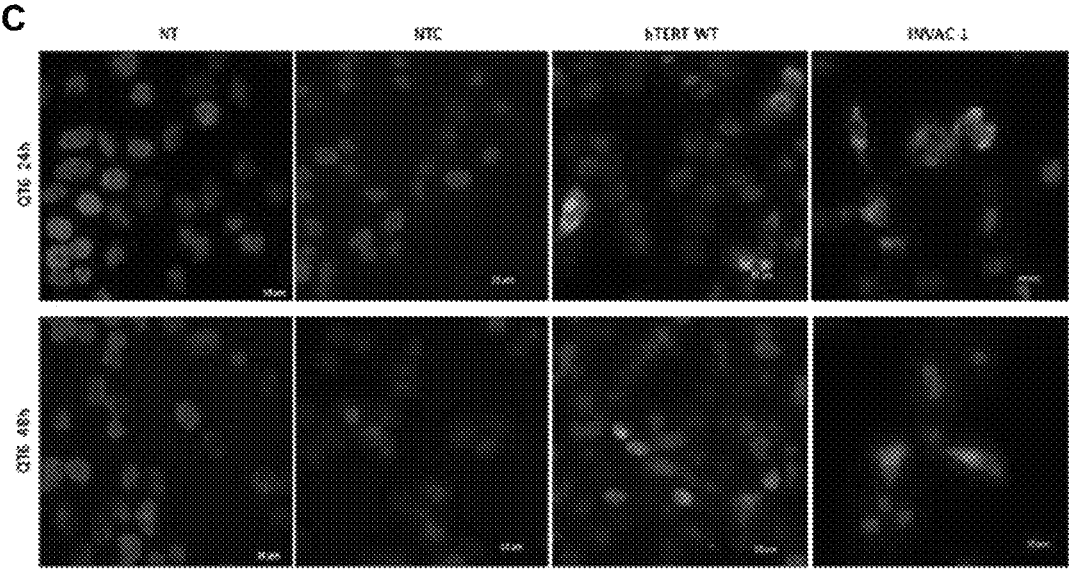
Figure 4D:
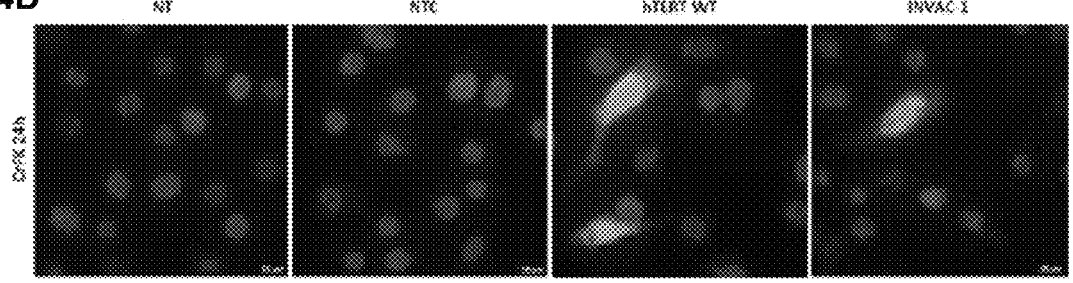

To overcome the non-specific fluorescence background due to endogenous hTERT protein expression, non-human cell lines, QT6 quail fibrosarcoma and CrFK feline kidney cells, were used for immunostaining. No background signal was observed in both cell lines after transient transfection with pNTC8685-eRNA41H empty backbone vector (FIGS. 4C & D). As expected, exogenous wild-type hTERT protein (pTRIP-CMV-hTERT) was mainly detected in nucleus and nucleolus of both cell lines (FIGS. 4C & D). INVAC-1 protein, as already observed in HEK293T and HeLa cells, had a nuclear and cytoplasmic distribution into CrFK cells at 24 h (FIG. 4D). Interestingly, expression of INVAC-1 into QT6 cells at 24 and 48 h was only cytoplasmic suggesting that the deletion of the nucleolar localization signal drastically altered the distribution of the protein in this cell line.

Taken together, these results showed that INVAC-1-derived hTERT protein has a modified subcellular distribution as compared to wild-type hTERT in different cell lines. This alteration may be an advantage for enhancing proteasomal degradation of the protein into peptides for MHC class I presentation to generate specific cellular immune responses (Andersson and Barry, 2004).

Transfection of QT6 and CrFK cells (without non specific hTERT background) with INVAC-1 derivatives (pUTD10Not, pUTD10Cog and pUTD23Tyn) confirmed a nucleolar exclusion pattern of these hTERT-derived proteins (data not shown). Their subcellular distribution was mostly cytoplasmic as compared to wild-type hTERT.

INVAC-1 and INVAC-1 Derivatives have No Enzymatic Activity

Human telomerase plays a critical role in tumor growth by participating to immortalization and preventing senescence of tumor cells. Therefore, the use of wild-type telomerase as a vaccine product may lead to safety concerns.

A TRAP assay was performed to evaluate the telomerase activity of Ubi-hTERT constructs in telomerase negative CrFK cell line. Telomerase activity was only detected in CrFK cells transfected with wild-type hTERT using pTRIP- CMV-hTERT plasmid. No telomerase activity was detected in CrFK cells transfected with INVAC-1 or INVAC-1 derivatives (FIG. 5).

Figure 5A:
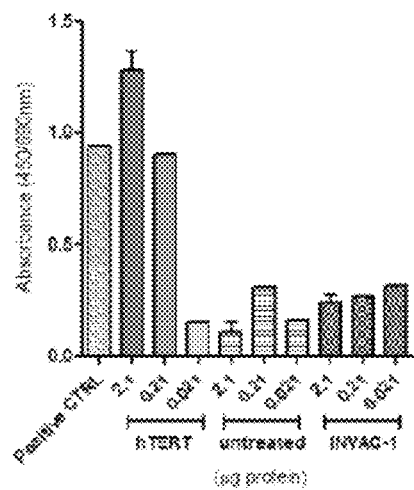
Figure 5B:
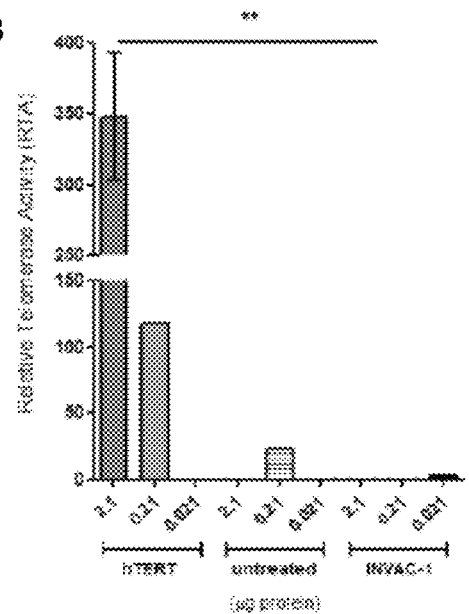
Figure 5C:
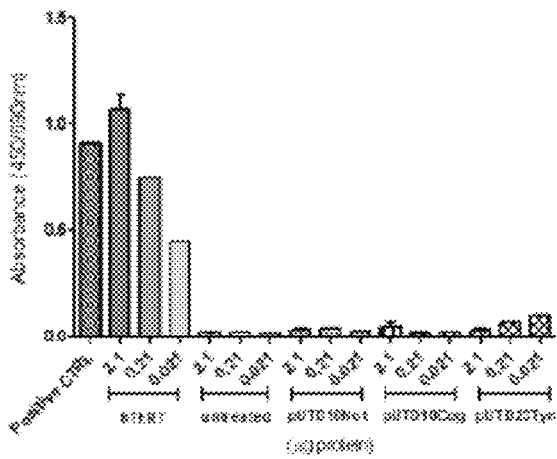
Figure 5D:
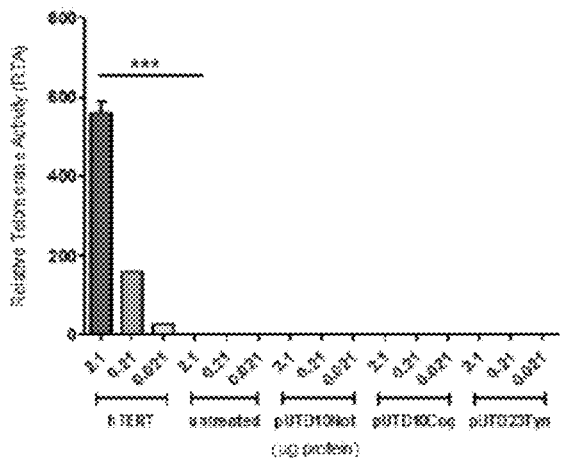

As shown in FIGS. 5A and 5C, raw absorbance data demonstrated that the level of telomerase activity of INVAC-1 and INVAC-1 derivatives is comparable to the level of untreated cells.

Relative Telomerase Activity (RTA) data (FIGS. 5B and 5D) which represent fully analyzed results taking into account the specificity of the assay by using various negative controls including heat-inactivated samples, shown that INVAC-1 and INVAC-1 derivatives are completely devoid of any telomerase activity.

All samples treated with the internal amplification standard (IS) control were highly positive confirming the absence of Taq DNA polymerase inhibitors in CrFK lysate samples and thus reemphasizing the specificity of the assay.

In conclusion, these results confirmed that INVAC-1 and INVAC-1 derivatives do not have any enzymatic activity. Therefore, with regards to the telomerase activity, there is no safety concern for using INVAC-1 in human.

Electroporation is Advantageous to Induce Significant Levels of hTERT Specific CD8 T-Cells Secreting Interferon-γ after ID Administration of INVAC-1

The intensity of hTERT specific CD8 T-cell responses was assessed in C57BL/6 mice previously immunized with INVAC-1 via the intradermal route followed or not by skin electroporation (FIG. 6). Fourteen days post-injection, mouse spleens were harvested and the induced immune responses were monitored via an IFN-γ ELISPOT assay using hTERT peptides restricted to H2. A significant difference in the frequency of IFNγ$^+$ CD8 T-cells was observed between the group of mice which received an electroporation after the ID injection of INVAC-1 and the group which did not (p<0.05). Thus, these results suggest that electroporation is advantageous to induce significant levels of hTERT specific CD8 T-cell responses after ID vaccination with INVAC-1.

INVAC-1 Vaccination Via Different Administration Routes Followed by Electroporation Induces hTERT Specific CD8 T-Cell Secreting Interferon-γ. The ID Vaccination Route Appears to be the Best Route Conventional vaccines are commonly administered via the SC or IM route. However, the intradermal route of immunization is now regaining interest in the field of vaccination (Combadiere and Liard, 2011). Consequently, the ID route was tested for the administration of INVAC-1 and compared to the conventional SC and IM routes.

In a first set of experiments different groups of transgenic HLA-B7 mice were immunized with INVAC-1 via the ID or SC route immediately followed by electroporation (FIG. 7A). Fourteen days after vaccination/electroporation, mouse spleens were harvested and the induced immune response was monitored in the spleen via an IFN-γ ELISPOT assay using hTERT peptides restricted to HLA-B7. In a second set of experiments one group of transgenic HLA-B7 mice was immunized with INVAC-1 via the ID route and the other one via the IM route immediately followed by electroporation (FIG. 7B). The frequency of hTERT specific CD8 T-cells was monitored in PBMCs via an IFN-γ ELISPOT assay using hTERT peptides restricted to HLA-B7. It was established that the vaccination with INVAC-1 followed by electroporation was able to induce hTERT specific CD8 T-cell responses in HLA-B7 mice whatever the route of vaccination used (FIGS. 7A and 7B).

Moreover, as shown in FIG. 7A, the number of responding animals was higher in the group of mice vaccinated via the ID route as compared to group vaccinated via the SC route, with 6 out of 8 vs. 3 out of 8 responders respectively. A significant difference was also observed in the frequency of hTERT specific CD8 T-cells between the group of mice vaccinated ID in comparison with the animals vaccinated IM (p<0.05) (FIG. 7B).

Both experiments demonstrated that the ID route of vaccination was more efficient than the IM and SC routes for the INVAC-1-mediated induction of hTERT specific CD8 T-cells. Similar data were obtained using other mouse models i.e HLA-A2-DR1 mice (data not shown). Consequently, all subsequent immunogenicity studies performed with INVAC-1 were then designed with an ID administration of the vaccine followed by electroporation.

Impact of the Vaccine Dose on hTERT Specific CD8 T-Cell Response after a Single ID Immunization with INVAC-1 and Electroporation Another important parameter to be tested was the impact of the vaccine dose on hTERT specific CD8 T-cell responses. C57BL/6 mice were immunized via the ID route followed by electroporation in both lower flanks with increasing doses of INVAC-1. The vaccine volume remained constant at 50 µL/site. Animals were vaccinated in 2 or 4 sites depending on the final vaccine dose received. Fourteen days after vaccination/electroporation, mouse spleens were harvested and the specific cellular immune responses were monitored via an IFN-γ ELISPOT assay using hTERT peptides restricted to H2.

In a first set of experiments, C57BL/6 mice received a single ID injection of INVAC-1/electroporation with doses ranging from 12.5 µg to 100 µg (FIG. 8A). A significant difference in the frequency of hTERT specific CD8 T-cells was observed in the group of animals vaccinated with 100 µg of INVAC-1 in comparison with control animals vaccinated with PBS (p<0.01) (FIG. 8A). It was also observed that the median number of hTERT specific CD8 T-cells increased in proportion to the dose of vaccine received (from 12.5 µg to 100 µg). The number of responding animals also increased along with the vaccine dose with respectively 4 out of 6 responders for the 12.5 µg dose, 4 out of 5 for the 25 µg dose and 6 out of 6 responders for the 50 and 100 µg doses.

In a second series of experiments, C57BL/6 mice received a single ID injection of INVAC-1/electroporation with doses ranging from 100 µg to 1200 µg (FIG. 8B). A significant difference in the frequency of hTERT specific CD8 T-cells was observed in the group of animals vaccinated with 800 µg of INVAC-1 administered at 4 mg/mL in comparison with control animals vaccinated with PBS (p<0.05) (FIG. 8B). It was noticed that the median number of hTERT specific CD8 T-cells increased proportionally to the dose of vaccine received from 100 µg to 800 µg and that this median number decreased when injecting 1200 µg. The number of responding animals increased with the vaccine dose with respectively 4 out of 5 responders for the 100 µg dose, 5 out of 5 or 4 out of 4 responders for the doses superior to 200 µg. For the 1200 µg dose, even if all animals were responders, there were still 2 out of 5 animals with a level of specific responses close to the cut-off value.

In conclusion, for the vaccine specific CD8 T-cell criterion in C57BL/6 mice, a dose response was observed as a consequence of the administration of different quantities of INVAC-1. Interestingly, no sign of vaccine toxicity was observed in animals injected with the highest doses of vaccine (800 and 1200 µg) in comparison with control mice (monitoring of body weight and macroscopic autopsy at sacrifice). Similar data were obtained in transgenic HLA-B7 mice (data not shown).

A Prime-Boost Regimen is Recommended for INVAC-1 Vaccination in Order to Increase the Level of hTERT Specific CD8 T-Cell Response Most of vaccination protocols recommended for conventional vaccines (BCG, measles, influenza . . . ) include a prime-boost regimen in order to improve the frequency of vaccine specific immune responses. Consequently, the impact of a prime-boost regimen on the generation of hTERT specific CD8 T-cell responses was tested for INVAC-1 ID vaccination and electroporation. Towards this aim, transgenic HLA-B7 mice were immunized ID with INVAC-1 and skin vaccination sites were electroporated directly after vaccine administration. Twenty one days after the first immunization, mice received a second injection of INVAC-1 using the same vaccination procedure. At different time points after prime and boost immunizations, peripheral blood was collected in order to monitor hTERT specific CD8 T-cell responses via an IFN-γ ELISPOT assay using hTERT peptides restricted to HLA-B7 (FIG. 9). A peak of hTERT specific CD8 T-cell response was observed at 14 days post-priming. However, the median frequency of hTERT specific CD8 T-cells in the group of vaccinated animals was relatively low (11.3 spots/200,000 PBMCs) and there were 2 out of 5 animals which did not respond to the vaccine. After boosting, a peak of hTERT specific CD8 T-cells was observed at day 10 post-injection. The median frequency of hTERT specific CD8 T-cells in the group of vaccinated animals at this time point (D31 post-prime, D10 post-boost) was significantly different from the median frequency of hTERT specific CD8 T-cells in pre-immune samples ($p<0.05$). There were 4 out of 5 responders after boosting.

In conclusion, a prime-boost vaccination regimen is recommended for INVAC-1 ID vaccination/electroporation because first it allows increasing the frequency of hTERT specific CD8 T-cells circulating in the blood (effector T-cells) and secondly it shortens the time necessary to reach the peak of the specific cellular immune response, which is an important parameter in the context of an anti-cancer vaccination.

ID Vaccination with Δ10Not, Δ10Cog or Δ23 Constructs Followed by Electroporation Also Induces hTERT Specific CD8 T-Cell Response. A Prime-Boost Vaccination Regimen is Recommended to Increase the Frequency of Vaccine Specific CD8 T-Cells.

Together with the development of INVAC-1, 3 other DNA plasmid constructs (INVAC-1 derivatives) were designed: Δ10Not (pUTD10Not), Δ10Cog (pUTD10Cog) or Δ23 (pUTD23Tyn). Three deletions were engineered into the catalytic site of the hTERT enzyme. They ranged from 10-23 amino acid residues and spanned the crucial trio of Valine-Aspartic acid-Aspartic acid residues (Val-Asp-Asp, or VDD in the one letter code) (FIG. 2A). These constructs were designed to show that any deletion eliminating the activity of the enzyme could retain immunogenicity.

In order to confirm this hypothesis, C57BL/6 mice were immunized via the ID route followed by electroporation with INVAC-1, Δ10Not, Δ10Cog, Δ23 or PBS (FIG. 10A). Half of the animals received a second injection of DNA or PBS 21 days after the first immunization using the same procedure. Animals were sacrificed fourteen days (group of mice which received a single injection) or ten days (group of mice which received 2 injections) after the last vaccination/electroporation. Mouse spleens were harvested and the induced CD8 T-cell response was monitored via an IFN-γ ELISPOT assay using hTERT peptides restricted to H2 (pool of 4 peptides).

For the animals which received a single DNA injection, a significant difference in the frequency of hTERT specific CD8 T-cells was observed only in the group of mice vaccinated with 100 μg of INVAC-1 in comparison with control animals vaccinated with PBS ($p<0.05$) (FIG. 10A, dark dots). When analysing the frequency of responders, there were 3 out of 4 responders in the group of mice vaccinated with INVAC-1 and Δ10Cog. However, for Δ10Cog, animals were low responders with hTERT specific CD8 T-cell responses inferior to 50/200,000 splenocytes. There was only 1 out of 4 responders in the group of animals vaccinated with Δ23 and no responder with animals treated by Δ10Not. For the animals which received two vaccinations (FIG. 10A, white dots), a significant median frequency of hTERT specific IFN-γ secreting CD8 T-cells was observed in the spleen of mice immunized with INVAC-1, Δ10Not, and Δ10Cog in comparison with control mice injected with PBS ($p<0.001$). There were only 2 out of 4 responding animals in the group of mice vaccinated with Δ23 which was not statistically significant. In conclusion, after one or two rounds of vaccination, INVAC-1 and INVAC-1 derivative constructs allowed the induction of hTERT specific CD8 T-cells, INVAC-1 being the more immunogenic one in C57BL/6 mice.

In a second set of experiments, transgenic HLA-B7 mice were vaccinated ID with INVAC-1, Δ10Not, Δ10Cog, Δ23 or PBS (FIG. 10B) followed by electroporation and received a second injection 21 days after the first one using the same procedure. Spleens were collected 10 days after the last injection and the induced CD8 T-cell response was monitored via an IFN-γ ELISPOT assay using hTERT peptides restricted to B7. As shown in FIG. 10B a significant median frequency of hTERT specific IFN-γ secreting CD8 T-cells was observed in the spleen of mice immunized with INVAC-1, Δ10Not, Δ10Cog and Δ23 in comparison with control mice injected with PBS ($p<0.001$).

As shown for INVAC-1, the 3 INVAC-1 derivatives Δ10Not, Δ10Cog and Δ23 were also capable of inducing hTERT specific CD8 T-cells in vivo after ID vaccination and electroporation in two different mouse strains. A prime-boost vaccination regimen was also recommended for INVAC-1 derivatives to reach significant levels of hTERT specific CD8 T-cell responses. Taken together, these results demonstrate that INVAC-1 is the construct which allows the induction of the best hTERT specific CD8 T-cell response. This is probably due to the difference observed in ΔhTERT protein expression levels after plasmid transfection as shown by western blotting (FIG. 3).

The Breadth of hTERT Specific T-Cell Response after ID Vaccination(s) Followed by Electroporation is Different According to the hTERT Plasmid Construct Used for Vaccination (INVAC-1, pNTC-hTERT or pNTC-hTERT-ΔVDD)

The impact of hTERT sequence modifications engineered within the INVAC-1 construct, i.e, (1) the deletion of the nucleolar localization signal, (2) the addition of the ubiquitin sequence and (3) the deletion within the catalytic site, on the repertoire of the T-cell immune response against hTERT has been assessed. INVAC-1 hTERT specific cellular immune responses were screened after ID immunization(s)/electroporation(s) with INVAC-1 and compared to responses induced by a DNA encoding the native/wild-type sequence of the human TERT (pNTC-hTERT) and a DNA encoding the hTERT sequence only deleted in the VDD region (pNTC-hTERT-ΔVDD). Control animals received ID injection(s) of 25 μg of pNTC empty vector followed by electroporation.

A first series of HLA-B7 transgenic mice received a single injection of either one of the 4 constructs using the vaccination protocol described before (25 µg/mouse). A second series of animals received a prime injection and a boost 21 days after the first vaccination with either one of the 4 constructs using the vaccination protocol described before (25 µg/mouse).

Fourteen days after a single injection or 10 days post-boost, splenocytes from vaccinated and control mice were tested in an IFNγ ELIspot assay using 269 peptides of 15 AA overlapping of 11 AA and recovering the whole protein sequence of hTERT (27 pools composed of 10 peptides each).

Immunization with INVAC-1 induced a large repertoire of T-cells against numerous hTERT epitopes since after the priming, about 12 pools of peptides were recognized (FIG. 11A). These data suggest that a minimum of 12 epitopes restricted to HLA-B7 were expressed after processing on the surface of dendritic cells with a density of MEW peptide complexes allowing the induction of a strong T-cell response. These important results show the capacity of INVAC-1 for processing and expression of numerous hTERT peptides on the surface of APC. The difference obtained with the other constructs (hTERT and hTERTΔVDD) validates the optimization features made in INVAC-1 leading to increase the breadth of the T-cell repertoire against hTERT. In addition, these results stress out the advantage of DNA vaccination versus peptide immunization.

The advantage for a second cycle of immunization (prime-boost) with INVAC-1 in transgenic mice was confirmed in this study. In vivo T-cell repertoire was improved as at least 5 new epitopes were revealed (FIG. 11B). A total of at least 17 epitopes were recognized after the boost. These data confirm that several injections in the patient will be beneficial to obtain a better anti-tumor response.

Analyzing these data globally by doing the sum of total median of frequency of specific T-cell detected for the 27 pools of peptides, no major differences were observed after one (prime) or two (prime-boost) cycles of immunizations between the three hTERT constructs (FIG. 11C). This suggests that the modifications made in INVAC-1 hTERT had no impact on the breadth of the immune response, even though a significant higher T-cell mediated immune response was observed after the boost with INVAC-1.

In conclusion, INVAC-1 vaccination mediated a large repertoire of T-cell immune response against numerous hTERT epitopes different from wild-type hTERT and hTERTΔVDD constructs in terms of peptides/epitopes recognized by T-cells.

ID Vaccination with INVAC-1 Followed by Electroporation Induces hTERT Specific T-Cell Responses with the Hallmark of an Anti-Cancer Immune Response: Cytotoxic CD8 T-Cells and Th1 CD4 T-Cells Among immune cells that are relevant in antitumor immune responses, cytotoxic CD8 T lymphocytes (CTL) and Th1 CD4 T-cells have been identified as the most powerful effector cells (Vesely et al., 2011) (Braumuller et al., 2013).

In a first step, the cytotoxic activity of hTERT specific CD8 T-cells was investigated in vivo after ID vaccination/electroporation with INVAC-1. Indeed, this activity is necessary to kill tumor cells. In order to measure the in vivo cytolytic strength of the hTERT specific CD8$^+$ T-cell response elicited by INVAC-1 immunization, an in vivo cytotoxicity assay was performed using carboxyfuorescein-diacetate succinimidyl ester (CFSE)-labelled, peptide-pulsed splenocytes as target cells. HLA-B7 transgenic mice which received a prime or a prime-boost vaccination with INVAC-1 (or PBS as control) via the ID route as described before were intravenously injected with $7.10^6$ target cells. Target cells were splenocytes from naive congenic mice independently labelled with 3 different concentrations of CFSE and pulsed with either a hTERT peptide restricted to HLA-B7 (p351, immuno-dominant peptide or p1123, sub-dominant peptide) or left unpulsed as an internal control. After 15-18 hours, spleen cells were harvested and the disappearance of peptide-pulsed cells in immunized vs. control mice was quantified by flow cytometry.

Results show that all mice developed specific CTLs against the immuno-dominant peptide p351 after a single injection (FIG. 12A, white dots) with a median specific lysis of 35%. One third of the animals developed specific CTLs against the sub-dominant peptide p1123 (FIG. 12A, black dots). It can be expected that multiple injection cycles would allow increasing the number of animals which develop a specific CTL lysis against the sub-dominant peptide 1123.

It has been recently described that a hTERT specific CD4 T-cell response may be associated with a better chemotherapy response in NSCLC patients (Godet et al., 2012). Therefore, the presence of a hTERT specific CD4 T-cell response after INVAC-1 ID injection was investigated. To this aim HLA-A2/DR1 transgenic mice were ID immunized with INVAC-1 followed by electroporation and the hTERT specific CD4 T-cell response was monitored in the spleen 14 days after vaccination via an IFN-γ ELISPOT assay using hTERT peptides restricted to DR1. As shown in FIG. 12B, a significant median frequency of hTERT specific IFN-γ secreting CD4 T-cells was observed in the spleen of ID vaccinated mice in comparison with control mice injected with PBS ($p<0.001$).

It has been emphasized that Th1 immunity had a clear positive effect on cancer cell elimination in vivo (Braumuller et al., 2013). As a matter of fact, CD4$^+$Th1 cells produce several cytokines (such as IFN-γ, TNF-α and IL-2) essential for the induction of cell-mediated immunity against tumors. Consequently, after INVAC-1 ID vaccination, the different cytokines secreted by hTERT specific CD4 T-cells were investigated. To this aim, splenocytes from INVAC-1-vaccinated HLA-A2/DR1 transgenic mice were stimulated in vitro for 24 hours with a pool of hTERT peptides or left unstimulated. Supernatants were recovered and assayed in a Cytokine Binding Assay (CBA) in order to evaluate the concentration of Th1, Th2 and Th17 cytokines secreted by hTERT specific CD4 T-cells.

As shown in FIG. 12C, significant concentrations of Th1 cytokines IL-2, TNFα and IFNγ were detected in supernatants from splenocytes recovered from mice vaccinated with INVAC-1 in comparison with supernatants from control mice ($p<0.05$).

Thus, ID vaccination/electroporation with INVAC-1 is able to promote the expansion of hTERT specific CD8 T-cells which exhibit a cytotoxic activity in vivo along with specific CD4 T-cells with a Th1 profile. Both types of response are the hallmark of a favourable anti-cancer immune response.

Therapeutic and Preventive ID Vaccination with INVAC-1 Followed by Electroporation Delay Tumor Growth after Syngeneic Tumor Inoculation in HLA-A2/DR1 Transgenic Mice Up to this point, results have shown that an ID injection of INVAC-1 followed by electroporation was able to induce cytotoxic CD8 T-cells and Th1 CD4 T-cells in mice. The next step was then to evaluate the protection of transgenic HLA-A2/DR1 mice conferred by INVAC-1 ID vaccination and electroporation after Sarc-2 (fibrosarcoma) tumor cells inoculation. In a first attempt, transgenic HLA-A2/DR1 mice were vaccinated ID with INVAC-1 followed by electroporation in a prime-boost strategy or mock vaccinated with PBS. One month after preventive vaccination, mice were challenged via the SC route with 50,000 Sarc-2 cells. Tumor volume was measured every 2-3 days. FIG. 13A shows the kinetics of the median tumor volume after challenge according to mice treatment. Tumor growth delay (TGD) at 500 mm$^3$ was then calculated. This criterion allows measuring a vaccine treatment effect on tumor growth by comparing the time to reach a defined tumor volume in control and treated groups. An eleven-day tumor growth delay was observed between the group of mice vaccinated with INVAC-1 and the group of animals which received PBS. Thus, preventive vaccination with INVAC-1 was responsible for a slow-down in tumor growth. Because tumor inoculation was performed one month after the last vaccination, anti-tumor effects could be to some extent attributed to the presence of hTERT specific memory T-cells.

In a second series of experiments, transgenic mice were engrafted with 20,000 Sarc-2 cells and were ID vaccinated with INVAC-1 followed by electroporation 4 days after cell inoculation (FIG. 13B). Control animals received an ID injection of an "empty" plasmid (NTC) which has the same backbone as INVAC-1 but which does not encode any tumor antigen. Two boost vaccinations were performed with the same procedure 21 and 35 days after tumor engraftment. Tumor growth delay at 500 mm$^3$ was calculated. A 4-day tumor growth delay was observed between the group of mice vaccinated with INVAC-1 and the group of animals which received the NTC empty plasmid. In conclusion, therapeutic vaccination with INVAC-1 allowed a relatively weak, nevertheless repeatedly observed, slow-down in tumor growth.

Administration of Murine GM-CSF Along with INVAC-1 ID Vaccination/Electroporation Improves the Intensity and Quality of hTERT Specific Cellular Immune Response and Delays Tumor Growth after a Syngeneic Tumor Challenge in HLA-A2/DR1 Transgenic Mice.

Different cytokines have been used so far as immunomodulators to facilitate antigen recognition and T-cell expansion in anti-cancer vaccination studies both in animal models and in humans.

One of the most frequently used cytokine is the GM-CSF (Granulocyte macrophage Colony Stimulating Factor). This cytokine is known to help the maturation of Antigen Presenting Cells and to favor the Th1 cellular immune responses (Parmiani et al., 2007). Regarding the major role played by GM-CSF in the context of anti-tumor vaccines, the impact of the addition of murine GM-CSF (mGM-CSF) on hTERT specific T-cell responses after INVAC-1 ID vaccination and electroporation was tested. To this aim, C57BL/6 mice received an ID injection of mGM-CSF 18 hours prior being vaccinated with INVAC-1 via the ID route followed by electroporation (FIG. 14A). Another group of mice was vaccinated ID with INVAC-1/electroporation without addition of mGM-CSF. Control animals were mock vaccinated with PBS and electroporation. Fourteen days post-injection, mouse spleens were harvested and the induced immune responses were monitored via an IFN-γ ELISPOT assay using hTERT peptides restricted to H2. A significant difference in the frequency of IFNγ$^+$ CD8 T-cells was observed between the group of mice which received mGM-CSF before the ID injection of INVAC-1 and the group which did not ($p<0.001$). Thus, addition of mGM-CSF allowed a major increase in the frequency of hTERT specific CD8 T-cells. A second step consisted in investigating the impact of this immunodulator on the quality of hTERT specific CD4 T-cells, and especially on the generation of Th1 specific T-cells. To this aim, splenocytes from INVAC-1 or INVAC-1/mGM-CSF vaccinated HLA-A2/DR1 transgenic mice were stimulated in vitro for 24 hours with a pool of hTERT peptides restricted to DR1 or left unstimulated. Supernatants were recovered and assayed in a Cytokine Binding Assay (CBA) in order to evaluate the concentration of Th1, Th2 and Th17 cytokines secreted by hTERT specific CD4 T-cells. As shown in FIG. 14B, significant concentrations of Th1 cytokines IL-2, TNFα and IFNγ were detected in supernatants from splenocytes recovered from mice vaccinated with INVAC-1/mGM-CSF in comparison with supernatants from mice vaccinated with INVAC-1 only. When adding mGM-CSF, there was a major increase in the concentration of TNFα ($p<0.01$), IFNγ ($p<0.05$) and IL-2 ($p<0.05$) which are Th1 anti-tumoral cytokines.

Thereafter, the combination mGM-CSF/INVAC-1 was studied in the Sarc-2 animal tumor model in order to evaluate if mGM-CSF could potentiate anti-tumor effects.

To this aim, HLA-A2/DR1 transgenic mice were engrafted with 20,000 Sarc-2 cells and were vaccinated ID with INVAC-1 and mGM-CSF followed by electroporation 4 days after cell engraftment (FIG. 14C). Control animals received an ID injection of an empty plasmid (NTC) and mGM-CSF or PBS and mGM-CSF. Two boost vaccinations were performed with the same procedure 21 and 35 days after tumor engraftment. Tumor growth delay (TGD) at 500 mm$^3$ was calculated. A 14-day TGD was observed between the group of mice vaccinated with INVAC-1/mGM-CSF and the group of animals which received NTC/mGM-CSF; 10-day TGD was observed between INVAC-1/mGM-CSF and PBS/mGM-CSF group. These results demonstrate that a therapeutic vaccination with INVAC-1 combined with mGM-CSF allowed a slow-down in tumor growth.

Administration of Murine IL-12 Along with INVAC-1 ID Vaccination/Electroporation Improves the Intensity of hTERT Specific CD8 T-Cell Response The impact of the IL-12 cytokine on hTERT specific CD8 T-cell response after INVAC-1 ID vaccination and electroporation was also investigated. To this aim, HLA-A2/DR1 mice received an ID injection of IL-12 along with the ID administration of INVAC-1 followed by electroporation (FIG. 15). Another group of mice was vaccinated ID with INVAC-1/electroporation without addition of IL-12. Control animals were mock vaccinated with PBS and IL-12 or PBS alone followed by electroporation. Fourteen days post-injection, mouse spleens were harvested and the induced immune responses were monitored via an IFN-γ ELISPOT assay using hTERT peptides restricted to A2. The frequency of responding mice was increased when adding IL-12. Indeed, there were 2 out of 5 and 4 out of 5 responding animals for the INVAC-1 vaccinated group and the INVAC-1/IL-12 vaccinated group respectively.

Example II

Abbreviations

AA: Amino Acid, bp: Base-pair, CTL: Cytotoxic T-Lymphocyte, CMV: Cytomegalovirus, DNA: Deoxyribonucleic Acid, EP: Electroporation, ID: Intradermal, NoLS: Nucleolar Localization Sequence, RNA: Ribonucleic Acid, RTA: Relative Telomerase Activity, TRAP: Telomeric Repeat Amplification Protocol, TERT: Telomerase Reverse Transcriptase, Ubi: Ubiquitin, VDD: Valine-Aspartic Acid-Aspartic Acid Materials and Methods Plasmid DNA Vectors
INVAC-1
The INVAC-1 construct was already described in EXAMPLE I.
INVAC-1 Shuffled Derivatives
pUTScram and pUTInv constructs are double stranded DNA plasmids of approximately 8.9 kb encoding human ubiquitin-telomerase-based fusion proteins which are enzymatically inactive. The Scrambled and Inverted transgenes were inserted into Invitrogen pcDNA3.1(+) vector (5.4 kb) derived from pcDNA3.0 which was designed for high-level of stable and transient expression in mammalian cells. Transgene expression is driven from human cytomegalovirus immediate-early (CMV) promoter to allow efficient high-level expression in a wide range of mammalian cells. The vector contains multiple cloning sites (MCS) to facilitate cloning. Efficient transcription termination is driven by the Bovine Growth Hormone (BGH) polyadenylation signal.
pUTScram (Named Scrambled)
The Ubi-Scrambled hTERT insert (Scrambled, 1184 AA) starts at position 923 and ends at position 4474 of the pUTScram plasmid (FIG. 20A). pUTScram encodes a human ubiquitin-telomerase-based fusion construct (Scrambled) of 1184 AA corresponding to a protein of approximately 130.2 kDa. hTERT protein was deleted of the 23 first amino-acids (1-23 AA) which were replaced by an ubiquitin polypeptide (76 AA). The catalytic site was inactivated by a 9 bp deletion coding for VDD (* mark; FIG. 28) and corresponding to AA 867-869 of wild-type human telomerase (hTERT; patent WO 2007/014740 and hTERT isoform 1 Accession number NM_198253). hTERT sequence was divided into ten immunogenic fragments and reassembled in the following specific order: fragment 7 (210 bp), fragment 2 (201 bp), fragment 6 (312 bp), fragment 4 (117 bp), fragment 9 (576 bp), fragment 3 (120 bp), fragment 1 (258 bp), fragment 8 (477 bp), fragment 10 (516 bp), fragment 5 (303 bp). These 10 fragments are bridged with 6×Gly linker (SEQ ID NO: 99) (G linker; 18 bp). Consequently, 76 non-immunogenic AA (228 bp) were deleted from hTERT sequence. The 14 amino acids at the C-terminal sequence of the Ubi-hTERT shuffled insert code for the V5 epitope tag (FIG. 22).
pUTInv (Named Inverted)
The Ubi-inverted hTERT insert (Inverted, 1184 AA) starts at position 923 and ends at position 4474 of the pUTInv plasmid (FIG. 20B). pUTInv encodes a human ubiquitin-telomerase-based fusion construct (Inverted) of 1184 AA corresponding to a protein of approximately 130.2 kDa. hTERT protein was deleted of the 23 first amino-acids (1-23 AA) which were replaced by an ubiquitin polypeptide (76 AA). The catalytic site was inactivated by a 9 bp deletion coding for VDD (* mark; FIG. 29) and corresponding to AA 867-869 of wild-type human telomerase (hTERT; patent WO 2007/014740; Accession number NM_198253). hTERT sequence was divided into ten immunogenic fragments and reassembled in the following specific order: fragment 10 (516 bp), fragment 9 (576 bp), fragment 8 (477 bp), fragment 7 (210 bp), fragment 6 (312 bp), fragment 5 (303 bp), fragment 4 (117 bp), fragment 3 (120 bp), fragment 2 (201 bp), fragment 1 (258 bp). These 10 fragments were bridged with 6×Gly linker (SEQ ID NO: 99) (G linker; 18 bp). Consequently, 76 non-immunogenic AA (228 bp) were deleted from hTERT sequence. The 14 amino acids at the C-terminal sequence of the Ubi-hTERT shuffled insert code for the V5 epitope tag (FIG. 22).
Genes Synthesis and Cloning
The genes were de novo synthesized as ubiquitin-telomerase-based fusion constructs through an overlapping 40-mer oligonucleotides assembly process (GeneCust, Luxembourg). Several conservative base changes were made to eliminate restriction sites and attenuate GC rich sequences. Gene synthesis included unique flanking restriction sites HindIII/XbaI to allow subcloning of the gene into desired expression system. The synthesized genes were cloned between HindIII and XbaI restriction sites of the pcDNA3.1 (+) expression vector (Invitrogen, Carlsbad, USA). The sequences of the plasmids were verified by sequencing using PEGFP-N5' CGGTGGGAGGTCTATATAAG (SEQ ID NO: 27) and BGH CAGGGTCAAGGAAGGCAC (SEQ ID NO: 28) primers.
Plasmids Production
These INVAC-1 shuffled derivatives synthetized by GeneCust were transformed and produced in *E. coli* 5-alpha cells (fhuA2Δ(argF-lacZ)U169 phoA glnV44 Φ80 Δ(lacZ)M15 gyrA96 recA1 relA1 endA1 thi-1 hsdR17) (Lucigen Corporation, Middleton, USA, ref. 60602-2) by RD Biotech (Besançon, France). Cells were plated and propagated on Lenox Broth media containing ampicillin (#EU04000D, Euromedex). After extraction and purification, concentrated endotoxin-free gigaprep plasmid stocks (2 mg/mL) resuspended in 1× sterile PBS were prepared. The vectors were verified by restriction mapping (HindIII-XbaI; FIG. 21).
pTRIP-CMV-hTERT
This DNA plasmid was already described in EXAMPLE I.
Cell Cultures and Transient Transfections for Western Blot and TRAP Assays
CrFK (Crandell Rees feline kidney) and HEK293T (Human embryonic kidney) cell lines were cultured in Dulbecco's modified Eagle's medium (DMEM) supplemented with 10% heat-inactivated fetal calf serum (PAA, Velizy-Villacoublay, France) and 1% penicillin/streptomycin (Life Technologies, Saint-Aubin, France).
Cells were grown as monolayers in 75 cm$^2$ flasks at 37° C. in a humidified atmosphere containing 5% $CO_2$. The cells were grown until 70-80% confluence on the day of transfection. For western blot assays, 5×10$^5$ cells were seeded in six-well tissue culture plates and incubated for 24 h. For TRAP assays, 7×10$^5$ cells were seeded in six-well tissue culture plates and incubated for 24 h. INVAC-1, pUTScram and pUTInv constructs were transfected into target cells using jetPrime cationic polymer transfection reagent according to manufacturer's instructions (Polyplus-transfection Inc., France). Cells transfected with pTRIP-CMV-hTERT plasmid was used as positive control and non-transfected cells as negative control. Transfection mediums were removed 4 hours later and replaced by 2 mL of DMEM culture medium. After appropriate time of transfection—18-96 hours for western blot assays and 24 hours for TRAP assays, cells were harvested and analyzed for telomerase expression and activity.
Western Blot
Western blot analyses were performed using transfected HEK293T cells. The western blot procedure is as described in EXAMPLE I.

TRAP Assay

This procedure is as described in EXAMPLE I.

Mice

HLA-B*0702 transgenic mouse strain was used in these experiments.

The HLA-B*0702 transgenic mice express the human HLA-B*0702 α1-α2 domains of the molecule and the murine α3 domain of the H2D molecule. These mice do not express the H2-D$^b$ and H2-K$^b$ molecules (Rohrlich, Cardinaud et al. 2003).

Mice were used between 9 and 15 weeks of age and were supplied by the Pasteur Institute of Paris. Animals were housed at the Specific Pathogen Free animal facility of the Pasteur Institute (Animal Facilities Lwoff n° 22, agreement number B 75 15-07). Prior to intradermal (ID) or intravenous (IV) injection, mice were anesthetized with a mix solution of 2% xylazine (Rompun, Bayer Santé, Loos, France) and 8% Ketamine (Imalgen 1000, Merial, Lyon, France) in 1× Phosphate Buffer Saline (1×PBS, Life Technologies, Saint-Aubin, France) through the intraperitoneal route (IP) according to individual animal weight and duration of anesthesia. All animals were handled in strict accordance with good animal practice and complied with local animal experimentation (Directive 2010/63/UE).

hTERT Peptides hTERT peptides restricted to HLA-B*0702, were previously described in EXAMPLE I. Lyophilized peptides were dissolved in sterile water at 2 mg/mL and stored at −20° C. prior use.

Mouse Immunization and In Vivo Electroporation Procedure

Intradermal (ID) immunization was performed on the lower part of the mouse flank with insulin syringes and specific needles (U-100, 29GX½"-0.33×12 mm, Terumo, Belgium) after shaving. No erythema was observed after shaving, during and after the immunization procedures. Each animal received a priming ID injection of plasmid (INVAC-1, pUTScram or pUTInv) with 100 µg of DNA or 1×PBS. According to the vaccine regimen, mice could receive a similar second injection of DNA or 1×PBS.

In vivo DNA electroporation was performed using the CLINIPORATOR® 2 electroporation system and software (IGEA, Italy) equipped with plate electrodes (P-30-8G, IGEA). Directly after ID vaccination, a skin fold was made at the injection site, entirely covered with conductive gel (Labo FH, blue contact gel, NM Médical, France) and placed between the plate electrodes. Two pulses of different voltages were applied (HV-LV): HV: 1250 V/cm, 1 Hz, 100 µs; 1 pulse, 1000 ms break; LV: 180 V/cm, 1 Hz, 400 ms, 1 pulse.

ELISpot Assay

ELISpot Assay was performed according to the method described in EXAMPLE I. Only a pool of three specific hTERT peptides restricted to HLA-B*0702 (p277, p351 and p1123) was used in Example II.

In Vivo Cytotoxicity Assay

In vivo lysis assay was performed according to the procedure described in EXAMPLE I. Only two specific hTERT peptides restricted to HLA-B*0702 (p351 and p1123) were used respectively as immunodominant and subdominant peptides in Example II.

Statistical Analysis and Data Handling

GraphPad Prism 5 software was used for data handling, analysis and graphic representations. Data are represented as the mean±standard deviation or as median. Statistical analyses of ELISpot assays were performed using a Mann Whitney non parametric and/or a Kruskal-Wallis analysis with Dunn's multiple comparison test. Significance was set at p-value<0.05.

Results

Characterization and Sequence Analysis of INVAC-1 Plasmid DNA

The characterization and sequence analysis of INVAC-1 plasmid DNA were already described in EXAMPLE I.

Characterization and Sequence Analysis of INVAC-1 Shuffled Derivative Constructs (pUTScram and pUTInv)

Two INVAC-1 shuffled derivative genes were synthesized and cloned (FIG. 20). These constructs were based on INVAC-1 nucleotide sequence described in EXAMPLE I and wild-type hTERT amino acid sequence described in international patent application WO 2007/014740.

Codon optimization was carried out for high level expression in mammalian cells (FIG. 27). Scrambled and Inverted Ubi-hTERT shuffled transgenes were successfully ligated into pcDNA3.1(+) Invitrogen expression vector as shown by HindIII and XbaI digestion and electrophoresis (FIG. 21). Inserts and junctions were sequenced using PEGFP-N5' and BGH primers matching the vector sequence flanking the DNA insert. Sequencing results confirmed that transgenes have been correctly cloned (FIGS. 28 and 29).

Figure 23A:
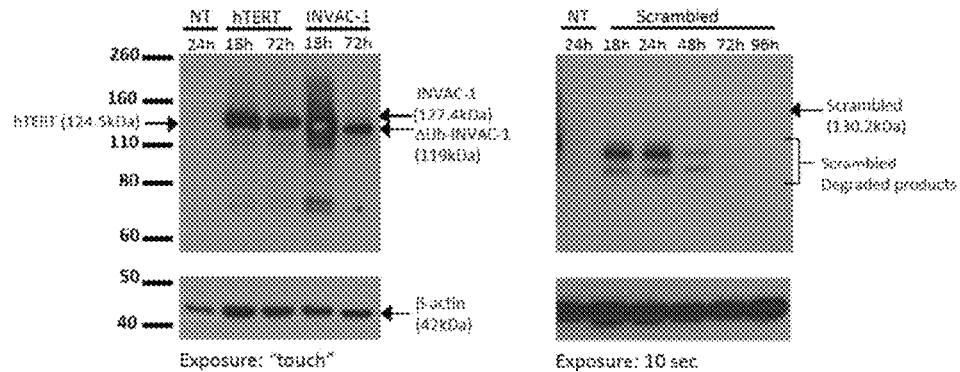
Figure 23B:
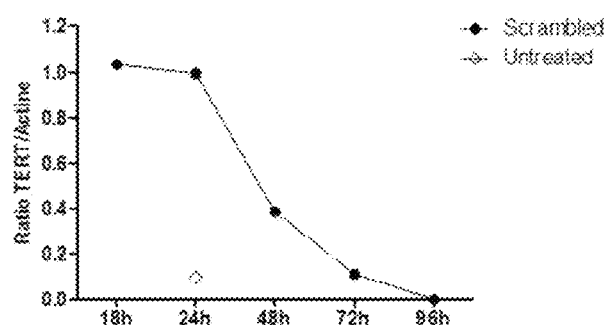
Figure 23C:
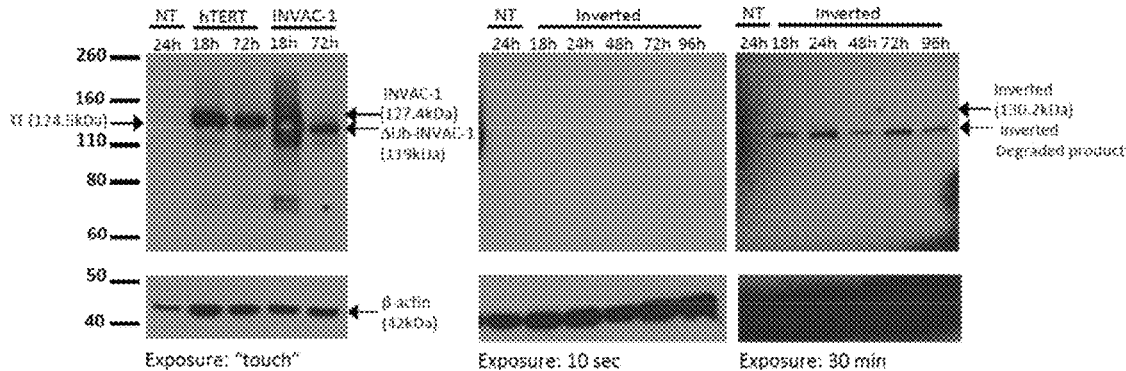
Figure 23D:
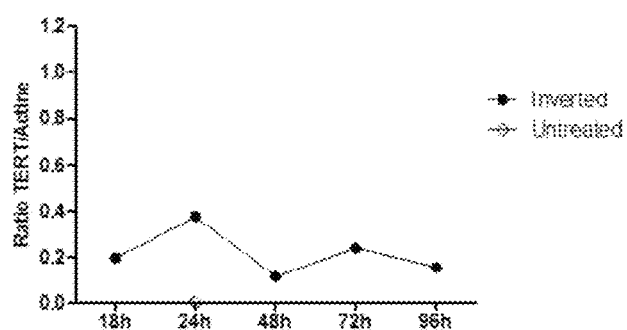

INVAC-1 Shuffled Derivative Proteins are Correctly Expressed In Vitro and Degraded by the Proteasome Pathway Western blot assay was performed to provide information about the global expression of wild-type hTERT, INVAC-1, pUTScram and pUTInv proteins after 18 h to 96 h of in vitro transient transfection into HEK293T cell lines. The bands of wild-type hTERT protein corresponded to the size of unmodified hTERT at 124.5 kDa (FIGS. 23A and 23C, left part of the Figures). In EXAMPLE I, INVAC-1 proteins have been shown to be rapidly degraded over time contrariwise to the wild type hTERT proteins expressed at a stable level. Specific bands for Scrambled and Inverted shuffled proteins were detected over time (FIGS. 23A and 23C, right part of the Figures). For both, these bands were observed at a smaller size (<110 kDa) than predicted size for entire proteins (130.2 kDa). These forms of Scrambled and Inverted proteins correspond to degraded products. Indeed, Scrambled and Inverted expression non-degraded products were not detectable on western blot analysis. These constructs gave respectively from 1 to 3 specific bands suggesting a fast degradation of these proteins just after production. As INVAC-1, the same pattern of degradation over time for Scrambled degraded products was demonstrated after normalization to β-actin loading control (ImageJ analysis; FIG. 23B). Inverted degraded products have a pattern more similar to the others INVAC-1 derivatives proteins (FIGS. 23C, 23D and FIG. 3C: pUTD10Not, pUTD10Cog and pUTD23Tyn, see EXAMPLE I).

INVAC-1 Shuffled Derivatives have a Predominant Cytoplasmic Distribution and a Nucleolar Exclusion Pattern As demonstrated for INVAC-1 and INVAC-1 derivatives (pUTD10Not, pUTD10Cog and pUTD23Tyn, see EXAMPLE I), Scrambled and Inverted shuffled proteins encoded by pUTScram and pUTInv were distributed between nucleus and cytoplasm with a nucleolar exclusion pattern (data not shown).

INVAC-1 Shuffled Derivatives have No Enzymatic Activity

A TRAP assay was performed to evaluate the telomerase activity of Ubi-hTERT shuffled constructs in telomerase negative CrFK cell line. Telomerase activity was only detected in CrFK cells transfected with wild-type hTERT using pTRIP-CMV-hTERT plasmid.

As shown in FIG. 24A, raw absorbance data demonstrated that the level of telomerase activity of Scrambled and Inverted proteins is comparable to the level of untreated cells. Relative Telomerase Activity (RTA) data (FIG. 24B) which represent fully analyzed results taking into account the specificity of the assay by using various negative controls including heat-inactivated samples, confirmed that these shuffled proteins are completely devoid of any telomerase activity.

Shuffled hTERT Constructs Induce hTERT Specific CD8 T-Cell Response pUTScram and pUTInv constructs were designed to induce antigen presentation of multiple hTERT epitopes increasing the scope of INVAC-1 features. Immunogenicity comparison of pUTScram, pUTInv and INVAC-1 was assessed in HLA-B7 mice ID immunized with the different constructs followed by skin electroporation after two cycles of immunization (prime-boost regimen). Animals were sacrificed ten days after the second vaccination/electroporation. Mouse spleens were harvested and the induced CD8 T-cell response was monitored via an IFN-γ ELISPOT assay using hTERT peptides restricted to HLA-B7 MEW class I (pool of 3 peptides p277, p351 and p1123). A significant difference in the frequency of hTERT specific CD8 T-cells was observed in mice vaccinated with INVAC-1, pUTScram (Scrambled) and pUTInv (Inverted) in comparison with control animals (FIG. 25).

These results demonstrate that artificial hTERT shuffled constructs, pUTScram (Scrambled) and pUTInv (Inverted), were capable to induce significant high levels of hTERT specific CD8 T-cell responses after two immunization cycles as INVAC-1 did. Indeed, as previously demonstrated for INVAC-1, the advantage of a prime-boost vaccination regimen is to selectively boost the previous activated specific T-cells and broaden epitope presentation in order to generate secondary hTERT specific T-cell involving new specific TCRs.

Vaccination with Artificial Shuffled hTERT Constructs pUTScram and pUTInv Induce in Vivo Cytotoxic hTERT Specific CD8 T-Cells Among immune cells that are relevant in antitumor immune responses, cytotoxic CD8 T lymphocytes (CTL) and Th1 CD4 T-cells have been identified as the most powerful effector cells (Vesely, Kershaw et al. 2011) (Braumuller, Wieder et al. 2013).

The cytotoxic activity of hTERT specific CD8 T-cells was investigated in vivo after ID vaccination/electroporation with INVAC-1, pUTScram and pUTInv. In order to measure the in vivo cytolytic strength of the hTERT specific CD8$^+$ T-cell response elicited by DNA immunization, an in vivo cytotoxicity assay was performed using carboxyfluorescein-diacetate succinimidyl ester (CFSE)-labelled and peptide-pulsed splenocytes as target cells. HLA-B7 transgenic mice which received one vaccination with DNA constructs (or PBS as control) via the ID route, as described before, were intravenously injected with $10^7$ target cells. Target cells were splenocytes from naive congenic mice independently labelled with 3 different concentrations of CFSE and pulsed with either a hTERT peptide restricted to HLA-B7 (p351, immunodominant peptide or p1123, subdominant peptide) or left unpulsed as an internal control. After 15-18 hours, spleens of immunized mice were harvested and splenocyte suspensions were analysed by flow cytometry. The percentage of specific lysis was evaluated by comparing the ratio of pulsed to unpulsed CFSE labeled cells in vaccinated mice versus control mice.

Results show that all mice immunized with the different constructs developed hTERT specific cytotoxic T lymphocytes (CTLs) after one immunization.

As expected, the cytotoxicity against the immunodominant peptide p351 was higher than against the subdominant peptide p1123 for the three groups (FIG. 26).

Immunization with INVAC-1 and pUTInv led to a specific lysis of telomerase immune-dominant (p351) epitopes-bearing target cells of 37% and 35%, respectively (FIG. 26, black dots). In comparison, immunization with pUTScram led to a specific lysis of 20%. Two INVAC-1 immunized mice out of five and one pUTScram out of six developed specific CTLs against the subdominant peptide p1123 (FIG. 26, grey dots).

As stated previously, it can be expected that multiple injection cycles would allow increasing the number of animals that develop a specific CTL lysis against both immunodominant and subdominant peptides. Indeed, previous results (see EXAMPLE I) demonstrated that a second immunization widens the breadth of the immune response against subdominant epitopes.

In conclusion, as INVAC-1, artificial shuffled hTERT Scrambled or Inverted-mediated immunization can generate hTERT specific CD8 T-cells that exhibit in vivo cytolytic activity.

REFERENCES

Adolph, K. 1996 ed. "Viral Genome Methods" CRC Press, Florida

Adotevi, O., Mollier, K., Neuveut, C., Cardinaud, S., Boulanger, E., Mignen, B., Fridman, W. H., Zanetti, M., Charneau, P., Tartour, E., et al. (2006). Immunogenic HLA-B*0702-restricted epitopes derived from human telomerase reverse transcriptase that elicit antitumor cytotoxic T-cell responses. Clin Cancer Res 12, 3158-3167.

Andersson, H. A., and Barry, M. A. (2004). Maximizing antigen targeting to the proteasome for gene-based vaccines. Mol Ther 10, 432-446.

Bachmair, A., Finley, D., and Varshaysky, A. (1986). In vivo half-life of a protein is a function of its amino-terminal residue. Science 234, 179-186.

Braumuller, H., Wieder, T., Brenner, E., Assmann, S., Hahn, M., Alkhaled, M., Schilbach, K., Essmann, F., Kneilling, M., Griessinger, C., et al. (2013). T-helper-1-cell cytokines drive cancer into senescence. Nature 494, 361-365.

Cadima-Couto, I., Freitas-Vieira, A., Nowarski, R., Britan-Rosich, E., Kotler, M., and Goncalves, J. (2009). Ubiquitin-fusion as a strategy to modulate protein half-life: A3G antiviral activity revisited. Virology 393, 286-294.

Cheever et al., The prioritization of cancer antigens: a national cancer institute pilot project for the acceleration of translational research. Clin Cancer Res, 2009. 15(17): p. 5323-37.

Combadiere, B., and Liard, C. (2011). Transcutaneous and intradermal vaccination. Human Vaccines 7, 811-827.

Cortez-Gonzalez, X., Sidney, J., Adotevi, O., Sette, A., Millard, F., Lemonnier, F., Langlade-Demoyen, P., and Zanetti, M. (2006). Immunogenic HLA-B7-restricted peptides of hTRT. Int Immunol 18, 1707-1718.

Dosset, M., Godet, Y., Vauchy, C., Beziaud, L., Lone, Y. C., Sedlik, C., Liard, C., Levionnois, E., Clerc, B., Sandoval, F., et al. (2012). Universal cancer peptide-based therapeutic vaccine breaks tolerance against telomerase and eradicates established tumor. Clin Cancer Res 18, 6284-6295.

Firat, H., Cochet, M., Rohrlich, P. S., Garcia-Pons, F., Darche, S., Danos, O., Lemonnier, F. A., and Langlade-Demoyen, P. (2002). Comparative analysis of the CD8(+) T cell repertoires of H-2 class I wild-type/HLA-A2.1 and H-2 class I knockout/HLA-A2.1 transgenic mice. Internat Immunol 14, 925-934.

Godet, Y., Fabre-Guillevin, E., Dosset, M., Lamuraglia, M., Levionnois, E., Ravel, P., Benhamouda, N., Cazes, A., Le Pimpec-Barthes, F., Gaugler, B., et al. (2012). Analysis of spontaneous tumor-specific CD4 T cell immunity in lung cancer using promiscuous HLA-DR telomerase-derived epitopes: potential synergistic effect with chemotherapy response. Clin Cancer Res 18, 2943-2953.

Lavigueur, A., H. La Branche, et al. (1993). A splicing enhancer in the human fibronectin alternate ED1 exon interacts with SR proteins and stimulates U2 snRNP binding. Genes Dev 7: 2405-2417.

Michalek, M. T., Grant, E. P., Gramm, C., Goldberg, A. L., and Rock, K. L. (1993). A role for the ubiquitin-dependent proteolytic pathway in MHC class I-restricted antigen presentation. Nature 363, 552-554.

Mir L M. 2008. Application of electroporation gene therapy: past, current, and future. Methods Mol Biol 423: 3-17.

Murray, 1991, ed. "Gene Transfer and Expression Protocols" Humana Pres, Clifton, N.J.

Pajot, A., Michel, M. L., Fazilleau, N., Pancre, V., Auriault, C., Ojcius, D. M., Lemonnier, F. A., and Lone, Y. C. (2004). A mouse model of human adaptive immune functions: HLA-A2.1-/HLA-DR1-transgenic H-2 class I-/class II-knockout mice. Eur J Immunol 34, 3060-3069.

Parmiani, G., Castelli, C., Pilla, L., Santinami, M., Colombo, M. P., and Rivoltini, L. (2007). Opposite immune functions of GM-CSF administered as vaccine adjuvant in cancer patients. Ann Oncol 18, 226-232.

Rohrlich, P. S., Cardinaud, S., Firat, H., Lamari, M., Briand, P., Escriou, N., and Lemonnier, F. A. (2003). HLA-B*0702 transgenic, H-2KbDb double-knockout mice: phenotypical and functional characterization in response to influenza virus. Int Immunol 15, 765-772.

Rosenberg S A, Yang J C, Restifo N P (2004). Cancer immunotherapy: moving beyond current vaccines. Nat Med. 10:909-15.

Sardesai N Y, Weiner D B. 2011. Electroporation delivery of DNA vaccines: prospects for success. Curr Opin Immunol 23: 421-429.

Tasaki, T., Sriram, S. M., Park, K. S., and Kwon, Y. T. (2012). The N-end rule pathway. Annu Rev Biochem 81, 261-289.

Varshaysky, A. (1996). The N-end rule: functions, mysteries, uses. Proc Natl Acad Sci USA 93, 12142-12149.

Vesely, M. D., Kershaw, M. H., Schreiber, R. D., and Smyth, M. J. (2011). Natural innate and adaptive immunity to cancer. Annu Rev Immunol 29, 235-271.

Yang, 1992, "Gene transfer into mammalian somatic cells in vivo", Crit. Rev. Biotech. 12: 335-356

Yang, Y., Chen, Y., Zhang, C., Huang, H., and Weissman, S. M. (2002). Nucleolar localization of hTERT protein is associated with telomerase function. Exp Cell Res 277, 201-209.

The invention claimed is:

1. A nucleic acid molecule comprising a sequence encoding a fusion protein which comprises the amino acid sequence of a human telomerase reverse transcriptase (hTERT) protein, wherein the hTERT protein
   (i) is devoid of telomerase catalytic activity by deletion of amino acids VDD corresponding to residues 867-869 of SEQ ID NO: 2 within the hTERT catalytic site and by deletion of 1 to 12 amino acids upstream and/or downstream from VDD as compared to wild-type hTERT protein,
   (ii) is devoid of a nucleolar localization signal sequence by deletion of at least amino acids 1-23 as compared to wild-type hTERT protein, and
   (iii) is fused to an amino acid sequence which enhances the addressing of the hTERT protein to a proteasome; wherein the amino acid sequence of the fusion protein consists of SEQ ID NO: 14, 16 or 18.

2. The nucleic acid molecule of claim 1, wherein the nucleic acid is a DNA molecule.

3. A method for triggering an immune response in a subject, against cells that overexpress telomerase, wherein the method comprises administering to the subject an effective amount of the nucleic acid molecule of claim 1.

4. The method of claim 3, wherein the cells that overexpress telomerase are dysplasia cells, tumor cells, or cells infected by an oncovirus.

5. A method for preventing or treating a tumor in a subject in need thereof, wherein the method comprises administering to the subject an effective amount of the nucleic acid-molecule of claim 1.

6. An immunogenic composition comprising (a) the nucleic acid molecule of claim 1 and (b) a carrier and/or excipient.

* * * * *

SEQUENCE LISTING

```
<160> NUMBER OF SEQ ID NOS: 101

<210> SEQ ID NO 1
<211> LENGTH: 4018
<212> TYPE: DNA
<213> ORGANISM: Homo sapiens
<220> FEATURE:
<221> NAME/KEY: CDS
<222> LOCATION: (59)..(3454)

<400> SEQUENCE: 1
caggcagcgc tgcgtcctgc tgcgcacgtg ggaagccctg gccccggcca ccccgcg        58 atg ccg cgc gct ccc cgc tgc cga gcc gtg cgc tcc ctg ctg cgc agc     106
Met Pro Arg Ala Pro Arg Cys Arg Ala Val Arg Ser Leu Leu Arg Ser
1               5                   10                  15 cac tac cgc gag gtg ctg ccg ctg gcc acg ttc gtg cgg cgc ctg ggg     154
His Tyr Arg Glu Val Leu Pro Leu Ala Thr Phe Val Arg Arg Leu Gly
            20                  25                  30 ccc cag ggc tgg cgg ctg gtg cag cgc ggg gac ccg gcg gct ttc cgc     202
Pro Gln Gly Trp Arg Leu Val Gln Arg Gly Asp Pro Ala Ala Phe Arg
        35                  40                  45 gcg ctg gtg gcc cag tgc ctg gtg tgc gtg ccc tgg gac gca cgg ccg     250
Ala Leu Val Ala Gln Cys Leu Val Cys Val Pro Trp Asp Ala Arg Pro
    50                  55                  60 ccc ccc gcc gcc ccc tcc ttc cgc cag gtg tcc tgc ctg aag gag ctg     298
Pro Pro Ala Ala Pro Ser Phe Arg Gln Val Ser Cys Leu Lys Glu Leu
65                  70                  75                  80 gtg gcc cga gtg ctg cag agg ctg tgc gag cgc ggc gcg aag aac gtg     346
Val Ala Arg Val Leu Gln Arg Leu Cys Glu Arg Gly Ala Lys Asn Val
                85                  90                  95
```

-continued

| | |
|---|---|
| ctg gcc ttc ggc ttc gcg ctg ctg gac ggg gcc cgg ggc ccc ccc<br>Leu Ala Phe Gly Phe Ala Leu Leu Asp Gly Ala Arg Gly Pro Pro<br>100           105                110 | 394 |
| gag gcc ttc acc acc agc gtg cgc agc tac ctg ccc aac acg gtg acc<br>Glu Ala Phe Thr Thr Ser Val Arg Ser Tyr Leu Pro Asn Thr Val Thr<br>115                120                125 | 442 |
| gac gca ctg cgg ggg agc ggg gcg tgg ggg ctg ctg cgc cgc gtg<br>Asp Ala Leu Arg Gly Ser Gly Ala Trp Gly Leu Leu Leu Arg Arg Val<br>130           135                140 | 490 |
| ggc gac gac gtg ctg gtt cac ctg ctg gca cgc tgc gcg ctc ttt gtg<br>Gly Asp Asp Val Leu Val His Leu Leu Ala Arg Cys Ala Leu Phe Val<br>145                150                155                160 | 538 |
| ctg gtg gct ccc agc tgc gcc tac cag gtg tgc ggg ccg ccg ctg tac<br>Leu Val Ala Pro Ser Cys Ala Tyr Gln Val Cys Gly Pro Pro Leu Tyr<br>                165                170                175 | 586 |
| cag ctc ggc gct gcc act cag gcc cgg ccc ccg cca cac gct agt gga<br>Gln Leu Gly Ala Ala Thr Gln Ala Arg Pro Pro Pro His Ala Ser Gly<br>          180                185                190 | 634 |
| ccc cga agg cgt ctg gga tgc gaa cgg gcc tgg aac cat agc gtc agg<br>Pro Arg Arg Arg Leu Gly Cys Glu Arg Ala Trp Asn His Ser Val Arg<br>195                200                205 | 682 |
| gag gcc ggg gtc ccc ctg ggc ctg cca gcc ccg ggt gcg agg agg cgc<br>Glu Ala Gly Val Pro Leu Gly Leu Pro Ala Pro Gly Ala Arg Arg Arg<br>210                215                220 | 730 |
| ggg ggc agt gcc agc cga agt ctg ccg ttg ccc aag agg ccc agg cgt<br>Gly Gly Ser Ala Ser Arg Ser Leu Pro Leu Pro Lys Arg Pro Arg Arg<br>225                230                235                240 | 778 |
| ggc gct gcc cct gag ccg gag cgg acg ccc gtt ggg cag ggg tcc tgg<br>Gly Ala Ala Pro Glu Pro Glu Arg Thr Pro Val Gly Gln Gly Ser Trp<br>                245                250                255 | 826 |
| gcc cac ccg ggc agg acg cgt gga ccg agt gac cgt ggt ttc tgt gtg<br>Ala His Pro Gly Arg Thr Arg Gly Pro Ser Asp Arg Gly Phe Cys Val<br>          260                265                270 | 874 |
| gtg tca cct gcc aga ccc gcc gaa gaa gcc acc tct ttg gag ggt gcg<br>Val Ser Pro Ala Arg Pro Ala Glu Glu Ala Thr Ser Leu Glu Gly Ala<br>275                280                285 | 922 |
| ctc tct ggc acg cgc cac tcc cac cca tcc gtg ggc cgc cag cac cac<br>Leu Ser Gly Thr Arg His Ser His Pro Ser Val Gly Arg Gln His His<br>290                295                300 | 970 |
| gcg ggc ccc cca tcc aca tcg cgg cca cca cgt ccc tgg gac acg cct<br>Ala Gly Pro Pro Ser Thr Ser Arg Pro Pro Arg Pro Trp Asp Thr Pro<br>305                310                315                320 | 1018 |
| tgt ccc ccg gtg tac gcc gag acc aag cac ttc ctc tac tcc tca ggc<br>Cys Pro Pro Val Tyr Ala Glu Thr Lys His Phe Leu Tyr Ser Ser Gly<br>                325                330                335 | 1066 |
| gac aag gag cag ctg cgg ccc tcc ttc cta ctc agc tct ctg agg ccc<br>Asp Lys Glu Gln Leu Arg Pro Ser Phe Leu Leu Ser Ser Leu Arg Pro<br>          340                345                350 | 1114 |
| agc ctg act ggc gct cgg agg ctc gtg gag acc atc ttt ctg ggt tcc<br>Ser Leu Thr Gly Ala Arg Arg Leu Val Glu Thr Ile Phe Leu Gly Ser<br>355                360                365 | 1162 |
| agg ccc tgg atg cca ggg act ccc cgc agg ttg ccc cgc ctg ccc cag<br>Arg Pro Trp Met Pro Gly Thr Pro Arg Arg Leu Pro Arg Leu Pro Gln<br>370                375                380 | 1210 |
| cgc tac tgg caa atg cgg ccc ctg ttt ctg gag ctg ctt ggg aac cac<br>Arg Tyr Trp Gln Met Arg Pro Leu Phe Leu Glu Leu Leu Gly Asn His<br>385                390                395                400 | 1258 |

-continued

```
gcg cag tgc ccc tac ggg gtg ctc ctc aag acg cac tgc ccg ctg cga    1306
Ala Gln Cys Pro Tyr Gly Val Leu Leu Lys Thr His Cys Pro Leu Arg
            405                 410                 415 gct gcg gtc acc cca gca gcc ggt gtc tgt gcc cgg gag aag ccc cag    1354
Ala Ala Val Thr Pro Ala Ala Gly Val Cys Ala Arg Glu Lys Pro Gln
        420                 425                 430 ggc tct gtg gcg gcc ccc gag gag gag gac aca gac ccc cgt cgc ctg    1402
Gly Ser Val Ala Ala Pro Glu Glu Glu Asp Thr Asp Pro Arg Arg Leu
    435                 440                 445 gtg cag ctg ctc cgc cag cac agc agc ccc tgg cag gtg tac ggc ttc    1450
Val Gln Leu Leu Arg Gln His Ser Ser Pro Trp Gln Val Tyr Gly Phe
450                 455                 460 gtg cgg gcc tgc ctg cgc cgg ctg gtg ccc cca ggc ctc tgg ggc tcc    1498
Val Arg Ala Cys Leu Arg Arg Leu Val Pro Pro Gly Leu Trp Gly Ser
465                 470                 475                 480 agg cac aac gaa cgc cgc ttc ctc agg aac acc aag aag ttc atc tcc    1546
Arg His Asn Glu Arg Arg Phe Leu Arg Asn Thr Lys Lys Phe Ile Ser
                485                 490                 495 ctg ggg aag cat gcc aag ctc tcg ctg cag gag ctg acg tgg aag atg    1594
Leu Gly Lys His Ala Lys Leu Ser Leu Gln Glu Leu Thr Trp Lys Met
            500                 505                 510 agc gtg cgg gac tgc gct tgg ctg cgc agg agc cca ggg gtt ggc tgt    1642
Ser Val Arg Asp Cys Ala Trp Leu Arg Arg Ser Pro Gly Val Gly Cys
        515                 520                 525 gtt ccg gcc gca gag cac cgt ctg cgt gag gag atc ctg gcc aag ttc    1690
Val Pro Ala Ala Glu His Arg Leu Arg Glu Glu Ile Leu Ala Lys Phe
    530                 535                 540 ctg cac tgg ctg atg agt gtg tac gtc gtc gag ctg ctc agg tct ttc    1738
Leu His Trp Leu Met Ser Val Tyr Val Val Glu Leu Leu Arg Ser Phe
545                 550                 555                 560 ttt tat gtc acg gag acc acg ttt caa aag aac agg ctc ttt ttc tac    1786
Phe Tyr Val Thr Glu Thr Thr Phe Gln Lys Asn Arg Leu Phe Phe Tyr
                565                 570                 575 cgg aag agt gtc tgg agc aag ttg caa agc att gga atc aga cag cac    1834
Arg Lys Ser Val Trp Ser Lys Leu Gln Ser Ile Gly Ile Arg Gln His
            580                 585                 590 ttg aag agg gtg cag ctg cgg gag ctg tcg gaa gca gag gtc agg cag    1882
Leu Lys Arg Val Gln Leu Arg Glu Leu Ser Glu Ala Glu Val Arg Gln
        595                 600                 605 cat cgg gaa gcc agg ccc gcc ctg ctg acg tcc aga ctc cgc ttc atc    1930
His Arg Glu Ala Arg Pro Ala Leu Leu Thr Ser Arg Leu Arg Phe Ile
    610                 615                 620 ccc aag cct gac ggg ctg cgg ccg att gtg aac atg gac tac gtc gtg    1978
Pro Lys Pro Asp Gly Leu Arg Pro Ile Val Asn Met Asp Tyr Val Val
625                 630                 635                 640 gga gcc aga acg ttc cgc aga gaa aag agg gcc gag cgt ctc acc tcg    2026
Gly Ala Arg Thr Phe Arg Arg Glu Lys Arg Ala Glu Arg Leu Thr Ser
                645                 650                 655 agg gtg aag gca ctg ttc agc gtg ctc aac tac gag cgg gcg cgg cgc    2074
Arg Val Lys Ala Leu Phe Ser Val Leu Asn Tyr Glu Arg Ala Arg Arg
            660                 665                 670 ccc ggc ctc ctg ggc gcc tct gtg ctg ggc ctg gac gat atc cac agg    2122
Pro Gly Leu Leu Gly Ala Ser Val Leu Gly Leu Asp Asp Ile His Arg
        675                 680                 685 gcc tgg cgc acc ttc gtg ctg cgt gtg cgg gcc cag gac ccg ccg cct    2170
Ala Trp Arg Thr Phe Val Leu Arg Val Arg Ala Gln Asp Pro Pro Pro
    690                 695                 700
```

```
gag ctg tac ttt gtc aag gtg gat gtg acg ggc gcg tac gac acc atc    2218
Glu Leu Tyr Phe Val Lys Val Asp Val Thr Gly Ala Tyr Asp Thr Ile
705                 710                 715                 720 ccc cag gac agg ctc acg gag gtc atc gcc agc atc atc aaa ccc cag    2266
Pro Gln Asp Arg Leu Thr Glu Val Ile Ala Ser Ile Ile Lys Pro Gln
            725                 730                 735 aac acg tac tgc gtg cgt cgg tat gcc gtg gtc cag aag gcc gcc cat    2314
Asn Thr Tyr Cys Val Arg Arg Tyr Ala Val Val Gln Lys Ala Ala His
        740                 745                 750 ggg cac gtc cgc aag gcc ttc aag agc cac gtc tct acc ttg aca gac    2362
Gly His Val Arg Lys Ala Phe Lys Ser His Val Ser Thr Leu Thr Asp
    755                 760                 765 ctc cag ccg tac atg cga cag ttc gtg gct cac ctg cag gag acc agc    2410
Leu Gln Pro Tyr Met Arg Gln Phe Val Ala His Leu Gln Glu Thr Ser
770                 775                 780 ccg ctg agg gat gcc gtc gtc atc gag cag agc tcc tcc ctg aat gag    2458
Pro Leu Arg Asp Ala Val Val Ile Glu Gln Ser Ser Ser Leu Asn Glu
785                 790                 795                 800 gcc agc agt ggc ctc ttc gac gtc ttc cta cgc ttc atg tgc cac cac    2506
Ala Ser Ser Gly Leu Phe Asp Val Phe Leu Arg Phe Met Cys His His
            805                 810                 815 gcc gtg cgc atc agg ggc aag tcc tac gtc cag tgc cag ggg atc ccg    2554
Ala Val Arg Ile Arg Gly Lys Ser Tyr Val Gln Cys Gln Gly Ile Pro
        820                 825                 830 cag ggc tcc atc ctc tcc acg ctg ctc tgc agc ctg tgc tac ggc gac    2602
Gln Gly Ser Ile Leu Ser Thr Leu Leu Cys Ser Leu Cys Tyr Gly Asp
    835                 840                 845 atg gag aac aag ctg ttt gcg ggg att cgg cgg gac ggg ctc ctc ctg    2650
Met Glu Asn Lys Leu Phe Ala Gly Ile Arg Arg Asp Gly Leu Leu Leu
850                 855                 860 cgt ttg gtg gat gat ttc ttg ttg gtg aca cct cac ctc acc cac gcg    2698
Arg Leu Val Asp Asp Phe Leu Leu Val Thr Pro His Leu Thr His Ala
865                 870                 875                 880 aaa acc ttc ctc agg acc ctg gtc cga ggt gtc cct gag tat ggc tgc    2746
Lys Thr Phe Leu Arg Thr Leu Val Arg Gly Val Pro Glu Tyr Gly Cys
            885                 890                 895 gtg gtg aac ttg cgg aag aca gtg gtg aac ttc cct gta gaa gac gag    2794
Val Val Asn Leu Arg Lys Thr Val Val Asn Phe Pro Val Glu Asp Glu
        900                 905                 910 gcc ctg ggt ggc acg gct ttt gtt cag atg ccg gcc cac ggc cta ttc    2842
Ala Leu Gly Gly Thr Ala Phe Val Gln Met Pro Ala His Gly Leu Phe
    915                 920                 925 ccc tgg tgc ggc ctg ctg ctg gat acc cgg acc ctg gag gtg cag agc    2890
Pro Trp Cys Gly Leu Leu Leu Asp Thr Arg Thr Leu Glu Val Gln Ser
930                 935                 940 gac tac tcc agc tat gcc cgg acc tcc atc aga gcc agt ctc acc ttc    2938
Asp Tyr Ser Ser Tyr Ala Arg Thr Ser Ile Arg Ala Ser Leu Thr Phe
945                 950                 955                 960 aac cgc ggc ttc aag gct ggg agg aac atg cgt cgc aaa ctc ttt ggg    2986
Asn Arg Gly Phe Lys Ala Gly Arg Asn Met Arg Arg Lys Leu Phe Gly
            965                 970                 975 gtc ttg cgg ctg aag tgt cac agc ctg ttt ctg gat ttg cag gtg aac    3034
Val Leu Arg Leu Lys Cys His Ser Leu Phe Leu Asp Leu Gln Val Asn
        980                 985                 990 agc ctc cag acg gtg tgc acc aac atc tac aag atc ctc ctg ctg cag    3082
Ser Leu Gln Thr Val Cys Thr Asn Ile Tyr Lys Ile Leu Leu Leu Gln
    995                 1000                1005
```

-continued

```
gcg tac agg ttt cac gca tgt gtg ctg cag ctc cca ttt cat cag      3127
Ala Tyr Arg Phe His Ala Cys Val Leu Gln Leu Pro Phe His Gln
    1010                1015                1020 caa gtt tgg aag aac ccc aca ttt ttc ctg cgc gtc atc tct gac      3172
Gln Val Trp Lys Asn Pro Thr Phe Phe Leu Arg Val Ile Ser Asp
1025                1030                1035 acg gcc tcc ctc tgc tac tcc atc ctg aaa gcc aag aac gca ggg      3217
Thr Ala Ser Leu Cys Tyr Ser Ile Leu Lys Ala Lys Asn Ala Gly
    1040                1045                1050 atg tcg ctg ggg gcc aag ggc gcc gcc ggc cct ctg ccc tcc gag      3262
Met Ser Leu Gly Ala Lys Gly Ala Ala Gly Pro Leu Pro Ser Glu
        1055                1060                1065 gcc gtg cag tgg ctg tgc cac caa gca ttc ctg ctc aag ctg act      3307
Ala Val Gln Trp Leu Cys His Gln Ala Phe Leu Leu Lys Leu Thr
    1070                1075                1080 cga cac cgt gtc acc tac gtg cca ctc ctg ggg tca ctc agg aca      3352
Arg His Arg Val Thr Tyr Val Pro Leu Leu Gly Ser Leu Arg Thr
1085                1090                1095 gcc cag acg cag ctg agt cgg aag ctc ccg ggg acg acg ctg act      3397
Ala Gln Thr Gln Leu Ser Arg Lys Leu Pro Gly Thr Thr Leu Thr
    1100                1105                1110 gcc ctg gag gcc gca gcc aac ccg gca ctg ccc tca gac ttc aag      3442
Ala Leu Glu Ala Ala Ala Asn Pro Ala Leu Pro Ser Asp Phe Lys
        1115                1120                1125 acc atc ctg gac tgatggccac ccgcccacag ccaggccgag agcagacacc     3494
Thr Ile Leu Asp
    1130 agcagccctg tcacgccggg ctctacgtcc cagggaggga ggggcggccc acacccaggc  3554 ccgcaccgct gggagtctga ggcctgagtg agtgtttggc cgaggcctgc atgtccggct  3614 gaaggctgag tgtccggctg aggcctgagc gagtgtccag ccaagggctg agtgtccagc  3674 acacctgccg tcttcacttc cccacaggct ggcgctcggc tccacccag ggccagcttt   3734 tcctcaccag gagcccggct tccactcccc acataggaat agtccatccc cagattcgcc   3794 attgttcacc cctcgccctg ccctcctttg ccttccaccc ccaccatcca ggtgagacc    3854 ctgagaagga ccctgggagc tctgggaatt tggagtgacc aaaggtgtgc cctgtacaca   3914 ggcgaggacc ctgcacctgg atggggggtcc ctgtgggtca aattgggggg aggtgctgtg   3974 ggagtaaaat actgaatata tgagtttttc agttttgaaa aaaa                    4018
```

<210> SEQ ID NO 2
<211> LENGTH: 1132
<212> TYPE: PRT
<213> ORGANISM: Homo sapiens

<400> SEQUENCE: 2

```
Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80
```

```
Val Ala Arg Val Leu Gln Arg Leu Cys Glu Arg Gly Ala Lys Asn Val
                 85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
            115                 120                 125

Asp Ala Leu Arg Gly Ser Gly Ala Trp Gly Leu Leu Arg Arg Val
130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro His Ala Ser Gly
            180                 185                 190

Pro Arg Arg Arg Leu Gly Cys Glu Arg Ala Trp Asn His Ser Val Arg
            195                 200                 205

Glu Ala Gly Val Pro Leu Gly Leu Pro Ala Pro Gly Ala Arg Arg Arg
210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
            275                 280                 285

Leu Ser Gly Thr Arg His Ser His Pro Ser Val Gly Arg Gln His His
            290                 295                 300

Ala Gly Pro Pro Ser Thr Ser Arg Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
            355                 360                 365

Arg Pro Trp Met Pro Gly Thr Pro Arg Arg Leu Pro Arg Leu Pro Gln
370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Asp Thr Asp Pro Arg Arg Leu
            435                 440                 445

Val Gln Leu Leu Arg Gln His Ser Ser Pro Trp Gln Val Tyr Gly Phe
450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495
```

```
Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
            515                 520                 525

Val Pro Ala Ala Glu His Arg Leu Arg Glu Ile Leu Ala Lys Phe
    530                 535                 540

Leu His Trp Leu Met Ser Val Tyr Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
            595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
    770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
        835                 840                 845

Met Glu Asn Lys Leu Phe Ala Gly Ile Arg Arg Asp Gly Leu Leu Leu
    850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
            900                 905                 910
```

Ala Leu Gly Gly Thr Ala Phe Val Gln Met Pro Ala His Gly Leu Phe
        915                 920                 925

Pro Trp Cys Gly Leu Leu Asp Thr Arg Thr Leu Glu Val Gln Ser
    930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Lys Leu Phe Gly
                965                 970                 975

Val Leu Arg Leu Lys Cys His Ser Leu Phe Leu Asp Leu Gln Val Asn
            980                 985                 990

Ser Leu Gln Thr Val Cys Thr Asn Ile Tyr Lys Ile Leu Leu Leu Gln
        995                 1000                1005

Ala Tyr Arg Phe His Ala Cys Val Leu Gln Leu Pro Phe His Gln
    1010                1015                1020

Gln Val Trp Lys Asn Pro Thr Phe Phe Leu Arg Val Ile Ser Asp
    1025                1030                1035

Thr Ala Ser Leu Cys Tyr Ser Ile Leu Lys Ala Lys Asn Ala Gly
    1040                1045                1050

Met Ser Leu Gly Ala Lys Gly Ala Ala Gly Pro Leu Pro Ser Glu
    1055                1060                1065

Ala Val Gln Trp Leu Cys His Gln Ala Phe Leu Leu Lys Leu Thr
    1070                1075                1080

Arg His Arg Val Thr Tyr Val Pro Leu Leu Gly Ser Leu Arg Thr
    1085                1090                1095

Ala Gln Thr Gln Leu Ser Arg Lys Leu Pro Gly Thr Thr Leu Thr
    1100                1105                1110

Ala Leu Glu Ala Ala Ala Asn Pro Ala Leu Pro Ser Asp Phe Lys
    1115                1120                1125

Thr Ile Leu Asp
    1130

<210> SEQ ID NO 3
<211> LENGTH: 3246
<212> TYPE: DNA
<213> ORGANISM: Homo sapiens
<220> FEATURE:
<221> NAME/KEY: CDS
<222> LOCATION: (1)..(3246)

<400> SEQUENCE: 3 cgc gct ctg gtg gcc cag tgc ctg gtg tgc gtg ccc tgg gac gca cgg      48
Arg Ala Leu Val Ala Gln Cys Leu Val Cys Val Pro Trp Asp Ala Arg
1               5                   10                  15 cca ccc cct gcc gca ccc tca ttc cgc caa gtg tcc tgc ctg aag gag      96
Pro Pro Pro Ala Ala Pro Ser Phe Arg Gln Val Ser Cys Leu Lys Glu
                20                  25                  30 ctg gtg gcc cga gtg ctg cag agg ctg tgc gag cgc ggc gcg aag aac     144
Leu Val Ala Arg Val Leu Gln Arg Leu Cys Glu Arg Gly Ala Lys Asn
            35                  40                  45 gtg ctg gcc ttc ggc ttc gcg ctg ctg gac ggg gct cgc gga ggc cca     192
Val Leu Ala Phe Gly Phe Ala Leu Leu Asp Gly Ala Arg Gly Gly Pro
        50                  55                  60 ccc gag gcc ttc acc acc agc gtg cgc agc tac ctg ccc aac acg gtg     240
Pro Glu Ala Phe Thr Thr Ser Val Arg Ser Tyr Leu Pro Asn Thr Val
65                  70                  75                  80

|     |     |     |     |     |     |     |     |     |     |     |     |     |     |     |     |     |
|---|---|---|---|---|---|---|---|---|---|---|---|---|---|---|---|---|
| acc | gac | gca | ctg | cgg | ggg | agc | ggg | gcg | tgg | ggg | ctg | ctg | ttg | cgc | cgc | 288 |
| Thr | Asp | Ala | Leu | Arg | Gly | Ser | Gly | Ala | Trp | Gly | Leu | Leu | Leu | Arg | Arg |  |
|  |  |  | 85 |  |  |  | 90 |  |  |  |  | 95 |  |  |  |  |
| gtg | ggc | gac | gac | gtg | ctg | gtt | cac | ctg | ctg | gca | cgc | tgc | gcg | ctc | ttt | 336 |
| Val | Gly | Asp | Asp | Val | Leu | Val | His | Leu | Leu | Ala | Arg | Cys | Ala | Leu | Phe |  |
|  |  |  | 100 |  |  |  | 105 |  |  |  |  | 110 |  |  |  |  |
| gtg | ctg | gtg | gct | ccc | agc | tgc | gcc | tac | cag | gtg | tgc | ggg | ccg | ccg | ctg | 384 |
| Val | Leu | Val | Ala | Pro | Ser | Cys | Ala | Tyr | Gln | Val | Cys | Gly | Pro | Pro | Leu |  |
|  |  | 115 |  |  |  |  | 120 |  |  |  |  | 125 |  |  |  |  |
| tac | cag | ctc | ggc | gct | gcc | act | cag | gca | cgg | cct | cca | cct | cac | gct | agt | 432 |
| Tyr | Gln | Leu | Gly | Ala | Ala | Thr | Gln | Ala | Arg | Pro | Pro | Pro | His | Ala | Ser |  |
|  | 130 |  |  |  |  | 135 |  |  |  |  | 140 |  |  |  |  |  |
| gga | ccc | cga | agg | cgt | ctg | gga | tgc | gaa | cgg | gcc | tgg | aac | cat | agc | gtc | 480 |
| Gly | Pro | Arg | Arg | Arg | Leu | Gly | Cys | Glu | Arg | Ala | Trp | Asn | His | Ser | Val |  |
| 145 |  |  |  |  | 150 |  |  |  |  | 155 |  |  |  |  | 160 |  |
| agg | gag | gcc | ggg | gtc | ccc | ctg | ggc | ctg | cca | gcc | ccg | ggt | gcg | agg | agg | 528 |
| Arg | Glu | Ala | Gly | Val | Pro | Leu | Gly | Leu | Pro | Ala | Pro | Gly | Ala | Arg | Arg |  |
|  |  |  |  | 165 |  |  |  |  | 170 |  |  |  |  | 175 |  |  |
| cgc | ggg | ggc | agt | gcc | agc | cga | agt | ctg | ccg | ttg | ccc | aag | agg | ccc | agg | 576 |
| Arg | Gly | Gly | Ser | Ala | Ser | Arg | Ser | Leu | Pro | Leu | Pro | Lys | Arg | Pro | Arg |  |
|  |  |  | 180 |  |  |  |  | 185 |  |  |  |  | 190 |  |  |  |
| cgt | ggc | gct | gcc | cct | gag | ccg | gag | cgg | acg | ccc | gtt | ggg | cag | ggg | tcc | 624 |
| Arg | Gly | Ala | Ala | Pro | Glu | Pro | Glu | Arg | Thr | Pro | Val | Gly | Gln | Gly | Ser |  |
|  |  | 195 |  |  |  |  | 200 |  |  |  |  | 205 |  |  |  |  |
| tgg | gcc | cac | ccg | ggc | agg | acg | cgt | gga | ccg | agt | gac | cgt | ggt | ttc | tgt | 672 |
| Trp | Ala | His | Pro | Gly | Arg | Thr | Arg | Gly | Pro | Ser | Asp | Arg | Gly | Phe | Cys |  |
|  | 210 |  |  |  |  | 215 |  |  |  |  | 220 |  |  |  |  |  |
| gtg | gtg | tca | cct | gcc | aga | ccc | gcc | gaa | gaa | gcc | acc | tct | ttg | gag | ggt | 720 |
| Val | Val | Ser | Pro | Ala | Arg | Pro | Ala | Glu | Glu | Ala | Thr | Ser | Leu | Glu | Gly |  |
| 225 |  |  |  |  | 230 |  |  |  |  | 235 |  |  |  |  | 240 |  |
| gcg | ctc | tct | ggc | acg | cgc | cac | tcc | cac | cca | tcc | gtg | ggc | cgc | cag | cac | 768 |
| Ala | Leu | Ser | Gly | Thr | Arg | His | Ser | His | Pro | Ser | Val | Gly | Arg | Gln | His |  |
|  |  |  |  | 245 |  |  |  |  | 250 |  |  |  |  | 255 |  |  |
| cac | gcg | ggc | ccc | cca | tcc | aca | tcg | cgg | cca | cca | cgt | ccc | tgg | gac | acg | 816 |
| His | Ala | Gly | Pro | Pro | Ser | Thr | Ser | Arg | Pro | Pro | Arg | Pro | Trp | Asp | Thr |  |
|  |  |  | 260 |  |  |  |  | 265 |  |  |  |  | 270 |  |  |  |
| cct | tgt | ccc | ccg | gtg | tac | gcc | gag | acc | aag | cac | ttc | ctc | tac | tcc | tca | 864 |
| Pro | Cys | Pro | Pro | Val | Tyr | Ala | Glu | Thr | Lys | His | Phe | Leu | Tyr | Ser | Ser |  |
|  |  | 275 |  |  |  |  | 280 |  |  |  |  | 285 |  |  |  |  |
| ggc | gac | aag | gag | cag | ctg | cgg | cca | tcc | ttc | ctg | ctg | agc | tct | ctg | agg | 912 |
| Gly | Asp | Lys | Glu | Gln | Leu | Arg | Pro | Ser | Phe | Leu | Leu | Ser | Ser | Leu | Arg |  |
|  | 290 |  |  |  |  | 295 |  |  |  |  | 300 |  |  |  |  |  |
| ccc | agc | ctg | act | ggc | gct | cgg | agg | ctc | gtg | gag | acc | atc | ttt | ctg | ggt | 960 |
| Pro | Ser | Leu | Thr | Gly | Ala | Arg | Arg | Leu | Val | Glu | Thr | Ile | Phe | Leu | Gly |  |
| 305 |  |  |  |  | 310 |  |  |  |  | 315 |  |  |  |  | 320 |  |
| tcc | agg | ccc | tgg | atg | cca | ggg | act | ccc | cgc | agg | ttg | ccc | cgc | ctg | ccc | 1008 |
| Ser | Arg | Pro | Trp | Met | Pro | Gly | Thr | Pro | Arg | Arg | Leu | Pro | Arg | Leu | Pro |  |
|  |  |  |  | 325 |  |  |  |  | 330 |  |  |  |  | 335 |  |  |
| cag | cgc | tac | tgg | caa | atg | cgg | ccc | ctg | ttt | ctg | gag | ctg | ctt | ggg | aac | 1056 |
| Gln | Arg | Tyr | Trp | Gln | Met | Arg | Pro | Leu | Phe | Leu | Glu | Leu | Leu | Gly | Asn |  |
|  |  |  | 340 |  |  |  |  | 345 |  |  |  |  | 350 |  |  |  |
| cac | gcg | cag | tgc | ccc | tac | ggg | gtg | ctc | ctc | aag | acg | cac | tgc | ccg | ctg | 1104 |
| His | Ala | Gln | Cys | Pro | Tyr | Gly | Val | Leu | Leu | Lys | Thr | His | Cys | Pro | Leu |  |
|  |  | 355 |  |  |  |  | 360 |  |  |  |  | 365 |  |  |  |  |
| cga | gct | gcg | gtc | acc | cca | gca | gcc | ggt | gtc | tgt | gcc | cgg | gag | aag | ccc | 1152 |
| Arg | Ala | Ala | Val | Thr | Pro | Ala | Ala | Gly | Val | Cys | Ala | Arg | Glu | Lys | Pro |  |
|  | 370 |  |  |  |  | 375 |  |  |  |  | 380 |  |  |  |  |  |

-continued

| | |
|---|---|
| cag ggc tct gtg gcg gcc ccc gag gag gag gac aca gac ccc cgt cgc<br>Gln Gly Ser Val Ala Ala Pro Glu Glu Glu Asp Thr Asp Pro Arg Arg<br>385                      390                  395                  400 | 1200 |
| ctg gtg cag ctg ctc cgc cag cac agc agc ccc tgg cag gtg tac ggc<br>Leu Val Gln Leu Leu Arg Gln His Ser Ser Pro Trp Gln Val Tyr Gly<br>                  405                  410                  415 | 1248 |
| ttc gtg cgg gcc tgc ctg cgc cgg ctg gtg ccc cca ggc ctc tgg ggc<br>Phe Val Arg Ala Cys Leu Arg Arg Leu Val Pro Pro Gly Leu Trp Gly<br>420                      425                  430 | 1296 |
| tcc agg cac aac gaa cgc cgc ttc ctc agg aac acc aag aag ttc atc<br>Ser Arg His Asn Glu Arg Arg Phe Leu Arg Asn Thr Lys Lys Phe Ile<br>             435                  440                  445 | 1344 |
| tcc ctg ggg aag cat gcc aag ctc tcg ctg cag gag ctg acg tgg aag<br>Ser Leu Gly Lys His Ala Lys Leu Ser Leu Gln Glu Leu Thr Trp Lys<br>450                      455                  460 | 1392 |
| atg agc gtg cgg ggc tgc gct tgg ctg cgc agg agc cca ggg gtt ggc<br>Met Ser Val Arg Gly Cys Ala Trp Leu Arg Arg Ser Pro Gly Val Gly<br>465                      470                  475                  480 | 1440 |
| tgt gtt ccg gcc gca gag cac cgt ctg cgt gag gag atc ctg gcc aag<br>Cys Val Pro Ala Ala Glu His Arg Leu Arg Glu Glu Ile Leu Ala Lys<br>                          485                  490                  495 | 1488 |
| ttc ctg cac tgg ctg atg agt gtg tac gtc gtc gag ctg ctc agg tca<br>Phe Leu His Trp Leu Met Ser Val Tyr Val Val Glu Leu Leu Arg Ser<br>             500                  505                  510 | 1536 |
| ttc ttt tac gtg acg gag acc acg ttt caa aag aac agg ctg ttt ttc<br>Phe Phe Tyr Val Thr Glu Thr Thr Phe Gln Lys Asn Arg Leu Phe Phe<br>             515                  520                  525 | 1584 |
| tac cgg aag agt gtc tgg agc aag ttg caa agc att gga atc aga cag<br>Tyr Arg Lys Ser Val Trp Ser Lys Leu Gln Ser Ile Gly Ile Arg Gln<br>530                      535                  540 | 1632 |
| cac ttg aag agg gtg cag ctg cgg gag ctg tcg gaa gca gag gtc agg<br>His Leu Lys Arg Val Gln Leu Arg Glu Leu Ser Glu Ala Glu Val Arg<br>545                      550                  555                  560 | 1680 |
| cag cat cgg gaa gcc agg ccc gcc ctg ctg acg tcc aga ctc cgc ttc<br>Gln His Arg Glu Ala Arg Pro Ala Leu Leu Thr Ser Arg Leu Arg Phe<br>                          565                  570                  575 | 1728 |
| atc ccc aag cct gac ggg ctg cgg ccg att gtg aac atg gac tac gtc<br>Ile Pro Lys Pro Asp Gly Leu Arg Pro Ile Val Asn Met Asp Tyr Val<br>             580                  585                  590 | 1776 |
| gtg gga gcc aga acg ttc cgc aga gaa aag agg gcc gag cgt ctc acc<br>Val Gly Ala Arg Thr Phe Arg Arg Glu Lys Arg Ala Glu Arg Leu Thr<br>595                      600                  605 | 1824 |
| tca cgg gtg aag gca ctg ttc agc gtg ctc aac tac gag cgg gct cgg<br>Ser Arg Val Lys Ala Leu Phe Ser Val Leu Asn Tyr Glu Arg Ala Arg<br>             610                  615                  620 | 1872 |
| cgc cct ggc ctc ctg ggc gcc tct gtg ctg ggc ctg gac gat atc cac<br>Arg Pro Gly Leu Leu Gly Ala Ser Val Leu Gly Leu Asp Asp Ile His<br>625                      630                  635                  640 | 1920 |
| agg gcc tgg cgc acc ttc gtg ctg cgt gtg cgg gcc cag gac ccg ccg<br>Arg Ala Trp Arg Thr Phe Val Leu Arg Val Arg Ala Gln Asp Pro Pro<br>                          645                  650                  655 | 1968 |
| cct gag ctg tac ttt gtc aag gtg gat gtg acg ggc gcg tac gac acc<br>Pro Glu Leu Tyr Phe Val Lys Val Asp Val Thr Gly Ala Tyr Asp Thr<br>                      660                  665                  670 | 2016 |
| atc ccc cag gac agg ctc acg gag gtc atc gcc agc atc atc aaa ccc<br>Ile Pro Gln Asp Arg Leu Thr Glu Val Ile Ala Ser Ile Ile Lys Pro<br>675                      680                  685 | 2064 |

```
cag aac acg tac tgc gtg cgt cgg tat gcc gtg gtc cag aag gcc gcc      2112
Gln Asn Thr Tyr Cys Val Arg Arg Tyr Ala Val Val Gln Lys Ala Ala
    690             695                 700 cat ggg cac gtc cgc aag gcc ttc aag agc cac gtc tct acc ttg aca      2160
His Gly His Val Arg Lys Ala Phe Lys Ser His Val Ser Thr Leu Thr
705             710                 715                 720 gac ctc cag ccg tac atg cga cag ttc gtg gct cac ctg cag gag acc      2208
Asp Leu Gln Pro Tyr Met Arg Gln Phe Val Ala His Leu Gln Glu Thr
                725                 730                 735 agc ccg ctg agg gat gcc gtc gtc atc gag cag agc tcc tcc ctg aat      2256
Ser Pro Leu Arg Asp Ala Val Val Ile Glu Gln Ser Ser Ser Leu Asn
    740                 745                 750 gag gcc agc agt ggc ctc ttc gac gtc ttc cta cgc ttc atg tgc cac      2304
Glu Ala Ser Ser Gly Leu Phe Asp Val Phe Leu Arg Phe Met Cys His
755                 760                 765 cac gcc gtg cgc atc agg ggc aag tcc tac gtc cag tgc cag ggc atc      2352
His Ala Val Arg Ile Arg Gly Lys Ser Tyr Val Gln Cys Gln Gly Ile
    770                 775                 780 ccg cag ggc tcc atc ctc tcc acg ctg ctc tgc agc ctg tgc tac ggc      2400
Pro Gln Gly Ser Ile Leu Ser Thr Leu Leu Cys Ser Leu Cys Tyr Gly
785             790                 795                 800 gac atg gag aac aag ctg ttt gcg ggg att cgg cgg gac ggg ctg ctc      2448
Asp Met Glu Asn Lys Leu Phe Ala Gly Ile Arg Arg Asp Gly Leu Leu
                805                 810                 815 ctg cgt ttg ttc ttg ttg gtg aca cct cac ctc acc cac gcg aaa acc      2496
Leu Arg Leu Phe Leu Leu Val Thr Pro His Leu Thr His Ala Lys Thr
    820                 825                 830 ttc ctc agg acc ctg gtc cga ggt gtc cct gag tat ggc tgc gtg gtg      2544
Phe Leu Arg Thr Leu Val Arg Gly Val Pro Glu Tyr Gly Cys Val Val
835                 840                 845 aac ttg cgg aag aca gtg gtg aac ttc cct gta gaa gac gag gcc ctg      2592
Asn Leu Arg Lys Thr Val Val Asn Phe Pro Val Glu Asp Glu Ala Leu
    850                 855                 860 ggt ggc acg gct ttt gtt cag atg ccg gcc cac ggc cta ttc ccc tgg      2640
Gly Gly Thr Ala Phe Val Gln Met Pro Ala His Gly Leu Phe Pro Trp
865                 870                 875                 880 tgc ggc ctg ctg ctg gat acc cgg acc ctg gag gtg cag agc gac tac      2688
Cys Gly Leu Leu Leu Asp Thr Arg Thr Leu Glu Val Gln Ser Asp Tyr
                885                 890                 895 tcc agc tat gcc cgg acc tcc atc aga gcc agt ctc acc ttc aac cgc      2736
Ser Ser Tyr Ala Arg Thr Ser Ile Arg Ala Ser Leu Thr Phe Asn Arg
            900                 905                 910 ggc ttc aag gct ggg agg aac atg cgt cgc aaa ctc ttt ggg gtc ttg      2784
Gly Phe Lys Ala Gly Arg Asn Met Arg Arg Lys Leu Phe Gly Val Leu
        915                 920                 925 cgg ctg aag tgt cac agc ctg ttt ctg gat ttg cag gtg aac agc ctc      2832
Arg Leu Lys Cys His Ser Leu Phe Leu Asp Leu Gln Val Asn Ser Leu
    930                 935                 940 cag acg gtg tgc acc aac atc tac aag atc ctc ctg cag gcg tac          2880
Gln Thr Val Cys Thr Asn Ile Tyr Lys Ile Leu Leu Gln Ala Tyr
945             950                 955                 960 agg ttt cac gca tgt gtg ctg cag ctc cca ttt cat cag caa gtt tgg      2928
Arg Phe His Ala Cys Val Leu Gln Leu Pro Phe His Gln Gln Val Trp
                965                 970                 975 aag aac ccc aca ttt ttc ctg cgc gtc atc tct gac acg gcc tcc ctc      2976
Lys Asn Pro Thr Phe Phe Leu Arg Val Ile Ser Asp Thr Ala Ser Leu
            980                 985                 990
```

```
tgc tac tcc atc ctg aaa gcc aag aac gca ggg atg tcg ctg ggg gcc      3024
Cys Tyr Ser Ile Leu Lys Ala Lys Asn Ala Gly Met Ser Leu Gly Ala
        995                 1000                1005 aag ggc gcc gcc ggc cct ctg ccc tcc gag gcc gtg cag tgg ctg          3069
Lys Gly Ala Ala Gly Pro Leu Pro Ser Glu Ala Val Gln Trp Leu
    1010                1015                1020 tgc cac caa gca ttc ctg ctc aag ctg act cga cac cgt gtc acc          3114
Cys His Gln Ala Phe Leu Leu Lys Leu Thr Arg His Arg Val Thr
    1025                1030                1035 tac gtg cca ctc ctg ggg tca ctc agg aca gcc cag acg cag ctg          3159
Tyr Val Pro Leu Leu Gly Ser Leu Arg Thr Ala Gln Thr Gln Leu
    1040                1045                1050 agt cgg aag ctc ccg ggg acg acg ctg act gcc ctg gag gcc gca          3204
Ser Arg Lys Leu Pro Gly Thr Thr Leu Thr Ala Leu Glu Ala Ala
    1055                1060                1065 gcc aac ccg gca ctg ccc tca gac ttc aag acc atc ctg gac              3246
Ala Asn Pro Ala Leu Pro Ser Asp Phe Lys Thr Ile Leu Asp
    1070                1075                1080

<210> SEQ ID NO 4
<211> LENGTH: 1082
<212> TYPE: PRT
<213> ORGANISM: Homo sapiens

<400> SEQUENCE: 4

Arg Ala Leu Val Ala Gln Cys Leu Val Cys Val Pro Trp Asp Ala Arg
1               5                   10                  15

Pro Pro Pro Ala Ala Pro Ser Phe Arg Gln Val Ser Cys Leu Lys Glu
            20                  25                  30

Leu Val Ala Arg Val Leu Gln Arg Leu Cys Glu Arg Gly Ala Lys Asn
        35                  40                  45

Val Leu Ala Phe Gly Phe Ala Leu Leu Asp Gly Ala Arg Gly Gly Pro
    50                  55                  60

Pro Glu Ala Phe Thr Thr Ser Val Arg Ser Tyr Leu Pro Asn Thr Val
65                  70                  75                  80

Thr Asp Ala Leu Arg Gly Ser Gly Ala Trp Gly Leu Leu Leu Arg Arg
                85                  90                  95

Val Gly Asp Asp Val Leu Val His Leu Leu Ala Arg Cys Ala Leu Phe
            100                 105                 110

Val Leu Val Ala Pro Ser Cys Ala Tyr Gln Val Cys Gly Pro Pro Leu
        115                 120                 125

Tyr Gln Leu Gly Ala Ala Thr Gln Ala Arg Pro Pro Pro His Ala Ser
    130                 135                 140

Gly Pro Arg Arg Arg Leu Gly Cys Glu Arg Ala Trp Asn His Ser Val
145                 150                 155                 160

Arg Glu Ala Gly Val Pro Leu Gly Leu Pro Ala Pro Gly Ala Arg Arg
                165                 170                 175

Arg Gly Gly Ser Ala Ser Arg Ser Leu Pro Leu Pro Lys Arg Pro Arg
            180                 185                 190

Arg Gly Ala Ala Pro Glu Pro Glu Arg Thr Pro Val Gly Gln Gly Ser
        195                 200                 205

Trp Ala His Pro Gly Arg Thr Arg Gly Pro Ser Asp Arg Gly Phe Cys
    210                 215                 220

Val Val Ser Pro Ala Arg Pro Ala Glu Glu Ala Thr Ser Leu Glu Gly
225                 230                 235                 240
```

```
Ala Leu Ser Gly Thr Arg His Ser His Pro Ser Val Gly Arg Gln His
                245                 250                 255

His Ala Gly Pro Pro Ser Thr Ser Arg Pro Pro Arg Pro Trp Asp Thr
                260                 265                 270

Pro Cys Pro Pro Val Tyr Ala Glu Thr Lys His Phe Leu Tyr Ser Ser
                275                 280                 285

Gly Asp Lys Glu Gln Leu Arg Pro Ser Phe Leu Leu Ser Ser Leu Arg
                290                 295                 300

Pro Ser Leu Thr Gly Ala Arg Arg Leu Val Glu Thr Ile Phe Leu Gly
305                 310                 315                 320

Ser Arg Pro Trp Met Pro Gly Thr Pro Arg Arg Leu Pro Arg Leu Pro
                325                 330                 335

Gln Arg Tyr Trp Gln Met Arg Pro Leu Phe Leu Glu Leu Leu Gly Asn
                340                 345                 350

His Ala Gln Cys Pro Tyr Gly Val Leu Leu Lys Thr His Cys Pro Leu
                355                 360                 365

Arg Ala Ala Val Thr Pro Ala Ala Gly Val Cys Ala Arg Glu Lys Pro
                370                 375                 380

Gln Gly Ser Val Ala Ala Pro Glu Glu Glu Asp Thr Asp Pro Arg Arg
385                 390                 395                 400

Leu Val Gln Leu Leu Arg Gln His Ser Ser Pro Trp Gln Val Tyr Gly
                405                 410                 415

Phe Val Arg Ala Cys Leu Arg Arg Leu Val Pro Pro Gly Leu Trp Gly
                420                 425                 430

Ser Arg His Asn Glu Arg Arg Phe Leu Arg Asn Thr Lys Lys Phe Ile
                435                 440                 445

Ser Leu Gly Lys His Ala Lys Leu Ser Leu Gln Glu Leu Thr Trp Lys
                450                 455                 460

Met Ser Val Arg Gly Cys Ala Trp Leu Arg Arg Ser Pro Gly Val Gly
465                 470                 475                 480

Cys Val Pro Ala Ala Glu His Arg Leu Arg Glu Ile Leu Ala Lys
                485                 490                 495

Phe Leu His Trp Leu Met Ser Val Tyr Val Val Glu Leu Leu Arg Ser
                500                 505                 510

Phe Phe Tyr Val Thr Glu Thr Thr Phe Gln Lys Asn Arg Leu Phe Phe
                515                 520                 525

Tyr Arg Lys Ser Val Trp Ser Lys Leu Gln Ser Ile Gly Ile Arg Gln
                530                 535                 540

His Leu Lys Arg Val Gln Leu Arg Glu Leu Ser Glu Ala Glu Val Arg
545                 550                 555                 560

Gln His Arg Glu Ala Arg Pro Ala Leu Leu Thr Ser Arg Leu Arg Phe
                565                 570                 575

Ile Pro Lys Pro Asp Gly Leu Arg Pro Ile Val Asn Met Asp Tyr Val
                580                 585                 590

Val Gly Ala Arg Thr Phe Arg Arg Glu Lys Arg Ala Glu Arg Leu Thr
                595                 600                 605

Ser Arg Val Lys Ala Leu Phe Ser Val Leu Asn Tyr Glu Arg Ala Arg
                610                 615                 620

Arg Pro Gly Leu Leu Gly Ala Ser Val Leu Gly Leu Asp Asp Ile His
625                 630                 635                 640

Arg Ala Trp Arg Thr Phe Val Leu Arg Val Arg Ala Gln Asp Pro Pro
                645                 650                 655
```

```
Pro Glu Leu Tyr Phe Val Lys Val Asp Val Thr Gly Ala Tyr Asp Thr
              660                 665                 670

Ile Pro Gln Asp Arg Leu Thr Glu Val Ile Ala Ser Ile Ile Lys Pro
        675                 680                 685

Gln Asn Thr Tyr Cys Val Arg Arg Tyr Ala Val Val Gln Lys Ala Ala
    690                 695                 700

His Gly His Val Arg Lys Ala Phe Lys Ser His Val Ser Thr Leu Thr
705                 710                 715                 720

Asp Leu Gln Pro Tyr Met Arg Gln Phe Val Ala His Leu Gln Glu Thr
                725                 730                 735

Ser Pro Leu Arg Asp Ala Val Val Ile Glu Gln Ser Ser Ser Leu Asn
            740                 745                 750

Glu Ala Ser Ser Gly Leu Phe Asp Val Phe Leu Arg Phe Met Cys His
        755                 760                 765

His Ala Val Arg Ile Arg Gly Lys Ser Tyr Val Gln Cys Gln Gly Ile
    770                 775                 780

Pro Gln Gly Ser Ile Leu Ser Thr Leu Leu Cys Ser Leu Cys Tyr Gly
785                 790                 795                 800

Asp Met Glu Asn Lys Leu Phe Ala Gly Ile Arg Arg Asp Gly Leu Leu
                805                 810                 815

Leu Arg Leu Phe Leu Leu Val Thr Pro His Leu Thr His Ala Lys Thr
            820                 825                 830

Phe Leu Arg Thr Leu Val Arg Gly Val Pro Glu Tyr Gly Cys Val Val
        835                 840                 845

Asn Leu Arg Lys Thr Val Val Asn Phe Pro Val Glu Asp Glu Ala Leu
    850                 855                 860

Gly Gly Thr Ala Phe Val Gln Met Pro Ala His Gly Leu Phe Pro Trp
865                 870                 875                 880

Cys Gly Leu Leu Leu Asp Thr Arg Thr Leu Glu Val Gln Ser Asp Tyr
                885                 890                 895

Ser Ser Tyr Ala Arg Thr Ser Ile Arg Ala Ser Leu Thr Phe Asn Arg
            900                 905                 910

Gly Phe Lys Ala Gly Arg Asn Met Arg Arg Lys Leu Phe Gly Val Leu
        915                 920                 925

Arg Leu Lys Cys His Ser Leu Phe Leu Asp Leu Gln Val Asn Ser Leu
    930                 935                 940

Gln Thr Val Cys Thr Asn Ile Tyr Lys Ile Leu Leu Leu Gln Ala Tyr
945                 950                 955                 960

Arg Phe His Ala Cys Val Leu Gln Leu Pro Phe His Gln Gln Val Trp
                965                 970                 975

Lys Asn Pro Thr Phe Phe Leu Arg Val Ile Ser Asp Thr Ala Ser Leu
            980                 985                 990

Cys Tyr Ser Ile Leu Lys Ala Lys Asn Ala Gly Met Ser Leu Gly Ala
        995                 1000                1005

Lys Gly Ala Ala Gly Pro Leu Pro Ser Glu Ala Val Gln Trp Leu
    1010                1015                1020

Cys His Gln Ala Phe Leu Leu Lys Leu Thr Arg His Arg Val Thr
    1025                1030                1035

Tyr Val Pro Leu Leu Gly Ser Leu Arg Thr Ala Gln Thr Gln Leu
    1040                1045                1050

Ser Arg Lys Leu Pro Gly Thr Thr Leu Thr Ala Leu Glu Ala Ala
    1055                1060                1065
```

Ala Asn Pro Ala Leu Pro Ser Asp Phe Lys Thr Ile Leu Asp
    1070            1075                1080

<210> SEQ ID NO 5
<211> LENGTH: 3297
<212> TYPE: DNA
<213> ORGANISM: Homo sapiens
<220> FEATURE:
<221> NAME/KEY: CDS
<222> LOCATION: (1)..(3297)

<400> SEQUENCE: 5

```
ctg gcc acc ttc gtg cgg cgc ctg gga ccc cag ggc tgg cgg ctg gtg      48
Leu Ala Thr Phe Val Arg Arg Leu Gly Pro Gln Gly Trp Arg Leu Val
1               5                   10                  15 cag cgc ggg gac cct gct gct ttc aga gct ctc gtc gcc cag tgt ctg      96
Gln Arg Gly Asp Pro Ala Ala Phe Arg Ala Leu Val Ala Gln Cys Leu
            20                  25                  30 gtc tgc gtt cct tgg gac gca cgg ccc cca ccc gcc gcc ccc agt ttc     144
Val Cys Val Pro Trp Asp Ala Arg Pro Pro Pro Ala Ala Pro Ser Phe
        35                  40                  45 cgg cag gtg agt tgt ctc aaa gag ttg gtt gct cgg gtg ttg cag cgg     192
Arg Gln Val Ser Cys Leu Lys Glu Leu Val Ala Arg Val Leu Gln Arg
    50                  55                  60 ctt tgt gaa agg gga gca aag aac gtc ctt gcc ttt ggc ttc gct ttg     240
Leu Cys Glu Arg Gly Ala Lys Asn Val Leu Ala Phe Gly Phe Ala Leu
65                  70                  75                  80 ctc gat gga gca cgc gga ggc cct cct gag gca ttc act act agc gtc     288
Leu Asp Gly Ala Arg Gly Gly Pro Pro Glu Ala Phe Thr Thr Ser Val
                85                  90                  95 cgg tcc tac ctg ccc aac aca gtg acc gac gct ctg aga ggt tca ggt     336
Arg Ser Tyr Leu Pro Asn Thr Val Thr Asp Ala Leu Arg Gly Ser Gly
            100                 105                 110 gcc tgg ggt ctg ctg ctg cgg agg gtg ggt gat gat gtt ctg gtt cac     384
Ala Trp Gly Leu Leu Leu Arg Arg Val Gly Asp Asp Val Leu Val His
        115                 120                 125 ctc ctg gcc cgg tgt gcc ctg ttc gtg ctg gtg gct ccc tcc tgc gca     432
Leu Leu Ala Arg Cys Ala Leu Phe Val Leu Val Ala Pro Ser Cys Ala
    130                 135                 140 tac cag gtc tgc gga ccc cca ctt tat cag ctc ggc gct gct act cag     480
Tyr Gln Val Cys Gly Pro Pro Leu Tyr Gln Leu Gly Ala Ala Thr Gln
145                 150                 155                 160 gcc cgc cca cca cca cac gcc tca ggt cca aga cgc agg ctg ggc tgc     528
Ala Arg Pro Pro Pro His Ala Ser Gly Pro Arg Arg Arg Leu Gly Cys
                165                 170                 175 gaa cgg gca tgg aat cat agc gtg cgg gag gca ggt gtg cct ctc ggc     576
Glu Arg Ala Trp Asn His Ser Val Arg Glu Ala Gly Val Pro Leu Gly
            180                 185                 190 ctg cca gcc ccc gga gca agg aga cgc ggt gga tcc gcc agt cgc tca     624
Leu Pro Ala Pro Gly Ala Arg Arg Arg Gly Gly Ser Ala Ser Arg Ser
        195                 200                 205 ctc ccc ttg cct aag agg cca aga aga gga gcc gcc cct gaa ccc gag     672
Leu Pro Leu Pro Lys Arg Pro Arg Arg Gly Ala Ala Pro Glu Pro Glu
    210                 215                 220 aga aca cct gtc ggc cag ggc tcc tgg gct cac ccc gga agg acc agg     720
Arg Thr Pro Val Gly Gln Gly Ser Trp Ala His Pro Gly Arg Thr Arg
225                 230                 235                 240 ggc cca agc gat agg ggc ttc tgt gtt gtg tca cca gcc agg cct gcc     768
Gly Pro Ser Asp Arg Gly Phe Cys Val Val Ser Pro Ala Arg Pro Ala
                245                 250                 255
```

| | | |
|---|---|---|
| gaa gag gct acc tcc ttg gaa gga gcc ctc agt ggc acc agg cat tct<br>Glu Glu Ala Thr Ser Leu Glu Gly Ala Leu Ser Gly Thr Arg His Ser<br>260                        265                   270 | 816 | |
| cat cca tct gtg ggt agg cag cat cat gcc ggc ccc ccc tct aca agc<br>His Pro Ser Val Gly Arg Gln His His Ala Gly Pro Pro Ser Thr Ser<br>275                     280                     285 | 864 | |
| aga cct ccc aga cct tgg gac aca ccc tgc cca cca gtg tat gcc gag<br>Arg Pro Pro Arg Pro Trp Asp Thr Pro Cys Pro Pro Val Tyr Ala Glu<br>290                        295                   300 | 912 | |
| acc aag cac ttt ttg tat tcc agt ggc gat aaa gag cag ctc cgg ccc<br>Thr Lys His Phe Leu Tyr Ser Ser Gly Asp Lys Glu Gln Leu Arg Pro<br>305                   310                     315                 320 | 960 | |
| tct ttt ctg ctc tca agc ctc cgc ccc tct ctg acc gga gct cgc agg<br>Ser Phe Leu Leu Ser Ser Leu Arg Pro Ser Leu Thr Gly Ala Arg Arg<br>                   325                     330                 335 | 1008 | |
| ctg gtg gag acc atc ttt ctg ggc tca aga cca tgg atg cca ggc acc<br>Leu Val Glu Thr Ile Phe Leu Gly Ser Arg Pro Trp Met Pro Gly Thr<br>                340                     345                     350 | 1056 | |
| ccc cgc aga ctg ccc agg ctc ccc cag cgg tac tgg cag atg cgc cct<br>Pro Arg Arg Leu Pro Arg Leu Pro Gln Arg Tyr Trp Gln Met Arg Pro<br>             355                     360                     365 | 1104 | |
| ctc ttt ctg gaa ctt ctg ggt aac cac gcc cag tgc cca tat ggc gtc<br>Leu Phe Leu Glu Leu Leu Gly Asn His Ala Gln Cys Pro Tyr Gly Val<br>370                        375                     380 | 1152 | |
| ctg ctg aag acc cac tgt cct ctg agg gcc gcc gtg acc cca gcc gcc<br>Leu Leu Lys Thr His Cys Pro Leu Arg Ala Ala Val Thr Pro Ala Ala<br>385                        390                     395                 400 | 1200 | |
| ggt gtg tgt gct aga gaa aaa ccc cag ggc tca gtg gct gca cct gaa<br>Gly Val Cys Ala Arg Glu Lys Pro Gln Gly Ser Val Ala Ala Pro Glu<br>                   405                     410                     415 | 1248 | |
| gag gag gac act gac cct cgc cgc ctt gtc cag ttg ctc agg cag cat<br>Glu Glu Asp Thr Asp Pro Arg Arg Leu Val Gln Leu Leu Arg Gln His<br>                 420                     425                     430 | 1296 | |
| tca tca cca tgg cag gtg tac ggc ttc gtg agg gct tgc ctg cgg aga<br>Ser Ser Pro Trp Gln Val Tyr Gly Phe Val Arg Ala Cys Leu Arg Arg<br>             435                     440                     445 | 1344 | |
| ctg gtc ccc ccc gga ttg tgg gga tct cgg cac aac gaa cgc gct ttt<br>Leu Val Pro Pro Gly Leu Trp Gly Ser Arg His Asn Glu Arg Arg Phe<br>450                        455                     460 | 1392 | |
| ctg agg aat aca aag aag ttt atc tcc ctg ggc aag cat gca aag ctc<br>Leu Arg Asn Thr Lys Lys Phe Ile Ser Leu Gly Lys His Ala Lys Leu<br>465                        470                     475                 480 | 1440 | |
| agc ttg cag gag ctg aca tgg aag atg agc gtt aga gga tgc gca tgg<br>Ser Leu Gln Glu Leu Thr Trp Lys Met Ser Val Arg Gly Cys Ala Trp<br>                   485                     490                     495 | 1488 | |
| ctc agg cgg tca cct gga gtt gga tgc gtt cca gca gca gag cac agg<br>Leu Arg Arg Ser Pro Gly Val Gly Cys Val Pro Ala Ala Glu His Arg<br>             500                     505                     510 | 1536 | |
| ctg cgc gaa gag att ctc gca aag ttc ctg cac tgg ctt atg agc gtc<br>Leu Arg Glu Glu Ile Leu Ala Lys Phe Leu His Trp Leu Met Ser Val<br>             515                     520                     525 | 1584 | |
| tac gtg gtc gaa ctg ctg cgg tct ttc ttc tac gtg aca gag acc act<br>Tyr Val Val Glu Leu Leu Arg Ser Phe Phe Tyr Val Thr Glu Thr Thr<br>530                        535                     540 | 1632 | |
| ttt cag aag aac aga ctg ttc ttc tac agg aag tcc gtc tgg agc aag<br>Phe Gln Lys Asn Arg Leu Phe Phe Tyr Arg Lys Ser Val Trp Ser Lys<br>545                        550                     555                 560 | 1680 | |
| ctc cag agt att ggt att aga cag cac ctt aag aga gtt cag ctt aga<br>Leu Gln Ser Ile Gly Ile Arg Gln His Leu Lys Arg Val Gln Leu Arg<br>                   565                     570                     575 | 1728 | |

```
gag ctg tcc gaa gct gaa gtc cgc cag cac cgc gaa gct cgc ccc gcc    1776
Glu Leu Ser Glu Ala Glu Val Arg Gln His Arg Glu Ala Arg Pro Ala
            580                 585                 590 ctc ctg acc tct cgg ctg cgg ttt att ccc aaa ccc gat ggc ctt aga    1824
Leu Leu Thr Ser Arg Leu Arg Phe Ile Pro Lys Pro Asp Gly Leu Arg
        595                 600                 605 cct atc gtg aat atg gat tac gtc gtg ggt gcc cgc act ttc aga agg    1872
Pro Ile Val Asn Met Asp Tyr Val Val Gly Ala Arg Thr Phe Arg Arg
    610                 615                 620 gag aag cgc gcc gag aga ctg aca tct cgc gtg aag gca ctt ttt tct    1920
Glu Lys Arg Ala Glu Arg Leu Thr Ser Arg Val Lys Ala Leu Phe Ser
625                 630                 635                 640 gtg ctt aat tat gaa aga gcc cgc aga cct ggt ctt ctc gga gcc agc    1968
Val Leu Asn Tyr Glu Arg Ala Arg Arg Pro Gly Leu Leu Gly Ala Ser
            645                 650                 655 gtc ctc ggc ctg gat gat atc cat cgg gct tgg cgc acc ttt gtg ctt    2016
Val Leu Gly Leu Asp Asp Ile His Arg Ala Trp Arg Thr Phe Val Leu
        660                 665                 670 cgg gtg agg gca cag gat cct cct cct gag ctt tat ttt gtg aaa gtt    2064
Arg Val Arg Ala Gln Asp Pro Pro Pro Glu Leu Tyr Phe Val Lys Val
    675                 680                 685 gat gtt act ggt gct tac gat aca atc cct cag gac cgg ctc acc gag    2112
Asp Val Thr Gly Ala Tyr Asp Thr Ile Pro Gln Asp Arg Leu Thr Glu
690                 695                 700 gtg atc gcc tct att atc aaa ccc cag aac acc tac tgc gtg aga agg    2160
Val Ile Ala Ser Ile Ile Lys Pro Gln Asn Thr Tyr Cys Val Arg Arg
705                 710                 715                 720 tac gcc gtc gtt cag aaa gcc gca cac gga cac gtg cgc aaa gct ttc    2208
Tyr Ala Val Val Gln Lys Ala Ala His Gly His Val Arg Lys Ala Phe
            725                 730                 735 aaa tcc cac gtg tct acc ttg aca gac ctc cag cct tat atg cgg cag    2256
Lys Ser His Val Ser Thr Leu Thr Asp Leu Gln Pro Tyr Met Arg Gln
        740                 745                 750 ttt gtc gca cac ctg cag gag act agc ccc ttg agg gac gct gtg gtc    2304
Phe Val Ala His Leu Gln Glu Thr Ser Pro Leu Arg Asp Ala Val Val
    755                 760                 765 atc gaa cag tcc agc tct ctc aat gag gca tcc tca ggc ctg ttt gat    2352
Ile Glu Gln Ser Ser Ser Leu Asn Glu Ala Ser Ser Gly Leu Phe Asp
770                 775                 780 gtg ttc ctg cgc ttt atg tgc cac cac gcc gtg cgg att agg ggc aag    2400
Val Phe Leu Arg Phe Met Cys His His Ala Val Arg Ile Arg Gly Lys
785                 790                 795                 800 tct tac gtg cag tgc cag ggc atc cca cag ggt agc atc ctg agc aca    2448
Ser Tyr Val Gln Cys Gln Gly Ile Pro Gln Gly Ser Ile Leu Ser Thr
            805                 810                 815 ctg ctg tgt agc ctg tgc tat ggc gat atg gag aat aaa ttg ttc gcc    2496
Leu Leu Cys Ser Leu Cys Tyr Gly Asp Met Glu Asn Lys Leu Phe Ala
        820                 825                 830 ggt atc aga aga ttc ctg ctg gtt acc ccc cat ctg act cat gcc aaa    2544
Gly Ile Arg Arg Phe Leu Leu Val Thr Pro His Leu Thr His Ala Lys
    835                 840                 845 aca ttt ttg cgg act ctg gtt agg ggc gtg cca gag tat ggc tgt gtt    2592
Thr Phe Leu Arg Thr Leu Val Arg Gly Val Pro Glu Tyr Gly Cys Val
850                 855                 860 gtg aat ttg cgg aaa act gtg gtt aat ttc cca gtg gag gac gaa gct    2640
Val Asn Leu Arg Lys Thr Val Val Asn Phe Pro Val Glu Asp Glu Ala
865                 870                 875                 880
```

```
ctc gga ggc aca gct ttt gtt cag atg cct gcc cac ggc ctg ttc cca    2688
Leu Gly Gly Thr Ala Phe Val Gln Met Pro Ala His Gly Leu Phe Pro
            885                 890                 895 tgg tgc gga ctg ctg ctc gat acc cgg acc ctc gag gtg cag tcc gat    2736
Trp Cys Gly Leu Leu Leu Asp Thr Arg Thr Leu Glu Val Gln Ser Asp
        900                 905                 910 tat agt tcc tat gca aga aca tca att cgg gct agc ctg act ttc aac    2784
Tyr Ser Ser Tyr Ala Arg Thr Ser Ile Arg Ala Ser Leu Thr Phe Asn
    915                 920                 925 agg ggc ttc aag gcc ggc cgg aat atg aga agg aaa ctg ttc gga gtg    2832
Arg Gly Phe Lys Ala Gly Arg Asn Met Arg Arg Lys Leu Phe Gly Val
930                 935                 940 ttg aga ctt aag tgt cat agt ctt ttt ttg gac ttg cag gtc aat tct    2880
Leu Arg Leu Lys Cys His Ser Leu Phe Leu Asp Leu Gln Val Asn Ser
945                 950                 955                 960 ctc cag aca gtg tgt acc aac att tat aaa atc ctc ttg ctg cag gct    2928
Leu Gln Thr Val Cys Thr Asn Ile Tyr Lys Ile Leu Leu Leu Gln Ala
            965                 970                 975 tac aga ttc cat gcc tgc gtc ctg cag ctg cct ttc cac cag cag gtg    2976
Tyr Arg Phe His Ala Cys Val Leu Gln Leu Pro Phe His Gln Gln Val
        980                 985                 990 tgg aaa aac cct acc ttc ttc ctg  cgg gtg att agc gac  acc gcc agt   3024
Trp Lys Asn Pro Thr Phe Phe Leu  Arg Val Ile Ser Asp  Thr Ala Ser
    995                 1000                 1005 ctt tgc  tac tcc atc ttg aaa  gca aaa aac gct ggc  atg agc ttg      3069
Leu Cys  Tyr Ser Ile Leu Lys  Ala Lys Asn Ala Gly  Met Ser Leu
    1010                1015                 1020 gga gct  aag ggc gcc gct gga  cct ctg ccc agt gaa  gca gtc cag      3114
Gly Ala  Lys Gly Ala Ala Gly  Pro Leu Pro Ser Glu  Ala Val Gln
    1025                1030                 1035 tgg ctg  tgt cat cag gct ttc  ctc ctt aaa ctg aca  cgc cac cgc      3159
Trp Leu  Cys His Gln Ala Phe  Leu Leu Lys Leu Thr  Arg His Arg
    1040                1045                 1050 gtg act  tac gtc cca ctc ctg  ggc tcc ctg aga act  gct cag acc      3204
Val Thr  Tyr Val Pro Leu Leu  Gly Ser Leu Arg Thr  Ala Gln Thr
    1055                1060                 1065 cag ctt  tcc cgg aag ctt cca  ggc act acc ctt acc  gca ctc gaa      3249
Gln Leu  Ser Arg Lys Leu Pro  Gly Thr Thr Leu Thr  Ala Leu Glu
    1070                1075                 1080 gca gcc  gcc aac cct gcc ctg  ccc tcc gac ttt aag  act atc ctg      3294
Ala Ala  Ala Asn Pro Ala Leu  Pro Ser Asp Phe Lys  Thr Ile Leu
    1085                1090                 1095 gac                                                                 3297
Asp

<210> SEQ ID NO 6
<211> LENGTH: 1099
<212> TYPE: PRT
<213> ORGANISM: Homo sapiens

<400> SEQUENCE: 6

Leu Ala Thr Phe Val Arg Arg Leu Gly Pro Gln Gly Trp Arg Leu Val
1               5                   10                  15

Gln Arg Gly Asp Pro Ala Ala Phe Arg Ala Leu Val Ala Gln Cys Leu
            20                  25                  30

Val Cys Val Pro Trp Asp Ala Arg Pro Pro Ala Ala Pro Ser Phe
        35                  40                  45

Arg Gln Val Ser Cys Leu Lys Glu Leu Val Ala Arg Val Leu Gln Arg
    50                  55                  60
```

```
Leu Cys Glu Arg Gly Ala Lys Asn Val Leu Ala Phe Gly Phe Ala Leu
 65                  70                  75                  80

Leu Asp Gly Ala Arg Gly Gly Pro Pro Glu Ala Phe Thr Thr Ser Val
                 85                  90                  95

Arg Ser Tyr Leu Pro Asn Thr Val Thr Asp Ala Leu Arg Gly Ser Gly
            100                 105                 110

Ala Trp Gly Leu Leu Arg Arg Val Gly Asp Asp Val Leu Val His
            115                 120                 125

Leu Leu Ala Arg Cys Ala Leu Phe Val Leu Val Ala Pro Ser Cys Ala
130                 135                 140

Tyr Gln Val Cys Gly Pro Pro Leu Tyr Gln Leu Gly Ala Ala Thr Gln
145                 150                 155                 160

Ala Arg Pro Pro His Ala Ser Gly Pro Arg Arg Leu Gly Cys
                165                 170                 175

Glu Arg Ala Trp Asn His Ser Val Arg Glu Ala Gly Val Pro Leu Gly
            180                 185                 190

Leu Pro Ala Pro Gly Ala Arg Arg Gly Gly Ser Ala Ser Arg Ser
        195                 200                 205

Leu Pro Leu Pro Lys Arg Pro Arg Gly Ala Ala Pro Glu Pro Glu
210                 215                 220

Arg Thr Pro Val Gly Gln Gly Ser Trp Ala His Pro Gly Arg Thr Arg
225                 230                 235                 240

Gly Pro Ser Asp Arg Gly Phe Cys Val Val Ser Pro Ala Arg Pro Ala
                245                 250                 255

Glu Glu Ala Thr Ser Leu Glu Gly Ala Leu Ser Gly Thr Arg His Ser
                260                 265                 270

His Pro Ser Val Gly Arg Gln His His Ala Gly Pro Pro Ser Thr Ser
            275                 280                 285

Arg Pro Pro Arg Pro Trp Asp Thr Pro Cys Pro Pro Val Tyr Ala Glu
290                 295                 300

Thr Lys His Phe Leu Tyr Ser Ser Gly Asp Lys Glu Gln Leu Arg Pro
305                 310                 315                 320

Ser Phe Leu Leu Ser Ser Leu Arg Pro Ser Leu Thr Gly Ala Arg Arg
                325                 330                 335

Leu Val Glu Thr Ile Phe Leu Gly Ser Arg Pro Trp Met Pro Gly Thr
            340                 345                 350

Pro Arg Arg Leu Pro Arg Leu Pro Gln Arg Tyr Trp Gln Met Arg Pro
        355                 360                 365

Leu Phe Leu Glu Leu Leu Gly Asn His Ala Gln Cys Pro Tyr Gly Val
370                 375                 380

Leu Leu Lys Thr His Cys Pro Leu Arg Ala Ala Val Thr Pro Ala Ala
385                 390                 395                 400

Gly Val Cys Ala Arg Glu Lys Pro Gln Gly Ser Val Ala Ala Pro Glu
                405                 410                 415

Glu Glu Asp Thr Asp Pro Arg Arg Leu Val Gln Leu Leu Arg Gln His
            420                 425                 430

Ser Ser Pro Trp Gln Val Tyr Gly Phe Val Arg Ala Cys Leu Arg Arg
        435                 440                 445

Leu Val Pro Pro Gly Leu Trp Gly Ser Arg His Asn Glu Arg Arg Phe
450                 455                 460

Leu Arg Asn Thr Lys Lys Phe Ile Ser Leu Gly Lys His Ala Lys Leu
465                 470                 475                 480
```

```
Ser Leu Gln Glu Leu Thr Trp Lys Met Ser Val Arg Gly Cys Ala Trp
            485                 490                 495

Leu Arg Arg Ser Pro Gly Val Gly Cys Val Pro Ala Ala Glu His Arg
        500                 505                 510

Leu Arg Glu Glu Ile Leu Ala Lys Phe Leu His Trp Leu Met Ser Val
        515                 520                 525

Tyr Val Val Glu Leu Leu Arg Ser Phe Phe Tyr Val Thr Glu Thr Thr
        530                 535                 540

Phe Gln Lys Asn Arg Leu Phe Phe Tyr Arg Lys Ser Val Trp Ser Lys
545                 550                 555                 560

Leu Gln Ser Ile Gly Ile Arg Gln His Leu Lys Arg Val Gln Leu Arg
            565                 570                 575

Glu Leu Ser Glu Ala Glu Val Arg Gln His Arg Glu Ala Arg Pro Ala
        580                 585                 590

Leu Leu Thr Ser Arg Leu Arg Phe Ile Pro Lys Pro Asp Gly Leu Arg
        595                 600                 605

Pro Ile Val Asn Met Asp Tyr Val Val Gly Ala Arg Thr Phe Arg Arg
    610                 615                 620

Glu Lys Arg Ala Glu Arg Leu Thr Ser Arg Val Lys Ala Leu Phe Ser
625                 630                 635                 640

Val Leu Asn Tyr Glu Arg Ala Arg Arg Pro Gly Leu Leu Gly Ala Ser
            645                 650                 655

Val Leu Gly Leu Asp Asp Ile His Arg Ala Trp Arg Thr Phe Val Leu
            660                 665                 670

Arg Val Arg Ala Gln Asp Pro Pro Glu Leu Tyr Phe Val Lys Val
        675                 680                 685

Asp Val Thr Gly Ala Tyr Asp Thr Ile Pro Gln Asp Arg Leu Thr Glu
        690                 695                 700

Val Ile Ala Ser Ile Ile Lys Pro Gln Asn Thr Tyr Cys Val Arg Arg
705                 710                 715                 720

Tyr Ala Val Val Gln Lys Ala Ala His Gly His Val Arg Lys Ala Phe
            725                 730                 735

Lys Ser His Val Ser Thr Leu Thr Asp Leu Gln Pro Tyr Met Arg Gln
            740                 745                 750

Phe Val Ala His Leu Gln Glu Thr Ser Pro Leu Arg Asp Ala Val Val
        755                 760                 765

Ile Glu Gln Ser Ser Ser Leu Asn Glu Ala Ser Ser Gly Leu Phe Asp
        770                 775                 780

Val Phe Leu Arg Phe Met Cys His His Ala Val Arg Ile Arg Gly Lys
785                 790                 795                 800

Ser Tyr Val Gln Cys Gln Gly Ile Pro Gln Gly Ser Ile Leu Ser Thr
            805                 810                 815

Leu Leu Cys Ser Leu Cys Tyr Gly Asp Met Glu Asn Lys Leu Phe Ala
            820                 825                 830

Gly Ile Arg Arg Phe Leu Leu Val Thr Pro His Leu Thr His Ala Lys
        835                 840                 845

Thr Phe Leu Arg Thr Leu Val Arg Gly Val Pro Glu Tyr Gly Cys Val
        850                 855                 860

Val Asn Leu Arg Lys Thr Val Val Asn Phe Pro Val Glu Asp Glu Ala
865                 870                 875                 880

Leu Gly Gly Thr Ala Phe Val Gln Met Pro Ala His Gly Leu Phe Pro
            885                 890                 895
```

```
Trp Cys Gly Leu Leu Leu Asp Thr Arg Thr Leu Glu Val Gln Ser Asp
            900                 905                 910

Tyr Ser Ser Tyr Ala Arg Thr Ser Ile Arg Ala Ser Leu Thr Phe Asn
            915                 920                 925

Arg Gly Phe Lys Ala Gly Arg Asn Met Arg Arg Lys Leu Phe Gly Val
            930                 935                 940

Leu Arg Leu Lys Cys His Ser Leu Phe Leu Asp Leu Gln Val Asn Ser
945                 950                 955                 960

Leu Gln Thr Val Cys Thr Asn Ile Tyr Lys Ile Leu Leu Gln Ala
            965                 970                 975

Tyr Arg Phe His Ala Cys Val Leu Gln Leu Pro Phe His Gln Val
            980                 985                 990

Trp Lys Asn Pro Thr Phe Phe Leu Arg Val Ile Ser Asp Thr Ala Ser
            995                 1000                1005

Leu Cys Tyr Ser Ile Leu Lys Ala Lys Asn Ala Gly Met Ser Leu
            1010                1015                1020

Gly Ala Lys Gly Ala Ala Gly Pro Leu Pro Ser Glu Ala Val Gln
            1025                1030                1035

Trp Leu Cys His Gln Ala Phe Leu Leu Lys Leu Thr Arg His Arg
            1040                1045                1050

Val Thr Tyr Val Pro Leu Leu Gly Ser Leu Arg Thr Ala Gln Thr
            1055                1060                1065

Gln Leu Ser Arg Lys Leu Pro Gly Thr Thr Leu Thr Ala Leu Glu
            1070                1075                1080

Ala Ala Ala Asn Pro Ala Leu Pro Ser Asp Phe Lys Thr Ile Leu
            1085                1090                1095

Asp

<210> SEQ ID NO 7
<211> LENGTH: 3297
<212> TYPE: DNA
<213> ORGANISM: Homo sapiens
<220> FEATURE:
<221> NAME/KEY: CDS
<222> LOCATION: (1)..(3297)

<400> SEQUENCE: 7 ctg gcc acc ttc gtg cgg cgc ctg gga ccc cag ggc tgg cgg ctg gtg     48
Leu Ala Thr Phe Val Arg Arg Leu Gly Pro Gln Gly Trp Arg Leu Val
1               5                   10                  15 cag cgc ggg gac cct gct gct ttc aga gct ctc gtc gcc cag tgt ctg     96
Gln Arg Gly Asp Pro Ala Ala Phe Arg Ala Leu Val Ala Gln Cys Leu
                20                  25                  30 gtc tgc gtt cct tgg gac gca cgg ccc cca ccc gcc gcc ccc agt ttc    144
Val Cys Val Pro Trp Asp Ala Arg Pro Pro Ala Ala Pro Ser Phe
            35                  40                  45 cgg cag gtg agt tgt ctc aaa gag ttg gtt gct cgg gtg ttg cag cgg    192
Arg Gln Val Ser Cys Leu Lys Glu Leu Val Ala Arg Val Leu Gln Arg
    50                  55                  60 ctt tgt gaa agg gga gca aag aac gtc ctt gcc ttt ggc ttc gct ttg    240
Leu Cys Glu Arg Gly Ala Lys Asn Val Leu Ala Phe Gly Phe Ala Leu
65                  70                  75                  80 ctc gat gga gca cgc gga ggc cct cct gag gca ttc act act agc gtc    288
Leu Asp Gly Ala Arg Gly Gly Pro Pro Glu Ala Phe Thr Thr Ser Val
                85                  90                  95
```

-continued

| | | |
|---|---|---|
| cgg tcc tac ctg ccc aac aca gtg acc gac gct ctg aga ggt tca ggt<br>Arg Ser Tyr Leu Pro Asn Thr Val Thr Asp Ala Leu Arg Gly Ser Gly<br>              100                  105              110 | 336 |
| gcc tgg ggt ctg ctg ctg cgg agg gtg ggt gat gat gtt ctg gtt cac<br>Ala Trp Gly Leu Leu Leu Arg Arg Val Gly Asp Asp Val Leu Val His<br>         115                  120                125 | 384 |
| ctc ctg gcc cgg tgt gcc ctg ttc gtg ctg gtg gct ccc tcc tgc gca<br>Leu Leu Ala Arg Cys Ala Leu Phe Val Leu Val Ala Pro Ser Cys Ala<br> 130                 135                140 | 432 |
| tac cag gtc tgc gga ccc cca ctt tat cag ctc ggc gct gct act cag<br>Tyr Gln Val Cys Gly Pro Pro Leu Tyr Gln Leu Gly Ala Ala Thr Gln<br>145                150                155              160 | 480 |
| gcc cgc cca cca cca cac gcc tca ggt cca aga cgc cgg ctg ggc tgc<br>Ala Arg Pro Pro Pro His Ala Ser Gly Pro Arg Arg Arg Leu Gly Cys<br>               165                170              175 | 528 |
| gaa cgg gca tgg aat cat agc gtg cgg gag gca ggt gtg cct ctc ggc<br>Glu Arg Ala Trp Asn His Ser Val Arg Glu Ala Gly Val Pro Leu Gly<br>         180                  185               190 | 576 |
| ctg cca gcc ccc gga gca agg aga cgc ggt gga tcc gcc agt cgc tca<br>Leu Pro Ala Pro Gly Ala Arg Arg Arg Gly Gly Ser Ala Ser Arg Ser<br>195                 200                205 | 624 |
| ctc ccc ttg cct aag agg cca aga aga gga gcc gcc cct gaa ccc gag<br>Leu Pro Leu Pro Lys Arg Pro Arg Arg Gly Ala Ala Pro Glu Pro Glu<br>     210                  215              220 | 672 |
| aga aca cct gtc ggc cag ggc tcc tgg gct cac ccc gga agg acc agg<br>Arg Thr Pro Val Gly Gln Gly Ser Trp Ala His Pro Gly Arg Thr Arg<br>225                230              235              240 | 720 |
| ggc cca agc gat agg ggc ttc tgt gtt gtg tca cca gcc agg cct gcc<br>Gly Pro Ser Asp Arg Gly Phe Cys Val Val Ser Pro Ala Arg Pro Ala<br>               245                250              255 | 768 |
| gaa gag gct acc tcc ttg gaa gga gcc ctc agt ggc acc agg cat tct<br>Glu Glu Ala Thr Ser Leu Glu Gly Ala Leu Ser Gly Thr Arg His Ser<br>         260                  265               270 | 816 |
| cat cca tct gtg ggt agg cag cat cat gcc ggc ccc ccc tct aca agc<br>His Pro Ser Val Gly Arg Gln His His Ala Gly Pro Pro Ser Thr Ser<br>     275                  280              285 | 864 |
| aga cct ccc aga cct tgg gac aca ccc tgc cca cca gtg tat gcc gag<br>Arg Pro Pro Arg Pro Trp Asp Thr Pro Cys Pro Pro Val Tyr Ala Glu<br>290                295              300 | 912 |
| acc aag cac ttt ttg tat tcc agt ggc gat aaa gag cag ctc cgg ccc<br>Thr Lys His Phe Leu Tyr Ser Ser Gly Asp Lys Glu Gln Leu Arg Pro<br>305                310              315              320 | 960 |
| tct ttt ctg ctc tca agc ctc cgc ccc tct ctg acc gga gct cgc agg<br>Ser Phe Leu Leu Ser Ser Leu Arg Pro Ser Leu Thr Gly Ala Arg Arg<br>               325                330              335 | 1008 |
| ctg gtg gag acc atc ttt ctg ggc tca aga cca tgg atg cca ggc acc<br>Leu Val Glu Thr Ile Phe Leu Gly Ser Arg Pro Trp Met Pro Gly Thr<br>             340                345              350 | 1056 |
| ccc cgc aga ctg ccc agg ctc ccc cag cgg tac tgg cag atg cgc cct<br>Pro Arg Arg Leu Pro Arg Leu Pro Gln Arg Tyr Trp Gln Met Arg Pro<br>         355                360              365 | 1104 |
| ctc ttt ctg gaa ctt ctg ggt aac cac gcc cag tgc cca tat ggc gtc<br>Leu Phe Leu Glu Leu Leu Gly Asn His Ala Gln Cys Pro Tyr Gly Val<br>     370                  375              380 | 1152 |
| ctg ctg aag acc cac tgt cct ctg agg gcc gcc gtg acc cca gcc gcc<br>Leu Leu Lys Thr His Cys Pro Leu Arg Ala Ala Val Thr Pro Ala Ala<br>385                390              395              400 | 1200 |

| | |
|---|---|
| ggt gtg tgt gct aga gaa aaa ccc cag ggc tca gtg gct gca cct gaa<br>Gly Val Cys Ala Arg Glu Lys Pro Gln Gly Ser Val Ala Ala Pro Glu<br>405 410 415 | 1248 |
| gag gag gac act gac cct cgc cgc ctt gtc cag ttg ctc agg cag cat<br>Glu Glu Asp Thr Asp Pro Arg Arg Leu Val Gln Leu Leu Arg Gln His<br>420 425 430 | 1296 |
| tca tca cca tgg cag gtg tac ggc ttc gtg agg gct tgc ctg cgg aga<br>Ser Ser Pro Trp Gln Val Tyr Gly Phe Val Arg Ala Cys Leu Arg Arg<br>435 440 445 | 1344 |
| ctg gtc ccc ccc gga ttg tgg gga tct cgg cac aac gaa cgg cgc ttt<br>Leu Val Pro Pro Gly Leu Trp Gly Ser Arg His Asn Glu Arg Arg Phe<br>450 455 460 | 1392 |
| ctg agg aat aca aag aag ttt atc tcc ctg ggc aag cat gca aag ctc<br>Leu Arg Asn Thr Lys Lys Phe Ile Ser Leu Gly Lys His Ala Lys Leu<br>465 470 475 480 | 1440 |
| agc ttg cag gag ctg aca tgg aag atg agc gtt aga gga tgc gca tgg<br>Ser Leu Gln Glu Leu Thr Trp Lys Met Ser Val Arg Gly Cys Ala Trp<br>485 490 495 | 1488 |
| ctc agg cgg tca cct gga gtt gga tgc gtt cca gca gca gag cac agg<br>Leu Arg Arg Ser Pro Gly Val Gly Cys Val Pro Ala Ala Glu His Arg<br>500 505 510 | 1536 |
| ctg cgc gaa gag att ctc gca aag ttc ctg cac tgg ctt atg agc gtc<br>Leu Arg Glu Glu Ile Leu Ala Lys Phe Leu His Trp Leu Met Ser Val<br>515 520 525 | 1584 |
| tac gtg gtc gaa ctg ctg cgg tct ttc ttc tac gtg aca gag acc act<br>Tyr Val Val Glu Leu Leu Arg Ser Phe Phe Tyr Val Thr Glu Thr Thr<br>530 535 540 | 1632 |
| ttt cag aag aac aga ctg ttc ttc tac agg aag tcc gtc tgg agc aag<br>Phe Gln Lys Asn Arg Leu Phe Phe Tyr Arg Lys Ser Val Trp Ser Lys<br>545 550 555 560 | 1680 |
| ctc cag agt att ggt att aga cag cac ctt aag aga gtt cag ctt aga<br>Leu Gln Ser Ile Gly Ile Arg Gln His Leu Lys Arg Val Gln Leu Arg<br>565 570 575 | 1728 |
| gag ctg tcc gaa gct gaa gtc cgc cag cac cgc gaa gct cgc ccc gcc<br>Glu Leu Ser Glu Ala Glu Val Arg Gln His Arg Glu Ala Arg Pro Ala<br>580 585 590 | 1776 |
| ctc ctg acc tct cgg ctg cgg ttt att ccc aaa ccc gat ggc ctt aga<br>Leu Leu Thr Ser Arg Leu Arg Phe Ile Pro Lys Pro Asp Gly Leu Arg<br>595 600 605 | 1824 |
| cct atc gtg aat atg gat tac gtc gtg ggt gcc cgc act ttc aga agg<br>Pro Ile Val Asn Met Asp Tyr Val Val Gly Ala Arg Thr Phe Arg Arg<br>610 615 620 | 1872 |
| gag aag cgc gcc gag aga ctg aca tct cgc gtg aag gca ctt ttt tct<br>Glu Lys Arg Ala Glu Arg Leu Thr Ser Arg Val Lys Ala Leu Phe Ser<br>625 630 635 640 | 1920 |
| gtg ctt aat tat gaa aga gcc cgc aga cct ggt ctt ctc gga gcc agc<br>Val Leu Asn Tyr Glu Arg Ala Arg Arg Pro Gly Leu Leu Gly Ala Ser<br>645 650 655 | 1968 |
| gtg ctc ggc ctg gat gat atc cat cgg gct tgg cgc acc ttt gtg ctt<br>Val Leu Gly Leu Asp Asp Ile His Arg Ala Trp Arg Thr Phe Val Leu<br>660 665 670 | 2016 |
| cgg gtg agg gca cag gat cct cct cct gag ctt tat ttt gtg aaa gtt<br>Arg Val Arg Ala Gln Asp Pro Pro Pro Glu Leu Tyr Phe Val Lys Val<br>675 680 685 | 2064 |
| gat gtt act ggt gct tac gat aca atc cct cag gac cgg ctc acc gag<br>Asp Val Thr Gly Ala Tyr Asp Thr Ile Pro Gln Asp Arg Leu Thr Glu<br>690 695 700 | 2112 |

```
gtg atc gcc tct att atc aaa ccc cag aac acc tac tgc gtg aga agg    2160
Val Ile Ala Ser Ile Ile Lys Pro Gln Asn Thr Tyr Cys Val Arg Arg
705             710                 715                 720 tac gcc gtc gtt cag aaa gcc gca cac gga cac gtg cgc aaa gct ttc    2208
Tyr Ala Val Val Gln Lys Ala Ala His Gly His Val Arg Lys Ala Phe
                725                 730                 735 aaa tcc cac gtg tct acc ttg aca gac ctc cag cct tat atg cgg cag    2256
Lys Ser His Val Ser Thr Leu Thr Asp Leu Gln Pro Tyr Met Arg Gln
            740                 745                 750 ttt gtc gca cac ctg cag gag act agc ccc ttg agg gac gct gtg gtc    2304
Phe Val Ala His Leu Gln Glu Thr Ser Pro Leu Arg Asp Ala Val Val
        755                 760                 765 atc gaa cag tcc agc tct ctc aat gag gca tcc tca ggc ctg ttt gat    2352
Ile Glu Gln Ser Ser Ser Leu Asn Glu Ala Ser Ser Gly Leu Phe Asp
    770                 775                 780 gtg ttc ctg cgc ttt atg tgc cac cac gcc gtg cgg att agg ggc aag    2400
Val Phe Leu Arg Phe Met Cys His His Ala Val Arg Ile Arg Gly Lys
785                 790                 795                 800 tct tac gtg cag tgc cag ggc atc cca cag ggt agc atc ctg agc aca    2448
Ser Tyr Val Gln Cys Gln Gly Ile Pro Gln Gly Ser Ile Leu Ser Thr
                805                 810                 815 ctg ctg tgt agc ctg tgc tat ggc gat atg gag aat aaa ttg ttc gcc    2496
Leu Leu Cys Ser Leu Cys Tyr Gly Asp Met Glu Asn Lys Leu Phe Ala
            820                 825                 830 ggt atc aga aga gac ggt ttg ctc ctg agg ctg ctg act cat gcc aaa    2544
Gly Ile Arg Arg Asp Gly Leu Leu Leu Arg Leu Leu Thr His Ala Lys
        835                 840                 845 aca ttt ttg cgg act ctg gtt agg ggc gtg cca gag tat ggc tgt gtt    2592
Thr Phe Leu Arg Thr Leu Val Arg Gly Val Pro Glu Tyr Gly Cys Val
    850                 855                 860 gtg aat ttg cgg aaa act gtg gtt aat ttc cca gtg gag gac gaa gct    2640
Val Asn Leu Arg Lys Thr Val Val Asn Phe Pro Val Glu Asp Glu Ala
865                 870                 875                 880 ctc gga ggc aca gct ttt gtt cag atg cct gcc cac ggc ctg ttc cca    2688
Leu Gly Gly Thr Ala Phe Val Gln Met Pro Ala His Gly Leu Phe Pro
                885                 890                 895 tgg tgc gga ctg ctg ctc gat acc cgg acc ctc gag gtg cag tcc gat    2736
Trp Cys Gly Leu Leu Leu Asp Thr Arg Thr Leu Glu Val Gln Ser Asp
            900                 905                 910 tat agt tcc tat gca aga aca tca att cgg gct agc ctg act ttc aac    2784
Tyr Ser Ser Tyr Ala Arg Thr Ser Ile Arg Ala Ser Leu Thr Phe Asn
        915                 920                 925 agg ggc ttc aag gcc ggc cgg aat atg aga agg aaa ctg ttc gga gtg    2832
Arg Gly Phe Lys Ala Gly Arg Asn Met Arg Arg Lys Leu Phe Gly Val
    930                 935                 940 ttg aga ctt aag tgt cat agt ctt ttt ttg gac ttg cag gtc aat tct    2880
Leu Arg Leu Lys Cys His Ser Leu Phe Leu Asp Leu Gln Val Asn Ser
945                 950                 955                 960 ctc cag aca gtg tgt acc aac att tat aaa atc ctc ttg ctg cag gct    2928
Leu Gln Thr Val Cys Thr Asn Ile Tyr Lys Ile Leu Leu Leu Gln Ala
                965                 970                 975 tac aga ttc cat gcc tgc gtc ctg cag ctg cct ttc cac cag cag gtg    2976
Tyr Arg Phe His Ala Cys Val Leu Gln Leu Pro Phe His Gln Gln Val
            980                 985                 990 tgg aaa aac cct acc ttc ttc ctg  cgg gtg att agc gac  acc gcc agt   3024
Trp Lys Asn Pro Thr Phe Phe Leu  Arg Val Ile Ser Asp  Thr Ala Ser
        995                 1000                 1005
```

-continued

| | | | | | | | | | | |
|---|---|---|---|---|---|---|---|---|---|---|
| ctt | tgc | tac | tcc | atc | ttg | aaa | gca | aaa | aac | gct | ggc | atg | agc | ttg | 3069 |
| Leu | Cys | Tyr | Ser | Ile | Leu | Lys | Ala | Lys | Asn | Ala | Gly | Met | Ser | Leu | |
| | 1010 | | | | 1015 | | | | 1020 | | | | | | |

```
ctt tgc tac tcc atc ttg aaa gca aaa aac gct ggc atg agc ttg     3069
Leu Cys Tyr Ser Ile Leu Lys Ala Lys Asn Ala Gly Met Ser Leu
    1010            1015                1020 gga gct aag ggc gcc gct gga cct ctg ccc agt gaa gca gtc cag     3114
Gly Ala Lys Gly Ala Ala Gly Pro Leu Pro Ser Glu Ala Val Gln
        1025            1030                1035 tgg ctg tgt cat cag gct ttc ctc ctt aaa ctg aca cgc cac cgc     3159
Trp Leu Cys His Gln Ala Phe Leu Leu Lys Leu Thr Arg His Arg
    1040            1045                1050 gtg act tac gtc cca ctc ctg ggc tcc ctg aga act gct cag acc     3204
Val Thr Tyr Val Pro Leu Leu Gly Ser Leu Arg Thr Ala Gln Thr
        1055            1060                1065 cag ctt tcc cgg aag ctt cca ggc act acc ctt acc gca ctc gaa     3249
Gln Leu Ser Arg Lys Leu Pro Gly Thr Thr Leu Thr Ala Leu Glu
    1070            1075                1080 gca gcc gcc aac cct gcc ctg ccc tcc gac ttt aag act atc ctg     3294
Ala Ala Ala Asn Pro Ala Leu Pro Ser Asp Phe Lys Thr Ile Leu
        1085            1090                1095 gac                                                              3297
Asp

<210> SEQ ID NO 8
<211> LENGTH: 1099
<212> TYPE: PRT
<213> ORGANISM: Homo sapiens

<400> SEQUENCE: 8

Leu Ala Thr Phe Val Arg Arg Leu Gly Pro Gln Gly Trp Arg Leu Val
1               5                   10                  15

Gln Arg Gly Asp Pro Ala Ala Phe Arg Ala Leu Val Ala Gln Cys Leu
            20                  25                  30

Val Cys Val Pro Trp Asp Ala Arg Pro Pro Ala Ala Pro Ser Phe
        35                  40                  45

Arg Gln Val Ser Cys Leu Lys Glu Leu Val Ala Arg Val Leu Gln Arg
    50                  55                  60

Leu Cys Glu Arg Gly Ala Lys Asn Val Leu Ala Phe Gly Phe Ala Leu
65                  70                  75                  80

Leu Asp Gly Ala Arg Gly Gly Pro Pro Glu Ala Phe Thr Thr Ser Val
                85                  90                  95

Arg Ser Tyr Leu Pro Asn Thr Val Thr Asp Ala Leu Arg Gly Ser Gly
            100                 105                 110

Ala Trp Gly Leu Leu Leu Arg Arg Val Gly Asp Asp Val Leu Val His
        115                 120                 125

Leu Leu Ala Arg Cys Ala Leu Phe Val Leu Val Ala Pro Ser Cys Ala
    130                 135                 140

Tyr Gln Val Cys Gly Pro Pro Leu Tyr Gln Leu Gly Ala Ala Thr Gln
145                 150                 155                 160

Ala Arg Pro Pro Pro His Ala Ser Gly Pro Arg Arg Arg Leu Gly Cys
                165                 170                 175

Glu Arg Ala Trp Asn His Ser Val Arg Glu Ala Gly Val Pro Leu Gly
            180                 185                 190

Leu Pro Ala Pro Gly Ala Arg Arg Arg Gly Gly Ser Ala Ser Arg Ser
        195                 200                 205

Leu Pro Leu Pro Lys Arg Pro Arg Arg Gly Ala Ala Pro Glu Pro Glu
    210                 215                 220
```

```
Arg Thr Pro Val Gly Gln Gly Ser Trp Ala His Pro Gly Arg Thr Arg
225                 230                 235                 240

Gly Pro Ser Asp Arg Gly Phe Cys Val Val Ser Pro Ala Arg Pro Ala
            245                 250                 255

Glu Glu Ala Thr Ser Leu Glu Gly Ala Leu Ser Gly Thr Arg His Ser
                260                 265                 270

His Pro Ser Val Gly Arg Gln His His Ala Gly Pro Pro Ser Thr Ser
        275                 280                 285

Arg Pro Pro Arg Pro Trp Asp Thr Pro Cys Pro Val Tyr Ala Glu
    290                 295                 300

Thr Lys His Phe Leu Tyr Ser Ser Gly Asp Lys Glu Gln Leu Arg Pro
305                 310                 315                 320

Ser Phe Leu Leu Ser Ser Leu Arg Pro Ser Leu Thr Gly Ala Arg Arg
                325                 330                 335

Leu Val Glu Thr Ile Phe Leu Gly Ser Arg Pro Trp Met Pro Gly Thr
                340                 345                 350

Pro Arg Arg Leu Pro Arg Leu Pro Gln Arg Tyr Trp Gln Met Arg Pro
            355                 360                 365

Leu Phe Leu Glu Leu Leu Gly Asn His Ala Gln Cys Pro Tyr Gly Val
370                 375                 380

Leu Leu Lys Thr His Cys Pro Leu Arg Ala Ala Val Thr Pro Ala Ala
385                 390                 395                 400

Gly Val Cys Ala Arg Glu Lys Pro Gln Gly Ser Val Ala Ala Pro Glu
                405                 410                 415

Glu Glu Asp Thr Asp Pro Arg Arg Leu Val Gln Leu Leu Arg Gln His
                420                 425                 430

Ser Ser Pro Trp Gln Val Tyr Gly Phe Val Arg Ala Cys Leu Arg Arg
            435                 440                 445

Leu Val Pro Pro Gly Leu Trp Gly Ser Arg His Asn Glu Arg Arg Phe
450                 455                 460

Leu Arg Asn Thr Lys Lys Phe Ile Ser Leu Gly Lys His Ala Lys Leu
465                 470                 475                 480

Ser Leu Gln Glu Leu Thr Trp Lys Met Ser Val Arg Gly Cys Ala Trp
                485                 490                 495

Leu Arg Arg Ser Pro Gly Val Gly Cys Val Pro Ala Ala Glu His Arg
            500                 505                 510

Leu Arg Glu Glu Ile Leu Ala Lys Phe Leu His Trp Leu Met Ser Val
            515                 520                 525

Tyr Val Val Glu Leu Leu Arg Ser Phe Phe Tyr Val Thr Glu Thr Thr
530                 535                 540

Phe Gln Lys Asn Arg Leu Phe Phe Tyr Arg Lys Ser Val Trp Ser Lys
545                 550                 555                 560

Leu Gln Ser Ile Gly Ile Arg Gln His Leu Lys Arg Val Gln Leu Arg
                565                 570                 575

Glu Leu Ser Glu Ala Glu Val Arg Gln His Arg Glu Ala Arg Pro Ala
            580                 585                 590

Leu Leu Thr Ser Arg Leu Arg Phe Ile Pro Lys Pro Asp Gly Leu Arg
            595                 600                 605

Pro Ile Val Asn Met Asp Tyr Val Val Gly Ala Arg Thr Phe Arg Arg
            610                 615                 620

Glu Lys Arg Ala Glu Arg Leu Thr Ser Arg Val Lys Ala Leu Phe Ser
625                 630                 635                 640
```

-continued

```
Val Leu Asn Tyr Glu Arg Ala Arg Arg Pro Gly Leu Leu Gly Ala Ser
                645                 650                 655

Val Leu Gly Leu Asp Asp Ile His Arg Ala Trp Arg Thr Phe Val Leu
            660                 665                 670

Arg Val Arg Ala Gln Asp Pro Pro Glu Leu Tyr Phe Val Lys Val
        675                 680                 685

Asp Val Thr Gly Ala Tyr Asp Thr Ile Pro Gln Asp Arg Leu Thr Glu
    690                 695                 700

Val Ile Ala Ser Ile Ile Lys Pro Gln Asn Thr Tyr Cys Val Arg Arg
705                 710                 715                 720

Tyr Ala Val Val Gln Lys Ala Ala His Gly His Val Arg Lys Ala Phe
                725                 730                 735

Lys Ser His Val Ser Thr Leu Thr Asp Leu Gln Pro Tyr Met Arg Gln
            740                 745                 750

Phe Val Ala His Leu Gln Glu Thr Ser Pro Leu Arg Asp Ala Val Val
        755                 760                 765

Ile Glu Gln Ser Ser Ser Leu Asn Glu Ala Ser Ser Gly Leu Phe Asp
    770                 775                 780

Val Phe Leu Arg Phe Met Cys His His Ala Val Arg Ile Arg Gly Lys
785                 790                 795                 800

Ser Tyr Val Gln Cys Gln Gly Ile Pro Gln Gly Ser Ile Leu Ser Thr
                805                 810                 815

Leu Leu Cys Ser Leu Cys Tyr Gly Asp Met Glu Asn Lys Leu Phe Ala
            820                 825                 830

Gly Ile Arg Arg Asp Gly Leu Leu Leu Arg Leu Leu Thr His Ala Lys
        835                 840                 845

Thr Phe Leu Arg Thr Leu Val Arg Gly Val Pro Glu Tyr Gly Cys Val
    850                 855                 860

Val Asn Leu Arg Lys Thr Val Asn Phe Pro Val Glu Asp Glu Ala
865                 870                 875                 880

Leu Gly Gly Thr Ala Phe Val Gln Met Pro Ala His Gly Leu Phe Pro
                885                 890                 895

Trp Cys Gly Leu Leu Leu Asp Thr Arg Thr Leu Glu Val Gln Ser Asp
            900                 905                 910

Tyr Ser Ser Tyr Ala Arg Thr Ser Ile Arg Ala Ser Leu Thr Phe Asn
        915                 920                 925

Arg Gly Phe Lys Ala Gly Arg Asn Met Arg Arg Lys Leu Phe Gly Val
    930                 935                 940

Leu Arg Leu Lys Cys His Ser Leu Phe Leu Asp Leu Gln Val Asn Ser
945                 950                 955                 960

Leu Gln Thr Val Cys Thr Asn Ile Tyr Lys Ile Leu Leu Leu Gln Ala
                965                 970                 975

Tyr Arg Phe His Ala Cys Val Leu Gln Leu Pro Phe His Gln Gln Val
            980                 985                 990

Trp Lys Asn Pro Thr Phe Phe Leu Arg Val Ile Ser Asp Thr Ala Ser
        995                 1000                1005

Leu Cys Tyr Ser Ile Leu Lys Ala Lys Asn Ala Gly Met Ser Leu
    1010                1015                1020

Gly Ala Lys Gly Ala Ala Gly Pro Leu Pro Ser Glu Ala Val Gln
    1025                1030                1035

Trp Leu Cys His Gln Ala Phe Leu Leu Lys Leu Thr Arg His Arg
    1040                1045                1050
```

-continued

```
Val Thr Tyr Val Pro Leu Leu Gly Ser Leu Arg Thr Ala Gln Thr
    1055                1060                1065

Gln Leu Ser Arg Lys Leu Pro Gly Thr Thr Leu Thr Ala Leu Glu
    1070                1075                1080

Ala Ala Ala Asn Pro Ala Leu Pro Ser Asp Phe Lys Thr Ile Leu
    1085                1090                1095

Asp

<210> SEQ ID NO 9
<211> LENGTH: 3258
<212> TYPE: DNA
<213> ORGANISM: Homo sapiens
<220> FEATURE:
<221> NAME/KEY: CDS
<222> LOCATION: (1)..(3258)

<400> SEQUENCE: 9
```

| | | |
|---|---|---|
| ctg gcc acc ttc gtg cgg cgc ctg gga ccc cag ggc tgg cgg ctg gtg<br>Leu Ala Thr Phe Val Arg Arg Leu Gly Pro Gln Gly Trp Arg Leu Val<br>1               5                   10                  15 | | 48 |
| cag cgc ggg gac cct gct gct ttc aga gct ctc gtc gcc cag tgt ctg<br>Gln Arg Gly Asp Pro Ala Ala Phe Arg Ala Leu Val Ala Gln Cys Leu<br>            20                  25                  30 | | 96 |
| gtc tgc gtt cct tgg gac gca cgg ccc cca ccc gcc gcc ccc agt ttc<br>Val Cys Val Pro Trp Asp Ala Arg Pro Pro Pro Ala Ala Pro Ser Phe<br>        35                  40                  45 | | 144 |
| cgg cag gtg agt tgt ctc aaa gag ttg gtt gct cgg gtg ttg cag cgg<br>Arg Gln Val Ser Cys Leu Lys Glu Leu Val Ala Arg Val Leu Gln Arg<br>    50                  55                  60 | | 192 |
| ctt tgt gaa agg gga gca aag aac gtc ctt gcc ttt ggc ttc gct ttg<br>Leu Cys Glu Arg Gly Ala Lys Asn Val Leu Ala Phe Gly Phe Ala Leu<br>65                  70                  75                  80 | | 240 |
| ctc gat gga gca cgc gga ggc cct cct gag gca ttc act act agc gtc<br>Leu Asp Gly Ala Arg Gly Gly Pro Pro Glu Ala Phe Thr Thr Ser Val<br>                85                  90                  95 | | 288 |
| cgg tcc tac ctg ccc aac aca gtg acc gac gct ctg aga ggt tca ggt<br>Arg Ser Tyr Leu Pro Asn Thr Val Thr Asp Ala Leu Arg Gly Ser Gly<br>            100                 105                 110 | | 336 |
| gcc tgg ggt ctg ctg ctg cgg agg gtg ggt gat gat gtt ctg gtt cac<br>Ala Trp Gly Leu Leu Leu Arg Arg Val Gly Asp Asp Val Leu Val His<br>        115                 120                 125 | | 384 |
| ctc ctg gcc cgg tgt gcc ctg ttc gtg ctg gtg gct ccc tcc tgc gca<br>Leu Leu Ala Arg Cys Ala Leu Phe Val Leu Val Ala Pro Ser Cys Ala<br>    130                 135                 140 | | 432 |
| tac cag gtc tgc gga ccc cca ctt tat cag ctc ggc gct gct act cag<br>Tyr Gln Val Cys Gly Pro Pro Leu Tyr Gln Leu Gly Ala Ala Thr Gln<br>145                 150                 155                 160 | | 480 |
| gcc cgc cca cca cca cac gcc tca ggt cca aga cgc ggc tgg cTg tgc<br>Ala Arg Pro Pro Pro His Ala Ser Gly Pro Arg Arg Leu Gly Cys<br>                165                 170                 175 | | 528 |
| gaa cgg gca tgg aat cat agc gtg cgg gag gca ggt gtg cct ctc ggc<br>Glu Arg Ala Trp Asn His Ser Val Arg Glu Ala Gly Val Pro Leu Gly<br>            180                 185                 190 | | 576 |
| ctg cca gcc ccc gga gca agg aga cgc ggt gga tcc gcc agt cgc tca<br>Leu Pro Ala Pro Gly Ala Arg Arg Arg Gly Gly Ser Ala Ser Arg Ser<br>        195                 200                 205 | | 624 |
| ctc ccc ttg cct aag agg cca aga aga gga gcc gcc cct gaa ccc gag<br>Leu Pro Leu Pro Lys Arg Pro Arg Arg Gly Ala Ala Pro Glu Pro Glu<br>    210                 215                 220 | | 672 |

| | | |
|---|---|---|
| aga aca cct gtc ggc cag ggc tcc tgg gct cac ccc gga agg acc agg<br>Arg Thr Pro Val Gly Gln Gly Ser Trp Ala His Pro Gly Arg Thr Arg<br>225                                230                         235                     240 | 720 |
| ggc cca agc gat agg ggc ttc tgt gtt gtg tca cca gcc agg cct gcc<br>Gly Pro Ser Asp Arg Gly Phe Cys Val Val Ser Pro Ala Arg Pro Ala<br>                      245                         250                     255 | 768 |
| gaa gag gct acc tcc ttg gaa gga gcc ctc agt ggc acc agg cat tct<br>Glu Glu Ala Thr Ser Leu Glu Gly Ala Leu Ser Gly Thr Arg His Ser<br>                260                         265                     270 | 816 |
| cat cca tct gtg ggt agg cag cat cat gcc ggc ccc ccc tct aca agc<br>His Pro Ser Val Gly Arg Gln His His Ala Gly Pro Pro Ser Thr Ser<br>            275                        280                     285 | 864 |
| aga cct ccc aga cct tgg gac aca ccc tgc cca gtg tat gcc gag<br>Arg Pro Pro Arg Pro Trp Asp Thr Pro Cys Pro Val Tyr Ala Glu<br>290                       295                         300 | 912 |
| acc aag cac ttt ttg tat tcc agt ggc gat aaa gag cag ctc cgg ccc<br>Thr Lys His Phe Leu Tyr Ser Ser Gly Asp Lys Glu Gln Leu Arg Pro<br>305                                310                         315                     320 | 960 |
| tct ttt ctg ctc tca agc ctc cgc ccc tct ctg acc gga gct cgc agg<br>Ser Phe Leu Leu Ser Ser Leu Arg Pro Ser Leu Thr Gly Ala Arg Arg<br>                        325                         330                     335 | 1008 |
| ctg gtg gag acc atc ttt ctg ggc tca aga cca tgg atg cca ggc acc<br>Leu Val Glu Thr Ile Phe Leu Gly Ser Arg Pro Trp Met Pro Gly Thr<br>                340                         345                     350 | 1056 |
| ccc cgc aga ctg ccc agg ctc ccc cag cgg tac tgg cag atg cgc cct<br>Pro Arg Arg Leu Pro Arg Leu Pro Gln Arg Tyr Trp Gln Met Arg Pro<br>                      355                         360                     365 | 1104 |
| ctc ttt ctg gaa ctt ctg ggt aac cac gcc cag tgc cca tat ggc gtc<br>Leu Phe Leu Glu Leu Leu Gly Asn His Ala Gln Cys Pro Tyr Gly Val<br>370                                375                         380 | 1152 |
| ctg ctg aag acc cac tgt cct ctg agg gcc gcc gtg acc cca gcc gcc<br>Leu Leu Lys Thr His Cys Pro Leu Arg Ala Ala Val Thr Pro Ala Ala<br>385                                390                         395                     400 | 1200 |
| ggt gtg tgt gct aga gaa aaa ccc cag ggc tca gtg gct gca cct gaa<br>Gly Val Cys Ala Arg Glu Lys Pro Gln Gly Ser Val Ala Ala Pro Glu<br>                      405                         410                     415 | 1248 |
| gag gag gac act gac cct cgc cgc ctt gtc cag ttg ctc agg cag cat<br>Glu Glu Asp Thr Asp Pro Arg Arg Leu Val Gln Leu Leu Arg Gln His<br>                    420                         425                     430 | 1296 |
| tca tca cca tgg cag gtg tac ggc ttc gtg agg gct tgc ctg cgg aga<br>Ser Ser Pro Trp Gln Val Tyr Gly Phe Val Arg Ala Cys Leu Arg Arg<br>            435                        440                     445 | 1344 |
| ctg gtc ccc ccc gga ttg tgg gga tct cgg cac aac gaa cgg cgc ttt<br>Leu Val Pro Pro Gly Leu Trp Gly Ser Arg His Asn Glu Arg Arg Phe<br>450                                455                         460 | 1392 |
| ctg agg aat aca aag aag ttt atc tcc ctg ggc aag cat gca aag ctc<br>Leu Arg Asn Thr Lys Lys Phe Ile Ser Leu Gly Lys His Ala Lys Leu<br>465                                470                         475                     480 | 1440 |
| agc ttg cag gag ctg aca tgg aag atg agc gtt aga gga tgc gca tgg<br>Ser Leu Gln Glu Leu Thr Trp Lys Met Ser Val Arg Gly Cys Ala Trp<br>                    485                         490                     495 | 1488 |
| ctc agg cgg tca cct gga gtt gga tgc gtt cca gca gca gag cac agg<br>Leu Arg Arg Ser Pro Gly Val Gly Cys Val Pro Ala Ala Glu His Arg<br>                      500                         505                     510 | 1536 |
| ctg cgc gaa gag att ctc gca aag ttc ctg cac tgg ctt atg agc gtc<br>Leu Arg Glu Glu Ile Leu Ala Lys Phe Leu His Trp Leu Met Ser Val<br>                515                         520                     525 | 1584 |
| tac gtg gtc gaa ctg ctg cgg tct ttc ttc tac gtg aca gag acc act<br>Tyr Val Val Glu Leu Leu Arg Ser Phe Phe Tyr Val Thr Glu Thr Thr<br>530                                535                         540 | 1632 |

-continued

| | |
|---|---|
| ttt cag aag aac aga ctg ttc ttc tac agg aag tcc gtc tgg agc aag<br>Phe Gln Lys Asn Arg Leu Phe Phe Tyr Arg Lys Ser Val Trp Ser Lys<br>545                            550                          555                          560 | 1680 |
| ctc cag agt att ggt att aga cag cac ctt aag aga gtt cag ctt aga<br>Leu Gln Ser Ile Gly Ile Arg Gln His Leu Lys Arg Val Gln Leu Arg<br>                        565                          570                          575 | 1728 |
| gag ctg tcc gaa gct gaa gtc cgc cag cac cgc gaa gct cgc ccc gcc<br>Glu Leu Ser Glu Ala Glu Val Arg Gln His Arg Glu Ala Arg Pro Ala<br>580                            585                          590 | 1776 |
| ctc ctg acc tct cgg ctg cgg ttt att ccc aaa ccc gat ggc ctt aga<br>Leu Leu Thr Ser Arg Leu Arg Phe Ile Pro Lys Pro Asp Gly Leu Arg<br>                        595                          600                          605 | 1824 |
| cct atc gtg aat atg gat tac gtc gtg ggt gcc cgc act ttc aga agg<br>Pro Ile Val Asn Met Asp Tyr Val Val Gly Ala Arg Thr Phe Arg Arg<br>610                            615                          620 | 1872 |
| gag aag cgc gcc gag aga ctg aca tct cgc gtg aag gca ctt ttt tct<br>Glu Lys Arg Ala Glu Arg Leu Thr Ser Arg Val Lys Ala Leu Phe Ser<br>625                            630                          635                          640 | 1920 |
| gtg ctt aat tat gaa aga gcc cgc aga cct ggt ctc ctc gga gcc agc<br>Val Leu Asn Tyr Glu Arg Ala Arg Arg Pro Gly Leu Leu Gly Ala Ser<br>                        645                          650                          655 | 1968 |
| gtg ctc ggc ctg gat gat atc cat cgg gct tgg cgc acc ttt gtg ctt<br>Val Leu Gly Leu Asp Asp Ile His Arg Ala Trp Arg Thr Phe Val Leu<br>660                            665                          670 | 2016 |
| cgg gtg agg gca cag gat cct cct cct gag ctt tat ttt gtg aaa gtt<br>Arg Val Arg Ala Gln Asp Pro Pro Pro Glu Leu Tyr Phe Val Lys Val<br>                        675                          680                          685 | 2064 |
| gat gtt act ggt gct tac gat aca atc cct cag gac cgg ctc acc gag<br>Asp Val Thr Gly Ala Tyr Asp Thr Ile Pro Gln Asp Arg Leu Thr Glu<br>690                            695                          700 | 2112 |
| gtg atc gcc tct att atc aaa ccc cag aac acc tac tgc gtg aga agg<br>Val Ile Ala Ser Ile Ile Lys Pro Gln Asn Thr Tyr Cys Val Arg Arg<br>705                            710                          715                          720 | 2160 |
| tac gcc gtc gtt cag aaa gcc gca cac gga cac gtg cgc aaa gct ttc<br>Tyr Ala Val Val Gln Lys Ala Ala His Gly His Val Arg Lys Ala Phe<br>                        725                          730                          735 | 2208 |
| aaa tcc cac gtg tct acc ttg aca gac ctc cag cct tat atg cgg cag<br>Lys Ser His Val Ser Thr Leu Thr Asp Leu Gln Pro Tyr Met Arg Gln<br>740                            745                          750 | 2256 |
| ttt gtc gca cac ctg cag gag act agc ccc ttg agg gac gct gtg gtc<br>Phe Val Ala His Leu Gln Glu Thr Ser Pro Leu Arg Asp Ala Val Val<br>                        755                          760                          765 | 2304 |
| atc gaa cag tcc agc tct ctc aat gag gca tcc tca ggc ctg ttt gat<br>Ile Glu Gln Ser Ser Ser Leu Asn Glu Ala Ser Ser Gly Leu Phe Asp<br>770                            775                          780 | 2352 |
| gtg ttc ctg cgc ttt atg tgc cac cac gcc gtg cgg att agg ggc aag<br>Val Phe Leu Arg Phe Met Cys His His Ala Val Arg Ile Arg Gly Lys<br>785                            790                          795                          800 | 2400 |
| tct tac gtg cag tgc cag ggc atc cca cag ggt agc atc ctg agc aca<br>Ser Tyr Val Gln Cys Gln Gly Ile Pro Gln Gly Ser Ile Leu Ser Thr<br>                        805                          810                          815 | 2448 |
| ctg ctg tgt agc ctg tgc tat ggc gat atg gag aat aaa ttg ttc gcc<br>Leu Leu Cys Ser Leu Cys Tyr Gly Asp Met Glu Asn Lys Leu Phe Ala<br>820                            825                          830 | 2496 |
| ggt gcc aaa aca ttt ttg cgg act ctg gtt agg ggc gtg cca gag tat<br>Gly Ala Lys Thr Phe Leu Arg Thr Leu Val Arg Gly Val Pro Glu Tyr<br>                        835                          840                          845 | 2544 |

```
ggc tgt gtt gtg aat ttg cgg aaa act gtg gtt aat ttc cca gtg gag      2592
Gly Cys Val Val Asn Leu Arg Lys Thr Val Val Asn Phe Pro Val Glu
850                 855                 860 gac gaa gct ctc gga ggc aca gct ttt gtt cag atg cct gcc cac ggc      2640
Asp Glu Ala Leu Gly Gly Thr Ala Phe Val Gln Met Pro Ala His Gly
865                 870                 875                 880 ctg ttc cca tgg tgc gga ctg ctc gat acc cgg acc ctc gag gtg          2688
Leu Phe Pro Trp Cys Gly Leu Leu Asp Thr Arg Thr Leu Glu Val
                885                 890                 895 cag tcc gat tat agt tcc tat gca aga aca tca att cgg gct agc ctg      2736
Gln Ser Asp Tyr Ser Ser Tyr Ala Arg Thr Ser Ile Arg Ala Ser Leu
            900                 905                 910 act ttc aac agg ggc ttc aag gcc ggc cgg aat atg aga agg aaa ctg      2784
Thr Phe Asn Arg Gly Phe Lys Ala Gly Arg Asn Met Arg Arg Lys Leu
        915                 920                 925 ttc gga gtg ttg aga ctt aag tgt cat agt ctt ttt ttg gac ttg cag      2832
Phe Gly Val Leu Arg Leu Lys Cys His Ser Leu Phe Leu Asp Leu Gln
    930                 935                 940 gtc aat tct ctc cag aca gtg tgt acc aac att tat aaa atc ctc ttg      2880
Val Asn Ser Leu Gln Thr Val Cys Thr Asn Ile Tyr Lys Ile Leu Leu
945                 950                 955                 960 ctg cag gct tac aga ttc cat gcc tgc gtc ctg cag ctg cct ttc cac      2928
Leu Gln Ala Tyr Arg Phe His Ala Cys Val Leu Gln Leu Pro Phe His
                965                 970                 975 cag cag gtg tgg aaa aac cct acc ttc ttc ctg cgg gtg att agc gac      2976
Gln Gln Val Trp Lys Asn Pro Thr Phe Phe Leu Arg Val Ile Ser Asp
            980                 985                 990 acc gcc agt ctt tgc tac tcc atc ttg aaa gca aaa aac gct ggc atg      3024
Thr Ala Ser Leu Cys Tyr Ser Ile Leu Lys Ala Lys Asn Ala Gly Met
        995                 1000                1005 agc ttg gga gct aag ggc gcc gct gga cct ctg ccc agt gaa gca           3069
Ser Leu Gly Ala Lys Gly Ala Ala Gly Pro Leu Pro Ser Glu Ala
    1010                1015                1020 gtc cag tgg ctg tgt cat cag gct ttc ctc ctt aaa ctg aca cgc           3114
Val Gln Trp Leu Cys His Gln Ala Phe Leu Leu Lys Leu Thr Arg
    1025                1030                1035 cac cgc gtg act tac gtc cca ctc ctg ggc tcc ctg aga act gct           3159
His Arg Val Thr Tyr Val Pro Leu Leu Gly Ser Leu Arg Thr Ala
    1040                1045                1050 cag acc cag ctt tcc cgg aag ctt cca ggc act acc ctt acc gca           3204
Gln Thr Gln Leu Ser Arg Lys Leu Pro Gly Thr Thr Leu Thr Ala
    1055                1060                1065 ctc gaa gca gcc gcc aac cct gcc ctg ccc tcc gac ttt aag act           3249
Leu Glu Ala Ala Ala Asn Pro Ala Leu Pro Ser Asp Phe Lys Thr
    1070                1075                1080 atc ctg gac                                                           3258
Ile Leu Asp
    1085

<210> SEQ ID NO 10
<211> LENGTH: 1086
<212> TYPE: PRT
<213> ORGANISM: Homo sapiens

<400> SEQUENCE: 10

Leu Ala Thr Phe Val Arg Arg Leu Gly Pro Gln Gly Trp Arg Leu Val
1               5                   10                  15

Gln Arg Gly Asp Pro Ala Ala Phe Arg Ala Leu Val Ala Gln Cys Leu
            20                  25                  30
```

Val Cys Val Pro Trp Asp Ala Arg Pro Pro Ala Ala Pro Ser Phe
         35                  40                  45

Arg Gln Val Ser Cys Leu Lys Glu Leu Val Ala Arg Val Leu Gln Arg
 50                  55                  60

Leu Cys Glu Arg Gly Ala Lys Asn Val Leu Ala Phe Gly Phe Ala Leu
 65                  70                  75                  80

Leu Asp Gly Ala Arg Gly Gly Pro Pro Glu Ala Phe Thr Thr Ser Val
                 85                  90                  95

Arg Ser Tyr Leu Pro Asn Thr Val Thr Asp Ala Leu Arg Gly Ser Gly
             100                 105                 110

Ala Trp Gly Leu Leu Arg Arg Val Gly Asp Asp Val Leu Val His
         115                 120                 125

Leu Leu Ala Arg Cys Ala Leu Phe Val Leu Val Ala Pro Ser Cys Ala
130                 135                 140

Tyr Gln Val Cys Gly Pro Pro Leu Tyr Gln Leu Gly Ala Ala Thr Gln
145                 150                 155                 160

Ala Arg Pro Pro His Ala Ser Gly Pro Arg Arg Leu Gly Cys
                 165                 170                 175

Glu Arg Ala Trp Asn His Ser Val Arg Glu Ala Gly Val Pro Leu Gly
             180                 185                 190

Leu Pro Ala Pro Gly Ala Arg Arg Gly Gly Ser Ala Ser Arg Ser
             195                 200                 205

Leu Pro Leu Pro Lys Arg Pro Arg Gly Ala Ala Pro Glu Pro Glu
             210                 215                 220

Arg Thr Pro Val Gly Gln Gly Ser Trp Ala His Pro Gly Arg Thr Arg
225                 230                 235                 240

Gly Pro Ser Asp Arg Gly Phe Cys Val Val Ser Pro Ala Arg Pro Ala
                 245                 250                 255

Glu Glu Ala Thr Ser Leu Glu Gly Ala Leu Ser Gly Thr Arg His Ser
             260                 265                 270

His Pro Ser Val Gly Arg Gln His His Ala Gly Pro Pro Ser Thr Ser
         275                 280                 285

Arg Pro Pro Arg Pro Trp Asp Thr Pro Cys Pro Pro Val Tyr Ala Glu
290                 295                 300

Thr Lys His Phe Leu Tyr Ser Ser Gly Asp Lys Glu Gln Leu Arg Pro
305                 310                 315                 320

Ser Phe Leu Leu Ser Ser Leu Arg Pro Ser Leu Thr Gly Ala Arg Arg
                 325                 330                 335

Leu Val Glu Thr Ile Phe Leu Gly Ser Arg Pro Trp Met Pro Gly Thr
             340                 345                 350

Pro Arg Arg Leu Pro Arg Leu Pro Gln Arg Tyr Trp Gln Met Arg Pro
             355                 360                 365

Leu Phe Leu Glu Leu Leu Gly Asn His Ala Gln Cys Pro Tyr Gly Val
             370                 375                 380

Leu Leu Lys Thr His Cys Pro Leu Arg Ala Ala Val Thr Pro Ala Ala
385                 390                 395                 400

Gly Val Cys Ala Arg Glu Lys Pro Gln Gly Ser Val Ala Ala Pro Glu
                 405                 410                 415

Glu Glu Asp Thr Asp Pro Arg Arg Leu Val Gln Leu Leu Arg Gln His
             420                 425                 430

Ser Ser Pro Trp Gln Val Tyr Gly Phe Val Arg Ala Cys Leu Arg Arg
         435                 440                 445

```
Leu Val Pro Pro Gly Leu Trp Gly Ser Arg His Asn Glu Arg Phe
    450                 455                 460

Leu Arg Asn Thr Lys Lys Phe Ile Ser Leu Gly Lys His Ala Lys Leu
465                 470                 475                 480

Ser Leu Gln Glu Leu Thr Trp Lys Met Ser Val Arg Gly Cys Ala Trp
                485                 490                 495

Leu Arg Arg Ser Pro Gly Val Gly Cys Val Pro Ala Ala Glu His Arg
                500                 505                 510

Leu Arg Glu Glu Ile Leu Ala Lys Phe Leu His Trp Leu Met Ser Val
                515                 520                 525

Tyr Val Val Glu Leu Leu Arg Ser Phe Phe Tyr Val Thr Glu Thr Thr
    530                 535                 540

Phe Gln Lys Asn Arg Leu Phe Phe Tyr Arg Lys Ser Val Trp Ser Lys
545                 550                 555                 560

Leu Gln Ser Ile Gly Ile Arg Gln His Leu Lys Arg Val Gln Leu Arg
                565                 570                 575

Glu Leu Ser Glu Ala Glu Val Arg Gln His Arg Glu Ala Arg Pro Ala
                580                 585                 590

Leu Leu Thr Ser Arg Leu Arg Phe Ile Pro Lys Pro Asp Gly Leu Arg
                595                 600                 605

Pro Ile Val Asn Met Asp Tyr Val Val Gly Ala Arg Thr Phe Arg Arg
    610                 615                 620

Glu Lys Arg Ala Glu Arg Leu Thr Ser Arg Val Lys Ala Leu Phe Ser
625                 630                 635                 640

Val Leu Asn Tyr Glu Arg Ala Arg Arg Pro Gly Leu Leu Gly Ala Ser
                645                 650                 655

Val Leu Gly Leu Asp Asp Ile His Arg Ala Trp Arg Thr Phe Val Leu
                660                 665                 670

Arg Val Arg Ala Gln Asp Pro Pro Glu Leu Tyr Phe Val Lys Val
    675                 680                 685

Asp Val Thr Gly Ala Tyr Asp Thr Ile Pro Gln Asp Arg Leu Thr Glu
    690                 695                 700

Val Ile Ala Ser Ile Ile Lys Pro Gln Asn Thr Tyr Cys Val Arg Arg
705                 710                 715                 720

Tyr Ala Val Val Gln Lys Ala Ala His Gly His Val Arg Lys Ala Phe
                725                 730                 735

Lys Ser His Val Ser Thr Leu Thr Asp Leu Gln Pro Tyr Met Arg Gln
                740                 745                 750

Phe Val Ala His Leu Gln Glu Thr Ser Pro Leu Arg Asp Ala Val Val
                755                 760                 765

Ile Glu Gln Ser Ser Ser Leu Asn Glu Ala Ser Ser Gly Leu Phe Asp
    770                 775                 780

Val Phe Leu Arg Phe Met Cys His His Ala Val Arg Ile Arg Gly Lys
785                 790                 795                 800

Ser Tyr Val Gln Cys Gln Gly Ile Pro Gln Gly Ser Ile Leu Ser Thr
                805                 810                 815

Leu Leu Cys Ser Leu Cys Tyr Gly Asp Met Glu Asn Lys Leu Phe Ala
                820                 825                 830

Gly Ala Lys Thr Phe Leu Arg Thr Leu Val Arg Gly Val Pro Glu Tyr
                835                 840                 845

Gly Cys Val Val Asn Leu Arg Lys Thr Val Val Asn Phe Pro Val Glu
    850                 855                 860
```

Asp Glu Ala Leu Gly Gly Thr Ala Phe Val Gln Met Pro Ala His Gly
865                 870                 875                 880

Leu Phe Pro Trp Cys Gly Leu Leu Leu Asp Thr Arg Thr Leu Glu Val
            885                 890                 895

Gln Ser Asp Tyr Ser Ser Tyr Ala Arg Thr Ser Ile Arg Ala Ser Leu
        900                 905                 910

Thr Phe Asn Arg Gly Phe Lys Ala Gly Arg Asn Met Arg Arg Lys Leu
    915                 920                 925

Phe Gly Val Leu Arg Leu Lys Cys His Ser Leu Phe Leu Asp Leu Gln
930                 935                 940

Val Asn Ser Leu Gln Thr Val Cys Thr Asn Ile Tyr Lys Ile Leu Leu
945                 950                 955                 960

Leu Gln Ala Tyr Arg Phe His Ala Cys Val Leu Gln Leu Pro Phe His
            965                 970                 975

Gln Gln Val Trp Lys Asn Pro Thr Phe Phe Leu Arg Val Ile Ser Asp
        980                 985                 990

Thr Ala Ser Leu Cys Tyr Ser Ile Leu Lys Ala Lys Asn Ala Gly Met
    995                 1000                1005

Ser Leu Gly Ala Lys Gly Ala Ala Gly Pro Leu Pro Ser Glu Ala
    1010                1015                1020

Val Gln Trp Leu Cys His Gln Ala Phe Leu Leu Lys Leu Thr Arg
    1025                1030                1035

His Arg Val Thr Tyr Val Pro Leu Leu Gly Ser Leu Arg Thr Ala
    1040                1045                1050

Gln Thr Gln Leu Ser Arg Lys Leu Pro Gly Thr Thr Leu Thr Ala
    1055                1060                1065

Leu Glu Ala Ala Ala Asn Pro Ala Leu Pro Ser Asp Phe Lys Thr
    1070                1075                1080

Ile Leu Asp
    1085

```
<210> SEQ ID NO 11
<211> LENGTH: 7120
<212> TYPE: DNA
<213> ORGANISM: Artificial Sequence
<220> FEATURE:
<223> OTHER INFORMATION: Description of Artificial Sequence: Synthetic
      INVAC-1 plasmid expression vector
<220> FEATURE:
<221> NAME/KEY: CDS
<222> LOCATION: (3488)..(6961)

<400> SEQUENCE: 11
gctagcaccg ttggtttccg tagtgtagtg gttatcacgt tcgcctaaca cgcgaaaggt    60
ccccggttcg aaaccgggca ctacaaacca acaacgttaa aaaacaggtc tccccatac   120 tctttcattg tacacaccgc aagctcgaca atcatcggat tgaagcattg tcgcacacat   180
cttccacaca ggatcagtac ctgctttcgc ttttaaccaa ggcttttctc caagggatat   240
ttatagtctc aaaacacaca attactttac agttagggtg agtttccttt tgtgctgttt   300
tttaaaataa taatttagta tttgtatctc ttatagaaat ccaagcctat catgtaaaat   360
gtagctagta ttaaaagaa cagattatct gtcttttatc gcacattaag cctctatagt   420
tactaggaaa tattatatgc aaattaaccg gggcagggga gtagccgagc ttctcccaca   480
agtctgtgcg aggggccgg cgcgggccta gagatggcgg cgtcggatcg ccagccccgc   540
ctaatgagcg ggcttttttt tcttagggtg caaaaggaga gcctgtaagc gggcactctt   600
```

-continued

```
ccgtggtctg gtggataaat tcgcaagggt atcatggcgg acgaccgggg ttcgagcccc      660
gtatccggcc gtccgccgtg atccatgcgg ttaccgcccg cgtgtcgaac ccaggtgtgc      720
gacgtcagac aacgggggag tgctccttttt ggcttccttc ccctaccggt ctgcctcgcg     780
cgtttcggtg atgacggtga aaacctctga cacatgcagc tcccggagac ggtcacagct      840
tgtctgtaag cggatgccgg gagcagacaa gcccgtcagg gcgcgtcagc gggtgttggc      900
gggtgtcggg gcgcagccat gacccagtca cgtagcgata gcggagtgta tactggctta     960
actatgcggc atcagagcag attgtactga gagtgcacca tatgcggtgt gaaataccgc     1020
acagatgcgt aaggagaaaa taccgcatca ggcgctcttc cgcttcctcg ctcactgact     1080
cgctgcgctc ggtcgttcgg ctgcggcgag cggtatcagc tcactcaaag gcggtaatac     1140
ggttatccac agaatcaggg gataacgcag gaaagaacat gtgagcaaaa ggccagcaaa     1200
aggccaggaa ccgtaaaaag gccgcgttgc tggcgttttt ccataggctc cgcccccctg     1260
acgagcatca aaaaatcga cgctcaagtc agaggtggcg aaacccgaca ggactataaa      1320
gataccaggc gtttccccct ggaagctccc tcgtgcgctc tcctgttccg accctgccgc     1380
ttaccggata cctgtccgcc tttctccctt cgggaagcgt ggcgctttct catagctcac     1440
gctgtaggta tctcagttcg gtgtaggtcg ttcgctccaa gctgggctgt gtgcacgaac     1500
cccccgttca gcccgaccgc tgcgccttat ccggtaacta tcgtcttgag tccaacccgg     1560
taagacacga cttatcgcca ctggcagcag ccactggtaa caggattagc agagcgaggt     1620
atgtaggcgg tgctacagag ttcttgaagt ggtggcctaa ctacggctac actagaagaa     1680
cagtatttgg tatctgcgct ctgctgaagc cagttacctt cggaaaaaga gttggtagct     1740
cttgatccgg caaacaaacc accgctggta gcggtggttt ttttgtttgc aagcagcaga     1800
ttacgcgcag aaaaaaagga tctcaagaag atcctttgat cttttctacg ggtctgacg      1860 ctcagtggaa cgaaaactca cgttaaggga ttttggtcat gagattatca aaaaggatct     1920
tcacctagat ccttttaaat taaaatgaa gttttaaatc aatctaaagt atatatgagt      1980
aaacttggtc tgacagttac caatgcttaa tcagtgaggc acctatctca gcgatctgtc     2040
tatttcgttc atccatagtt gcctgactcc tgcaaaccac gttgtggtag aattggtaaa     2100
gagagtcgtg taaaatatcg agttcgcaca tcttgttgtc tgattattga ttttggcga     2160 aaccatttga tcatatgaca agatgtgtat ctaccttaac ttaatgattt tgataaaaat     2220
cattaggtac ccctgatcac tgtggaatgt gtgtcagtta gggtgtggaa agtccccagg     2280
ctccccagca ggcagaagta tgcaaagcat gcatctcaat tagtcagcaa ccaggtgtgg     2340
aaagtcccca ggctccccag caggcagaag tatgcaaagc atgcatctca attagtcagc     2400
aaccatagtc cgcccctaa ctccgcccat cccgccccta actccgccca gttacgggt      2460 cattagttca tagcccatat atggagttcc gcgttacata acttacggta atggcccgc      2520 ctggctgacc gcccaacgac ccccgcccat tgacgtcaat aatgacgtat gttcccatag     2580
taacgccaat agggactttc cattgacgtc aatgggtgga gtatttacgg taaactgccc     2640
acttggcagt acatcaagtg tatcatatgc caagtacgcc ccctattgac gtcaatgacg     2700
gtaaatggcc cgcctggcat tatgcccagt acatgacctt atgggacttt cctacttggc     2760
agtacatcta cgtattagtc atcgctatta ccatggtgat gcggttttgg cagtacatca     2820
atgggcgtgg atagcggttt gactcacggg gatttccaag tctccacccc attgacgtca     2880
atgggagttt gttttggcac caaaatcaac gggactttcc aaaatgtcgt aacaactccg     2940
ccccattgac gcaaatgggc ggtaggcgtg tacggtggga ggtctatata agcagagctc     3000
```

-continued

```
gtttagtgaa ccgtcagatc gcctggagac gccatccacg ctgttttgac ctccatagaa    3060
gacaccggga ccgatccagc ctccgcggct cgcatctctc cttcacgcgc cgccgcccct    3120
acctgaggcc gccatccacg ccggttgagt cgcgttctgc cgcctcccgc tgtggtgcc     3180 tcctgaactg cgtccgccgt ctaggtaagt ttaaagctca ggtcgagacc gggcctttgt    3240
ccggcgctcc cttggagcct acctagactc agccggctct ccacgctttg cctgaccctg    3300
cttgctcaac tctagttctc tcgttaactt aatgagacag atagaaactg gtcttgtaga    3360
aacagagtag tcgcctgctt ttctgccagg tgctgacttc tctcccctgg gcttttttct    3420
ttttctcagg ttgaaaagaa gaagacgaag aagacgaaga agacaaaccg tcgtcgacaa    3480
```

| | | | |
|---|---|---|---|
| gcttacc atg cag atc ttc gtg aag acc ctg acc ggc aag acc atc act | | | 3529 |
| Met Gln Ile Phe Val Lys Thr Leu Thr Gly Lys Thr Ile Thr | | | |
| 1               5                  10 | | | |
| ctc gag gtg gag ccc agt gac acc atc gaa aat gtg aag gcc aag atc | | | 3577 |
| Leu Glu Val Glu Pro Ser Asp Thr Ile Glu Asn Val Lys Ala Lys Ile | | | |
| 15              20                 25                  30 | | | |
| caa gat aaa gaa ggc atc cca ccc gac cag cag agg ctc atc ttt gct | | | 3625 |
| Gln Asp Lys Glu Gly Ile Pro Pro Asp Gln Gln Arg Leu Ile Phe Ala | | | |
|                 35                 40                  45 | | | |
| ggc aag cag ctg gaa gat ggc cgc act ctg tct gac tac aac atc cag | | | 3673 |
| Gly Lys Gln Leu Glu Asp Gly Arg Thr Leu Ser Asp Tyr Asn Ile Gln | | | |
|              50                 55                  60 | | | |
| aaa gag tcg acc ctg cac ctg gtc ctg cgt ctg aga ggc ggc cgc gct | | | 3721 |
| Lys Glu Ser Thr Leu His Leu Val Leu Arg Leu Arg Gly Gly Arg Ala | | | |
| 65                 70                 75 | | | |
| ctg gtg gcc cag tgc ctg gtg tgc gtg ccc tgg gac gca cgg cca ccc | | | 3769 |
| Leu Val Ala Gln Cys Leu Val Cys Val Pro Trp Asp Ala Arg Pro Pro | | | |
| 80                 85                 90 | | | |
| cct gcc gca ccc tca ttc cgc caa gtg tcc tgc ctg aag gag ctg gtg | | | 3817 |
| Pro Ala Ala Pro Ser Phe Arg Gln Val Ser Cys Leu Lys Glu Leu Val | | | |
| 95                 100                105                 110 | | | |
| gcc cga gtg ctg cag agg ctg tgc gag cgc ggc gcg aag aac gtg ctg | | | 3865 |
| Ala Arg Val Leu Gln Arg Leu Cys Glu Arg Gly Ala Lys Asn Val Leu | | | |
|                 115                120                 125 | | | |
| gcc ttc ggc ttc gcg ctg ctg gac ggg gct cgc gga ggc cca ccc gag | | | 3913 |
| Ala Phe Gly Phe Ala Leu Leu Asp Gly Ala Arg Gly Gly Pro Pro Glu | | | |
|             130                135                 140 | | | |
| gcc ttc acc acc agc gtg cgc agc tac ctg ccc aac acg gtg acc gac | | | 3961 |
| Ala Phe Thr Thr Ser Val Arg Ser Tyr Leu Pro Asn Thr Val Thr Asp | | | |
| 145                150                155 | | | |
| gca ctg cgg ggg agc ggg gcg tgg ggg ctg ctg ttg cgc cgc gtg ggc | | | 4009 |
| Ala Leu Arg Gly Ser Gly Ala Trp Gly Leu Leu Leu Arg Arg Val Gly | | | |
|     160                165                 170 | | | |
| gac gac gtg ctg gtt cac ctg ctg gca cgc tgc gcg ctc ttt gtg ctg | | | 4057 |
| Asp Asp Val Leu Val His Leu Leu Ala Arg Cys Ala Leu Phe Val Leu | | | |
| 175                180                185                 190 | | | |
| gtg gct ccc agc tgc gcc tac cag gtg tgc ggg ccg ccg ctg tac cag | | | 4105 |
| Val Ala Pro Ser Cys Ala Tyr Gln Val Cys Gly Pro Pro Leu Tyr Gln | | | |
|                 195                200                 205 | | | |
| ctc ggc gct gcc act cag gca cgg cct cca cct cac gct agt gga ccc | | | 4153 |
| Leu Gly Ala Ala Thr Gln Ala Arg Pro Pro Pro His Ala Ser Gly Pro | | | |
|             210                215                 220 | | | |
| cga agg cgt ctg gga tgc gaa cgg gcc tgg aac cat agc gtc agg gag | | | 4201 |
| Arg Arg Arg Leu Gly Cys Glu Arg Ala Trp Asn His Ser Val Arg Glu | | | |
|                 225                230                 235 | | | |

```
gcc ggg gtc ccc ctg ggc ctg cca gcc ccg ggt gcg agg agg cgc ggg         4249
Ala Gly Val Pro Leu Gly Leu Pro Ala Pro Gly Ala Arg Arg Arg Gly
    240                 245                 250 ggc agt gcc agc cga agt ctg ccg ttg ccc aag agg ccc agg cgt ggc         4297
Gly Ser Ala Ser Arg Ser Leu Pro Leu Pro Lys Arg Pro Arg Arg Gly
255                 260                 265                 270 gct gcc cct gag ccg gag cgg acg ccc gtt ggg cag ggg tcc tgg gcc         4345
Ala Ala Pro Glu Pro Glu Arg Thr Pro Val Gly Gln Gly Ser Trp Ala
                275                 280                 285 cac ccg ggc agg acg cgt gga ccg agt gac cgt ggt ttc tgt gtg gtg         4393
His Pro Gly Arg Thr Arg Gly Pro Ser Asp Arg Gly Phe Cys Val Val
        290                 295                 300 tca cct gcc aga ccc gcc gaa gaa gcc acc tct ttg gag ggt gcg ctc         4441
Ser Pro Ala Arg Pro Ala Glu Glu Ala Thr Ser Leu Glu Gly Ala Leu
            305                 310                 315 tct ggc acg cgc cac tcc cac cca tcc gtg ggc cgc cag cac cac gcg         4489
Ser Gly Thr Arg His Ser His Pro Ser Val Gly Arg Gln His His Ala
320                 325                 330 ggc ccc cca tcc aca tcg cgg cca cca cgt ccc tgg gac acg cct tgt         4537
Gly Pro Pro Ser Thr Ser Arg Pro Pro Arg Pro Trp Asp Thr Pro Cys
335                 340                 345                 350 ccc ccg gtg tac gcc gag acc aag cac ttc ctc tac tcc tca ggc gac         4585
Pro Pro Val Tyr Ala Glu Thr Lys His Phe Leu Tyr Ser Ser Gly Asp
                355                 360                 365 aag gag cag ctg cgg cca tcc ttc ctg ctg agc tct ctg agg ccc agc         4633
Lys Glu Gln Leu Arg Pro Ser Phe Leu Leu Ser Ser Leu Arg Pro Ser
        370                 375                 380 ctg act ggc gct cgg agg ctc gtg gag acc atc ttt ctg ggt tcc agg         4681
Leu Thr Gly Ala Arg Arg Leu Val Glu Thr Ile Phe Leu Gly Ser Arg
            385                 390                 395 ccc tgg atg cca ggg act ccc cgc agg ttg ccc cgc ctg ccc cag cgc         4729
Pro Trp Met Pro Gly Thr Pro Arg Arg Leu Pro Arg Leu Pro Gln Arg
400                 405                 410 tac tgg caa atg cgg ccc ctg ttt ctg gag ctg ctt ggg aac cac gcg         4777
Tyr Trp Gln Met Arg Pro Leu Phe Leu Glu Leu Leu Gly Asn His Ala
415                 420                 425                 430 cag tgc ccc tac ggg gtg ctc ctc aag acg cac tgc ccg ctg cga gct         4825
Gln Cys Pro Tyr Gly Val Leu Leu Lys Thr His Cys Pro Leu Arg Ala
                435                 440                 445 gcg gtc acc cca gca gcc ggt gtc tgt gcc cgg gag aag ccc cag ggc         4873
Ala Val Thr Pro Ala Ala Gly Val Cys Ala Arg Glu Lys Pro Gln Gly
        450                 455                 460 tct gtg gcg gcc ccc gag gag gag gac aca gac ccc cgt cgc ctg gtg         4921
Ser Val Ala Ala Pro Glu Glu Glu Asp Thr Asp Pro Arg Arg Leu Val
            465                 470                 475 cag ctg ctc cgc cag cac agc agc ccc tgg cag gtg tac ggc ttc gtg         4969
Gln Leu Leu Arg Gln His Ser Ser Pro Trp Gln Val Tyr Gly Phe Val
480                 485                 490 cgg gcc tgc ctg cgc cgg ctg gtg ccc cca ggc ctc tgg ggc tcc agg         5017
Arg Ala Cys Leu Arg Arg Leu Val Pro Pro Gly Leu Trp Gly Ser Arg
495                 500                 505                 510 cac aac gaa cgc cgc ttc ctc agg aac acc aag aag ttc atc tcc ctg         5065
His Asn Glu Arg Arg Phe Leu Arg Asn Thr Lys Lys Phe Ile Ser Leu
                515                 520                 525 ggg aag cat gcc aag ctc tcg ctg cag gag ctg acg tgg aag atg agc         5113
Gly Lys His Ala Lys Leu Ser Leu Gln Glu Leu Thr Trp Lys Met Ser
        530                 535                 540
```

```
gtg cgg ggc tgc gct tgg ctg cgc agg agc cca ggg gtt ggc tgt gtt      5161
Val Arg Gly Cys Ala Trp Leu Arg Arg Ser Pro Gly Val Gly Cys Val
            545                 550                 555 ccg gcc gca gag cac cgt ctg cgt gag gag atc ctg gcc aag ttc ctg      5209
Pro Ala Ala Glu His Arg Leu Arg Glu Glu Ile Leu Ala Lys Phe Leu
        560                 565                 570 cac tgg ctg atg agt gtg tac gtc gtc gag ctg ctc agg tca ttc ttt      5257
His Trp Leu Met Ser Val Tyr Val Val Glu Leu Leu Arg Ser Phe Phe
575                 580                 585                 590 tac gtg acg gag acc acg ttt caa aag aac agg ctg ttt ttc tac cgg      5305
Tyr Val Thr Glu Thr Thr Phe Gln Lys Asn Arg Leu Phe Phe Tyr Arg
                595                 600                 605 aag agt gtc tgg agc aag ttg caa agc att gga atc aga cag cac ttg      5353
Lys Ser Val Trp Ser Lys Leu Gln Ser Ile Gly Ile Arg Gln His Leu
            610                 615                 620 aag agg gtg cag ctg cgg gag ctg tcg gaa gca gag gtc agg cag cat      5401
Lys Arg Val Gln Leu Arg Glu Leu Ser Glu Ala Glu Val Arg Gln His
        625                 630                 635 cgg gaa gcc agg ccc gcc ctg ctg acg tcc aga ctc cgc ttc atc ccc      5449
Arg Glu Ala Arg Pro Ala Leu Leu Thr Ser Arg Leu Arg Phe Ile Pro
640                 645                 650 aag cct gac ggg ctg cgg ccg att gtg aac atg gac tac gtc gtg gga      5497
Lys Pro Asp Gly Leu Arg Pro Ile Val Asn Met Asp Tyr Val Val Gly
655                 660                 665                 670 gcc aga acg ttc cgc aga gaa aag agg gcc gag cgt ctc acc tca cgg      5545
Ala Arg Thr Phe Arg Arg Glu Lys Arg Ala Glu Arg Leu Thr Ser Arg
                675                 680                 685 gtg aag gca ctg ttc agc gtg ctc aac tac gag cgg gct cgg cgc cct      5593
Val Lys Ala Leu Phe Ser Val Leu Asn Tyr Glu Arg Ala Arg Arg Pro
            690                 695                 700 ggc ctc ctg ggc gcc tct gtg ctg ggc ctg gac gat atc cac agg gcc      5641
Gly Leu Leu Gly Ala Ser Val Leu Gly Leu Asp Asp Ile His Arg Ala
        705                 710                 715 tgg cgc acc ttc gtg ctg cgt gtg cgg gcc cag gac ccg ccg cct gag      5689
Trp Arg Thr Phe Val Leu Arg Val Arg Ala Gln Asp Pro Pro Pro Glu
720                 725                 730 ctg tac ttt gtc aag gtg gat gtg acg ggc gcg tac gac acc atc ccc      5737
Leu Tyr Phe Val Lys Val Asp Val Thr Gly Ala Tyr Asp Thr Ile Pro
735                 740                 745                 750 cag gac agg ctc acg gag gtc atc gcc agc atc atc aaa ccc cag aac      5785
Gln Asp Arg Leu Thr Glu Val Ile Ala Ser Ile Ile Lys Pro Gln Asn
                755                 760                 765 acg tac tgc gtg cgt cgg tat gcc gtg gtc cag aag gcc gcc cat ggg      5833
Thr Tyr Cys Val Arg Arg Tyr Ala Val Val Gln Lys Ala Ala His Gly
            770                 775                 780 cac gtc cgc aag gcc ttc aag agc cac gtc tct acc ttg aca gac ctc      5881
His Val Arg Lys Ala Phe Lys Ser His Val Ser Thr Leu Thr Asp Leu
        785                 790                 795 cag ccg tac atg cga cag ttc gtg gct cac ctg cag gag acc agc ccg      5929
Gln Pro Tyr Met Arg Gln Phe Val Ala His Leu Gln Glu Thr Ser Pro
800                 805                 810 ctg agg gat gcc gtc gtc atc gag cag agc tcc tcc ctg aat gag gcc      5977
Leu Arg Asp Ala Val Val Ile Glu Gln Ser Ser Ser Leu Asn Glu Ala
815                 820                 825                 830 agc agt ggc ctc ttc gac gtc ttc cta cgc ttc atg tgc cac cac gcc      6025
Ser Ser Gly Leu Phe Asp Val Phe Leu Arg Phe Met Cys His His Ala
                835                 840                 845
```

```
gtg cgc atc agg ggc aag tcc tac gtc cag tgc cag ggc atc ccg cag      6073
Val Arg Ile Arg Gly Lys Ser Tyr Val Gln Cys Gln Gly Ile Pro Gln
            850                 855                 860 ggc tcc atc ctc tcc acg ctg ctc tgc agc ctg tgc tac ggc gac atg      6121
Gly Ser Ile Leu Ser Thr Leu Leu Cys Ser Leu Cys Tyr Gly Asp Met
            865                 870                 875 gag aac aag ctg ttt gcg ggg att cgg cgg gac ggg ctg ctc ctg cgt      6169
Glu Asn Lys Leu Phe Ala Gly Ile Arg Arg Asp Gly Leu Leu Leu Arg
880                 885                 890 ttg ttc ttg ttg gtg aca cct cac ctc acc cac gcg aaa acc ttc ctc      6217
Leu Phe Leu Leu Val Thr Pro His Leu Thr His Ala Lys Thr Phe Leu
895                 900                 905                 910 agg acc ctg gtc cga ggt gtc cct gag tat ggc tgc gtg gtg aac ttg      6265
Arg Thr Leu Val Arg Gly Val Pro Glu Tyr Gly Cys Val Val Asn Leu
                915                 920                 925 cgg aag aca gtg gtg aac ttc cct gta gaa gac gag gcc ctg ggt ggc      6313
Arg Lys Thr Val Val Asn Phe Pro Val Glu Asp Glu Ala Leu Gly Gly
            930                 935                 940 acg gct ttt gtt cag atg ccg gcc cac ggc cta ttc ccc tgg tgc ggc      6361
Thr Ala Phe Val Gln Met Pro Ala His Gly Leu Phe Pro Trp Cys Gly
            945                 950                 955 ctg ctg ctg gat acc cgg acc ctg gag gtg cag agc gac tac tcc agc      6409
Leu Leu Leu Asp Thr Arg Thr Leu Glu Val Gln Ser Asp Tyr Ser Ser
            960                 965                 970 tat gcc cgg acc tcc atc aga gcc agt ctc acc ttc aac cgc ggc ttc      6457
Tyr Ala Arg Thr Ser Ile Arg Ala Ser Leu Thr Phe Asn Arg Gly Phe
975                 980                 985                 990 aag gct ggg agg aac atg cgt cgc aaa ctc ttt ggg gtc ttg cgg ctg      6505
Lys Ala Gly Arg Asn Met Arg Arg Lys Leu Phe Gly Val Leu Arg Leu
                995                 1000                1005 aag tgt cac agc ctg ttt ctg gat ttg cag gtg aac agc ctc cag           6550
Lys Cys His Ser Leu Phe Leu Asp Leu Gln Val Asn Ser Leu Gln
                1010                1015                1020 acg gtg tgc acc aac atc tac aag atc ctc ctg ctg cag gcg tac           6595
Thr Val Cys Thr Asn Ile Tyr Lys Ile Leu Leu Leu Gln Ala Tyr
                1025                1030                1035 agg ttt cac gca tgt gtg ctg cag ctc cca ttt cat cag caa gtt           6640
Arg Phe His Ala Cys Val Leu Gln Leu Pro Phe His Gln Gln Val
                1040                1045                1050 tgg aag aac ccc aca ttt ttc ctg cgc gtc atc tct gac acg gcc           6685
Trp Lys Asn Pro Thr Phe Phe Leu Arg Val Ile Ser Asp Thr Ala
                1055                1060                1065 tcc ctc tgc tac tcc atc ctg aaa gcc aag aac gca ggg atg tcg           6730
Ser Leu Cys Tyr Ser Ile Leu Lys Ala Lys Asn Ala Gly Met Ser
                1070                1075                1080 ctg ggg gcc aag ggc gcc gcc ggc cct ctg ccc tcc gag gcc gtg           6775
Leu Gly Ala Lys Gly Ala Ala Gly Pro Leu Pro Ser Glu Ala Val
                1085                1090                1095 cag tgg ctg tgc cac caa gca ttc ctg ctc aag ctg act cga cac           6820
Gln Trp Leu Cys His Gln Ala Phe Leu Leu Lys Leu Thr Arg His
                1100                1105                1110 cgt gtc acc tac gtg cca ctc ctg ggg tca ctc agg aca gcc cag           6865
Arg Val Thr Tyr Val Pro Leu Leu Gly Ser Leu Arg Thr Ala Gln
                1115                1120                1125 acg cag ctg agt cgg aag ctc ccg ggg acg acg ctg act gcc ctg           6910
Thr Gln Leu Ser Arg Lys Leu Pro Gly Thr Thr Leu Thr Ala Leu
                1130                1135                1140
```

-continued

```
gag gcc gca gcc  aac ccg gca ctg ccc  tca gac ttc aag acc  atc        6955
Glu Ala Ala Ala  Asn Pro Ala Leu Pro  Ser Asp Phe Lys Thr  Ile
            1145             1150                 1155 ctg gac taataatcta gaagatcttt ttccctctgc caaaaattat ggggacatca         7011
Leu Asp tgaagcccct tgagcatctg acttctggct aataaaggaa atttattttc attgcaatag     7071
tgtgttggaa ttttttgtgt ctctcactcg gaaggacata agggcggcc                 7120
```

<210> SEQ ID NO 12
<211> LENGTH: 1158
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 12

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Arg Ala Leu Val
65                  70                  75                  80

Ala Gln Cys Leu Val Cys Val Pro Trp Asp Ala Arg Pro Pro Pro Ala
                85                  90                  95

Ala Pro Ser Phe Arg Gln Val Ser Cys Leu Lys Glu Leu Val Ala Arg
            100                 105                 110

Val Leu Gln Arg Leu Cys Glu Arg Gly Ala Lys Asn Val Leu Ala Phe
        115                 120                 125

Gly Phe Ala Leu Leu Asp Gly Ala Arg Gly Gly Pro Pro Glu Ala Phe
    130                 135                 140

Thr Thr Ser Val Arg Ser Tyr Leu Pro Asn Thr Val Thr Asp Ala Leu
145                 150                 155                 160

Arg Gly Ser Gly Ala Trp Gly Leu Leu Leu Arg Arg Val Gly Asp Asp
                165                 170                 175

Val Leu Val His Leu Leu Ala Arg Cys Ala Leu Phe Val Leu Val Ala
            180                 185                 190

Pro Ser Cys Ala Tyr Gln Val Cys Gly Pro Pro Leu Tyr Gln Leu Gly
        195                 200                 205

Ala Ala Thr Gln Ala Arg Pro Pro His Ala Ser Gly Pro Arg Arg
    210                 215                 220

Arg Leu Gly Cys Glu Arg Ala Trp Asn His Ser Val Arg Glu Ala Gly
225                 230                 235                 240

Val Pro Leu Gly Leu Pro Ala Pro Gly Ala Arg Arg Arg Gly Gly Ser
                245                 250                 255

Ala Ser Arg Ser Leu Pro Leu Pro Lys Arg Pro Arg Arg Gly Ala Ala
            260                 265                 270

Pro Glu Pro Glu Arg Thr Pro Val Gly Gln Gly Ser Trp Ala His Pro
        275                 280                 285

Gly Arg Thr Arg Gly Pro Ser Asp Arg Gly Phe Cys Val Val Ser Pro
    290                 295                 300
```

```
Ala Arg Pro Ala Glu Glu Ala Thr Ser Leu Glu Gly Ala Leu Ser Gly
305                 310                 315                 320

Thr Arg His Ser His Pro Ser Val Gly Arg Gln His His Ala Gly Pro
            325                 330                 335

Pro Ser Thr Ser Arg Pro Pro Arg Pro Trp Asp Thr Pro Cys Pro Pro
            340                 345                 350

Val Tyr Ala Glu Thr Lys His Phe Leu Tyr Ser Ser Gly Asp Lys Glu
            355                 360                 365

Gln Leu Arg Pro Ser Phe Leu Leu Ser Ser Leu Arg Pro Ser Leu Thr
        370                 375                 380

Gly Ala Arg Arg Leu Val Glu Thr Ile Phe Leu Gly Ser Arg Pro Trp
385                 390                 395                 400

Met Pro Gly Thr Pro Arg Arg Leu Pro Arg Leu Pro Gln Arg Tyr Trp
                405                 410                 415

Gln Met Arg Pro Leu Phe Leu Glu Leu Leu Gly Asn His Ala Gln Cys
            420                 425                 430

Pro Tyr Gly Val Leu Leu Lys Thr His Cys Pro Leu Arg Ala Ala Val
            435                 440                 445

Thr Pro Ala Ala Gly Val Cys Ala Arg Glu Lys Pro Gln Gly Ser Val
450                 455                 460

Ala Ala Pro Glu Glu Glu Asp Thr Asp Pro Arg Arg Leu Val Gln Leu
465                 470                 475                 480

Leu Arg Gln His Ser Ser Pro Trp Gln Val Tyr Gly Phe Val Arg Ala
                485                 490                 495

Cys Leu Arg Arg Leu Val Pro Pro Gly Leu Trp Gly Ser Arg His Asn
            500                 505                 510

Glu Arg Arg Phe Leu Arg Asn Thr Lys Lys Phe Ile Ser Leu Gly Lys
        515                 520                 525

His Ala Lys Leu Ser Leu Gln Glu Leu Thr Trp Lys Met Ser Val Arg
530                 535                 540

Gly Cys Ala Trp Leu Arg Arg Ser Pro Gly Val Gly Cys Val Pro Ala
545                 550                 555                 560

Ala Glu His Arg Leu Arg Glu Glu Ile Leu Ala Lys Phe Leu His Trp
                565                 570                 575

Leu Met Ser Val Tyr Val Val Glu Leu Leu Arg Ser Phe Phe Tyr Val
            580                 585                 590

Thr Glu Thr Thr Phe Gln Lys Asn Arg Leu Phe Phe Tyr Arg Lys Ser
        595                 600                 605

Val Trp Ser Lys Leu Gln Ser Ile Gly Ile Arg Gln His Leu Lys Arg
610                 615                 620

Val Gln Leu Arg Glu Leu Ser Glu Ala Glu Val Arg Gln His Arg Glu
625                 630                 635                 640

Ala Arg Pro Ala Leu Leu Thr Ser Arg Leu Arg Phe Ile Pro Lys Pro
                645                 650                 655

Asp Gly Leu Arg Pro Ile Val Asn Met Asp Tyr Val Val Gly Ala Arg
            660                 665                 670

Thr Phe Arg Arg Glu Lys Arg Ala Glu Arg Leu Thr Ser Arg Val Lys
        675                 680                 685

Ala Leu Phe Ser Val Leu Asn Tyr Glu Arg Ala Arg Arg Pro Gly Leu
690                 695                 700

Leu Gly Ala Ser Val Leu Gly Leu Asp Asp Ile His Arg Ala Trp Arg
705                 710                 715                 720
```

```
Thr Phe Val Leu Arg Val Arg Ala Gln Asp Pro Pro Glu Leu Tyr
            725                 730                 735

Phe Val Lys Val Asp Val Thr Gly Ala Tyr Asp Thr Ile Pro Gln Asp
            740                 745                 750

Arg Leu Thr Glu Val Ile Ala Ser Ile Ile Lys Pro Gln Asn Thr Tyr
            755                 760                 765

Cys Val Arg Arg Tyr Ala Val Gln Lys Ala Ala His Gly His Val
            770                 775                 780

Arg Lys Ala Phe Lys Ser His Val Ser Thr Leu Thr Asp Leu Gln Pro
785                 790                 795                 800

Tyr Met Arg Gln Phe Val Ala His Leu Gln Glu Thr Ser Pro Leu Arg
            805                 810                 815

Asp Ala Val Ile Glu Gln Ser Ser Ser Leu Asn Glu Ala Ser Ser
            820                 825                 830

Gly Leu Phe Asp Val Phe Leu Arg Phe Met Cys His His Ala Val Arg
            835                 840                 845

Ile Arg Gly Lys Ser Tyr Val Gln Cys Gln Gly Ile Pro Gln Gly Ser
            850                 855                 860

Ile Leu Ser Thr Leu Leu Cys Ser Leu Cys Tyr Gly Asp Met Glu Asn
865                 870                 875                 880

Lys Leu Phe Ala Gly Ile Arg Arg Asp Gly Leu Leu Leu Arg Leu Phe
            885                 890                 895

Leu Leu Val Thr Pro His Leu Thr His Ala Lys Thr Phe Leu Arg Thr
            900                 905                 910

Leu Val Arg Gly Val Pro Glu Tyr Gly Cys Val Val Asn Leu Arg Lys
            915                 920                 925

Thr Val Val Asn Phe Pro Val Glu Asp Glu Ala Leu Gly Gly Thr Ala
            930                 935                 940

Phe Val Gln Met Pro Ala His Gly Leu Phe Pro Trp Cys Gly Leu Leu
945                 950                 955                 960

Leu Asp Thr Arg Thr Leu Glu Val Gln Ser Asp Tyr Ser Ser Tyr Ala
            965                 970                 975

Arg Thr Ser Ile Arg Ala Ser Leu Thr Phe Asn Arg Gly Phe Lys Ala
            980                 985                 990

Gly Arg Asn Met Arg Arg Lys Leu Phe Gly Val Leu Arg Leu Lys Cys
            995                 1000                1005

His Ser Leu Phe Leu Asp Leu Gln Val Asn Ser Leu Gln Thr Val
            1010                1015                1020

Cys Thr Asn Ile Tyr Lys Ile Leu Leu Leu Gln Ala Tyr Arg Phe
            1025                1030                1035

His Ala Cys Val Leu Gln Leu Pro Phe His Gln Val Trp Lys
            1040                1045                1050

Asn Pro Thr Phe Phe Leu Arg Val Ile Ser Asp Thr Ala Ser Leu
            1055                1060                1065

Cys Tyr Ser Ile Leu Lys Ala Lys Asn Ala Gly Met Ser Leu Gly
            1070                1075                1080

Ala Lys Gly Ala Ala Gly Pro Leu Pro Ser Glu Ala Val Gln Trp
            1085                1090                1095

Leu Cys His Gln Ala Phe Leu Leu Lys Leu Thr Arg His Arg Val
            1100                1105                1110

Thr Tyr Val Pro Leu Leu Gly Ser Leu Arg Thr Ala Gln Thr Gln
            1115                1120                1125
```

```
Leu Ser  Arg Lys Leu Pro Gly  Thr Thr Leu Thr Ala  Leu Glu Ala
    1130             1135                  1140

Ala Ala  Asn Pro Ala Leu Pro  Ser Asp Phe Lys Thr  Ile Leu Asp
    1145             1150                  1155

<210> SEQ ID NO 13
<211> LENGTH: 3570
<212> TYPE: DNA
<213> ORGANISM: Artificial Sequence
<220> FEATURE:
<223> OTHER INFORMATION: Description of Artificial Sequence: Synthetic
      pUTD10Not insert sequence
<220> FEATURE:
<221> NAME/KEY: CDS
<222> LOCATION: (1)..(3567)

<400> SEQUENCE: 13 atg cag att ttc gtc aaa aca ttg aca gga aag acc atc aca ctg gaa      48
Met Gln Ile Phe Val Lys Thr Leu Thr Gly Lys Thr Ile Thr Leu Glu
1               5                   10                  15 gtg gag cca agc gac act att gag aac gtc aaa gcc aag att cag gac      96
Val Glu Pro Ser Asp Thr Ile Glu Asn Val Lys Ala Lys Ile Gln Asp
            20                  25                  30 aag gag ggc atc cca cca gac cag cag agg ctg att ttt gcc gga aag     144
Lys Glu Gly Ile Pro Pro Asp Gln Gln Arg Leu Ile Phe Ala Gly Lys
        35                  40                  45 cag ctg gag gac gga cgc aca ctc agt gac tac aat atc cag aag gaa     192
Gln Leu Glu Asp Gly Arg Thr Leu Ser Asp Tyr Asn Ile Gln Lys Glu
    50                  55                  60 agt act ctg cat ctg gtc ctt cgc ctg cgc ggc gga ctg gcc acc ttc     240
Ser Thr Leu His Leu Val Leu Arg Leu Arg Gly Gly Leu Ala Thr Phe
65                  70                  75                  80 gtg cgg cgc ctg gga ccc cag ggc tgg cgg ctg gtg cag cgc ggg gac     288
Val Arg Arg Leu Gly Pro Gln Gly Trp Arg Leu Val Gln Arg Gly Asp
                85                  90                  95 cct gct gct ttc aga gct ctc gtc gcc cag tgt ctg gtc tgc gtt cct     336
Pro Ala Ala Phe Arg Ala Leu Val Ala Gln Cys Leu Val Cys Val Pro
            100                 105                 110 tgg gac gca cgg ccc cca ccc gcc gcc ccc agt ttc cgg cag gtg agt     384
Trp Asp Ala Arg Pro Pro Ala Ala Pro Ser Phe Arg Gln Val Ser
        115                 120                 125 tgt ctc aaa gag ttg gtt gct cgg gtg ttg cag cgg ctt tgt gaa agg     432
Cys Leu Lys Glu Leu Val Ala Arg Val Leu Gln Arg Leu Cys Glu Arg
    130                 135                 140 gga gca aag aac gtc ctt gcc ttt ggc ttc gct ttg ctc gat gga gca     480
Gly Ala Lys Asn Val Leu Ala Phe Gly Phe Ala Leu Leu Asp Gly Ala
145                 150                 155                 160 cgc gga ggc cct cct gag gca ttc act act agc gtc cgg tcc tac ctg     528
Arg Gly Gly Pro Pro Glu Ala Phe Thr Thr Ser Val Arg Ser Tyr Leu
                165                 170                 175 ccc aac aca gtg acc gac gct ctg aga ggt tca ggt gcc tgg ggt ctg     576
Pro Asn Thr Val Thr Asp Ala Leu Arg Gly Ser Gly Ala Trp Gly Leu
            180                 185                 190 ctg ctg cgg agg gtg ggt gat gat gtt ctg gtt cac ctc ctg gcc cgg     624
Leu Leu Arg Arg Val Gly Asp Asp Val Leu Val His Leu Leu Ala Arg
        195                 200                 205 tgt gcc ctg ttc gtg ctg gtg gct ccc tcc tgc gca tac cag gtc tgc     672
Cys Ala Leu Phe Val Leu Val Ala Pro Ser Cys Ala Tyr Gln Val Cys
    210                 215                 220
```

| | | | | | | | | | | | | | | | | |
|---|---|---|---|---|---|---|---|---|---|---|---|---|---|---|---|---|
| gga | ccc | cca | ctt | tat | cag | ctc | ggc | gct | gct | act | cag | gcc | cgc | cca | cca | 720 |
| Gly | Pro | Pro | Leu | Tyr | Gln | Leu | Gly | Ala | Ala | Thr | Gln | Ala | Arg | Pro | Pro | |
| 225 | | | | 230 | | | | | 235 | | | | | 240 | | |

| | | | | | | | | | | | | | | | |
|---|---|---|---|---|---|---|---|---|---|---|---|---|---|---|---|
| cca | cac | gcc | tca | ggt | cca | aga | cgc | cgg | ctg | ggc | tgc | gaa | cgg | gca | tgg | 768 |
| Pro | His | Ala | Ser | Gly | Pro | Arg | Arg | Arg | Leu | Gly | Cys | Glu | Arg | Ala | Trp | |
| | | | | 245 | | | | | 250 | | | | | 255 | | |

| aat | cat | agc | gtg | cgg | gag | gca | ggt | gtg | cct | ctc | ggc | ctg | cca | gcc | ccc | 816 |
|---|---|---|---|---|---|---|---|---|---|---|---|---|---|---|---|---|
| Asn | His | Ser | Val | Arg | Glu | Ala | Gly | Val | Pro | Leu | Gly | Leu | Pro | Ala | Pro | |
| | | | 260 | | | | | 265 | | | | | 270 | | | |

| gga | gca | agg | aga | cgc | ggt | gga | tcc | gcc | agt | cgc | tca | ctc | ccc | ttg | cct | 864 |
|---|---|---|---|---|---|---|---|---|---|---|---|---|---|---|---|---|
| Gly | Ala | Arg | Arg | Arg | Gly | Gly | Ser | Ala | Ser | Arg | Ser | Leu | Pro | Leu | Pro | |
| | | | 275 | | | | | 280 | | | | | 285 | | | |

| aag | agg | cca | aga | aga | gga | gcc | gcc | cct | gaa | ccc | gag | aga | aca | cct | gtc | 912 |
|---|---|---|---|---|---|---|---|---|---|---|---|---|---|---|---|---|
| Lys | Arg | Pro | Arg | Arg | Gly | Ala | Ala | Pro | Glu | Pro | Glu | Arg | Thr | Pro | Val | |
| | 290 | | | | | 295 | | | | | 300 | | | | | |

| ggc | cag | ggc | tcc | tgg | gct | cac | ccc | gga | agg | acc | agg | ggc | cca | agc | gat | 960 |
|---|---|---|---|---|---|---|---|---|---|---|---|---|---|---|---|---|
| Gly | Gln | Gly | Ser | Trp | Ala | His | Pro | Gly | Arg | Thr | Arg | Gly | Pro | Ser | Asp | |
| 305 | | | | 310 | | | | | 315 | | | | | 320 | | |

| agg | ggc | ttc | tgt | gtt | gtg | tca | cca | gcc | agg | cct | gcc | gaa | gag | gct | acc | 1008 |
|---|---|---|---|---|---|---|---|---|---|---|---|---|---|---|---|---|
| Arg | Gly | Phe | Cys | Val | Val | Ser | Pro | Ala | Arg | Pro | Ala | Glu | Glu | Ala | Thr | |
| | | | | 325 | | | | | 330 | | | | | 335 | | |

| tcc | ttg | gaa | gga | gcc | ctc | agt | ggc | acc | agg | cat | tct | cat | cca | tct | gtg | 1056 |
|---|---|---|---|---|---|---|---|---|---|---|---|---|---|---|---|---|
| Ser | Leu | Glu | Gly | Ala | Leu | Ser | Gly | Thr | Arg | His | Ser | His | Pro | Ser | Val | |
| | | | 340 | | | | | 345 | | | | | 350 | | | |

| ggt | agg | cag | cat | cat | gcc | ggc | ccc | ccc | tct | aca | agc | aga | cct | ccc | aga | 1104 |
|---|---|---|---|---|---|---|---|---|---|---|---|---|---|---|---|---|
| Gly | Arg | Gln | His | His | Ala | Gly | Pro | Pro | Ser | Thr | Ser | Arg | Pro | Pro | Arg | |
| | | 355 | | | | | 360 | | | | | 365 | | | | |

| cct | tgg | gac | aca | ccc | tgc | cca | cca | gtg | tat | gcc | gag | acc | aag | cac | ttt | 1152 |
|---|---|---|---|---|---|---|---|---|---|---|---|---|---|---|---|---|
| Pro | Trp | Asp | Thr | Pro | Cys | Pro | Pro | Val | Tyr | Ala | Glu | Thr | Lys | His | Phe | |
| 370 | | | | 375 | | | | | 380 | | | | | | | |

| ttg | tat | tcc | agt | ggc | gat | aaa | gag | cag | ctc | cgg | ccc | tct | ttt | ctg | ctc | 1200 |
|---|---|---|---|---|---|---|---|---|---|---|---|---|---|---|---|---|
| Leu | Tyr | Ser | Ser | Gly | Asp | Lys | Glu | Gln | Leu | Arg | Pro | Ser | Phe | Leu | Leu | |
| 385 | | | | 390 | | | | | 395 | | | | | 400 | | |

| tca | agc | ctc | cgc | ccc | tct | ctg | acc | gga | gct | cgc | agg | ctg | gtg | gag | acc | 1248 |
|---|---|---|---|---|---|---|---|---|---|---|---|---|---|---|---|---|
| Ser | Ser | Leu | Arg | Pro | Ser | Leu | Thr | Gly | Ala | Arg | Arg | Leu | Val | Glu | Thr | |
| | | | 405 | | | | | 410 | | | | | 415 | | | |

| atc | ttt | ctg | ggc | tca | aga | cca | tgg | atg | cca | ggc | acc | ccc | cgc | aga | ctg | 1296 |
|---|---|---|---|---|---|---|---|---|---|---|---|---|---|---|---|---|
| Ile | Phe | Leu | Gly | Ser | Arg | Pro | Trp | Met | Pro | Gly | Thr | Pro | Arg | Arg | Leu | |
| | | | 420 | | | | | 425 | | | | | 430 | | | |

| ccc | agg | ctc | ccc | cag | cgg | tac | tgg | cag | atg | cgc | cct | ctc | ttt | ctg | gaa | 1344 |
|---|---|---|---|---|---|---|---|---|---|---|---|---|---|---|---|---|
| Pro | Arg | Leu | Pro | Gln | Arg | Tyr | Trp | Gln | Met | Arg | Pro | Leu | Phe | Leu | Glu | |
| | | 435 | | | | | 440 | | | | | 445 | | | | |

| ctt | ctg | ggt | aac | cac | gcc | cag | tgc | cca | tat | ggc | gtc | ctg | ctg | aag | acc | 1392 |
|---|---|---|---|---|---|---|---|---|---|---|---|---|---|---|---|---|
| Leu | Leu | Gly | Asn | His | Ala | Gln | Cys | Pro | Tyr | Gly | Val | Leu | Leu | Lys | Thr | |
| | 450 | | | | | 455 | | | | | 460 | | | | | |

| cac | tgt | cct | ctg | agg | gcc | gcc | gtg | acc | cca | gcc | gcc | ggt | gtg | tgt | gct | 1440 |
|---|---|---|---|---|---|---|---|---|---|---|---|---|---|---|---|---|
| His | Cys | Pro | Leu | Arg | Ala | Ala | Val | Thr | Pro | Ala | Ala | Gly | Val | Cys | Ala | |
| 465 | | | | 470 | | | | | 475 | | | | | 480 | | |

| aga | gaa | aaa | ccc | cag | ggc | tca | gtg | gct | gca | cct | gaa | gag | gag | gac | act | 1488 |
|---|---|---|---|---|---|---|---|---|---|---|---|---|---|---|---|---|
| Arg | Glu | Lys | Pro | Gln | Gly | Ser | Val | Ala | Ala | Pro | Glu | Glu | Glu | Asp | Thr | |
| | | | 485 | | | | | 490 | | | | | 495 | | | |

| gac | cct | cgc | cgc | ctt | gtc | cag | ttg | ctc | agg | cag | cat | tca | tca | cca | tgg | 1536 |
|---|---|---|---|---|---|---|---|---|---|---|---|---|---|---|---|---|
| Asp | Pro | Arg | Arg | Leu | Val | Gln | Leu | Leu | Arg | Gln | His | Ser | Ser | Pro | Trp | |
| | | 500 | | | | | 505 | | | | | 510 | | | | |

| cag | gtg | tac | ggc | ttc | gtg | agg | gct | tgc | ctg | cgg | aga | ctg | gtc | ccc | ccc | 1584 |
|---|---|---|---|---|---|---|---|---|---|---|---|---|---|---|---|---|
| Gln | Val | Tyr | Gly | Phe | Val | Arg | Ala | Cys | Leu | Arg | Arg | Leu | Val | Pro | Pro | |
| | | | | 515 | | | | | 520 | | | | | 525 | | |

```
gga ttg tgg gga tct cgg cac aac gaa cgg cgc ttt ctg agg aat aca    1632
Gly Leu Trp Gly Ser Arg His Asn Glu Arg Arg Phe Leu Arg Asn Thr
        530             535                 540 aag aag ttt atc tcc ctg ggc aag cat gca aag ctc agc ttg cag gag    1680
Lys Lys Phe Ile Ser Leu Gly Lys His Ala Lys Leu Ser Leu Gln Glu
545             550                 555                 560 ctg aca tgg aag atg agc gtt aga gga tgc gca tgg ctc agg cgg tca    1728
Leu Thr Trp Lys Met Ser Val Arg Gly Cys Ala Trp Leu Arg Arg Ser
                565                 570                 575 cct gga gtt gga tgc gtt cca gca gca gag cac agg ctg cgc gaa gag    1776
Pro Gly Val Gly Cys Val Pro Ala Ala Glu His Arg Leu Arg Glu Glu
            580                 585                 590 att ctc gca aag ttc ctg cac tgg ctt atg agc gtc tac gtg gtc gaa    1824
Ile Leu Ala Lys Phe Leu His Trp Leu Met Ser Val Tyr Val Val Glu
        595                 600                 605 ctg ctg cgg tct ttc ttc tac gtg aca gag acc act ttt cag aag aac    1872
Leu Leu Arg Ser Phe Phe Tyr Val Thr Glu Thr Thr Phe Gln Lys Asn
610             615                 620 aga ctg ttc ttc tac agg aag tcc gtc tgg agc aag ctc cag agt att    1920
Arg Leu Phe Phe Tyr Arg Lys Ser Val Trp Ser Lys Leu Gln Ser Ile
625             630                 635                 640 ggt att aga cag cac ctt aag aga gtt cag ctt aga gag ctg tcc gaa    1968
Gly Ile Arg Gln His Leu Lys Arg Val Gln Leu Arg Glu Leu Ser Glu
                645                 650                 655 gct gaa gtc cgc cag cac cgc gaa gct cgc ccc gcc ctc ctg acc tct    2016
Ala Glu Val Arg Gln His Arg Glu Ala Arg Pro Ala Leu Leu Thr Ser
            660                 665                 670 cgg ctg cgg ttt att ccc aaa ccc gat ggc ctt aga cct atc gtg aat    2064
Arg Leu Arg Phe Ile Pro Lys Pro Asp Gly Leu Arg Pro Ile Val Asn
        675                 680                 685 atg gat tac gtc gtg ggt gcc cgc act ttc aga agg gag aag cgc gcc    2112
Met Asp Tyr Val Val Gly Ala Arg Thr Phe Arg Arg Glu Lys Arg Ala
690             695                 700 gag aga ctg aca tct cgc gtg aag gca ctt ttt tct gtg ctt aat tat    2160
Glu Arg Leu Thr Ser Arg Val Lys Ala Leu Phe Ser Val Leu Asn Tyr
705             710                 715                 720 gaa aga gcc cgc aga cct ggt ctt ctc gga gcc agc gtg ctc ggc ctg    2208
Glu Arg Ala Arg Arg Pro Gly Leu Leu Gly Ala Ser Val Leu Gly Leu
                725                 730                 735 gat gat atc cat cgg gct tgg cgc acc ttt gtg ctt cgg gtg agg gca    2256
Asp Asp Ile His Arg Ala Trp Arg Thr Phe Val Leu Arg Val Arg Ala
            740                 745                 750 cag gat cct cct cct gag ctt tat ttt gtg aaa gtt gat gtt act ggt    2304
Gln Asp Pro Pro Pro Glu Leu Tyr Phe Val Lys Val Asp Val Thr Gly
        755                 760                 765 gct tac gat aca atc cct cag gac cgg ctc acc gag gtg atc gcc tct    2352
Ala Tyr Asp Thr Ile Pro Gln Asp Arg Leu Thr Glu Val Ile Ala Ser
770             775                 780 att atc aaa ccc cag aac acc tac tgc gtg aga agg tac gcc gtc gtt    2400
Ile Ile Lys Pro Gln Asn Thr Tyr Cys Val Arg Arg Tyr Ala Val Val
785             790                 795                 800 cag aaa gcc gca cac gga cac gtg cgc aaa gct ttc aaa tcc cac gtg    2448
Gln Lys Ala Ala His Gly His Val Arg Lys Ala Phe Lys Ser His Val
                805                 810                 815 tct acc ttg aca gac ctc cag cct tat atg cgg cag ttt gtc gca cac    2496
Ser Thr Leu Thr Asp Leu Gln Pro Tyr Met Arg Gln Phe Val Ala His
            820                 825                 830
```

```
ctg cag gag act agc ccc ttg agg gac gct gtg gtc atc gaa cag tcc     2544
Leu Gln Glu Thr Ser Pro Leu Arg Asp Ala Val Val Ile Glu Gln Ser
            835                 840                 845 agc tct ctc aat gag gca tcc tca ggc ctg ttt gat gtg ttc ctg cgc     2592
Ser Ser Leu Asn Glu Ala Ser Ser Gly Leu Phe Asp Val Phe Leu Arg
850                 855                 860 ttt atg tgc cac cac gcc gtg cgg att agg ggc aag tct tac gtg cag     2640
Phe Met Cys His His Ala Val Arg Ile Arg Gly Lys Ser Tyr Val Gln
865                 870                 875                 880 tgc cag ggc atc cca cag ggt agc atc ctg agc aca ctg ctg tgt agc     2688
Cys Gln Gly Ile Pro Gln Gly Ser Ile Leu Ser Thr Leu Leu Cys Ser
                885                 890                 895 ctg tgc tat ggc gat atg gag aat aaa ttg ttc gcc ggt atc aga aga     2736
Leu Cys Tyr Gly Asp Met Glu Asn Lys Leu Phe Ala Gly Ile Arg Arg
            900                 905                 910 ttc ctg ctg gtt acc ccc cat ctg act cat gcc aaa aca ttt ttg cgg     2784
Phe Leu Leu Val Thr Pro His Leu Thr His Ala Lys Thr Phe Leu Arg
            915                 920                 925 act ctg gtt agg ggc gtg cca gag tat ggc tgt gtt gtg aat ttg cgg     2832
Thr Leu Val Arg Gly Val Pro Glu Tyr Gly Cys Val Val Asn Leu Arg
930                 935                 940 aaa act gtg gtt aat ttc cca gtg gag gac gaa gct ctc gga ggc aca     2880
Lys Thr Val Val Asn Phe Pro Val Glu Asp Glu Ala Leu Gly Gly Thr
945                 950                 955                 960 gct ttt gtt cag atg cct gcc cac ggc ctg ttc cca tgg tgc gga ctg     2928
Ala Phe Val Gln Met Pro Ala His Gly Leu Phe Pro Trp Cys Gly Leu
                965                 970                 975 ctg ctc gat acc cgg acc ctc gag gtg cag tcc gat tat agt tcc tat     2976
Leu Leu Asp Thr Arg Thr Leu Glu Val Gln Ser Asp Tyr Ser Ser Tyr
            980                 985                 990 gca aga aca tca att cgg gct agc ctg act ttc aac agg ggc ttc aag     3024
Ala Arg Thr Ser Ile Arg Ala Ser Leu Thr Phe Asn Arg Gly Phe Lys
            995                 1000                1005 gcc ggc cgg aat atg aga agg aaa ctg ttc gga gtg ttg aga ctt        3069
Ala Gly Arg Asn Met Arg Arg Lys Leu Phe Gly Val Leu Arg Leu
    1010                1015                1020 aag tgt cat agt ctt ttt ttg gac ttg cag gtc aat tct ctc cag        3114
Lys Cys His Ser Leu Phe Leu Asp Leu Gln Val Asn Ser Leu Gln
1025                1030                1035 aca gtg tgt acc aac att tat aaa atc ctc ttg ctg cag gct tac        3159
Thr Val Cys Thr Asn Ile Tyr Lys Ile Leu Leu Leu Gln Ala Tyr
    1040                1045                1050 aga ttc cat gcc tgc gtc ctg cag ctg cct ttc cac cag cag gtg        3204
Arg Phe His Ala Cys Val Leu Gln Leu Pro Phe His Gln Gln Val
    1055                1060                1065 tgg aaa aac cct acc ttc ttc ctg cgg gtg att agc gac acc gcc        3249
Trp Lys Asn Pro Thr Phe Phe Leu Arg Val Ile Ser Asp Thr Ala
    1070                1075                1080 agt ctt tgc tac tcc atc ttg aaa gca aaa aac gct ggc atg agc        3294
Ser Leu Cys Tyr Ser Ile Leu Lys Ala Lys Asn Ala Gly Met Ser
    1085                1090                1095 ttg gga gct aag ggc gcc gct gga cct ctg ccc agt gaa gca gtc        3339
Leu Gly Ala Lys Gly Ala Ala Gly Pro Leu Pro Ser Glu Ala Val
    1100                1105                1110 cag tgg ctg tgt cat cag gct ttc ctc ctt aaa ctg aca cgc cac        3384
Gln Trp Leu Cys His Gln Ala Phe Leu Leu Lys Leu Thr Arg His
    1115                1120                1125
```

```
cgc gtg act tac gtc cca ctc ctg ggc tcc ctg aga act gct cag    3429
Arg Val Thr Tyr Val Pro Leu Leu Gly Ser Leu Arg Thr Ala Gln
    1130                1135                1140 acc cag ctt tcc cgg aag ctt cca ggc act acc ctt acc gca ctc    3474
Thr Gln Leu Ser Arg Lys Leu Pro Gly Thr Thr Leu Thr Ala Leu
    1145                1150                1155 gaa gca gcc gcc aac cct gcc ctg ccc tcc gac ttt aag act atc    3519
Glu Ala Ala Ala Asn Pro Ala Leu Pro Ser Asp Phe Lys Thr Ile
    1160                1165                1170 ctg gac ggc aag cca att cct aat cca ttg ctg ggc ctg gac tca    3564
Leu Asp Gly Lys Pro Ile Pro Asn Pro Leu Leu Gly Leu Asp Ser
    1175                1180                1185 act tga                                                         3570
Thr

<210> SEQ ID NO 14
<211> LENGTH: 1189
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 14

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
        50                  55                  60

Ser Thr Leu His Leu Val Leu Arg Leu Arg Gly Gly Leu Ala Thr Phe
65                  70                  75                  80

Val Arg Arg Leu Gly Pro Gln Gly Trp Arg Leu Val Gln Arg Gly Asp
                85                  90                  95

Pro Ala Ala Phe Arg Ala Leu Val Ala Gln Cys Leu Val Cys Val Pro
            100                 105                 110

Trp Asp Ala Arg Pro Pro Ala Ala Pro Ser Phe Arg Gln Val Ser
        115                 120                 125

Cys Leu Lys Glu Leu Val Ala Arg Val Leu Gln Arg Leu Cys Glu Arg
    130                 135                 140

Gly Ala Lys Asn Val Leu Ala Phe Gly Phe Ala Leu Leu Asp Gly Ala
145                 150                 155                 160

Arg Gly Gly Pro Pro Glu Ala Phe Thr Thr Ser Val Arg Ser Tyr Leu
                165                 170                 175

Pro Asn Thr Val Thr Asp Ala Leu Arg Gly Ser Gly Ala Trp Gly Leu
            180                 185                 190

Leu Leu Arg Arg Val Gly Asp Asp Val Leu Val His Leu Leu Ala Arg
        195                 200                 205

Cys Ala Leu Phe Val Leu Val Ala Pro Ser Cys Ala Tyr Gln Val Cys
    210                 215                 220

Gly Pro Pro Leu Tyr Gln Leu Gly Ala Ala Thr Gln Ala Arg Pro Pro
225                 230                 235                 240

Pro His Ala Ser Gly Pro Arg Arg Arg Leu Gly Cys Glu Arg Ala Trp
                245                 250                 255
```

```
Asn His Ser Val Arg Glu Ala Gly Val Pro Leu Gly Leu Pro Ala Pro
                260                 265                 270

Gly Ala Arg Arg Gly Gly Ser Ala Ser Arg Ser Leu Pro Leu Pro
            275                 280                 285

Lys Arg Pro Arg Arg Gly Ala Ala Pro Glu Pro Glu Arg Thr Pro Val
        290                 295                 300

Gly Gln Gly Ser Trp Ala His Pro Gly Arg Thr Arg Gly Pro Ser Asp
305                 310                 315                 320

Arg Gly Phe Cys Val Val Ser Pro Ala Arg Pro Ala Glu Glu Ala Thr
                325                 330                 335

Ser Leu Glu Gly Ala Leu Ser Gly Thr Arg His Ser His Pro Ser Val
                340                 345                 350

Gly Arg Gln His His Ala Gly Pro Pro Ser Thr Ser Arg Pro Pro Arg
            355                 360                 365

Pro Trp Asp Thr Pro Cys Pro Pro Val Tyr Ala Glu Thr Lys His Phe
        370                 375                 380

Leu Tyr Ser Ser Gly Asp Lys Glu Gln Leu Arg Pro Ser Phe Leu Leu
385                 390                 395                 400

Ser Ser Leu Arg Pro Ser Leu Thr Gly Ala Arg Arg Leu Val Glu Thr
                405                 410                 415

Ile Phe Leu Gly Ser Arg Pro Trp Met Pro Gly Thr Pro Arg Arg Leu
                420                 425                 430

Pro Arg Leu Pro Gln Arg Tyr Trp Gln Met Arg Pro Leu Phe Leu Glu
            435                 440                 445

Leu Leu Gly Asn His Ala Gln Cys Pro Tyr Gly Val Leu Leu Lys Thr
450                 455                 460

His Cys Pro Leu Arg Ala Val Thr Pro Ala Ala Gly Val Cys Ala
465                 470                 475                 480

Arg Glu Lys Pro Gln Gly Ser Val Ala Ala Pro Glu Glu Asp Thr
                485                 490                 495

Asp Pro Arg Arg Leu Val Gln Leu Leu Arg Gln His Ser Ser Pro Trp
            500                 505                 510

Gln Val Tyr Gly Phe Val Arg Ala Cys Leu Arg Arg Leu Val Pro Pro
    515                 520                 525

Gly Leu Trp Gly Ser Arg His Asn Glu Arg Arg Phe Leu Arg Asn Thr
530                 535                 540

Lys Lys Phe Ile Ser Leu Gly Lys His Ala Lys Leu Ser Leu Gln Glu
545                 550                 555                 560

Leu Thr Trp Lys Met Ser Val Arg Gly Cys Ala Trp Leu Arg Arg Ser
                565                 570                 575

Pro Gly Val Gly Cys Val Pro Ala Ala Glu His Arg Leu Arg Glu Glu
            580                 585                 590

Ile Leu Ala Lys Phe Leu His Trp Leu Met Ser Val Tyr Val Val Glu
            595                 600                 605

Leu Leu Arg Ser Phe Phe Tyr Val Thr Glu Thr Thr Phe Gln Lys Asn
610                 615                 620

Arg Leu Phe Phe Tyr Arg Lys Ser Val Trp Ser Lys Leu Gln Ser Ile
625                 630                 635                 640

Gly Ile Arg Gln His Leu Lys Arg Val Gln Leu Arg Glu Leu Ser Glu
                645                 650                 655

Ala Glu Val Arg Gln His Arg Glu Ala Arg Pro Ala Leu Leu Thr Ser
                660                 665                 670
```

```
Arg Leu Arg Phe Ile Pro Lys Pro Asp Gly Leu Arg Pro Ile Val Asn
        675                 680                 685

Met Asp Tyr Val Gly Ala Arg Thr Phe Arg Arg Glu Lys Arg Ala
690                 695                 700

Glu Arg Leu Thr Ser Arg Val Lys Ala Leu Phe Ser Val Leu Asn Tyr
705                 710                 715                 720

Glu Arg Ala Arg Arg Pro Gly Leu Leu Gly Ala Ser Val Leu Gly Leu
                725                 730                 735

Asp Asp Ile His Arg Ala Trp Arg Thr Phe Val Leu Arg Val Arg Ala
                740                 745                 750

Gln Asp Pro Pro Glu Leu Tyr Phe Val Lys Val Asp Val Thr Gly
                755                 760                 765

Ala Tyr Asp Thr Ile Pro Gln Asp Arg Leu Thr Glu Val Ile Ala Ser
770                 775                 780

Ile Ile Lys Pro Gln Asn Thr Tyr Cys Val Arg Arg Tyr Ala Val Val
785                 790                 795                 800

Gln Lys Ala Ala His Gly His Val Arg Lys Ala Phe Lys Ser His Val
                805                 810                 815

Ser Thr Leu Thr Asp Leu Gln Pro Tyr Met Arg Gln Phe Val Ala His
                820                 825                 830

Leu Gln Glu Thr Ser Pro Leu Arg Asp Ala Val Val Ile Glu Gln Ser
        835                 840                 845

Ser Ser Leu Asn Glu Ala Ser Ser Gly Leu Phe Asp Val Phe Leu Arg
850                 855                 860

Phe Met Cys His His Ala Val Arg Ile Arg Gly Lys Ser Tyr Val Gln
865                 870                 875                 880

Cys Gln Gly Ile Pro Gln Gly Ser Ile Leu Ser Thr Leu Leu Cys Ser
                885                 890                 895

Leu Cys Tyr Gly Asp Met Glu Asn Lys Leu Phe Ala Gly Ile Arg Arg
                900                 905                 910

Phe Leu Leu Val Thr Pro His Leu Thr His Ala Lys Thr Phe Leu Arg
        915                 920                 925

Thr Leu Val Arg Gly Val Pro Glu Tyr Gly Cys Val Val Asn Leu Arg
        930                 935                 940

Lys Thr Val Val Asn Phe Pro Val Glu Asp Glu Ala Leu Gly Gly Thr
945                 950                 955                 960

Ala Phe Val Gln Met Pro Ala His Gly Leu Phe Pro Trp Cys Gly Leu
                965                 970                 975

Leu Leu Asp Thr Arg Thr Leu Glu Val Gln Ser Asp Tyr Ser Ser Tyr
                980                 985                 990

Ala Arg Thr Ser Ile Arg Ala Ser Leu Thr Phe Asn Arg Gly Phe Lys
                995                 1000                1005

Ala Gly Arg Asn Met Arg Arg Lys Leu Phe Gly Val Leu Arg Leu
        1010                1015                1020

Lys Cys His Ser Leu Phe Leu Asp Leu Gln Val Asn Ser Leu Gln
        1025                1030                1035

Thr Val Cys Thr Asn Ile Tyr Lys Ile Leu Leu Leu Gln Ala Tyr
        1040                1045                1050

Arg Phe His Ala Cys Val Leu Gln Leu Pro Phe His Gln Gln Val
        1055                1060                1065

Trp Lys Asn Pro Thr Phe Phe Leu Arg Val Ile Ser Asp Thr Ala
        1070                1075                1080
```

-continued

```
Ser Leu Cys Tyr Ser Ile Leu Lys Ala Lys Asn Ala Gly Met Ser
    1085                1090                1095

Leu Gly Ala Lys Gly Ala Ala Gly Pro Leu Pro Ser Glu Ala Val
1100                1105                1110

Gln Trp Leu Cys His Gln Ala Phe Leu Leu Lys Leu Thr Arg His
    1115                1120                1125

Arg Val Thr Tyr Val Pro Leu Leu Gly Ser Leu Arg Thr Ala Gln
    1130                1135                1140

Thr Gln Leu Ser Arg Lys Leu Pro Gly Thr Thr Leu Thr Ala Leu
    1145                1150                1155

Glu Ala Ala Ala Asn Pro Ala Leu Pro Ser Asp Phe Lys Thr Ile
    1160                1165                1170

Leu Asp Gly Lys Pro Ile Pro Asn Pro Leu Leu Gly Leu Asp Ser
    1175                1180                1185

Thr
```

<210> SEQ ID NO 15
<211> LENGTH: 3570
<212> TYPE: DNA
<213> ORGANISM: Artificial Sequence
<220> FEATURE:
<223> OTHER INFORMATION: Description of Artificial Sequence: Synthetic pUTD10Cog insert sequence
<220> FEATURE:
<221> NAME/KEY: CDS
<222> LOCATION: (1)..(3567)

<400> SEQUENCE: 15

```
atg cag att ttc gtc aaa aca ttg aca gga aag acc atc aca ctg gaa        48
Met Gln Ile Phe Val Lys Thr Leu Thr Gly Lys Thr Ile Thr Leu Glu
1               5                   10                  15 gtg gag cca agc gac act att gag aac gtc aaa gcc aag att cag gac        96
Val Glu Pro Ser Asp Thr Ile Glu Asn Val Lys Ala Lys Ile Gln Asp
            20                  25                  30 aag gag ggc atc cca cca gac cag cag agg ctg att ttt gcc gga aag       144
Lys Glu Gly Ile Pro Pro Asp Gln Gln Arg Leu Ile Phe Ala Gly Lys
        35                  40                  45 cag ctg gag gac gga cgc aca ctc agt gac tac aat atc cag aag gaa       192
Gln Leu Glu Asp Gly Arg Thr Leu Ser Asp Tyr Asn Ile Gln Lys Glu
    50                  55                  60 agt act ctg cat ctg gtc ctt cgc ctg cgc ggc gga ctg gcc acc ttc       240
Ser Thr Leu His Leu Val Leu Arg Leu Arg Gly Gly Leu Ala Thr Phe
65                  70                  75                  80 gtg cgg cgc ctg gga ccc cag ggc tgg cgg ctg gtg cag cgc ggg gac       288
Val Arg Arg Leu Gly Pro Gln Gly Trp Arg Leu Val Gln Arg Gly Asp
                85                  90                  95 cct gct gct ttc aga gct ctc gtc gcc cag tgt ctg gtc tgc gtt cct       336
Pro Ala Ala Phe Arg Ala Leu Val Ala Gln Cys Leu Val Cys Val Pro
            100                 105                 110 tgg gac gca cgg ccc cca ccc gcc gcc ccc agt ttc cgg cag gtg agt       384
Trp Asp Ala Arg Pro Pro Pro Ala Ala Pro Ser Phe Arg Gln Val Ser
        115                 120                 125 tgt ctc aaa gag ttg gtt gct cgg gtg ttg cag cgg ctt tgt gaa agg       432
Cys Leu Lys Glu Leu Val Ala Arg Val Leu Gln Arg Leu Cys Glu Arg
    130                 135                 140 gga gca aag aac gtc ctt gcc ttt ggc ttc gct ttg ctc gat gga gca       480
Gly Ala Lys Asn Val Leu Ala Phe Gly Phe Ala Leu Leu Asp Gly Ala
145                 150                 155                 160
```

-continued

| | | |
|---|---|---|
| cgc gga ggc cct cct gag gca ttc act act agc gtc cgg tcc tac ctg<br>Arg Gly Gly Pro Pro Glu Ala Phe Thr Thr Ser Val Arg Ser Tyr Leu<br>                              165                          170                        175 | | 528 |
| ccc aac aca gtg acc gac gct ctg aga ggt tca ggt gcc tgg ggt ctg<br>Pro Asn Thr Val Thr Asp Ala Leu Arg Gly Ser Gly Ala Trp Gly Leu<br>                        180                          185                        190 | | 576 |
| ctg ctg cgg agg gtg ggt gat gat gtt ctg gtt cac ctc ctg gcc cgg<br>Leu Leu Arg Arg Val Gly Asp Asp Val Leu Val His Leu Leu Ala Arg<br>                195                          200                        205 | | 624 |
| tgt gcc ctg ttc gtg ctg gtg gct ccc tcc tgc gca tac cag gtc tgc<br>Cys Ala Leu Phe Val Leu Val Ala Pro Ser Cys Ala Tyr Gln Val Cys<br>        210                          215                        220 | | 672 |
| gga ccc cca ctt tat cag ctc ggc gct gct act cag gcc cgc cca cca<br>Gly Pro Pro Leu Tyr Gln Leu Gly Ala Ala Thr Gln Ala Arg Pro Pro<br>225                        230                        235                        240 | | 720 |
| cca cac gcc tca ggt cca aga cgc cgg ctg ggc tgc gaa cgg gca tgg<br>Pro His Ala Ser Gly Pro Arg Arg Arg Leu Gly Cys Glu Arg Ala Trp<br>                        245                          250                        255 | | 768 |
| aat cat agc gtg cgg gag gca ggt gtg cct ctc ggc ctg cca gcc ccc<br>Asn His Ser Val Arg Glu Ala Gly Val Pro Leu Gly Leu Pro Ala Pro<br>                260                          265                        270 | | 816 |
| gga gca agg aga cgc ggt gga tcc gcc agt cgc tca ctc ccc ttg cct<br>Gly Ala Arg Arg Arg Gly Gly Ser Ala Ser Arg Ser Leu Pro Leu Pro<br>        275                          280                        285 | | 864 |
| aag agg cca aga aga gga gcc gcc cct gaa ccc gag aga aca cct gtc<br>Lys Arg Pro Arg Arg Gly Ala Ala Pro Glu Pro Glu Arg Thr Pro Val<br>                        290                          295                        300 | | 912 |
| ggc cag ggc tcc tgg gct cac ccc gga agg acc agg ggc cca agc gat<br>Gly Gln Gly Ser Trp Ala His Pro Gly Arg Thr Arg Gly Pro Ser Asp<br>305                        310                        315                        320 | | 960 |
| agg ggc ttc tgt gtt gtg tca cca gcc agg cct gcc gaa gag gct acc<br>Arg Gly Phe Cys Val Val Ser Pro Ala Arg Pro Ala Glu Glu Ala Thr<br>                        325                          330                        335 | | 1008 |
| tcc ttg gaa gga gcc ctc agt ggc acc agg cat tct cat cca tct gtg<br>Ser Leu Glu Gly Ala Leu Ser Gly Thr Arg His Ser His Pro Ser Val<br>                        340                          345                        350 | | 1056 |
| ggt agg cag cat cat gcc ggc ccc ccc tct aca agc aga cct ccc aga<br>Gly Arg Gln His His Ala Gly Pro Pro Ser Thr Ser Arg Pro Pro Arg<br>        355                          360                        365 | | 1104 |
| cct tgg gac aca ccc tgc cca cca gtg tat gcc gag acc aag cac ttt<br>Pro Trp Asp Thr Pro Cys Pro Pro Val Tyr Ala Glu Thr Lys His Phe<br>370                        375                        380 | | 1152 |
| ttg tat tcc agt ggc gat aaa gag cag ctc cgg ccc tct ttt ctg ctc<br>Leu Tyr Ser Ser Gly Asp Lys Glu Gln Leu Arg Pro Ser Phe Leu Leu<br>385                        390                        395                        400 | | 1200 |
| tca agc ctc cgc ccc tct ctg acc gga gct cgc agg ctg gtg gag acc<br>Ser Ser Leu Arg Pro Ser Leu Thr Gly Ala Arg Arg Leu Val Glu Thr<br>                        405                          410                        415 | | 1248 |
| atc ttt ctg ggc tca aga cca tgg atg cca ggc acc ccc cgc aga ctg<br>Ile Phe Leu Gly Ser Arg Pro Trp Met Pro Gly Thr Pro Arg Arg Leu<br>                        420                          425                        430 | | 1296 |
| ccc agg ctc ccc cag cgg tac tgg cag atg cgc cct ctc ttt ctg gaa<br>Pro Arg Leu Pro Gln Arg Tyr Trp Gln Met Arg Pro Leu Phe Leu Glu<br>                        435                          440                        445 | | 1344 |
| ctt ctg ggt aac cac gcc cag tgc cca tat ggc gtc ctg ctg aag acc<br>Leu Leu Gly Asn His Ala Gln Cys Pro Tyr Gly Val Leu Leu Lys Thr<br>        450                          455                        460 | | 1392 |

```
cac tgt cct ctg agg gcc gcc gtg acc cca gcc gcc ggt gtg tgt gct    1440
His Cys Pro Leu Arg Ala Ala Val Thr Pro Ala Ala Gly Val Cys Ala
465                 470                 475                 480 aga gaa aaa ccc cag ggc tca gtg gct gca cct gaa gag gag gac act    1488
Arg Glu Lys Pro Gln Gly Ser Val Ala Ala Pro Glu Glu Glu Asp Thr
                485                 490                 495 gac cct cgc cgc ctt gtc cag ttg ctc agg cag cat tca tca cca tgg    1536
Asp Pro Arg Arg Leu Val Gln Leu Leu Arg Gln His Ser Ser Pro Trp
            500                 505                 510 cag gtg tac ggc ttc gtg agg gct tgc ctg cgg aga ctg gtc ccc ccc    1584
Gln Val Tyr Gly Phe Val Arg Ala Cys Leu Arg Arg Leu Val Pro Pro
        515                 520                 525 gga ttg tgg gga tct cgg cac aac gaa cgg cgc ttt ctg agg aat aca    1632
Gly Leu Trp Gly Ser Arg His Asn Glu Arg Arg Phe Leu Arg Asn Thr
    530                 535                 540 aag aag ttt atc tcc ctg ggc aag cat gca aag ctc agc ttg cag gag    1680
Lys Lys Phe Ile Ser Leu Gly Lys His Ala Lys Leu Ser Leu Gln Glu
545                 550                 555                 560 ctg aca tgg aag atg agc gtt aga gga tgc gca tgg ctc agg cgg tca    1728
Leu Thr Trp Lys Met Ser Val Arg Gly Cys Ala Trp Leu Arg Arg Ser
                565                 570                 575 cct gga gtt gga tgc gtt cca gca gca gag cac agg ctg cgc gaa gag    1776
Pro Gly Val Gly Cys Val Pro Ala Ala Glu His Arg Leu Arg Glu Glu
            580                 585                 590 att ctc gca aag ttc ctg cac tgg ctt atg agc gtc tac gtg gtc gaa    1824
Ile Leu Ala Lys Phe Leu His Trp Leu Met Ser Val Tyr Val Val Glu
        595                 600                 605 ctg ctg cgg tct ttc ttc tac gtg aca gag acc act ttt cag aag aac    1872
Leu Leu Arg Ser Phe Phe Tyr Val Thr Glu Thr Thr Phe Gln Lys Asn
    610                 615                 620 aga ctg ttc ttc tac agg aag tcc gtc tgg agc aag ctc cag agt att    1920
Arg Leu Phe Phe Tyr Arg Lys Ser Val Trp Ser Lys Leu Gln Ser Ile
625                 630                 635                 640 ggt att aga cag cac ctt aag aga gtt cag ctt aga gag ctg tcc gaa    1968
Gly Ile Arg Gln His Leu Lys Arg Val Gln Leu Arg Glu Leu Ser Glu
                645                 650                 655 gct gaa gtc cgc cag cac cgc gaa gct cgc ccc gcc ctc ctg acc tct    2016
Ala Glu Val Arg Gln His Arg Glu Ala Arg Pro Ala Leu Leu Thr Ser
            660                 665                 670 cgg ctg cgg ttt att ccc aaa ccc gat ggc ctt aga cct atc gtg aat    2064
Arg Leu Arg Phe Ile Pro Lys Pro Asp Gly Leu Arg Pro Ile Val Asn
        675                 680                 685 atg gat tac gtc gtg ggt gcc cgc act ttc aga agg gag aag cgc gcc    2112
Met Asp Tyr Val Val Gly Ala Arg Thr Phe Arg Arg Glu Lys Arg Ala
    690                 695                 700 gag aga ctg aca tct cgc gtg aag gca ctt ttt tct gtg ctt aat tat    2160
Glu Arg Leu Thr Ser Arg Val Lys Ala Leu Phe Ser Val Leu Asn Tyr
705                 710                 715                 720 gaa aga gcc cgc aga cct ggt ctt ctc gga gcc agc gtg ctc ggc ctg    2208
Glu Arg Ala Arg Arg Pro Gly Leu Leu Gly Ala Ser Val Leu Gly Leu
                725                 730                 735 gat gat atc cat cgg gct tgg cgc acc ttt gtg ctt cgg gtg agg gca    2256
Asp Asp Ile His Arg Ala Trp Arg Thr Phe Val Leu Arg Val Arg Ala
            740                 745                 750 cag gat cct cct cct gag ctt tat ttt gtg aaa gtt gat gtt act ggt    2304
Gln Asp Pro Pro Pro Glu Leu Tyr Phe Val Lys Val Asp Val Thr Gly
        755                 760                 765
```

| | |
|---|---|
| gct tac gat aca atc cct cag gac cgg ctc acc gag gtg atc gcc tct<br>Ala Tyr Asp Thr Ile Pro Gln Asp Arg Leu Thr Glu Val Ile Ala Ser<br>770                   775                       780 | 2352 |
| att atc aaa ccc cag aac acc tac tgc gtg aga agg tac gcc gtc gtt<br>Ile Ile Lys Pro Gln Asn Thr Tyr Cys Val Arg Arg Tyr Ala Val Val<br>785                   790                    795                   800 | 2400 |
| cag aaa gcc gca cac gga cac gtg cgc aaa gct ttc aaa tcc cac gtg<br>Gln Lys Ala Ala His Gly His Val Arg Lys Ala Phe Lys Ser His Val<br>                        805                    810                   815 | 2448 |
| tct acc ttg aca gac ctc cag cct tat atg cgg cag ttt gtc gca cac<br>Ser Thr Leu Thr Asp Leu Gln Pro Tyr Met Arg Gln Phe Val Ala His<br>         820                   825                   830 | 2496 |
| ctg cag gag act agc ccc ttg agg gac gct gtg gtc atc gaa cag tcc<br>Leu Gln Glu Thr Ser Pro Leu Arg Asp Ala Val Val Ile Glu Gln Ser<br>835                   840                    845 | 2544 |
| agc tct ctc aat gag gca tcc tca ggc ctg ttt gat gtg ttc ctg cgc<br>Ser Ser Leu Asn Glu Ala Ser Ser Gly Leu Phe Asp Val Phe Leu Arg<br>850                   855                    860 | 2592 |
| ttt atg tgc cac cac gcc gtg cgg att agg ggc aag tct tac gtg cag<br>Phe Met Cys His His Ala Val Arg Ile Arg Gly Lys Ser Tyr Val Gln<br>865                   870                   875                   880 | 2640 |
| tgc cag ggc atc cca cag ggt agc atc ctg agc aca ctg ctg tgt agc<br>Cys Gln Gly Ile Pro Gln Gly Ser Ile Leu Ser Thr Leu Leu Cys Ser<br>                        885                    890                   895 | 2688 |
| ctg tgc tat ggc gat atg gag aat aaa ttg ttc gcc ggt atc aga aga<br>Leu Cys Tyr Gly Asp Met Glu Asn Lys Leu Phe Ala Gly Ile Arg Arg<br>         900                   905                   910 | 2736 |
| gac ggt ttg ctc ctg agg ctg ctg act cat gcc aaa aca ttt ttg cgg<br>Asp Gly Leu Leu Leu Arg Leu Leu Thr His Ala Lys Thr Phe Leu Arg<br>                        915                    920                   925 | 2784 |
| act ctg gtt agg ggc gtg cca gag tat ggc tgt gtt gtg aat ttg cgg<br>Thr Leu Val Arg Gly Val Pro Glu Tyr Gly Cys Val Val Asn Leu Arg<br>930                   935                    940 | 2832 |
| aaa act gtg gtt aat ttc cca gtg gag gac gaa gct ctc gga ggc aca<br>Lys Thr Val Val Asn Phe Pro Val Glu Asp Glu Ala Leu Gly Gly Thr<br>945                   950                    955                   960 | 2880 |
| gct ttt gtt cag atg cct gcc cac ggc ctg ttc cca tgg tgc gga ctg<br>Ala Phe Val Gln Met Pro Ala His Gly Leu Phe Pro Trp Cys Gly Leu<br>                        965                    970                   975 | 2928 |
| ctg ctc gat acc cgg acc ctc gag gtg cag tcc gat tat agt tcc tat<br>Leu Leu Asp Thr Arg Thr Leu Glu Val Gln Ser Asp Tyr Ser Ser Tyr<br>         980                   985                   990 | 2976 |
| gca aga aca tca att cgg gct agc ctg act ttc aac agg ggc ttc aag<br>Ala Arg Thr Ser Ile Arg Ala Ser Leu Thr Phe Asn Arg Gly Phe Lys<br>                        995                    1000                  1005 | 3024 |
| gcc ggc cgg aat atg aga agg aaa ctg ttc gga gtg ttg aga ctt<br>Ala Gly Arg Asn Met Arg Arg Lys Leu Phe Gly Val Leu Arg Leu<br>1010                    1015                  1020 | 3069 |
| aag tgt cat agt ctt ttt ttg gac ttg cag gtc aat tct ctc cag<br>Lys Cys His Ser Leu Phe Leu Asp Leu Gln Val Asn Ser Leu Gln<br>1025                    1030                  1035 | 3114 |
| aca gtg tgt acc aac att tat aaa atc ctc ttg ctg cag gct tac<br>Thr Val Cys Thr Asn Ile Tyr Lys Ile Leu Leu Leu Gln Ala Tyr<br>1040                    1045                  1050 | 3159 |
| aga ttc cat gcc tgc gtc ctg cag ctg cct ttc cac cag cag gtg<br>Arg Phe His Ala Cys Val Leu Gln Leu Pro Phe His Gln Gln Val<br>1055                    1060                  1065 | 3204 |

| | | | | | | | | | | | | | | |
|---|---|---|---|---|---|---|---|---|---|---|---|---|---|---|
| tgg | aaa | aac | cct | acc | ttc | ttc | ctg | cgg | gtg | att | agc | gac | acc | gcc | 3249 |
| Trp | Lys | Asn | Pro | Thr | Phe | Phe | Leu | Arg | Val | Ile | Ser | Asp | Thr | Ala | |
| | 1070 | | | | 1075 | | | | | 1080 | | | | | |

| agt | ctt | tgc | tac | tcc | atc | ttg | aaa | gca | aaa | aac | gct | ggc | atg | agc | 3294 |
|---|---|---|---|---|---|---|---|---|---|---|---|---|---|---|---|
| Ser | Leu | Cys | Tyr | Ser | Ile | Leu | Lys | Ala | Lys | Asn | Ala | Gly | Met | Ser | |
| 1085 | | | | | 1090 | | | | | 1095 | | | | | |

| ttg | gga | gct | aag | ggc | gcc | gct | gga | cct | ctg | ccc | agt | gaa | gca | gtc | 3339 |
|---|---|---|---|---|---|---|---|---|---|---|---|---|---|---|---|
| Leu | Gly | Ala | Lys | Gly | Ala | Ala | Gly | Pro | Leu | Pro | Ser | Glu | Ala | Val | |
| 1100 | | | | 1105 | | | | | 1110 | | | | | | |

| cag | tgg | ctg | tgt | cat | cag | gct | ttc | ctc | ctt | aaa | ctg | aca | cgc | cac | 3384 |
|---|---|---|---|---|---|---|---|---|---|---|---|---|---|---|---|
| Gln | Trp | Leu | Cys | His | Gln | Ala | Phe | Leu | Leu | Lys | Leu | Thr | Arg | His | |
| | 1115 | | | | 1120 | | | | | 1125 | | | | | |

| cgc | gtg | act | tac | gtc | cca | ctc | ctg | ggc | tcc | ctg | aga | act | gct | cag | 3429 |
|---|---|---|---|---|---|---|---|---|---|---|---|---|---|---|---|
| Arg | Val | Thr | Tyr | Val | Pro | Leu | Leu | Gly | Ser | Leu | Arg | Thr | Ala | Gln | |
| 1130 | | | | | 1135 | | | | | 1140 | | | | | |

| acc | cag | ctt | tcc | cgg | aag | ctt | cca | ggc | act | acc | ctt | acc | gca | ctc | 3474 |
|---|---|---|---|---|---|---|---|---|---|---|---|---|---|---|---|
| Thr | Gln | Leu | Ser | Arg | Lys | Leu | Pro | Gly | Thr | Thr | Leu | Thr | Ala | Leu | |
| 1145 | | | | | 1150 | | | | | 1155 | | | | | |

| gaa | gca | gcc | gcc | aac | cct | gcc | ctg | ccc | tcc | gac | ttt | aag | act | atc | 3519 |
|---|---|---|---|---|---|---|---|---|---|---|---|---|---|---|---|
| Glu | Ala | Ala | Ala | Asn | Pro | Ala | Leu | Pro | Ser | Asp | Phe | Lys | Thr | Ile | |
| 1160 | | | | | 1165 | | | | | 1170 | | | | | |

| ctg | gac | ggc | aag | cca | att | cct | aat | cca | ttg | ctg | ggc | ctg | gac | tca | 3564 |
|---|---|---|---|---|---|---|---|---|---|---|---|---|---|---|---|
| Leu | Asp | Gly | Lys | Pro | Ile | Pro | Asn | Pro | Leu | Leu | Gly | Leu | Asp | Ser | |
| 1175 | | | | | 1180 | | | | | 1185 | | | | | |

| act | tga | | | | | | | | | | | | | | 3570 |
|---|---|---|---|---|---|---|---|---|---|---|---|---|---|---|---|
| Thr | | | | | | | | | | | | | | | |

<210> SEQ ID NO 16
<211> LENGTH: 1189
<212> TYPE: PRT
<213> ORGANISM: Artificial Sequence
<220> FEATURE:
<223> OTHER INFORMATION: Description of Artificial Sequence: Synthetic
    construct

<400> SEQUENCE: 16

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Leu Ala Thr Phe
65                  70                  75                  80

Val Arg Arg Leu Gly Pro Gln Gly Trp Arg Leu Val Gln Arg Gly Asp
                85                  90                  95

Pro Ala Ala Phe Arg Ala Leu Val Ala Gln Cys Leu Val Cys Val Pro
            100                 105                 110

Trp Asp Ala Arg Pro Pro Pro Ala Ala Pro Ser Phe Arg Gln Val Ser
        115                 120                 125

Cys Leu Lys Glu Leu Val Ala Arg Val Leu Gln Arg Leu Cys Glu Arg
    130                 135                 140

Gly Ala Lys Asn Val Leu Ala Phe Gly Phe Ala Leu Leu Asp Gly Ala
145                 150                 155                 160

Arg Gly Gly Pro Pro Glu Ala Phe Thr Thr Ser Val Arg Ser Tyr Leu
                165                 170                 175

```
Pro Asn Thr Val Thr Asp Ala Leu Arg Gly Ser Gly Ala Trp Gly Leu
            180                 185                 190

Leu Leu Arg Arg Val Gly Asp Asp Val Leu Val His Leu Leu Ala Arg
        195                 200                 205

Cys Ala Leu Phe Val Leu Val Ala Pro Ser Cys Ala Tyr Gln Val Cys
    210                 215                 220

Gly Pro Pro Leu Tyr Gln Leu Gly Ala Ala Thr Gln Ala Arg Pro Pro
225                 230                 235                 240

Pro His Ala Ser Gly Pro Arg Arg Leu Gly Cys Glu Arg Ala Trp
                245                 250                 255

Asn His Ser Val Arg Glu Ala Gly Val Pro Leu Gly Leu Pro Ala Pro
            260                 265                 270

Gly Ala Arg Arg Arg Gly Gly Ser Ala Ser Arg Ser Leu Pro Leu Pro
        275                 280                 285

Lys Arg Pro Arg Arg Gly Ala Ala Pro Glu Pro Glu Arg Thr Pro Val
    290                 295                 300

Gly Gln Gly Ser Trp Ala His Pro Gly Arg Thr Arg Gly Pro Ser Asp
305                 310                 315                 320

Arg Gly Phe Cys Val Val Ser Pro Ala Arg Pro Ala Glu Glu Ala Thr
                325                 330                 335

Ser Leu Glu Gly Ala Leu Ser Gly Thr Arg His Ser His Pro Ser Val
            340                 345                 350

Gly Arg Gln His His Ala Gly Pro Pro Ser Thr Ser Arg Pro Pro Arg
        355                 360                 365

Pro Trp Asp Thr Pro Cys Pro Pro Val Tyr Ala Glu Thr Lys His Phe
    370                 375                 380

Leu Tyr Ser Ser Gly Asp Lys Glu Gln Leu Arg Pro Ser Phe Leu Leu
385                 390                 395                 400

Ser Ser Leu Arg Pro Ser Leu Thr Gly Ala Arg Arg Leu Val Glu Thr
                405                 410                 415

Ile Phe Leu Gly Ser Arg Pro Trp Met Pro Gly Thr Pro Arg Arg Leu
            420                 425                 430

Pro Arg Leu Pro Gln Arg Tyr Trp Gln Met Arg Pro Leu Phe Leu Glu
        435                 440                 445

Leu Leu Gly Asn His Ala Gln Cys Pro Tyr Gly Val Leu Leu Lys Thr
    450                 455                 460

His Cys Pro Leu Arg Ala Ala Val Thr Pro Ala Ala Gly Val Cys Ala
465                 470                 475                 480

Arg Glu Lys Pro Gln Gly Ser Val Ala Ala Pro Glu Glu Glu Asp Thr
                485                 490                 495

Asp Pro Arg Arg Leu Val Gln Leu Leu Arg Gln His Ser Ser Pro Trp
            500                 505                 510

Gln Val Tyr Gly Phe Val Arg Ala Cys Leu Arg Arg Leu Val Pro Pro
        515                 520                 525

Gly Leu Trp Gly Ser Arg His Asn Glu Arg Arg Phe Leu Arg Asn Thr
    530                 535                 540

Lys Lys Phe Ile Ser Leu Gly Lys His Ala Lys Leu Ser Leu Gln Glu
545                 550                 555                 560

Leu Thr Trp Lys Met Ser Val Arg Gly Cys Ala Trp Leu Arg Arg Ser
                565                 570                 575

Pro Gly Val Gly Cys Val Pro Ala Ala Glu His Arg Leu Arg Glu Glu
            580                 585                 590
```

```
Ile Leu Ala Lys Phe Leu His Trp Leu Met Ser Val Tyr Val Glu
            595                 600                 605

Leu Leu Arg Ser Phe Phe Tyr Val Thr Glu Thr Thr Phe Gln Lys Asn
            610                 615                 620

Arg Leu Phe Phe Tyr Arg Lys Ser Val Trp Ser Lys Leu Gln Ser Ile
625                 630                 635                 640

Gly Ile Arg Gln His Leu Lys Arg Val Gln Leu Arg Glu Leu Ser Glu
                645                 650                 655

Ala Glu Val Arg Gln His Arg Glu Ala Arg Pro Ala Leu Leu Thr Ser
                660                 665                 670

Arg Leu Arg Phe Ile Pro Lys Pro Asp Gly Leu Arg Pro Ile Val Asn
675                 680                 685

Met Asp Tyr Val Val Gly Ala Arg Thr Phe Arg Arg Glu Lys Arg Ala
690                 695                 700

Glu Arg Leu Thr Ser Arg Val Lys Ala Leu Phe Ser Val Leu Asn Tyr
705                 710                 715                 720

Glu Arg Ala Arg Arg Pro Gly Leu Leu Gly Ala Ser Val Leu Gly Leu
                725                 730                 735

Asp Asp Ile His Arg Ala Trp Arg Thr Phe Val Leu Arg Val Arg Ala
                740                 745                 750

Gln Asp Pro Pro Glu Leu Tyr Phe Val Lys Val Asp Val Thr Gly
            755                 760                 765

Ala Tyr Asp Thr Ile Pro Gln Asp Arg Leu Thr Glu Val Ile Ala Ser
770                 775                 780

Ile Ile Lys Pro Gln Asn Thr Tyr Cys Val Arg Arg Tyr Ala Val Val
785                 790                 795                 800

Gln Lys Ala Ala His Gly His Val Arg Lys Ala Phe Lys Ser His Val
                805                 810                 815

Ser Thr Leu Thr Asp Leu Gln Pro Tyr Met Arg Gln Phe Val Ala His
                820                 825                 830

Leu Gln Glu Thr Ser Pro Leu Arg Asp Ala Val Val Ile Glu Gln Ser
            835                 840                 845

Ser Ser Leu Asn Glu Ala Ser Ser Gly Leu Phe Asp Val Phe Leu Arg
850                 855                 860

Phe Met Cys His His Ala Val Arg Ile Arg Gly Lys Ser Tyr Val Gln
865                 870                 875                 880

Cys Gln Gly Ile Pro Gln Gly Ser Ile Leu Ser Thr Leu Leu Cys Ser
                885                 890                 895

Leu Cys Tyr Gly Asp Met Glu Asn Lys Leu Phe Ala Gly Ile Arg Arg
                900                 905                 910

Asp Gly Leu Leu Leu Arg Leu Leu Thr His Ala Lys Thr Phe Leu Arg
            915                 920                 925

Thr Leu Val Arg Gly Val Pro Glu Tyr Gly Cys Val Val Asn Leu Arg
            930                 935                 940

Lys Thr Val Val Asn Phe Pro Val Glu Asp Glu Ala Leu Gly Gly Thr
945                 950                 955                 960

Ala Phe Val Gln Met Pro Ala His Gly Leu Phe Pro Trp Cys Gly Leu
                965                 970                 975

Leu Leu Asp Thr Arg Thr Leu Glu Val Gln Ser Asp Tyr Ser Ser Tyr
                980                 985                 990

Ala Arg Thr Ser Ile Arg Ala Ser Leu Thr Phe Asn Arg Gly Phe Lys
            995                 1000                1005
```

```
Ala Gly Arg Asn Met Arg Arg Lys Leu Phe Gly Val Leu Arg Leu
    1010                1015                1020

Lys Cys His Ser Leu Phe Leu Asp Leu Gln Val Asn Ser Leu Gln
    1025                1030                1035

Thr Val Cys Thr Asn Ile Tyr Lys Ile Leu Leu Leu Gln Ala Tyr
    1040                1045                1050

Arg Phe His Ala Cys Val Leu Gln Leu Pro Phe His Gln Gln Val
    1055                1060                1065

Trp Lys Asn Pro Thr Phe Phe Leu Arg Val Ile Ser Asp Thr Ala
    1070                1075                1080

Ser Leu Cys Tyr Ser Ile Leu Lys Ala Lys Asn Ala Gly Met Ser
    1085                1090                1095

Leu Gly Ala Lys Gly Ala Ala Gly Pro Leu Pro Ser Glu Ala Val
    1100                1105                1110

Gln Trp Leu Cys His Gln Ala Phe Leu Leu Lys Leu Thr Arg His
    1115                1120                1125

Arg Val Thr Tyr Val Pro Leu Leu Gly Ser Leu Arg Thr Ala Gln
    1130                1135                1140

Thr Gln Leu Ser Arg Lys Leu Pro Gly Thr Thr Leu Thr Ala Leu
    1145                1150                1155

Glu Ala Ala Ala Asn Pro Ala Leu Pro Ser Asp Phe Lys Thr Ile
    1160                1165                1170

Leu Asp Gly Lys Pro Ile Pro Asn Pro Leu Leu Gly Leu Asp Ser
    1175                1180                1185

Thr
```

<210> SEQ ID NO 17
<211> LENGTH: 3531
<212> TYPE: DNA
<213> ORGANISM: Artificial Sequence
<220> FEATURE:
<223> OTHER INFORMATION: Description of Artificial Sequence: Synthetic
      pUTD23Tyn insert sequence
<220> FEATURE:
<221> NAME/KEY: CDS
<222> LOCATION: (1)..(3528)

<400> SEQUENCE: 17

```
atg cag att ttc gtc aaa aca ttg aca gga aag acc atc aca ctg gaa    48
Met Gln Ile Phe Val Lys Thr Leu Thr Gly Lys Thr Ile Thr Leu Glu
1               5                   10                  15 gtg gag cca agc gac act att gag aac gtc aaa gcc aag att cag gac    96
Val Glu Pro Ser Asp Thr Ile Glu Asn Val Lys Ala Lys Ile Gln Asp
                20                  25                  30 aag gag ggc atc cca cca gac cag cag agg ctg att ttt gcc gga aag   144
Lys Glu Gly Ile Pro Pro Asp Gln Gln Arg Leu Ile Phe Ala Gly Lys
            35                  40                  45 cag ctg gag gac gga cgc aca ctc agt gac tac aat atc cag aag gaa   192
Gln Leu Glu Asp Gly Arg Thr Leu Ser Asp Tyr Asn Ile Gln Lys Glu
        50                  55                  60 agt act ctg cat ctg gtc ctt cgc ctg cgc ggc gga ctg gcc acc ttc   240
Ser Thr Leu His Leu Val Leu Arg Leu Arg Gly Gly Leu Ala Thr Phe
65                  70                  75                  80 gtg cgg cgc ctg gga ccc cag ggc tgg cgg ctg gtg cag cgc ggg gac   288
Val Arg Arg Leu Gly Pro Gln Gly Trp Arg Leu Val Gln Arg Gly Asp
                85                  90                  95
```

| | | |
|---|---|---|
| cct gct gct ttc aga gct ctc gtc gcc cag tgt ctg gtc tgc gtt cct<br>Pro Ala Ala Phe Arg Ala Leu Val Ala Gln Cys Leu Val Cys Val Pro<br>                100               105            110 | 336 |
| tgg gac gca cgg ccc cca ccc gcc gcc ccc agt ttc cgg cag gtg agt<br>Trp Asp Ala Arg Pro Pro Pro Ala Ala Pro Ser Phe Arg Gln Val Ser<br>         115               120              125 | 384 |
| tgt ctc aaa gag ttg gtt gct cgg gtg ttg cag cgg ctt tgt gaa agg<br>Cys Leu Lys Glu Leu Val Ala Arg Val Leu Gln Arg Leu Cys Glu Arg<br>130               135              140 | 432 |
| gga gca aag aac gtc ctt gcc ttt ggc ttc gct ttg ctc gat gga gca<br>Gly Ala Lys Asn Val Leu Ala Phe Gly Phe Ala Leu Leu Asp Gly Ala<br>145               150              155              160 | 480 |
| cgc gga ggc cct cct gag gca ttc act act agc gtc cgg tcc tac ctg<br>Arg Gly Gly Pro Pro Glu Ala Phe Thr Thr Ser Val Arg Ser Tyr Leu<br>                165              170           175 | 528 |
| ccc aac aca gtg acc gac gct ctg aga ggt tca ggt gcc tgg ggt ctg<br>Pro Asn Thr Val Thr Asp Ala Leu Arg Gly Ser Gly Ala Trp Gly Leu<br>         180               185              190 | 576 |
| ctg ctg cgg agg gtg ggt gat gat gtt ctg gtt cac ctc ctg gcc cgg<br>Leu Leu Arg Arg Val Gly Asp Asp Val Leu Val His Leu Leu Ala Arg<br>             195              200           205 | 624 |
| tgt gcc ctg ttc gtg ctg gtg gct ccc tcc tgc gca tac cag gtc tgc<br>Cys Ala Leu Phe Val Leu Val Ala Pro Ser Cys Ala Tyr Gln Val Cys<br>210               215              220 | 672 |
| gga ccc cca ctt tat cag ctc ggc gct gct act cag gcc cgc cca cca<br>Gly Pro Pro Leu Tyr Gln Leu Gly Ala Ala Thr Gln Ala Arg Pro Pro<br>225               230              235              240 | 720 |
| cca cac gcc tca ggt cca aga cgc cgg ctg ggc tgc gaa cgg gca tgg<br>Pro His Ala Ser Gly Pro Arg Arg Arg Leu Gly Cys Glu Arg Ala Trp<br>                245              250           255 | 768 |
| aat cat agc gtg cgg gag gca ggt gtg cct ctc ggc ctg cca gcc ccc<br>Asn His Ser Val Arg Glu Ala Gly Val Pro Leu Gly Leu Pro Ala Pro<br>         260               265              270 | 816 |
| gga gca agg aga cgc ggt gga tcc gcc agt cgc tca ctc ccc ttg cct<br>Gly Ala Arg Arg Arg Gly Gly Ser Ala Ser Arg Ser Leu Pro Leu Pro<br>             275              280           285 | 864 |
| aag agg cca aga aga gga gcc gcc cct gaa ccc gag aga aca cct gtc<br>Lys Arg Pro Arg Arg Gly Ala Ala Pro Glu Pro Glu Arg Thr Pro Val<br>290               295              300 | 912 |
| ggc cag ggc tcc tgg gct cac ccc gga agg acc agg ggc cca agc gat<br>Gly Gln Gly Ser Trp Ala His Pro Gly Arg Thr Arg Gly Pro Ser Asp<br>305               310              315              320 | 960 |
| agg ggc ttc tgt gtt gtg tca cca gcc agg cct gcc gaa gag gct acc<br>Arg Gly Phe Cys Val Val Ser Pro Ala Arg Pro Ala Glu Glu Ala Thr<br>                325              330           335 | 1008 |
| tcc ttg gaa gga gcc ctc agt ggc acc agg cat tct cat cca tct gtg<br>Ser Leu Glu Gly Ala Leu Ser Gly Thr Arg His Ser His Pro Ser Val<br>         340               345              350 | 1056 |
| ggt agg cag cat cat gcc ggc ccc ccc tct aca agc aga cct ccc aga<br>Gly Arg Gln His His Ala Gly Pro Pro Ser Thr Ser Arg Pro Pro Arg<br>             355              360           365 | 1104 |
| cct tgg gac aca ccc tgc cca cca gtg tat gcc gag acc aag cac ttt<br>Pro Trp Asp Thr Pro Cys Pro Pro Val Tyr Ala Glu Thr Lys His Phe<br>370               375              380 | 1152 |
| ttg tat tcc agt ggc gat aaa gag cag ctc cgg ccc tct ttt ctg ctc<br>Leu Tyr Ser Ser Gly Asp Lys Glu Gln Leu Arg Pro Ser Phe Leu Leu<br>385               390              395              400 | 1200 |

-continued

| | | |
|---|---|---|
| tca agc ctc cgc ccc tct ctg acc gga gct cgc agg ctg gtg gag acc<br>Ser Ser Leu Arg Pro Ser Leu Thr Gly Ala Arg Arg Leu Val Glu Thr<br>405 410 415 | | 1248 |
| atc ttt ctg ggc tca aga cca tgg atg cca ggc acc ccc cgc aga ctg<br>Ile Phe Leu Gly Ser Arg Pro Trp Met Pro Gly Thr Pro Arg Arg Leu<br>420 425 430 | | 1296 |
| ccc agg ctc ccc cag cgg tac tgg cag atg cgc cct ctc ttt ctg gaa<br>Pro Arg Leu Pro Gln Arg Tyr Trp Gln Met Arg Pro Leu Phe Leu Glu<br>435 440 445 | | 1344 |
| ctt ctg ggt aac cac gcc cag tgc cca tat ggc gtc ctg ctg aag acc<br>Leu Leu Gly Asn His Ala Gln Cys Pro Tyr Gly Val Leu Leu Lys Thr<br>450 455 460 | | 1392 |
| cac tgt cct ctg agg gcc gcc gtg acc cca gcc gcc ggt gtg tgt gct<br>His Cys Pro Leu Arg Ala Ala Val Thr Pro Ala Ala Gly Val Cys Ala<br>465 470 475 480 | | 1440 |
| aga gaa aaa ccc cag ggc tca gtg gct gca cct gaa gag gag gac act<br>Arg Glu Lys Pro Gln Gly Ser Val Ala Ala Pro Glu Glu Glu Asp Thr<br>485 490 495 | | 1488 |
| gac cct cgc cgc ctt gtc cag ttg ctc agg cag cat tca tca cca tgg<br>Asp Pro Arg Arg Leu Val Gln Leu Leu Arg Gln His Ser Ser Pro Trp<br>500 505 510 | | 1536 |
| cag gtg tac ggc ttc gtg agg gct tgc ctg cgg aga ctg gtc ccc ccc<br>Gln Val Tyr Gly Phe Val Arg Ala Cys Leu Arg Arg Leu Val Pro Pro<br>515 520 525 | | 1584 |
| gga ttg tgg gga tct cgg cac aac gaa cgg cgc ttt ctg agg aat aca<br>Gly Leu Trp Gly Ser Arg His Asn Glu Arg Arg Phe Leu Arg Asn Thr<br>530 535 540 | | 1632 |
| aag aag ttt atc tcc ctg ggc aag cat gca aag ctc agc ttg cag gag<br>Lys Lys Phe Ile Ser Leu Gly Lys His Ala Lys Leu Ser Leu Gln Glu<br>545 550 555 560 | | 1680 |
| ctg aca tgg aag atg agc gtt aga gga tgc gca tgg ctc agg cgg tca<br>Leu Thr Trp Lys Met Ser Val Arg Gly Cys Ala Trp Leu Arg Arg Ser<br>565 570 575 | | 1728 |
| cct gga gtt gga tgc gtt cca gca gca gag cac agg ctg cgc gaa gag<br>Pro Gly Val Gly Cys Val Pro Ala Ala Glu His Arg Leu Arg Glu Glu<br>580 585 590 | | 1776 |
| att ctc gca aag ttc ctg cac tgg ctt atg agc gtc tac gtg gtc gaa<br>Ile Leu Ala Lys Phe Leu His Trp Leu Met Ser Val Tyr Val Val Glu<br>595 600 605 | | 1824 |
| ctg ctg cgg tct ttc ttc tac gtg aca gag acc act ttt cag aag aac<br>Leu Leu Arg Ser Phe Phe Tyr Val Thr Glu Thr Thr Phe Gln Lys Asn<br>610 615 620 | | 1872 |
| aga ctg ttc ttc tac agg aag tcc gtc tgg agc aag ctc cag agt att<br>Arg Leu Phe Phe Tyr Arg Lys Ser Val Trp Ser Lys Leu Gln Ser Ile<br>625 630 635 640 | | 1920 |
| ggt att aga cag cac ctt aag aga gtt cag ctt aga gag ctg tcc gaa<br>Gly Ile Arg Gln His Leu Lys Arg Val Gln Leu Arg Glu Leu Ser Glu<br>645 650 655 | | 1968 |
| gct gaa gtc cgc cag cac cgc gaa gct cgc ccc gcc ctc ctg acc tct<br>Ala Glu Val Arg Gln His Arg Glu Ala Arg Pro Ala Leu Leu Thr Ser<br>660 665 670 | | 2016 |
| cgg ctg cgg ttt att ccc aaa ccc gat ggc ctt aga cct atc gtg aat<br>Arg Leu Arg Phe Ile Pro Lys Pro Asp Gly Leu Arg Pro Ile Val Asn<br>675 680 685 | | 2064 |
| atg gat tac gtc gtg ggt gcc cgc act ttc aga agg gag aag cgc gcc<br>Met Asp Tyr Val Val Gly Ala Arg Thr Phe Arg Arg Glu Lys Arg Ala<br>690 695 700 | | 2112 |

-continued

| | |
|---|---|
| gag aga ctg aca tct cgc gtg aag gca ctt ttt tct gtg ctt aat tat<br>Glu Arg Leu Thr Ser Arg Val Lys Ala Leu Phe Ser Val Leu Asn Tyr<br>705     710     715     720 | 2160 |
| gaa aga gcc cgc aga cct ggt ctt ctc gga gcc agc gtg ctc ggc ctg<br>Glu Arg Ala Arg Arg Pro Gly Leu Leu Gly Ala Ser Val Leu Gly Leu<br>    725     730     735 | 2208 |
| gat gat atc cat cgg gct tgg cgc acc ttt gtg ctt cgg gtg agg gca<br>Asp Asp Ile His Arg Ala Trp Arg Thr Phe Val Leu Arg Val Arg Ala<br>740     745     750 | 2256 |
| cag gat cct cct cct gag ctt tat ttt gtg aaa gtt gat gtt act ggt<br>Gln Asp Pro Pro Pro Glu Leu Tyr Phe Val Lys Val Asp Val Thr Gly<br> 755     760     765 | 2304 |
| gct tac gat aca atc cct cag gac cgg ctc acc gag gtg atc gcc tct<br>Ala Tyr Asp Thr Ile Pro Gln Asp Arg Leu Thr Glu Val Ile Ala Ser<br>770     775     780 | 2352 |
| att atc aaa ccc cag aac acc tac tgc gtg aga agg tac gcc gtc gtt<br>Ile Ile Lys Pro Gln Asn Thr Tyr Cys Val Arg Arg Tyr Ala Val Val<br>785     790     795     800 | 2400 |
| cag aaa gcc gca cac gga cac gtg cgc aaa gct ttc aaa tcc cac gtg<br>Gln Lys Ala Ala His Gly His Val Arg Lys Ala Phe Lys Ser His Val<br>    805     810     815 | 2448 |
| tct acc ttg aca gac ctc cag cct tat atg cgg cag ttt gtc gca cac<br>Ser Thr Leu Thr Asp Leu Gln Pro Tyr Met Arg Gln Phe Val Ala His<br>820     825     830 | 2496 |
| ctg cag gag act agc ccc ttg agg gac gct gtg gtc atc gaa cag tcc<br>Leu Gln Glu Thr Ser Pro Leu Arg Asp Ala Val Val Ile Glu Gln Ser<br> 835     840     845 | 2544 |
| agc tct ctc aat gag gca tcc tca ggc ctg ttt gat gtg ttc ctg cgc<br>Ser Ser Leu Asn Glu Ala Ser Ser Gly Leu Phe Asp Val Phe Leu Arg<br>850     855     860 | 2592 |
| ttt atg tgc cac cac gcc gtg cgg att agg ggc aag tct tac gtg cag<br>Phe Met Cys His His Ala Val Arg Ile Arg Gly Lys Ser Tyr Val Gln<br>865     870     875     880 | 2640 |
| tgc cag ggc atc cca cag ggt agc atc ctg agc aca ctg ctg tgt agc<br>Cys Gln Gly Ile Pro Gln Gly Ser Ile Leu Ser Thr Leu Leu Cys Ser<br>    885     890     895 | 2688 |
| ctg tgc tat ggc gat atg gag aat aaa ttg ttc gcc ggt gcc aaa aca<br>Leu Cys Tyr Gly Asp Met Glu Asn Lys Leu Phe Ala Gly Ala Lys Thr<br>900     905     910 | 2736 |
| ttt ttg cgg act ctg gtt agg ggc gtg cca gag tat ggc tgt gtt gtg<br>Phe Leu Arg Thr Leu Val Arg Gly Val Pro Glu Tyr Gly Cys Val Val<br> 915     920     925 | 2784 |
| aat ttg cgg aaa act gtg gtt aat ttc cca gtg gag gac gaa gct ctc<br>Asn Leu Arg Lys Thr Val Val Asn Phe Pro Val Glu Asp Glu Ala Leu<br>930     935     940 | 2832 |
| gga ggc aca gct ttt gtt cag atg cct gcc cac ggc ctg ttc cca tgg<br>Gly Gly Thr Ala Phe Val Gln Met Pro Ala His Gly Leu Phe Pro Trp<br>945     950     955     960 | 2880 |
| tgc gga ctg ctg ctc gat acc cgg acc ctc gag gtg cag tcc gat tat<br>Cys Gly Leu Leu Leu Asp Thr Arg Thr Leu Glu Val Gln Ser Asp Tyr<br>    965     970     975 | 2928 |
| agt tcc tat gca aga aca tca att cgg gct agc ctg act ttc aac agg<br>Ser Ser Tyr Ala Arg Thr Ser Ile Arg Ala Ser Leu Thr Phe Asn Arg<br>980     985     990 | 2976 |
| ggc ttc aag gcc ggc cgg aat atg aga agg aaa ctg ttc gga gtg ttg<br>Gly Phe Lys Ala Gly Arg Asn Met Arg Arg Lys Leu Phe Gly Val Leu<br> 995     1000     1005 | 3024 |

```
aga ctt aag tgt cat agt ctt ttt ttg gac ttg cag gtc aat tct      3069
Arg Leu Lys Cys His Ser Leu Phe Leu Asp Leu Gln Val Asn Ser
    1010                1015                1020 ctc cag aca gtg tgt acc aac att tat aaa atc ctc ttg ctg cag      3114
Leu Gln Thr Val Cys Thr Asn Ile Tyr Lys Ile Leu Leu Leu Gln
1025                1030                1035 gct tac aga ttc cat gcc tgc gtc ctg cag ctg cct ttc cac cag      3159
Ala Tyr Arg Phe His Ala Cys Val Leu Gln Leu Pro Phe His Gln
        1040                1045                1050 cag gtg tgg aaa aac cct acc ttc ttc ctg cgg gtg att agc gac      3204
Gln Val Trp Lys Asn Pro Thr Phe Phe Leu Arg Val Ile Ser Asp
    1055                1060                1065 acc gcc agt ctt tgc tac tcc atc ttg aaa gca aaa aac gct ggc      3249
Thr Ala Ser Leu Cys Tyr Ser Ile Leu Lys Ala Lys Asn Ala Gly
1070                1075                1080 atg agc ttg gga gct aag ggc gcc gct gga cct ctg ccc agt gaa      3294
Met Ser Leu Gly Ala Lys Gly Ala Ala Gly Pro Leu Pro Ser Glu
        1085                1090                1095 gca gtc cag tgg ctg tgt cat cag gct ttc ctc ctt aaa ctg aca      3339
Ala Val Gln Trp Leu Cys His Gln Ala Phe Leu Leu Lys Leu Thr
    1100                1105                1110 cgc cac cgc gtg act tac gtc cca ctc ctg ggc tcc ctg aga act      3384
Arg His Arg Val Thr Tyr Val Pro Leu Leu Gly Ser Leu Arg Thr
1115                1120                1125 gct cag acc cag ctt tcc cgg aag ctt cca ggc act acc ctt acc      3429
Ala Gln Thr Gln Leu Ser Arg Lys Leu Pro Gly Thr Thr Leu Thr
        1130                1135                1140 gca ctc gaa gca gcc gcc aac cct gcc ctg ccc tcc gac ttt aag      3474
Ala Leu Glu Ala Ala Ala Asn Pro Ala Leu Pro Ser Asp Phe Lys
    1145                1150                1155 act atc ctg gac ggc aag cca att cct aat cca ttg ctg ggc ctg      3519
Thr Ile Leu Asp Gly Lys Pro Ile Pro Asn Pro Leu Leu Gly Leu
1160                1165                1170 gac tca act tga                                                   3531
Asp Ser Thr
        1175

<210> SEQ ID NO 18
<211> LENGTH: 1176
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 18

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Leu Ala Thr Phe
65                  70                  75                  80

Val Arg Arg Leu Gly Pro Gln Gly Trp Arg Leu Val Gln Arg Gly Asp
                85                  90                  95
```

-continued

```
Pro Ala Ala Phe Arg Ala Leu Val Ala Gln Cys Leu Val Cys Val Pro
            100                 105                 110

Trp Asp Ala Arg Pro Pro Ala Ala Pro Ser Phe Arg Gln Val Ser
        115                 120                 125

Cys Leu Lys Glu Leu Val Ala Arg Val Leu Gln Arg Leu Cys Glu Arg
        130                 135                 140

Gly Ala Lys Asn Val Leu Ala Phe Gly Phe Ala Leu Leu Asp Gly Ala
145                 150                 155                 160

Arg Gly Gly Pro Pro Glu Ala Phe Thr Thr Ser Val Arg Ser Tyr Leu
                165                 170                 175

Pro Asn Thr Val Thr Asp Ala Leu Arg Gly Ser Gly Ala Trp Gly Leu
                180                 185                 190

Leu Leu Arg Arg Val Gly Asp Asp Val Leu Val His Leu Leu Ala Arg
            195                 200                 205

Cys Ala Leu Phe Val Leu Val Ala Pro Ser Cys Ala Tyr Gln Val Cys
        210                 215                 220

Gly Pro Pro Leu Tyr Gln Leu Gly Ala Ala Thr Gln Ala Arg Pro Pro
225                 230                 235                 240

Pro His Ala Ser Gly Pro Arg Arg Leu Gly Cys Glu Arg Ala Trp
                245                 250                 255

Asn His Ser Val Arg Glu Ala Gly Val Pro Leu Gly Leu Pro Ala Pro
                260                 265                 270

Gly Ala Arg Arg Arg Gly Gly Ser Ala Ser Arg Ser Leu Pro Leu Pro
            275                 280                 285

Lys Arg Pro Arg Arg Gly Ala Ala Pro Glu Pro Glu Arg Thr Pro Val
        290                 295                 300

Gly Gln Gly Ser Trp Ala His Pro Gly Arg Thr Arg Gly Pro Ser Asp
305                 310                 315                 320

Arg Gly Phe Cys Val Val Ser Pro Ala Arg Pro Ala Glu Glu Ala Thr
                325                 330                 335

Ser Leu Glu Gly Ala Leu Ser Gly Thr Arg His Ser His Pro Ser Val
                340                 345                 350

Gly Arg Gln His His Ala Gly Pro Pro Ser Thr Ser Arg Pro Pro Arg
            355                 360                 365

Pro Trp Asp Thr Pro Cys Pro Pro Val Tyr Ala Glu Thr Lys His Phe
        370                 375                 380

Leu Tyr Ser Ser Gly Asp Lys Glu Gln Leu Arg Pro Ser Phe Leu Leu
385                 390                 395                 400

Ser Ser Leu Arg Pro Ser Leu Thr Gly Ala Arg Arg Leu Val Glu Thr
                405                 410                 415

Ile Phe Leu Gly Ser Arg Pro Trp Met Pro Gly Thr Pro Arg Arg Leu
            420                 425                 430

Pro Arg Leu Pro Gln Arg Tyr Trp Gln Met Arg Pro Leu Phe Leu Glu
        435                 440                 445

Leu Leu Gly Asn His Ala Gln Cys Pro Tyr Gly Val Leu Leu Lys Thr
        450                 455                 460

His Cys Pro Leu Arg Ala Ala Val Thr Pro Ala Ala Gly Val Cys Ala
465                 470                 475                 480

Arg Glu Lys Pro Gln Gly Ser Val Ala Ala Pro Glu Glu Asp Thr
                485                 490                 495

Asp Pro Arg Arg Leu Val Gln Leu Leu Arg Gln His Ser Ser Pro Trp
                500                 505                 510
```

```
Gln Val Tyr Gly Phe Val Arg Ala Cys Leu Arg Arg Leu Val Pro Pro
            515                 520                 525

Gly Leu Trp Gly Ser Arg His Asn Glu Arg Arg Phe Leu Arg Asn Thr
530                 535                 540

Lys Lys Phe Ile Ser Leu Gly Lys His Ala Lys Leu Ser Leu Gln Glu
545                 550                 555                 560

Leu Thr Trp Lys Met Ser Val Arg Gly Cys Ala Trp Leu Arg Arg Ser
                565                 570                 575

Pro Gly Val Gly Cys Val Pro Ala Ala Glu His Arg Leu Arg Glu Glu
                580                 585                 590

Ile Leu Ala Lys Phe Leu His Trp Leu Met Ser Val Tyr Val Val Glu
            595                 600                 605

Leu Leu Arg Ser Phe Phe Tyr Val Thr Glu Thr Thr Phe Gln Lys Asn
            610                 615                 620

Arg Leu Phe Phe Tyr Arg Lys Ser Val Trp Ser Lys Leu Gln Ser Ile
625                 630                 635                 640

Gly Ile Arg Gln His Leu Lys Arg Val Gln Leu Arg Glu Leu Ser Glu
                645                 650                 655

Ala Glu Val Arg Gln His Arg Glu Ala Arg Pro Ala Leu Leu Thr Ser
                660                 665                 670

Arg Leu Arg Phe Ile Pro Lys Pro Asp Gly Leu Arg Pro Ile Val Asn
            675                 680                 685

Met Asp Tyr Val Val Gly Ala Arg Thr Phe Arg Arg Glu Lys Arg Ala
            690                 695                 700

Glu Arg Leu Thr Ser Arg Val Lys Ala Leu Phe Ser Val Leu Asn Tyr
705                 710                 715                 720

Glu Arg Ala Arg Arg Pro Gly Leu Leu Gly Ala Ser Val Leu Gly Leu
                725                 730                 735

Asp Asp Ile His Arg Ala Trp Arg Thr Phe Val Leu Arg Val Arg Ala
                740                 745                 750

Gln Asp Pro Pro Pro Glu Leu Tyr Phe Val Lys Val Asp Val Thr Gly
            755                 760                 765

Ala Tyr Asp Thr Ile Pro Gln Asp Arg Leu Thr Glu Val Ile Ala Ser
            770                 775                 780

Ile Ile Lys Pro Gln Asn Thr Tyr Cys Val Arg Arg Tyr Ala Val Val
785                 790                 795                 800

Gln Lys Ala Ala His Gly His Val Arg Lys Ala Phe Lys Ser His Val
                805                 810                 815

Ser Thr Leu Thr Asp Leu Gln Pro Tyr Met Arg Gln Phe Val Ala His
                820                 825                 830

Leu Gln Glu Thr Ser Pro Leu Arg Asp Ala Val Val Ile Glu Gln Ser
            835                 840                 845

Ser Ser Leu Asn Glu Ala Ser Ser Gly Leu Phe Asp Val Phe Leu Arg
            850                 855                 860

Phe Met Cys His His Ala Val Arg Ile Arg Gly Lys Ser Tyr Val Gln
865                 870                 875                 880

Cys Gln Gly Ile Pro Gln Gly Ser Ile Leu Ser Thr Leu Leu Cys Ser
                885                 890                 895

Leu Cys Tyr Gly Asp Met Glu Asn Lys Leu Phe Ala Gly Ala Lys Thr
                900                 905                 910

Phe Leu Arg Thr Leu Val Arg Gly Val Pro Glu Tyr Gly Cys Val Val
            915                 920                 925
```

```
Asn Leu Arg Lys Thr Val Val Asn Phe Pro Val Glu Asp Glu Ala Leu
    930                 935                 940

Gly Gly Thr Ala Phe Val Gln Met Pro Ala His Gly Leu Phe Pro Trp
945                 950                 955                 960

Cys Gly Leu Leu Leu Asp Thr Arg Thr Leu Glu Val Gln Ser Asp Tyr
                965                 970                 975

Ser Ser Tyr Ala Arg Thr Ser Ile Arg Ala Ser Leu Thr Phe Asn Arg
            980                 985                 990

Gly Phe Lys Ala Gly Arg Asn Met Arg Arg Lys Leu Phe Gly Val Leu
        995                 1000                1005

Arg Leu Lys Cys His Ser Leu Phe Leu Asp Leu Gln Val Asn Ser
    1010                1015                1020

Leu Gln Thr Val Cys Thr Asn Ile Tyr Lys Ile Leu Leu Leu Gln
    1025                1030                1035

Ala Tyr Arg Phe His Ala Cys Val Leu Gln Leu Pro Phe His Gln
    1040                1045                1050

Gln Val Trp Lys Asn Pro Thr Phe Phe Leu Arg Val Ile Ser Asp
    1055                1060                1065

Thr Ala Ser Leu Cys Tyr Ser Ile Leu Lys Ala Lys Asn Ala Gly
    1070                1075                1080

Met Ser Leu Gly Ala Lys Gly Ala Ala Gly Pro Leu Pro Ser Glu
    1085                1090                1095

Ala Val Gln Trp Leu Cys His Gln Ala Phe Leu Leu Lys Leu Thr
    1100                1105                1110

Arg His Arg Val Thr Tyr Val Pro Leu Leu Gly Ser Leu Arg Thr
    1115                1120                1125

Ala Gln Thr Gln Leu Ser Arg Lys Leu Pro Gly Thr Thr Leu Thr
    1130                1135                1140

Ala Leu Glu Ala Ala Ala Asn Pro Ala Leu Pro Ser Asp Phe Lys
    1145                1150                1155

Thr Ile Leu Asp Gly Lys Pro Ile Pro Asn Pro Leu Leu Gly Leu
    1160                1165                1170

Asp Ser Thr
    1175

<210> SEQ ID NO 19
<211> LENGTH: 7
<212> TYPE: PRT
<213> ORGANISM: Homo sapiens

<400> SEQUENCE: 19

Asp Gly Leu Leu Leu Arg Leu
1               5

<210> SEQ ID NO 20
<211> LENGTH: 7
<212> TYPE: PRT
<213> ORGANISM: Homo sapiens

<400> SEQUENCE: 20

Phe Leu Leu Val Thr Pro His
1               5

<210> SEQ ID NO 21
<211> LENGTH: 10
<212> TYPE: PRT
<213> ORGANISM: Homo sapiens
```

<400> SEQUENCE: 21

Asp Gly Leu Leu Leu Arg Leu Val Asp Asp
1               5                   10

<210> SEQ ID NO 22
<211> LENGTH: 10
<212> TYPE: PRT
<213> ORGANISM: Homo sapiens

<400> SEQUENCE: 22

Val Asp Asp Phe Leu Leu Val Thr Pro His
1               5                   10

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      restriction site

<400> SEQUENCE: 23
gtcgacaagc ttcccgggtc tagaagatct                                      30

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gcttttctgc caggtgctga                                                 20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gccagaagtc agatgctcaa                                                 20

<210> SEQ ID NO 26
<211> LENGTH: 23
<212> TYPE: PRT
<213> ORGANISM: Homo sapiens

<400> SEQUENCE: 26

Ile Arg Arg Asp Gly Leu Leu Leu Arg Leu Val Asp Asp Phe Leu Leu
1               5                   10                  15

Val Thr Pro His Leu Thr His
            20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 27
cggtgggagg tctatataag                                              20

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cagggtcaag gaaggcac                                                18

<210> SEQ ID NO 29
<211> LENGTH: 10
<212> TYPE: PRT
<213> ORGANISM: Homo sapiens

<400> SEQUENCE: 29

Arg Pro Ser Leu Thr Gly Ala Arg Arg Leu
1               5                   10

<210> SEQ ID NO 30
<211> LENGTH: 9
<212> TYPE: PRT
<213> ORGANISM: Homo sapiens

<400> SEQUENCE: 30

Arg Pro Ala Glu Glu Ala Thr Ser Leu
1               5

<210> SEQ ID NO 31
<211> LENGTH: 9
<212> TYPE: PRT
<213> ORGANISM: Homo sapiens

<400> SEQUENCE: 31

Leu Pro Ser Asp Phe Lys Thr Ile Leu
1               5

<210> SEQ ID NO 32
<211> LENGTH: 9
<212> TYPE: PRT
<213> ORGANISM: Homo sapiens

<400> SEQUENCE: 32

Ile Leu Ala Lys Phe Leu His Trp Leu
1               5

<210> SEQ ID NO 33
<211> LENGTH: 9
<212> TYPE: PRT
<213> ORGANISM: Homo sapiens

<400> SEQUENCE: 33

Tyr Leu Phe Phe Tyr Arg Lys Ser Val
1               5

<210> SEQ ID NO 34
<211> LENGTH: 10
<212> TYPE: PRT
<213> ORGANISM: Homo sapiens
```

```
<400> SEQUENCE: 34

Tyr Leu Gln Val Asn Ser Leu Gln Thr Val
1               5                   10

<210> SEQ ID NO 35
<211> LENGTH: 9
<212> TYPE: PRT
<213> ORGANISM: Homo sapiens

<400> SEQUENCE: 35

Ser Val Trp Ser Lys Leu Gln Ser Ile
1               5

<210> SEQ ID NO 36
<211> LENGTH: 9
<212> TYPE: PRT
<213> ORGANISM: Homo sapiens

<400> SEQUENCE: 36

Ser Leu Cys Tyr Ser Ile Leu Lys Ala
1               5

<210> SEQ ID NO 37
<211> LENGTH: 15
<212> TYPE: PRT
<213> ORGANISM: Homo sapiens

<400> SEQUENCE: 37

Lys Ser Val Trp Ser Lys Leu Gln Ser Ile Gly Ile Arg Gln His
1               5                   10                  15

<210> SEQ ID NO 38
<211> LENGTH: 15
<212> TYPE: PRT
<213> ORGANISM: Homo sapiens

<400> SEQUENCE: 38

Gly Thr Ala Phe Val Gln Met Pro Ala His Gly Leu Phe Pro Trp
1               5                   10                  15

<210> SEQ ID NO 39
<211> LENGTH: 15
<212> TYPE: PRT
<213> ORGANISM: Homo sapiens

<400> SEQUENCE: 39

Ser Leu Cys Tyr Ser Ile Leu Lys Ala Lys Asn Ala Gly Met Ser
1               5                   10                  15

<210> SEQ ID NO 40
<211> LENGTH: 9
<212> TYPE: PRT
<213> ORGANISM: Homo sapiens

<400> SEQUENCE: 40

Arg Pro Ile Val Asn Met Asp Tyr Val
1               5

<210> SEQ ID NO 41
<211> LENGTH: 9
<212> TYPE: PRT
<213> ORGANISM: Homo sapiens
```

<400> SEQUENCE: 41

His Ala Gln Cys Pro Tyr Gly Val Leu
1               5

<210> SEQ ID NO 42
<211> LENGTH: 10
<212> TYPE: PRT
<213> ORGANISM: Homo sapiens

<400> SEQUENCE: 42

Gln Ala Tyr Arg Phe His Ala Cys Val Leu
1               5                   10

<210> SEQ ID NO 43
<211> LENGTH: 11
<212> TYPE: PRT
<213> ORGANISM: Homo sapiens

<400> SEQUENCE: 43

Gln Thr Val Cys Thr Ile Asn Ile Tyr Lys Ile
1               5                   10

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ggcaagtcct acgtccagtg                                               20

<210> SEQ ID NO 45
<211> LENGTH: 3591
<212> TYPE: DNA
<213> ORGANISM: Artificial Sequence
<220> FEATURE:
<223> OTHER INFORMATION: Description of Artificial Sequence: Synthetic
      Ubi-hTERT fusion optimized sequence
<220> FEATURE:
<221> NAME/KEY: CDS
<222> LOCATION: (1)..(3588)

<400> SEQUENCE: 45 atg cag att ttc gtc aaa aca ttg aca gga aag acc atc aca ctg gaa    48
Met Gln Ile Phe Val Lys Thr Leu Thr Gly Lys Thr Ile Thr Leu Glu
1               5                   10                  15 gtg gag cca agc gac act att gag aac gtc aaa gcc aag att cag gac    96
Val Glu Pro Ser Asp Thr Ile Glu Asn Val Lys Ala Lys Ile Gln Asp
                20                  25                  30 aag gag ggc atc cca cca gac cag cag agg ctg att ttt gcc gga aag   144
Lys Glu Gly Ile Pro Pro Asp Gln Gln Arg Leu Ile Phe Ala Gly Lys
            35                  40                  45 cag ctg gag gac gga cgc aca ctc agt gac tac aat atc cag aag gaa   192
Gln Leu Glu Asp Gly Arg Thr Leu Ser Asp Tyr Asn Ile Gln Lys Glu
        50                  55                  60 agt act ctg cat ctg gtc ctt cgc ctg cgc ggc gga ctg gcc acc ttc   240
Ser Thr Leu His Leu Val Leu Arg Leu Arg Gly Gly Leu Ala Thr Phe
65                  70                  75                  80 gtg cgg cgc ctg gga ccc cag ggc tgg cgg ctg gtg cag cgc ggg gac   288
Val Arg Arg Leu Gly Pro Gln Gly Trp Arg Leu Val Gln Arg Gly Asp
                85                  90                  95

| | |
|---|---|
| cct gct gct ttc aga gct ctc gtc gcc cag tgt ctg gtc tgc gtt cct<br>Pro Ala Ala Phe Arg Ala Leu Val Ala Gln Cys Leu Val Cys Val Pro<br>                100                105              110 | 336 |
| tgg gac gca cgg ccc cca ccc gcc gcc ccc agt ttc cgg cag gtg agt<br>Trp Asp Ala Arg Pro Pro Pro Ala Ala Pro Ser Phe Arg Gln Val Ser<br>                115                120              125 | 384 |
| tgt ctc aaa gag ttg gtt gct cgg gtg ttg cag cgg ctt tgt gaa agg<br>Cys Leu Lys Glu Leu Val Ala Arg Val Leu Gln Arg Leu Cys Glu Arg<br>    130                135              140 | 432 |
| gga gca aag aac gtc ctt gcc ttt ggc ttc gct ttg ctc gat gga gca<br>Gly Ala Lys Asn Val Leu Ala Phe Gly Phe Ala Leu Leu Asp Gly Ala<br>145                150              155              160 | 480 |
| cgc gga ggc cct cct gag gca ttc act act agc gtc cgg tcc tac ctg<br>Arg Gly Gly Pro Pro Glu Ala Phe Thr Thr Ser Val Arg Ser Tyr Leu<br>                    165              170              175 | 528 |
| ccc aac aca gtg acc gac gct ctg aga ggt tca ggt gcc tgg ggt ctg<br>Pro Asn Thr Val Thr Asp Ala Leu Arg Gly Ser Gly Ala Trp Gly Leu<br>                180                185              190 | 576 |
| ctg ctg cgg agg gtg ggt gat gat gtt ctg gtt cac ctc ctg gcc cgg<br>Leu Leu Arg Arg Val Gly Asp Asp Val Leu Val His Leu Leu Ala Arg<br>           195                200              205 | 624 |
| tgt gcc ctg ttc gtg ctg gtg gct ccc tcc tgc gca tac cag gtc tgc<br>Cys Ala Leu Phe Val Leu Val Ala Pro Ser Cys Ala Tyr Gln Val Cys<br>210                215              220 | 672 |
| gga ccc cca ctt tat cag ctc ggc gct gct act cag gcc cgc cca cca<br>Gly Pro Pro Leu Tyr Gln Leu Gly Ala Ala Thr Gln Ala Arg Pro Pro<br>225                230              235              240 | 720 |
| cca cac gcc tca ggt cca aga cgc cgg ctg ggc tgc gaa cgg gca tgg<br>Pro His Ala Ser Gly Pro Arg Arg Arg Leu Gly Cys Glu Arg Ala Trp<br>                    245              250              255 | 768 |
| aat cat agc gtg cgg gag gca ggt gtg cct ctc ggc ctg cca gcc ccc<br>Asn His Ser Val Arg Glu Ala Gly Val Pro Leu Gly Leu Pro Ala Pro<br>                260                265              270 | 816 |
| gga gca agg aga cgc ggt gga tcc gcc agt cgc tca ctc ccc ttg cct<br>Gly Ala Arg Arg Arg Gly Gly Ser Ala Ser Arg Ser Leu Pro Leu Pro<br>        275                280              285 | 864 |
| aag agg cca aga aga gga gcc gcc cct gaa ccc gag aga aca cct gtc<br>Lys Arg Pro Arg Arg Gly Ala Ala Pro Glu Pro Glu Arg Thr Pro Val<br>290                295              300 | 912 |
| ggc cag ggc tcc tgg gct cac ccc gga agg acc agg ggc cca agc gat<br>Gly Gln Gly Ser Trp Ala His Pro Gly Arg Thr Arg Gly Pro Ser Asp<br>305                310              315              320 | 960 |
| agg ggc ttc tgt gtt gtg tca cca gcc agg cct gcc gaa gag gct acc<br>Arg Gly Phe Cys Val Val Ser Pro Ala Arg Pro Ala Glu Glu Ala Thr<br>                    325              330              335 | 1008 |
| tcc ttg gaa gga gcc ctc agt ggc acc agg cat tct cat cca tct gtg<br>Ser Leu Glu Gly Ala Leu Ser Gly Thr Arg His Ser His Pro Ser Val<br>           340                345              350 | 1056 |
| ggt agg cag cat cat gcc ggc ccc ccc tct aca agc aga cct ccc aga<br>Gly Arg Gln His His Ala Gly Pro Pro Ser Thr Ser Arg Pro Pro Arg<br>                355                360              365 | 1104 |
| cct tgg gac aca ccc tgc cca cca gtg tat gcc gag acc aag cac ttt<br>Pro Trp Asp Thr Pro Cys Pro Pro Val Tyr Ala Glu Thr Lys His Phe<br>370                375              380 | 1152 |
| ttg tat tcc agt ggc gat aaa gag cag ctc cgg ccc tct ttt ctg ctc<br>Leu Tyr Ser Ser Gly Asp Lys Glu Gln Leu Arg Pro Ser Phe Leu Leu<br>385                390              395              400 | 1200 |
| tca agc ctc cgc ccc tct ctg acc gga gct cgc agg ctg gtg gag acc<br>Ser Ser Leu Arg Pro Ser Leu Thr Gly Ala Arg Arg Leu Val Glu Thr<br>                    405              410              415 | 1248 |

```
atc ttt ctg ggc tca aga cca tgg atg cca ggc acc ccc cgc aga ctg      1296
Ile Phe Leu Gly Ser Arg Pro Trp Met Pro Gly Thr Pro Arg Arg Leu
        420                 425                 430 ccc agg ctc ccc cag cgg tac tgg cag atg cgc cct ctc ttt ctg gaa      1344
Pro Arg Leu Pro Gln Arg Tyr Trp Gln Met Arg Pro Leu Phe Leu Glu
            435                 440                 445 ctt ctg ggt aac cac gcc cag tgc cca tat ggc gtc ctg ctg aag acc      1392
Leu Leu Gly Asn His Ala Gln Cys Pro Tyr Gly Val Leu Leu Lys Thr
    450                 455                 460 cac tgt cct ctg agg gcc gcc gtg acc cca gcc gcc ggt gtg tgt gct      1440
His Cys Pro Leu Arg Ala Ala Val Thr Pro Ala Ala Gly Val Cys Ala
465                 470                 475                 480 aga gaa aaa ccc cag ggc tca gtg gct gca cct gaa gag gag gac act      1488
Arg Glu Lys Pro Gln Gly Ser Val Ala Ala Pro Glu Glu Glu Asp Thr
                485                 490                 495 gac cct cgc cgc ctt gtc cag ttg ctc agg cag cat tca tca cca tgg      1536
Asp Pro Arg Arg Leu Val Gln Leu Leu Arg Gln His Ser Ser Pro Trp
            500                 505                 510 cag gtg tac ggc ttc gtg agg gct tgc ctg cgg aga ctg gtc ccc ccc      1584
Gln Val Tyr Gly Phe Val Arg Ala Cys Leu Arg Arg Leu Val Pro Pro
    515                 520                 525 gga ttg tgg gga tct cgg cac aac gaa cgg cgc ttt ctg agg aat aca      1632
Gly Leu Trp Gly Ser Arg His Asn Glu Arg Arg Phe Leu Arg Asn Thr
530                 535                 540 aag aag ttt atc tcc ctg ggc aag cat gca aag ctc agc ttg cag gag      1680
Lys Lys Phe Ile Ser Leu Gly Lys His Ala Lys Leu Ser Leu Gln Glu
545                 550                 555                 560 ctg aca tgg aag atg agc gtt aga gga tgc gca tgg ctc agg cgg tca      1728
Leu Thr Trp Lys Met Ser Val Arg Gly Cys Ala Trp Leu Arg Arg Ser
                565                 570                 575 cct gga gtt gga tgc gtt cca gca gca gag cac agg ctg cgc gaa gag      1776
Pro Gly Val Gly Cys Val Pro Ala Ala Glu His Arg Leu Arg Glu Glu
            580                 585                 590 att ctc gca aag ttc ctg cac tgg ctt atg agc gtc tac gtg gtc gaa      1824
Ile Leu Ala Lys Phe Leu His Trp Leu Met Ser Val Tyr Val Val Glu
    595                 600                 605 ctg ctg cgg tct ttc ttc tac gtg aca gag acc act ttt cag aag aac      1872
Leu Leu Arg Ser Phe Phe Tyr Val Thr Glu Thr Thr Phe Gln Lys Asn
610                 615                 620 aga ctg ttc ttc tac agg aag tcc gtc tgg agc aag ctc cag agt att      1920
Arg Leu Phe Phe Tyr Arg Lys Ser Val Trp Ser Lys Leu Gln Ser Ile
625                 630                 635                 640 ggt att aga cag cac ctt aag aga gtt cag ctt aga gag ctg tcc gaa      1968
Gly Ile Arg Gln His Leu Lys Arg Val Gln Leu Arg Glu Leu Ser Glu
                645                 650                 655 gct gaa gtc cgc cag cac cgc gaa gct cgc ccc gcc ctc ctg acc tct      2016
Ala Glu Val Arg Gln His Arg Glu Ala Arg Pro Ala Leu Leu Thr Ser
            660                 665                 670 cgg ctg cgg ttt att ccc aaa ccc gat ggc ctt aga cct atc gtg aat      2064
Arg Leu Arg Phe Ile Pro Lys Pro Asp Gly Leu Arg Pro Ile Val Asn
    675                 680                 685 atg gat tac gtc gtg ggt gcc cgc act ttc aga agg gag aag cgc gcc      2112
Met Asp Tyr Val Val Gly Ala Arg Thr Phe Arg Arg Glu Lys Arg Ala
690                 695                 700 gag aga ctg aca tct cgc gtg aag gca ctt ttt tct gtg ctt aat tat      2160
Glu Arg Leu Thr Ser Arg Val Lys Ala Leu Phe Ser Val Leu Asn Tyr
705                 710                 715                 720
```

```
gaa aga gcc cgc aga cct ggt ctt ctc gga gcc agc gtg ctc ggc ctg     2208
Glu Arg Ala Arg Arg Pro Gly Leu Leu Gly Ala Ser Val Leu Gly Leu
            725                 730                 735 gat gat atc cat cgg gct tgg cgc acc ttt gtg ctt cgg gtg agg gca     2256
Asp Asp Ile His Arg Ala Trp Arg Thr Phe Val Leu Arg Val Arg Ala
        740                 745                 750 cag gat cct cct cct gag ctt tat ttt gtg aaa gtt gat gtt act ggt     2304
Gln Asp Pro Pro Pro Glu Leu Tyr Phe Val Lys Val Asp Val Thr Gly
        755                 760                 765 gct tac gat aca atc cct cag gac cgg ctc acc gag gtg atc gcc tct     2352
Ala Tyr Asp Thr Ile Pro Gln Asp Arg Leu Thr Glu Val Ile Ala Ser
        770                 775                 780 att atc aaa ccc cag aac acc tac tgc gtg aga agg tac gcc gtc gtt     2400
Ile Ile Lys Pro Gln Asn Thr Tyr Cys Val Arg Arg Tyr Ala Val Val
785                 790                 795                 800 cag aaa gcc gca cac gga cac gtg cgc aaa gct ttc aaa tcc cac gtg     2448
Gln Lys Ala Ala His Gly His Val Arg Lys Ala Phe Lys Ser His Val
            805                 810                 815 tct acc ttg aca gac ctc cag cct tat atg cgg cag ttt gtc gca cac     2496
Ser Thr Leu Thr Asp Leu Gln Pro Tyr Met Arg Gln Phe Val Ala His
            820                 825                 830 ctg cag gag act agc ccc ttg agg gac gct gtg gtc atc gaa cag tcc     2544
Leu Gln Glu Thr Ser Pro Leu Arg Asp Ala Val Val Ile Glu Gln Ser
            835                 840                 845 agc tct ctc aat gag gca tcc tca ggc ctg ttt gat gtg ttc ctg cgc     2592
Ser Ser Leu Asn Glu Ala Ser Ser Gly Leu Phe Asp Val Phe Leu Arg
            850                 855                 860 ttt atg tgc cac cac gcc gtg cgg att agg ggc aag tct tac gtg cag     2640
Phe Met Cys His His Ala Val Arg Ile Arg Gly Lys Ser Tyr Val Gln
865                 870                 875                 880 tgc cag ggc atc cca cag ggt agc atc ctg agc aca ctg ctg tgt agc     2688
Cys Gln Gly Ile Pro Gln Gly Ser Ile Leu Ser Thr Leu Leu Cys Ser
            885                 890                 895 ctg tgc tat ggc gat atg gag aat aaa ttg ttc gcc ggt atc aga aga     2736
Leu Cys Tyr Gly Asp Met Glu Asn Lys Leu Phe Ala Gly Ile Arg Arg
            900                 905                 910 gac ggt ttg ctc ctg agg ctg ttc ctg ctg gtt acc ccc cat ctg act     2784
Asp Gly Leu Leu Leu Arg Leu Phe Leu Leu Val Thr Pro His Leu Thr
            915                 920                 925 cat gcc aaa aca ttt ttg cgg act ctg gtt agg ggc gtg cca gag tat     2832
His Ala Lys Thr Phe Leu Arg Thr Leu Val Arg Gly Val Pro Glu Tyr
        930                 935                 940 ggc tgt gtt gtg aat ttg cgg aaa act gtg gtt aat ttc cca gtg gag     2880
Gly Cys Val Val Asn Leu Arg Lys Thr Val Val Asn Phe Pro Val Glu
945                 950                 955                 960 gac gaa gct ctc gga ggc aca gct ttt gtt cag atg cct gcc cac ggc     2928
Asp Glu Ala Leu Gly Gly Thr Ala Phe Val Gln Met Pro Ala His Gly
            965                 970                 975 ctg ttc cca tgg tgc gga ctg ctc ctc gat acc cgg acc ctc gag gtg     2976
Leu Phe Pro Trp Cys Gly Leu Leu Leu Asp Thr Arg Thr Leu Glu Val
            980                 985                 990 cag tcc gat tat agt tcc tat gca aga aca tca att cgg gct agc ctg     3024
Gln Ser Asp Tyr Ser Ser Tyr Ala Arg Thr Ser Ile Arg Ala Ser Leu
            995                 1000                1005 act ttc aac agg ggc ttc aag gcc ggc cgg aat atg aga agg aaa         3069
Thr Phe Asn Arg Gly Phe Lys Ala Gly Arg Asn Met Arg Arg Lys
        1010                1015                1020
```

```
ctg ttc gga gtg ttg aga ctt aag tgt cat agt ctt ttt ttg gac      3114
Leu Phe Gly Val Leu Arg Leu Lys Cys His Ser Leu Phe Leu Asp
    1025                1030                1035 ttg cag gtc aat tct ctc cag aca gtg tgt acc aac att tat aaa      3159
Leu Gln Val Asn Ser Leu Gln Thr Val Cys Thr Asn Ile Tyr Lys
1040                1045                1050 atc ctc ttg ctg cag gct tac aga ttc cat gcc tgc gtc ctg cag      3204
Ile Leu Leu Leu Gln Ala Tyr Arg Phe His Ala Cys Val Leu Gln
        1055                1060                1065 ctg cct ttc cac cag cag gtg tgg aaa aac cct acc ttc ttc ctg      3249
Leu Pro Phe His Gln Gln Val Trp Lys Asn Pro Thr Phe Phe Leu
            1070                1075                1080 cgg gtg att agc gac acc gcc agt ctt tgc tac tcc atc ttg aaa      3294
Arg Val Ile Ser Asp Thr Ala Ser Leu Cys Tyr Ser Ile Leu Lys
    1085                1090                1095 gca aaa aac gct ggc atg agc ttg gga gct aag ggc gcc gct gga      3339
Ala Lys Asn Ala Gly Met Ser Leu Gly Ala Lys Gly Ala Ala Gly
1100                1105                1110 cct ctg ccc agt gaa gca gtc cag tgg ctg tgt cat cag gct ttc      3384
Pro Leu Pro Ser Glu Ala Val Gln Trp Leu Cys His Gln Ala Phe
        1115                1120                1125 ctc ctt aaa ctg aca cgc cac cgc gtg act tac gtc cca ctc ctg      3429
Leu Leu Lys Leu Thr Arg His Arg Val Thr Tyr Val Pro Leu Leu
            1130                1135                1140 ggc tcc ctg aga act gct cag acc cag ctt tcc cgg aag ctt cca      3474
Gly Ser Leu Arg Thr Ala Gln Thr Gln Leu Ser Arg Lys Leu Pro
    1145                1150                1155 ggc act acc ctt acc gca ctc gaa gca gcc gcc aac cct gcc ctg      3519
Gly Thr Thr Leu Thr Ala Leu Glu Ala Ala Ala Asn Pro Ala Leu
1160                1165                1170 ccc tcc gac ttt aag act atc ctg gac ggc aag cca att cct aat      3564
Pro Ser Asp Phe Lys Thr Ile Leu Asp Gly Lys Pro Ile Pro Asn
        1175                1180                1185 cca ttg ctg ggc ctg gac tca act tga                              3591
Pro Leu Leu Gly Leu Asp Ser Thr
            1190                1195
```

<210> SEQ ID NO 46
<211> LENGTH: 1196
<212> TYPE: PRT
<213> ORGANISM: Artificial Sequence
<220> FEATURE:
<223> OTHER INFORMATION: Description of Artificial Sequence: Synthetic construct

<400> SEQUENCE: 46

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Leu Ala Thr Phe
65                  70                  75                  80

Val Arg Arg Leu Gly Pro Gln Gly Trp Arg Leu Val Gln Arg Gly Asp
                85                  90                  95
```

```
Pro Ala Ala Phe Arg Ala Leu Val Ala Gln Cys Leu Val Cys Val Pro
            100                 105                 110
Trp Asp Ala Arg Pro Pro Ala Ala Pro Ser Phe Arg Gln Val Ser
            115                 120                 125
Cys Leu Lys Glu Leu Val Ala Arg Val Leu Gln Arg Leu Cys Glu Arg
            130                 135                 140
Gly Ala Lys Asn Val Leu Ala Phe Gly Phe Ala Leu Leu Asp Gly Ala
145                 150                 155                 160
Arg Gly Gly Pro Pro Glu Ala Phe Thr Thr Ser Val Arg Ser Tyr Leu
                165                 170                 175
Pro Asn Thr Val Thr Asp Ala Leu Arg Gly Ser Gly Ala Trp Gly Leu
            180                 185                 190
Leu Leu Arg Arg Val Gly Asp Asp Val Leu Val His Leu Leu Ala Arg
            195                 200                 205
Cys Ala Leu Phe Val Leu Val Ala Pro Ser Cys Ala Tyr Gln Val Cys
            210                 215                 220
Gly Pro Pro Leu Tyr Gln Leu Gly Ala Ala Thr Gln Ala Arg Pro Pro
225                 230                 235                 240
Pro His Ala Ser Gly Pro Arg Arg Leu Gly Cys Glu Arg Ala Trp
                245                 250                 255
Asn His Ser Val Arg Glu Ala Gly Val Pro Leu Gly Leu Pro Ala Pro
            260                 265                 270
Gly Ala Arg Arg Arg Gly Gly Ser Ala Ser Arg Ser Leu Pro Leu Pro
            275                 280                 285
Lys Arg Pro Arg Arg Gly Ala Ala Pro Glu Pro Glu Arg Thr Pro Val
            290                 295                 300
Gly Gln Gly Ser Trp Ala His Pro Gly Arg Thr Arg Gly Pro Ser Asp
305                 310                 315                 320
Arg Gly Phe Cys Val Val Ser Pro Ala Arg Pro Ala Glu Glu Ala Thr
                325                 330                 335
Ser Leu Glu Gly Ala Leu Ser Gly Thr Arg His Ser His Pro Ser Val
            340                 345                 350
Gly Arg Gln His His Ala Gly Pro Pro Ser Thr Ser Arg Pro Pro Arg
            355                 360                 365
Pro Trp Asp Thr Pro Cys Pro Pro Val Tyr Ala Glu Thr Lys His Phe
            370                 375                 380
Leu Tyr Ser Ser Gly Asp Lys Glu Gln Leu Arg Pro Ser Phe Leu Leu
385                 390                 395                 400
Ser Ser Leu Arg Pro Ser Leu Thr Gly Ala Arg Arg Leu Val Glu Thr
                405                 410                 415
Ile Phe Leu Gly Ser Arg Pro Trp Met Pro Gly Thr Pro Arg Arg Leu
            420                 425                 430
Pro Arg Leu Pro Gln Arg Tyr Trp Gln Met Arg Pro Leu Phe Leu Glu
            435                 440                 445
Leu Leu Gly Asn His Ala Gln Cys Pro Tyr Gly Val Leu Leu Lys Thr
            450                 455                 460
His Cys Pro Leu Arg Ala Ala Val Thr Pro Ala Ala Gly Val Cys Ala
465                 470                 475                 480
Arg Glu Lys Pro Gln Gly Ser Val Ala Ala Pro Glu Glu Asp Thr
                485                 490                 495
Asp Pro Arg Arg Leu Val Gln Leu Leu Arg Gln His Ser Ser Pro Trp
            500                 505                 510
```

```
Gln Val Tyr Gly Phe Val Arg Ala Cys Leu Arg Arg Leu Val Pro Pro
    515                 520                 525

Gly Leu Trp Gly Ser Arg His Asn Glu Arg Arg Phe Leu Arg Asn Thr
530                 535                 540

Lys Lys Phe Ile Ser Leu Gly Lys His Ala Lys Leu Ser Leu Gln Glu
545                 550                 555                 560

Leu Thr Trp Lys Met Ser Val Arg Gly Cys Ala Trp Leu Arg Arg Ser
                565                 570                 575

Pro Gly Val Gly Cys Val Pro Ala Ala Glu His Arg Leu Arg Glu Glu
                580                 585                 590

Ile Leu Ala Lys Phe Leu His Trp Leu Met Ser Val Tyr Val Val Glu
                595                 600                 605

Leu Leu Arg Ser Phe Phe Tyr Val Thr Glu Thr Thr Phe Gln Lys Asn
            610                 615                 620

Arg Leu Phe Phe Tyr Arg Lys Ser Val Trp Ser Lys Leu Gln Ser Ile
625                 630                 635                 640

Gly Ile Arg Gln His Leu Lys Arg Val Gln Leu Arg Glu Leu Ser Glu
                645                 650                 655

Ala Glu Val Arg Gln His Arg Glu Ala Arg Pro Ala Leu Leu Thr Ser
                660                 665                 670

Arg Leu Arg Phe Ile Pro Lys Pro Asp Gly Leu Arg Pro Ile Val Asn
    675                 680                 685

Met Asp Tyr Val Val Gly Ala Arg Thr Phe Arg Arg Glu Lys Arg Ala
    690                 695                 700

Glu Arg Leu Thr Ser Arg Val Lys Ala Leu Phe Ser Val Leu Asn Tyr
705                 710                 715                 720

Glu Arg Ala Arg Arg Pro Gly Leu Leu Gly Ala Ser Val Leu Gly Leu
                725                 730                 735

Asp Asp Ile His Arg Ala Trp Arg Thr Phe Val Leu Arg Val Arg Ala
                740                 745                 750

Gln Asp Pro Pro Glu Leu Tyr Phe Val Lys Val Asp Val Thr Gly
    755                 760                 765

Ala Tyr Asp Thr Ile Pro Gln Asp Arg Leu Thr Glu Val Ile Ala Ser
    770                 775                 780

Ile Ile Lys Pro Gln Asn Thr Tyr Cys Val Arg Arg Tyr Ala Val Val
785                 790                 795                 800

Gln Lys Ala Ala His Gly His Val Arg Lys Ala Phe Lys Ser His Val
                805                 810                 815

Ser Thr Leu Thr Asp Leu Gln Pro Tyr Met Arg Gln Phe Val Ala His
                820                 825                 830

Leu Gln Glu Thr Ser Pro Leu Arg Asp Ala Val Val Ile Glu Gln Ser
            835                 840                 845

Ser Ser Leu Asn Glu Ala Ser Ser Gly Leu Phe Asp Val Phe Leu Arg
        850                 855                 860

Phe Met Cys His His Ala Val Arg Ile Arg Gly Lys Ser Tyr Val Gln
865                 870                 875                 880

Cys Gln Gly Ile Pro Gln Gly Ser Ile Leu Ser Thr Leu Leu Cys Ser
                885                 890                 895

Leu Cys Tyr Gly Asp Met Glu Asn Lys Leu Phe Ala Gly Ile Arg Arg
            900                 905                 910

Asp Gly Leu Leu Leu Arg Leu Phe Leu Leu Val Thr Pro His Leu Thr
        915                 920                 925
```

His Ala Lys Thr Phe Leu Arg Thr Leu Val Arg Gly Val Pro Glu Tyr
    930                 935                 940

Gly Cys Val Val Asn Leu Arg Lys Thr Val Val Asn Phe Pro Val Glu
945                 950                 955                 960

Asp Glu Ala Leu Gly Gly Thr Ala Phe Val Gln Met Pro Ala His Gly
                965                 970                 975

Leu Phe Pro Trp Cys Gly Leu Leu Asp Thr Arg Thr Leu Glu Val
            980                 985                 990

Gln Ser Asp Tyr Ser Ser Tyr Ala Arg Thr Ser Ile Arg Ala Ser Leu
        995                 1000                1005

Thr Phe Asn Arg Gly Phe Lys Ala Gly Arg Asn Met Arg Arg Lys
    1010                1015                1020

Leu Phe Gly Val Leu Arg Leu Lys Cys His Ser Leu Phe Leu Asp
    1025                1030                1035

Leu Gln Val Asn Ser Leu Gln Thr Val Cys Thr Asn Ile Tyr Lys
    1040                1045                1050

Ile Leu Leu Leu Gln Ala Tyr Arg Phe His Ala Cys Val Leu Gln
    1055                1060                1065

Leu Pro Phe His Gln Gln Val Trp Lys Asn Pro Thr Phe Phe Leu
    1070                1075                1080

Arg Val Ile Ser Asp Thr Ala Ser Leu Cys Tyr Ser Ile Leu Lys
    1085                1090                1095

Ala Lys Asn Ala Gly Met Ser Leu Gly Ala Lys Gly Ala Ala Gly
    1100                1105                1110

Pro Leu Pro Ser Glu Ala Val Gln Trp Leu Cys His Gln Ala Phe
    1115                1120                1125

Leu Leu Lys Leu Thr Arg His Arg Val Thr Tyr Val Pro Leu Leu
    1130                1135                1140

Gly Ser Leu Arg Thr Ala Gln Thr Gln Leu Ser Arg Lys Leu Pro
    1145                1150                1155

Gly Thr Thr Leu Thr Ala Leu Glu Ala Ala Ala Asn Pro Ala Leu
    1160                1165                1170

Pro Ser Asp Phe Lys Thr Ile Leu Asp Gly Lys Pro Ile Pro Asn
    1175                1180                1185

Pro Leu Leu Gly Leu Asp Ser Thr
    1190                1195

<210> SEQ ID NO 47
<211> LENGTH: 3555
<212> TYPE: DNA
<213> ORGANISM: Artificial Sequence
<220> FEATURE:
<223> OTHER INFORMATION: Description of Artificial Sequence: Synthetic
      pUTSCram insert
<220> FEATURE:
<221> NAME/KEY: CDS
<222> LOCATION: (1)..(3552)

<400> SEQUENCE: 47 atg cag att ttc gtc aaa aca ttg aca gga aag acc atc aca ctg gaa     48
Met Gln Ile Phe Val Lys Thr Leu Thr Gly Lys Thr Ile Thr Leu Glu
1               5                   10                  15 gtg gag cca agc gac act att gag aac gtc aaa gcc aag att cag gac     96
Val Glu Pro Ser Asp Thr Ile Glu Asn Val Lys Ala Lys Ile Gln Asp
            20                  25                  30

-continued

```
aag gag ggc atc cca cca gac cag cag agg ctg att ttt gcc gga aag        144
Lys Glu Gly Ile Pro Pro Asp Gln Gln Arg Leu Ile Phe Ala Gly Lys
         35                  40                  45 cag ctg gag gac gga cgc aca ctc agt gac tac aat atc cag aag gaa        192
Gln Leu Glu Asp Gly Arg Thr Leu Ser Asp Tyr Asn Ile Gln Lys Glu
 50                  55                  60 agt act ctg cat ctg gtc ctt cgc ctg cgc ggc gga ggt gga ggt gga        240
Ser Thr Leu His Leu Val Leu Arg Leu Arg Gly Gly Gly Gly Gly Gly
 65                  70                  75                  80 tgc gtt cca gca gca gag cac agg ctg cgc gaa gag att ctc gca aag        288
Cys Val Pro Ala Ala Glu His Arg Leu Arg Glu Glu Ile Leu Ala Lys
                 85                  90                  95 ttc ctg cac tgg ctt atg agc gtc tac gtg gtc gaa ctg ctg cgg tct        336
Phe Leu His Trp Leu Met Ser Val Tyr Val Val Glu Leu Leu Arg Ser
            100                 105                 110 ttc ttc tac gtg aca gag acc act ttt cag aag aac aga ctg ttc ttc        384
Phe Phe Tyr Val Thr Glu Thr Thr Phe Gln Lys Asn Arg Leu Phe Phe
            115                 120                 125 tac agg aag tcc gtc tgg agc aag ctc cag agt att ggt att aga cag        432
Tyr Arg Lys Ser Val Trp Ser Lys Leu Gln Ser Ile Gly Ile Arg Gln
130                 135                 140 cac ctt aag aga gtt cag gga ggt ggt gga ggt gga ttc act act agc        480
His Leu Lys Arg Val Gln Gly Gly Gly Gly Gly Gly Phe Thr Thr Ser
145                 150                 155                 160 gtc cgg tcc tac ctg ccc aac aca gtg acc gac gct ctg aga ggt tca        528
Val Arg Ser Tyr Leu Pro Asn Thr Val Thr Asp Ala Leu Arg Gly Ser
                165                 170                 175 ggt gcc tgg ggt ctg ctg ctg cgg agg gtg ggt gat gat gtt ctg gtt        576
Gly Ala Trp Gly Leu Leu Leu Arg Arg Val Gly Asp Asp Val Leu Val
                180                 185                 190 cac ctc ctg gcc cgg tgt gcc ctg ttc gtg ctg gtg gct ccc tcc tgc        624
His Leu Leu Ala Arg Cys Ala Leu Phe Val Leu Val Ala Pro Ser Cys
            195                 200                 205 gca tac cag gtc tgc gga ccc cca ctt tat cag ctc ggc gct gct ggt        672
Ala Tyr Gln Val Cys Gly Pro Pro Leu Tyr Gln Leu Gly Ala Ala Gly
 210                 215                 220 gga ggt ggt gga ggt gcc ggt gtg tgt gct aga gaa aaa ccc cag ggc        720
Gly Gly Gly Gly Gly Ala Gly Val Cys Ala Arg Glu Lys Pro Gln Gly
225                 230                 235                 240 tca gtg gct gca cct gaa gag gag gac act gac cct cgc cgc ctt gtc        768
Ser Val Ala Ala Pro Glu Glu Glu Asp Thr Asp Pro Arg Arg Leu Val
                245                 250                 255 cag ttg ctc agg cag cat tca tca cca tgg cag gtg tac ggc ttc gtg        816
Gln Leu Leu Arg Gln His Ser Ser Pro Trp Gln Val Tyr Gly Phe Val
                260                 265                 270 agg gct tgc ctg cgg aga ctg gtc ccc ccc gga ttg tgg gga tct cgg        864
Arg Ala Cys Leu Arg Arg Leu Val Pro Pro Gly Leu Trp Gly Ser Arg
            275                 280                 285 cac aac gaa cgg cgc ttt ctg agg aat aca aag aag ttt atc tcc ctg        912
His Asn Glu Arg Arg Phe Leu Arg Asn Thr Lys Lys Phe Ile Ser Leu
 290                 295                 300 ggc aag cat gca aag ctc agc ttg cag gag ctg aca tgg aag atg agc        960
Gly Lys His Ala Lys Leu Ser Leu Gln Glu Leu Thr Trp Lys Met Ser
305                 310                 315                 320 gtt aga gga tgc gca tgg ctc agg cgg tca cct gga gtt gga ggt gga      1008
Val Arg Gly Cys Ala Trp Leu Arg Arg Ser Pro Gly Val Gly Gly Gly
                325                 330                 335
```

```
ggt gga gga tcc tgg gct cac ccc gga agg acc agg ggc cca agc gat       1056
Gly Gly Gly Ser Trp Ala His Pro Gly Arg Thr Arg Gly Pro Ser Asp
            340                 345                 350 agg ggc ttc tgt gtt gtg tca cca gcc agg cct gcc gaa gag gct acc       1104
Arg Gly Phe Cys Val Val Ser Pro Ala Arg Pro Ala Glu Glu Ala Thr
        355                 360                 365 tcc ttg gaa gga gcc ctc agt ggc acc agg ggt ggt gga ggt gga gga       1152
Ser Leu Glu Gly Ala Leu Ser Gly Thr Arg Gly Gly Gly Gly Gly Gly
    370                 375                 380 aaa tcc cac gtg tct acc ttg aca gac ctc cag cct tat atg cgg cag       1200
Lys Ser His Val Ser Thr Leu Thr Asp Leu Gln Pro Tyr Met Arg Gln
385                 390                 395                 400 ttt gtc gca cac ctg cag gag act agc ccc ttg agg gac gct gtg gtc       1248
Phe Val Ala His Leu Gln Glu Thr Ser Pro Leu Arg Asp Ala Val Val
            405                 410                 415 atc gaa cag tcc agc tct ctc aat gag gca tcc tca ggc ctg ttt gat       1296
Ile Glu Gln Ser Ser Ser Leu Asn Glu Ala Ser Ser Gly Leu Phe Asp
        420                 425                 430 gtg ttc ctg cgc ttt atg tgc cac cac gcc gtg cgg att agg ggc aag       1344
Val Phe Leu Arg Phe Met Cys His His Ala Val Arg Ile Arg Gly Lys
    435                 440                 445 tct tac gtg cag tgc cag ggc atc cca cag ggt agc atc ctg agc aca       1392
Ser Tyr Val Gln Cys Gln Gly Ile Pro Gln Gly Ser Ile Leu Ser Thr
450                 455                 460 ctg ctg tgt agc ctg tgc tat ggc gat atg gag aat aaa ttg ttc gcc       1440
Leu Leu Cys Ser Leu Cys Tyr Gly Asp Met Glu Asn Lys Leu Phe Ala
465                 470                 475                 480 ggt atc aga aga gac ggt ttg ctc ctg agg ctg ttc ctg ctg gtt acc       1488
Gly Ile Arg Arg Asp Gly Leu Leu Leu Arg Leu Phe Leu Leu Val Thr
            485                 490                 495 ccc cat ctg act cat gcc aaa aca ttt ttg cgg act ctg gtt agg ggc       1536
Pro His Leu Thr His Ala Lys Thr Phe Leu Arg Thr Leu Val Arg Gly
        500                 505                 510 gtg cca gag tat ggc tgt gtt gtg aat ttg cgg aaa act gtg gtt aat       1584
Val Pro Glu Tyr Gly Cys Val Val Asn Leu Arg Lys Thr Val Val Asn
    515                 520                 525 ttc cca gtg gag gac gaa gct ctc gga ggc aca gct ttt gtt cag atg       1632
Phe Pro Val Glu Asp Glu Ala Leu Gly Gly Thr Ala Phe Val Gln Met
530                 535                 540 cct gcc cac ggc ctg ttc cca tgg tgc gga ctg ctc ctc gat acc cgg       1680
Pro Ala His Gly Leu Phe Pro Trp Cys Gly Leu Leu Leu Asp Thr Arg
545                 550                 555                 560 acc ctc gag gtg cag tcc gat tat agt tcc tat gca aga aca tca att       1728
Thr Leu Glu Val Gln Ser Asp Tyr Ser Ser Tyr Ala Arg Thr Ser Ile
            565                 570                 575 gga gga ggt ggt gga ggt tgg aat cat agc gtg cgg gag gca ggt gtg       1776
Gly Gly Gly Gly Gly Gly Trp Asn His Ser Val Arg Glu Ala Gly Val
        580                 585                 590 cct ctc ggc ctg cca gcc ccc gga gca agg aga cgt ggt gga tcc gcc       1824
Pro Leu Gly Leu Pro Ala Pro Gly Ala Arg Arg Arg Gly Gly Ser Ala
    595                 600                 605 agt cgc tca ctc ccc ttg cct aag agg cca aga aga gga gcc ggt gga       1872
Ser Arg Ser Leu Pro Leu Pro Lys Arg Pro Arg Arg Gly Ala Gly Gly
610                 615                 620 gga ggt ggt gga ctg gcc acc ttc gtg cgg cgc ctg gga ccc cag ggc       1920
Gly Gly Gly Gly Leu Ala Thr Phe Val Arg Arg Leu Gly Pro Gln Gly
625                 630                 635                 640
```

| | | |
|---|---|---|
| tgg cgg ctg gtg cag cgc ggg gac cct gct gct ttc aga gct ctc gtc<br>Trp Arg Leu Val Gln Arg Gly Asp Pro Ala Ala Phe Arg Ala Leu Val<br>                645                  650            655 | | 1968 |
| gcc cag tgt ctg gtc tgc gtt cct tgg gac gca cgg ccc cca ccc gcc<br>Ala Gln Cys Leu Val Cys Val Pro Trp Asp Ala Arg Pro Pro Pro Ala<br>660                  665                  670 | | 2016 |
| gcc ccc agt ttc cgg cag gtg agt tgt ctc aaa gag ttg gtt gct cgg<br>Ala Pro Ser Phe Arg Gln Val Ser Cys Leu Lys Glu Leu Val Ala Arg<br>       675                  680                  685 | | 2064 |
| gtg ttg cag cgg ctt tgt gaa agg gga gca aag aac gtc ctt gcc ttt<br>Val Leu Gln Arg Leu Cys Glu Arg Gly Ala Lys Asn Val Leu Ala Phe<br>690                  695                  700 | | 2112 |
| ggc ttc gct ttg ctc gat gga gca cgc gga gga ggt ggt gga ggt gga<br>Gly Phe Ala Leu Leu Asp Gly Ala Arg Gly Gly Gly Gly Gly Gly Gly<br>705                  710                  715                  720 | | 2160 |
| aga gag ctg tcc gaa gct gaa gtc cgc cag cac cgc gaa gct cgc ccc<br>Arg Glu Leu Ser Glu Ala Glu Val Arg Gln His Arg Glu Ala Arg Pro<br>                725                  730                  735 | | 2208 |
| gcc ctc ctg acc tct cgg ctg cgg ttt att ccc aaa ccc gat ggc ctt<br>Ala Leu Leu Thr Ser Arg Leu Arg Phe Ile Pro Lys Pro Asp Gly Leu<br>740                  745                  750 | | 2256 |
| aga cct atc gtg aat atg gat tac gtc gtg ggt gcc cgc act ttc aga<br>Arg Pro Ile Val Asn Met Asp Tyr Val Val Gly Ala Arg Thr Phe Arg<br>       755                  760                  765 | | 2304 |
| agg gag aag cgc gcc gag aga ctg aca tct cgc gtg aag gca ctt ttt<br>Arg Glu Lys Arg Ala Glu Arg Leu Thr Ser Arg Val Lys Ala Leu Phe<br>770                  775                  780 | | 2352 |
| tct gtg ctt aat tat gaa aga gcc cgc aga cct ggt ctt ctc gga gcc<br>Ser Val Leu Asn Tyr Glu Arg Ala Arg Arg Pro Gly Leu Leu Gly Ala<br>785                  790                  795                  800 | | 2400 |
| agc gtg ctc ggc ctg gat gat atc cat cgg gct tgg cgc acc ttt gtg<br>Ser Val Leu Gly Leu Asp Asp Ile His Arg Ala Trp Arg Thr Phe Val<br>                805                  810                  815 | | 2448 |
| ctt cgg gtg agg gca cag gat cct cct cct gag ctt tat ttt gtg aaa<br>Leu Arg Val Arg Ala Gln Asp Pro Pro Pro Glu Leu Tyr Phe Val Lys<br>                820                  825                  830 | | 2496 |
| gtt gat gtt act ggt gct tac gat aca atc cct cag gac cgg ctc acc<br>Val Asp Val Thr Gly Ala Tyr Asp Thr Ile Pro Gln Asp Arg Leu Thr<br>835                  840                  845 | | 2544 |
| gag gtg atc gcc tct att atc aaa ccc cag aac acc tac tgc gtg aga<br>Glu Val Ile Ala Ser Ile Ile Lys Pro Gln Asn Thr Tyr Cys Val Arg<br>       850                  855                  860 | | 2592 |
| agg tac gcc gtc gtt cag aaa gcc gca cac gga cac gtg cgc aaa ggt<br>Arg Tyr Ala Val Val Gln Lys Ala Ala His Gly His Val Arg Lys Gly<br>865                  870                  875                  880 | | 2640 |
| gga gga ggt ggt gga aac agg ggc ttc aag gcc ggc cgg aat atg aga<br>Gly Gly Gly Gly Gly Asn Arg Gly Phe Lys Ala Gly Arg Asn Met Arg<br>                885                  890                  895 | | 2688 |
| agg aaa ctg ttc gga gtg ttg aga ctt aag tgt cat agt ctt ttt ttg<br>Arg Lys Leu Phe Gly Val Leu Arg Leu Lys Cys His Ser Leu Phe Leu<br>900                  905                  910 | | 2736 |
| gac ttg cag gtc aat tct ctc cag aca gtg tgt acc aac att tat aaa<br>Asp Leu Gln Val Asn Ser Leu Gln Thr Val Cys Thr Asn Ile Tyr Lys<br>                915                  920                  925 | | 2784 |
| atc ctc ttg ctg cag gct tac aga ttc cat gcc tgc gtc ctg cag ctg<br>Ile Leu Leu Leu Gln Ala Tyr Arg Phe His Ala Cys Val Leu Gln Leu<br>930                  935                  940 | | 2832 |

```
cct ttc cac cag cag gtg tgg aaa aac cct acc ttc ttc ctg cgg gtg    2880
Pro Phe His Gln Gln Val Trp Lys Asn Pro Thr Phe Phe Leu Arg Val
945                 950                 955                 960 att agc gac acc gcc agt ctt tgc tac tcc atc ttg aaa gca aaa aac    2928
Ile Ser Asp Thr Ala Ser Leu Cys Tyr Ser Ile Leu Lys Ala Lys Asn
            965                 970                 975 gct ggc atg agc ttg gga gct aag ggc gcc gct gga cct ctg ccc agt    2976
Ala Gly Met Ser Leu Gly Ala Lys Gly Ala Ala Gly Pro Leu Pro Ser
980                 985                 990 gaa gca gtc cag tgg ctg tgt cat cag gct ttc ctc ctt aaa ctg aca    3024
Glu Ala Val Gln Trp Leu Cys His Gln Ala Phe Leu Leu Lys Leu Thr
            995                 1000                1005 cgc cac cgc gtg act tac gtc cca ctc ctg ggc tcc ctg aga act        3069
Arg His Arg Val Thr Tyr Val Pro Leu Leu Gly Ser Leu Arg Thr
1010                1015                1020 gct cag acc cag ctt tcc cgg aaa ctt cca ggc act acc ctt acc        3114
Ala Gln Thr Gln Leu Ser Arg Lys Leu Pro Gly Thr Thr Leu Thr
1025                1030                1035 gca ctc gaa gca gcc gcc aac cct gcc ctg ccc tcc gac ttt aag        3159
Ala Leu Glu Ala Ala Ala Asn Pro Ala Leu Pro Ser Asp Phe Lys
1040                1045                1050 act atc ctg gac gga ggt gga ggt gga gtc ccc tgc cca cca gtg        3204
Thr Ile Leu Asp Gly Gly Gly Gly Gly Pro Cys Pro Pro Val
1055                1060                1065 tat gcc gag acc aag cac ttt ttg tat tcc agt ggc gat aaa gag        3249
Tyr Ala Glu Thr Lys His Phe Leu Tyr Ser Ser Gly Asp Lys Glu
1070                1075                1080 cag ctc cgg ccc tct ttt ctg ctc tca agc ctc cgc ccc tct ctg        3294
Gln Leu Arg Pro Ser Phe Leu Leu Ser Ser Leu Arg Pro Ser Leu
1085                1090                1095 acc gga gct cgc agg ctg gtg gag acc atc ttt ctg ggc tca aga        3339
Thr Gly Ala Arg Arg Leu Val Glu Thr Ile Phe Leu Gly Ser Arg
1100                1105                1110 cca tgg atg cca ggc acc ccc cgc aga ctg ccc agg ctc ccc cag        3384
Pro Trp Met Pro Gly Thr Pro Arg Arg Leu Pro Arg Leu Pro Gln
1115                1120                1125 cgg tac tgg cag atg cgc cct ctc ttt ctg gaa ctt ctg ggt aac        3429
Arg Tyr Trp Gln Met Arg Pro Leu Phe Leu Glu Leu Leu Gly Asn
1130                1135                1140 cac gcc cag tgc cca tat ggc gtc ctg ctg aag acc cac tgt cct        3474
His Ala Gln Cys Pro Tyr Gly Val Leu Leu Lys Thr His Cys Pro
1145                1150                1155 ctg agg gcc gcc gtg acc gga ggt ggt gga gga ggt ggc aag cca        3519
Leu Arg Ala Ala Val Thr Gly Gly Gly Gly Gly Gly Lys Pro
1160                1165                1170 att cct aat cca ttg ctg ggc ctg gac tca act tga                    3555
Ile Pro Asn Pro Leu Leu Gly Leu Asp Ser Thr
1175                1180

<210> SEQ ID NO 48
<211> LENGTH: 1184
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 48

Met Gln Ile Phe Val Lys Thr Leu Thr Gly Lys Thr Ile Thr Leu Glu
1               5                   10                  15
```

```
Val Glu Pro Ser Asp Thr Ile Glu Asn Val Lys Ala Lys Ile Gln Asp
             20                  25                  30

Lys Glu Gly Ile Pro Pro Asp Gln Gln Arg Leu Ile Phe Ala Gly Lys
         35                  40                  45

Gln Leu Glu Asp Gly Arg Thr Leu Ser Asp Tyr Asn Ile Gln Lys Glu
 50                  55                  60

Ser Thr Leu His Leu Val Leu Arg Leu Arg Gly Gly Gly Gly Gly Gly
 65                  70                  75                  80

Cys Val Pro Ala Ala Glu His Arg Leu Arg Glu Ile Leu Ala Lys
                 85                  90                  95

Phe Leu His Trp Leu Met Ser Val Tyr Val Glu Leu Leu Arg Ser
                100                 105                 110

Phe Phe Tyr Val Thr Glu Thr Thr Phe Gln Lys Asn Arg Leu Phe Phe
             115                 120                 125

Tyr Arg Lys Ser Val Trp Ser Lys Leu Gln Ser Ile Gly Ile Arg Gln
     130                 135                 140

His Leu Lys Arg Val Gln Gly Gly Gly Gly Gly Phe Thr Thr Ser
145                 150                 155                 160

Val Arg Ser Tyr Leu Pro Asn Thr Val Thr Asp Ala Leu Arg Gly Ser
                    165                 170                 175

Gly Ala Trp Gly Leu Leu Leu Arg Arg Val Gly Asp Asp Val Leu Val
             180                 185                 190

His Leu Leu Ala Arg Cys Ala Leu Phe Val Leu Val Ala Pro Ser Cys
                 195                 200                 205

Ala Tyr Gln Val Cys Gly Pro Pro Leu Tyr Gln Leu Gly Ala Ala Gly
     210                 215                 220

Gly Gly Gly Gly Gly Gly Val Cys Ala Arg Glu Lys Pro Gln Gly
225                 230                 235                 240

Ser Val Ala Ala Pro Glu Glu Asp Thr Asp Pro Arg Arg Leu Val
                 245                 250                 255

Gln Leu Leu Arg Gln His Ser Ser Pro Trp Gln Val Tyr Gly Phe Val
                 260                 265                 270

Arg Ala Cys Leu Arg Arg Leu Val Pro Pro Gly Leu Trp Gly Ser Arg
     275                 280                 285

His Asn Glu Arg Arg Phe Leu Arg Asn Thr Lys Lys Phe Ile Ser Leu
 290                 295                 300

Gly Lys His Ala Lys Leu Ser Leu Gln Glu Leu Thr Trp Lys Met Ser
305                 310                 315                 320

Val Arg Gly Cys Ala Trp Leu Arg Arg Ser Pro Gly Val Gly Gly Gly
                325                 330                 335

Gly Gly Gly Ser Trp Ala His Pro Gly Arg Thr Arg Gly Pro Ser Asp
             340                 345                 350

Arg Gly Phe Cys Val Val Ser Pro Ala Arg Pro Ala Glu Glu Ala Thr
         355                 360                 365

Ser Leu Glu Gly Ala Leu Ser Gly Thr Arg Gly Gly Gly Gly Gly
         370                 375                 380

Lys Ser His Val Ser Thr Leu Thr Asp Leu Gln Pro Tyr Met Arg Gln
385                 390                 395                 400

Phe Val Ala His Leu Gln Glu Thr Ser Pro Leu Arg Asp Ala Val Val
                 405                 410                 415

Ile Glu Gln Ser Ser Ser Leu Asn Glu Ala Ser Ser Gly Leu Phe Asp
             420                 425                 430
```

```
Val Phe Leu Arg Phe Met Cys His His Ala Val Arg Ile Arg Gly Lys
            435                 440                 445

Ser Tyr Val Gln Cys Gln Gly Ile Pro Gln Gly Ser Ile Leu Ser Thr
450                 455                 460

Leu Leu Cys Ser Leu Cys Tyr Gly Asp Met Glu Asn Lys Leu Phe Ala
465                 470                 475                 480

Gly Ile Arg Arg Asp Gly Leu Leu Arg Leu Phe Leu Leu Val Thr
            485                 490                 495

Pro His Leu Thr His Ala Lys Thr Phe Leu Arg Thr Leu Val Arg Gly
            500                 505                 510

Val Pro Glu Tyr Gly Cys Val Val Asn Leu Arg Lys Thr Val Val Asn
            515                 520                 525

Phe Pro Val Glu Asp Glu Ala Leu Gly Gly Thr Ala Phe Val Gln Met
530                 535                 540

Pro Ala His Gly Leu Phe Pro Trp Cys Gly Leu Leu Leu Asp Thr Arg
545                 550                 555                 560

Thr Leu Glu Val Gln Ser Asp Tyr Ser Ser Tyr Ala Arg Thr Ser Ile
            565                 570                 575

Gly Gly Gly Gly Gly Trp Asn His Ser Val Arg Glu Ala Gly Val
            580                 585                 590

Pro Leu Gly Leu Pro Ala Pro Gly Ala Arg Arg Gly Gly Ser Ala
            595                 600                 605

Ser Arg Ser Leu Pro Leu Pro Lys Arg Pro Arg Gly Ala Gly Gly
610                 615                 620

Gly Gly Gly Gly Leu Ala Thr Phe Val Arg Arg Leu Gly Pro Gln Gly
625                 630                 635                 640

Trp Arg Leu Val Gln Arg Gly Asp Pro Ala Ala Phe Arg Ala Leu Val
            645                 650                 655

Ala Gln Cys Leu Val Cys Val Pro Trp Asp Ala Arg Pro Pro Pro Ala
            660                 665                 670

Ala Pro Ser Phe Arg Gln Val Ser Cys Leu Lys Glu Leu Val Ala Arg
            675                 680                 685

Val Leu Gln Arg Leu Cys Glu Arg Gly Ala Lys Asn Val Leu Ala Phe
            690                 695                 700

Gly Phe Ala Leu Leu Asp Gly Ala Arg Gly Gly Gly Gly Gly Gly
705                 710                 715                 720

Arg Glu Leu Ser Glu Ala Glu Val Arg Gln His Arg Glu Ala Arg Pro
            725                 730                 735

Ala Leu Leu Thr Ser Arg Leu Arg Phe Ile Pro Lys Pro Asp Gly Leu
            740                 745                 750

Arg Pro Ile Val Asn Met Asp Tyr Val Val Gly Ala Arg Thr Phe Arg
            755                 760                 765

Arg Glu Lys Arg Ala Glu Arg Leu Thr Ser Arg Val Lys Ala Leu Phe
770                 775                 780

Ser Val Leu Asn Tyr Glu Arg Ala Arg Pro Gly Leu Leu Gly Ala
785                 790                 795                 800

Ser Val Leu Gly Leu Asp Asp Ile His Arg Ala Trp Arg Thr Phe Val
            805                 810                 815

Leu Arg Val Arg Ala Gln Asp Pro Pro Glu Leu Tyr Phe Val Lys
            820                 825                 830

Val Asp Val Thr Gly Ala Tyr Asp Thr Ile Pro Gln Asp Arg Leu Thr
            835                 840                 845
```

Glu Val Ile Ala Ser Ile Ile Lys Pro Gln Asn Thr Tyr Cys Val Arg
850                 855                 860

Arg Tyr Ala Val Val Gln Lys Ala Ala His Gly His Val Arg Lys Gly
865                 870                 875                 880

Gly Gly Gly Gly Gly Asn Arg Gly Phe Lys Ala Gly Arg Asn Met Arg
                885                 890                 895

Arg Lys Leu Phe Gly Val Leu Arg Leu Lys Cys His Ser Leu Phe Leu
            900                 905                 910

Asp Leu Gln Val Asn Ser Leu Gln Thr Val Cys Thr Asn Ile Tyr Lys
        915                 920                 925

Ile Leu Leu Leu Gln Ala Tyr Arg Phe His Ala Cys Val Leu Gln Leu
    930                 935                 940

Pro Phe His Gln Gln Val Trp Lys Asn Pro Thr Phe Phe Leu Arg Val
945                 950                 955                 960

Ile Ser Asp Thr Ala Ser Leu Cys Tyr Ser Ile Leu Lys Ala Lys Asn
                965                 970                 975

Ala Gly Met Ser Leu Gly Ala Lys Gly Ala Ala Gly Pro Leu Pro Ser
            980                 985                 990

Glu Ala Val Gln Trp Leu Cys His Gln Ala Phe Leu Leu Lys Leu Thr
        995                 1000                1005

Arg His Arg Val Thr Tyr Val Pro Leu Leu Gly Ser Leu Arg Thr
    1010                1015                1020

Ala Gln Thr Gln Leu Ser Arg Lys Leu Pro Gly Thr Thr Leu Thr
    1025                1030                1035

Ala Leu Glu Ala Ala Ala Asn Pro Ala Leu Pro Ser Asp Phe Lys
    1040                1045                1050

Thr Ile Leu Asp Gly Gly Gly Gly Gly Pro Cys Pro Pro Val
    1055                1060                1065

Tyr Ala Glu Thr Lys His Phe Leu Tyr Ser Ser Gly Asp Lys Glu
    1070                1075                1080

Gln Leu Arg Pro Ser Phe Leu Leu Ser Ser Leu Arg Pro Ser Leu
    1085                1090                1095

Thr Gly Ala Arg Arg Leu Val Glu Thr Ile Phe Leu Gly Ser Arg
    1100                1105                1110

Pro Trp Met Pro Gly Thr Pro Arg Arg Leu Pro Arg Leu Pro Gln
    1115                1120                1125

Arg Tyr Trp Gln Met Arg Pro Leu Phe Leu Glu Leu Leu Gly Asn
    1130                1135                1140

His Ala Gln Cys Pro Tyr Gly Val Leu Leu Lys Thr His Cys Pro
    1145                1150                1155

Leu Arg Ala Ala Val Thr Gly Gly Gly Gly Gly Gly Lys Pro
    1160                1165                1170

Ile Pro Asn Pro Leu Leu Gly Leu Asp Ser Thr
    1175                1180

<210> SEQ ID NO 49
<211> LENGTH: 3555
<212> TYPE: DNA
<213> ORGANISM: Artificial Sequence
<220> FEATURE:
<223> OTHER INFORMATION: Description of Artificial Sequence: Synthetic
      pUTInv insert
<220> FEATURE:
<221> NAME/KEY: CDS
<222> LOCATION: (1)..(3552)

<400> SEQUENCE: 49

| | | | | | | | | | | | | | | | | |
|---|---|---|---|---|---|---|---|---|---|---|---|---|---|---|---|---|
| atg | cag | att | ttc | gtc | aaa | aca | ttg | aca | gga | aag | acc | atc | aca | ctg | gaa | 48 |
| Met | Gln | Ile | Phe | Val | Lys | Thr | Leu | Thr | Gly | Lys | Thr | Ile | Thr | Leu | Glu | |
| 1 | | | | 5 | | | | | 10 | | | | | 15 | | |
| gtg | gag | cca | agc | gac | act | att | gag | aac | gtc | aaa | gcc | aag | att | cag | gac | 96 |
| Val | Glu | Pro | Ser | Asp | Thr | Ile | Glu | Asn | Val | Lys | Ala | Lys | Ile | Gln | Asp | |
| | | | | 20 | | | | | 25 | | | | | 30 | | |
| aag | gag | ggc | atc | cca | cca | gac | cag | cag | agg | ctg | att | ttt | gcc | gga | aag | 144 |
| Lys | Glu | Gly | Ile | Pro | Pro | Asp | Gln | Gln | Arg | Leu | Ile | Phe | Ala | Gly | Lys | |
| | | | 35 | | | | | 40 | | | | | 45 | | | |
| cag | ctg | gag | gac | gga | cgc | aca | ctc | agt | gac | tac | aat | atc | cag | aag | gaa | 192 |
| Gln | Leu | Glu | Asp | Gly | Arg | Thr | Leu | Ser | Asp | Tyr | Asn | Ile | Gln | Lys | Glu | |
| 50 | | | | | 55 | | | | | 60 | | | | | | |
| agt | act | ctg | cat | ctg | gtc | ctt | cgc | ctg | cgc | ggc | gga | ggt | gga | ggt | gga | 240 |
| Ser | Thr | Leu | His | Leu | Val | Leu | Arg | Leu | Arg | Gly | Gly | Gly | Gly | Gly | Gly | |
| 65 | | | | 70 | | | | | 75 | | | | | 80 | | |
| aac | agg | ggc | ttc | aag | gcc | ggc | cgg | aat | atg | aga | agg | aaa | ctg | ttc | gga | 288 |
| Asn | Arg | Gly | Phe | Lys | Ala | Gly | Arg | Asn | Met | Arg | Arg | Lys | Leu | Phe | Gly | |
| | | | | 85 | | | | | 90 | | | | | 95 | | |
| gtg | ttg | aga | ctt | aag | tgt | cat | agt | ctt | ttt | ttg | gac | ttg | cag | gtc | aat | 336 |
| Val | Leu | Arg | Leu | Lys | Cys | His | Ser | Leu | Phe | Leu | Asp | Leu | Gln | Val | Asn | |
| | | | 100 | | | | | 105 | | | | | 110 | | | |
| tct | ctc | cag | aca | gtg | tgt | acc | aac | att | tat | aaa | atc | ctc | ttg | ctg | cag | 384 |
| Ser | Leu | Gln | Thr | Val | Cys | Thr | Asn | Ile | Tyr | Lys | Ile | Leu | Leu | Leu | Gln | |
| | | | 115 | | | | | 120 | | | | | 125 | | | |
| gct | tac | aga | ttc | cat | gcc | tgc | gtc | ctg | cag | ctg | cct | ttc | cac | cag | cag | 432 |
| Ala | Tyr | Arg | Phe | His | Ala | Cys | Val | Leu | Gln | Leu | Pro | Phe | His | Gln | Gln | |
| 130 | | | | | 135 | | | | | 140 | | | | | | |
| gtg | tgg | aaa | aac | cct | acc | ttc | ttc | ctg | cgg | gtg | att | agc | gac | acc | gcc | 480 |
| Val | Trp | Lys | Asn | Pro | Thr | Phe | Phe | Leu | Arg | Val | Ile | Ser | Asp | Thr | Ala | |
| 145 | | | | | 150 | | | | | 155 | | | | | 160 | |
| agt | ctt | tgc | tac | tcc | atc | ttg | aaa | gca | aaa | aac | gct | ggc | atg | agc | ttg | 528 |
| Ser | Leu | Cys | Tyr | Ser | Ile | Leu | Lys | Ala | Lys | Asn | Ala | Gly | Met | Ser | Leu | |
| | | | | 165 | | | | | 170 | | | | | 175 | | |
| gga | gct | aag | ggc | gcc | gct | gga | cct | ctg | ccc | agt | gaa | gca | gtc | cag | tgg | 576 |
| Gly | Ala | Lys | Gly | Ala | Ala | Gly | Pro | Leu | Pro | Ser | Glu | Ala | Val | Gln | Trp | |
| | | | 180 | | | | | 185 | | | | | 190 | | | |
| ctg | tgt | cat | cag | gct | ttc | ctc | ctt | aaa | ctg | aca | cgc | cac | cgc | gtg | act | 624 |
| Leu | Cys | His | Gln | Ala | Phe | Leu | Leu | Lys | Leu | Thr | Arg | His | Arg | Val | Thr | |
| | | | 195 | | | | | 200 | | | | | 205 | | | |
| tac | gtc | cca | ctc | ctg | ggc | tcc | ctg | aga | act | gct | cag | acc | cag | ctt | tcc | 672 |
| Tyr | Val | Pro | Leu | Leu | Gly | Ser | Leu | Arg | Thr | Ala | Gln | Thr | Gln | Leu | Ser | |
| | | 210 | | | | | 215 | | | | | 220 | | | | |
| cgg | aaa | ctt | cca | ggc | act | acc | ctt | acc | gca | ctc | gaa | gca | gcc | gcc | aac | 720 |
| Arg | Lys | Leu | Pro | Gly | Thr | Thr | Leu | Thr | Ala | Leu | Glu | Ala | Ala | Ala | Asn | |
| 225 | | | | | 230 | | | | | 235 | | | | | 240 | |
| cct | gcc | ctg | ccc | tcc | gac | ttt | aag | act | atc | ctg | gac | gga | ggt | ggt | gga | 768 |
| Pro | Ala | Leu | Pro | Ser | Asp | Phe | Lys | Thr | Ile | Leu | Asp | Gly | Gly | Gly | Gly | |
| | | | | 245 | | | | | 250 | | | | | 255 | | |
| ggt | gga | aaa | tcc | cac | gtg | tct | acc | ttg | aca | gac | ctc | cag | cct | tat | atg | 816 |
| Gly | Gly | Lys | Ser | His | Val | Ser | Thr | Leu | Thr | Asp | Leu | Gln | Pro | Tyr | Met | |
| | | | 260 | | | | | 265 | | | | | 270 | | | |
| cgg | cag | ttt | gtc | gca | cac | ctg | cag | gag | act | agc | ccc | ttg | agg | gac | gct | 864 |
| Arg | Gln | Phe | Val | Ala | His | Leu | Gln | Glu | Thr | Ser | Pro | Leu | Arg | Asp | Ala | |
| | | 275 | | | | | 280 | | | | | 285 | | | | |
| gtg | gtc | atc | gaa | cag | tcc | agc | tct | ctc | aat | gag | gca | tcc | tca | ggc | ctg | 912 |
| Val | Val | Ile | Glu | Gln | Ser | Ser | Ser | Leu | Asn | Glu | Ala | Ser | Ser | Gly | Leu | |
| 290 | | | | | 295 | | | | | 300 | | | | | | |

| | | |
|---|---|---|
| ttt gat gtg ttc ctg cgc ttt atg tgc cac cac gcc gtg cgg att agg<br>Phe Asp Val Phe Leu Arg Phe Met Cys His His Ala Val Arg Ile Arg<br>305                          310                      315                      320 | | 960 |
| ggc aag tct tac gtg cag tgc cag ggc atc cca cag ggt agc atc ctg<br>Gly Lys Ser Tyr Val Gln Cys Gln Gly Ile Pro Gln Gly Ser Ile Leu<br>                      325                              330                      335 | | 1008 |
| agc aca ctg ctg tgt agc ctg tgc tat ggc gat atg gag aat aaa ttg<br>Ser Thr Leu Leu Cys Ser Leu Cys Tyr Gly Asp Met Glu Asn Lys Leu<br>        340                          345                        350 | | 1056 |
| ttc gcc ggt atc aga aga gac ggt ttg ctc ctg agg ctg ttc ctg ctg<br>Phe Ala Gly Ile Arg Arg Asp Gly Leu Leu Leu Arg Leu Phe Leu Leu<br>            355                        360                      365 | | 1104 |
| gtt acc ccc cat ctg act cat gcc aaa aca ttt ttg cgg act ctg gtt<br>Val Thr Pro His Leu Thr His Ala Lys Thr Phe Leu Arg Thr Leu Val<br>370                          375                      380 | | 1152 |
| agg ggc gtg cca gag tat ggc tgt gtt gtg aat ttg cgg aaa act gtg<br>Arg Gly Val Pro Glu Tyr Gly Cys Val Val Asn Leu Arg Lys Thr Val<br>385                          390                      395                      400 | | 1200 |
| gtt aat ttc cca gtg gag gac gaa gct ctc gga ggc aca gct ttt gtt<br>Val Asn Phe Pro Val Glu Asp Glu Ala Leu Gly Gly Thr Ala Phe Val<br>                            405                          410                      415 | | 1248 |
| cag atg cct gcc cac ggc ctg ttc cca tgg tgc gga ctg ctc ctc gat<br>Gln Met Pro Ala His Gly Leu Phe Pro Trp Cys Gly Leu Leu Leu Asp<br>            420                        425                      430 | | 1296 |
| acc cgg acc ctc gag gtg cag tcc gat tat agt tcc tat gca aga aca<br>Thr Arg Thr Leu Glu Val Gln Ser Asp Tyr Ser Ser Tyr Ala Arg Thr<br>                      435                        440                      445 | | 1344 |
| tca att ggt gga ggt ggt gga ggt aga gag ctg tcc gaa gct gaa gtc<br>Ser Ile Gly Gly Gly Gly Gly Gly Arg Glu Leu Ser Glu Ala Glu Val<br>            450                        455                      460 | | 1392 |
| cgc cag cac cgc gaa gct cgc ccc gcc ctc ctg acc tct cgg ctg cgg<br>Arg Gln His Arg Glu Ala Arg Pro Ala Leu Leu Thr Ser Arg Leu Arg<br>465                          470                      475                      480 | | 1440 |
| ttt att ccc aaa ccc gat ggc ctt aga cct atc gtg aat atg gat tac<br>Phe Ile Pro Lys Pro Asp Gly Leu Arg Pro Ile Val Asn Met Asp Tyr<br>                        485                          490                      495 | | 1488 |
| gtc gtg ggt gcc cgc act ttc aga agg gag aag cgc gcc gag aga ctg<br>Val Val Gly Ala Arg Thr Phe Arg Arg Glu Lys Arg Ala Glu Arg Leu<br>            500                        505                      510 | | 1536 |
| aca tct cgc gtg aag gca ctt ttt tct gtg ctt aat tat gaa aga gcc<br>Thr Ser Arg Val Lys Ala Leu Phe Ser Val Leu Asn Tyr Glu Arg Ala<br>                515                        520                      525 | | 1584 |
| cgc aga cct ggt ctt ctc gga gcc agc gtg ctc ggc ctg gat gat atc<br>Arg Arg Pro Gly Leu Leu Gly Ala Ser Val Leu Gly Leu Asp Asp Ile<br>        530                        535                        540 | | 1632 |
| cat cgg gct tgg cgc acc ttt gtg ctt cgg gtg agg gca cag gat cct<br>His Arg Ala Trp Arg Thr Phe Val Leu Arg Val Arg Ala Gln Asp Pro<br>545                          550                      555                      560 | | 1680 |
| cct cct gag ctt tat ttt gtg aaa gtt gat gtt act ggt gct tac gat<br>Pro Pro Glu Leu Tyr Phe Val Lys Val Asp Val Thr Gly Ala Tyr Asp<br>                        565                          570                      575 | | 1728 |
| aca atc cct cag gac cgg ctc acc gag gtg atc gcc tct att atc aaa<br>Thr Ile Pro Gln Asp Arg Leu Thr Glu Val Ile Ala Ser Ile Ile Lys<br>                580                        585                      590 | | 1776 |
| ccc cag aac acc tac tgc gtg aga agg tac gcc gtc gtt cag aaa gcc<br>Pro Gln Asn Thr Tyr Cys Val Arg Arg Tyr Ala Val Val Gln Lys Ala<br>        595                        600                        605 | | 1824 |
| gca cac gga cac gtg cgc aaa gga ggt gga ggt gga tgc gtt cca<br>Ala His Gly His Val Arg Lys Gly Gly Gly Gly Gly Cys Val Pro<br>610                          615                      620 | | 1872 |

-continued

| | | |
|---|---|---|
| gca gca gag cac agg ctg cgc gaa gag att ctc gca aag ttc ctg cac<br>Ala Ala Glu His Arg Leu Arg Glu Glu Ile Leu Ala Lys Phe Leu His<br>625                              630                             635                           640 | 1920 |

```
gca gca gag cac agg ctg cgc gaa gag att ctc gca aag ttc ctg cac    1920
Ala Ala Glu His Arg Leu Arg Glu Glu Ile Leu Ala Lys Phe Leu His
625                 630                 635                 640 tgg ctt atg agc gtc tac gtg gtc gaa ctg ctg cgg tct ttc ttc tac    1968
Trp Leu Met Ser Val Tyr Val Val Glu Leu Leu Arg Ser Phe Phe Tyr
                645                 650                 655 gtg aca gag acc act ttt cag aag aac aga ctg ttc ttc tac agg aag    2016
Val Thr Glu Thr Thr Phe Gln Lys Asn Arg Leu Phe Phe Tyr Arg Lys
            660                 665                 670 tcc gtc tgg agc aag ctc cag agt att ggt att aga cag cac ctt aag    2064
Ser Val Trp Ser Lys Leu Gln Ser Ile Gly Ile Arg Gln His Leu Lys
        675                 680                 685 aga gtt cag ggt ggt gga ggt gga gcc ggt gtg tgt gct aga gaa        2112
Arg Val Gln Gly Gly Gly Gly Gly Ala Gly Val Cys Ala Arg Glu
    690                 695                 700 aaa ccc cag ggc tca gtg gct gca cct gaa gag gag gac act gac cct    2160
Lys Pro Gln Gly Ser Val Ala Ala Pro Glu Glu Glu Asp Thr Asp Pro
705                 710                 715                 720 cgc cgc ctt gtc cag ttg ctc agg cag cat tca tca cca tgg cag gtg    2208
Arg Arg Leu Val Gln Leu Leu Arg Gln His Ser Ser Pro Trp Gln Val
                725                 730                 735 tac ggc ttc gtg agg gct tgc ctg cgg aga ctg gtc ccc ccc gga ttg    2256
Tyr Gly Phe Val Arg Ala Cys Leu Arg Arg Leu Val Pro Pro Gly Leu
            740                 745                 750 tgg gga tct cgg cac aac gaa cgg cgc ttt ctg agg aat aca aag aag    2304
Trp Gly Ser Arg His Asn Glu Arg Arg Phe Leu Arg Asn Thr Lys Lys
        755                 760                 765 ttt atc tcc ctg ggc aag cat gca aag ctc agc ttg cag gag ctg aca    2352
Phe Ile Ser Leu Gly Lys His Ala Lys Leu Ser Leu Gln Glu Leu Thr
770                 775                 780 tgg aag atg agc gtt aga gga tgc gca tgg ctc agg cgg tca cct gga    2400
Trp Lys Met Ser Val Arg Gly Cys Ala Trp Leu Arg Arg Ser Pro Gly
785                 790                 795                 800 gtt gga gga ggt ggt gga ggt ccc tgc cca cca gtg tat gcc gag acc    2448
Val Gly Gly Gly Gly Gly Gly Pro Cys Pro Pro Val Tyr Ala Glu Thr
                805                 810                 815 aag cac ttt ttg tat tcc agt ggc gat aaa gag cag ctc cgg ccc tct    2496
Lys His Phe Leu Tyr Ser Ser Gly Asp Lys Glu Gln Leu Arg Pro Ser
            820                 825                 830 ttt ctg ctc tca agc ctc cgc ccc tct ctg acc gga gct cgc agg ctg    2544
Phe Leu Leu Ser Ser Leu Arg Pro Ser Leu Thr Gly Ala Arg Arg Leu
        835                 840                 845 gtg gag acc atc ttt ctg ggc tca aga cca tgg atg cca ggc acc ccc    2592
Val Glu Thr Ile Phe Leu Gly Ser Arg Pro Trp Met Pro Gly Thr Pro
850                 855                 860 cgc aga ctg ccc agg ctc ccc cag cgg tac tgg cag atg cgc cct ctc    2640
Arg Arg Leu Pro Arg Leu Pro Gln Arg Tyr Trp Gln Met Arg Pro Leu
865                 870                 875                 880 ttt ctg gaa ctt ctg ggt aac cac gcc cag tgc cca tat ggc gtc ctg    2688
Phe Leu Glu Leu Leu Gly Asn His Ala Gln Cys Pro Tyr Gly Val Leu
                885                 890                 895 ctg aag acc cac tgt cct ctg agg gcc gcc gtg acc ggt gga gga ggt    2736
Leu Lys Thr His Cys Pro Leu Arg Ala Ala Val Thr Gly Gly Gly Gly
            900                 905                 910 ggt gga tcc tgg gct cac ccc gga agg acc agg ggc cca agc gat agg    2784
Gly Gly Ser Trp Ala His Pro Gly Arg Thr Arg Gly Pro Ser Asp Arg
        915                 920                 925
```

```
ggc ttc tgt gtt gtg tca cca gcc agg cct gcc gaa gag gct acc tcc      2832
Gly Phe Cys Val Val Ser Pro Ala Arg Pro Ala Glu Glu Ala Thr Ser
    930                 935                 940 ttg gaa gga gcc ctc agt ggc acc agg gga ggt gga ggt gga tgg          2880
Leu Glu Gly Ala Leu Ser Gly Thr Arg Gly Gly Gly Gly Gly Trp
945                 950                 955                 960 aat cat agc gtg cgg gag gca ggt gtg cct ctc ggc ctg cca gcc ccc      2928
Asn His Ser Val Arg Glu Ala Gly Val Pro Leu Gly Leu Pro Ala Pro
                965                 970                 975 gga gca agg aga cgc ggt gga tcc gcc agt cgc tca ctc ccc ttg cct      2976
Gly Ala Arg Arg Arg Gly Gly Ser Ala Ser Arg Ser Leu Pro Leu Pro
            980                 985                 990 aag agg cca aga aga gga gcc ggt gga gga ggt ggt gga ttc act act      3024
Lys Arg Pro Arg Arg Gly Ala Gly Gly Gly Gly Gly Gly Phe Thr Thr
        995                 1000                1005 agc gtc cgg tcc tac ctg ccc aac aca gtg acc gac gct ctg aga          3069
Ser Val Arg Ser Tyr Leu Pro Asn Thr Val Thr Asp Ala Leu Arg
    1010                1015                1020 ggt tca ggt gcc tgg ggt ctg ctg ctg cgg agg gtg ggt gat gat          3114
Gly Ser Gly Ala Trp Gly Leu Leu Leu Arg Arg Val Gly Asp Asp
    1025                1030                1035 gtt ctg gtt cac ctc ctg gcc cgg tgt gcc ctg ttc gtg ctg gtg          3159
Val Leu Val His Leu Leu Ala Arg Cys Ala Leu Phe Val Leu Val
    1040                1045                1050 gct ccc tcc tgc gca tac cag gtc tgc gga ccc cca ctt tat cag          3204
Ala Pro Ser Cys Ala Tyr Gln Val Cys Gly Pro Pro Leu Tyr Gln
    1055                1060                1065 ctc ggc gct gct gga ggt gga ggt gga ggt ctg gcc acc ttc gtg          3249
Leu Gly Ala Ala Gly Gly Gly Gly Gly Leu Ala Thr Phe Val
    1070                1075                1080 cgg cgc ctg gga ccc cag ggc tgg cgg ctg gtg cag cgc ggg gac          3294
Arg Arg Leu Gly Pro Gln Gly Trp Arg Leu Val Gln Arg Gly Asp
    1085                1090                1095 cct gct gct ttc aga gct ctc gtc gcc cag tgt ctg gtc tgc gtt          3339
Pro Ala Ala Phe Arg Ala Leu Val Ala Gln Cys Leu Val Cys Val
    1100                1105                1110 cct tgg gac gca cgg ccc cca ccc gcc gcc ccc agt ttc cgg cag          3384
Pro Trp Asp Ala Arg Pro Pro Ala Ala Pro Ser Phe Arg Gln
    1115                1120                1125 gtg agt tgt ctc aaa gag ttg gtt gct cgg gtg ttg cag cgg ctt          3429
Val Ser Cys Leu Lys Glu Leu Val Ala Arg Val Leu Gln Arg Leu
    1130                1135                1140 tgt gaa agg gga gca aag aac gtc ctt gcc ttt ggc ttc gct ttg          3474
Cys Glu Arg Gly Ala Lys Asn Val Leu Ala Phe Gly Phe Ala Leu
    1145                1150                1155 ctc gat gga gca cgc gga gga ggt ggt gga gga ggt ggc aag cca          3519
Leu Asp Gly Ala Arg Gly Gly Gly Gly Gly Gly Gly Lys Pro
    1160                1165                1170 att cct aat cca ttg ctg ggc ctg gac tca act tga                      3555
Ile Pro Asn Pro Leu Leu Gly Leu Asp Ser Thr
    1175                1180
```

<210> SEQ ID NO 50
<211> LENGTH: 1184
<212> TYPE: PRT
<213> ORGANISM: Artificial Sequence
<220> FEATURE:
<223> OTHER INFORMATION: Description of Artificial Sequence: Synthetic construct

<400> SEQUENCE: 50

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Gly Gly Gly Gly
65                  70                  75                  80

Asn Arg Gly Phe Lys Ala Gly Arg Asn Met Arg Arg Lys Leu Phe Gly
                85                  90                  95

Val Leu Arg Leu Lys Cys His Ser Leu Phe Leu Asp Leu Gln Val Asn
            100                 105                 110

Ser Leu Gln Thr Val Cys Thr Asn Ile Tyr Lys Ile Leu Leu Leu Gln
        115                 120                 125

Ala Tyr Arg Phe His Ala Cys Val Leu Gln Leu Pro Phe His Gln Gln
    130                 135                 140

Val Trp Lys Asn Pro Thr Phe Phe Leu Arg Val Ile Ser Asp Thr Ala
145                 150                 155                 160

Ser Leu Cys Tyr Ser Ile Leu Lys Ala Lys Asn Ala Gly Met Ser Leu
                165                 170                 175

Gly Ala Lys Gly Ala Ala Gly Pro Leu Pro Ser Glu Ala Val Gln Trp
            180                 185                 190

Leu Cys His Gln Ala Phe Leu Leu Lys Leu Thr Arg His Arg Val Thr
        195                 200                 205

Tyr Val Pro Leu Leu Gly Ser Leu Arg Thr Ala Gln Thr Gln Leu Ser
    210                 215                 220

Arg Lys Leu Pro Gly Thr Thr Leu Thr Ala Leu Glu Ala Ala Ala Asn
225                 230                 235                 240

Pro Ala Leu Pro Ser Asp Phe Lys Thr Ile Leu Asp Gly Gly Gly Gly
                245                 250                 255

Gly Gly Lys Ser His Val Ser Thr Leu Thr Asp Leu Gln Pro Tyr Met
            260                 265                 270

Arg Gln Phe Val Ala His Leu Gln Glu Thr Ser Pro Leu Arg Asp Ala
        275                 280                 285

Val Val Ile Glu Gln Ser Ser Ser Leu Asn Glu Ala Ser Ser Gly Leu
    290                 295                 300

Phe Asp Val Phe Leu Arg Phe Met Cys His His Ala Val Arg Ile Arg
305                 310                 315                 320

Gly Lys Ser Tyr Val Gln Cys Gln Gly Ile Pro Gln Gly Ser Ile Leu
                325                 330                 335

Ser Thr Leu Leu Cys Ser Leu Cys Tyr Gly Asp Met Glu Asn Lys Leu
            340                 345                 350

Phe Ala Gly Ile Arg Arg Asp Gly Leu Leu Leu Arg Leu Phe Leu Leu
        355                 360                 365

Val Thr Pro His Leu Thr His Ala Lys Thr Phe Leu Arg Thr Leu Val
    370                 375                 380

Arg Gly Val Pro Glu Tyr Gly Cys Val Val Asn Leu Arg Lys Thr Val
385                 390                 395                 400
```

```
Val Asn Phe Pro Val Glu Asp Glu Ala Leu Gly Thr Ala Phe Val
            405                 410                 415

Gln Met Pro Ala His Gly Leu Phe Pro Trp Cys Gly Leu Leu Leu Asp
            420                 425                 430

Thr Arg Thr Leu Glu Val Gln Ser Asp Tyr Ser Ser Tyr Ala Arg Thr
            435                 440                 445

Ser Ile Gly Gly Gly Gly Gly Arg Glu Leu Ser Glu Ala Glu Val
            450                 455                 460

Arg Gln His Arg Glu Ala Arg Pro Ala Leu Leu Thr Ser Arg Leu Arg
465                 470                 475                 480

Phe Ile Pro Lys Pro Asp Gly Leu Arg Pro Ile Val Asn Met Asp Tyr
            485                 490                 495

Val Val Gly Ala Arg Thr Phe Arg Arg Glu Lys Arg Ala Glu Arg Leu
            500                 505                 510

Thr Ser Arg Val Lys Ala Leu Phe Ser Val Leu Asn Tyr Glu Arg Ala
            515                 520                 525

Arg Arg Pro Gly Leu Leu Gly Ala Ser Val Leu Gly Leu Asp Asp Ile
530                 535                 540

His Arg Ala Trp Arg Thr Phe Val Leu Arg Val Arg Ala Gln Asp Pro
545                 550                 555                 560

Pro Pro Glu Leu Tyr Phe Val Lys Val Asp Val Thr Gly Ala Tyr Asp
            565                 570                 575

Thr Ile Pro Gln Asp Arg Leu Thr Glu Val Ile Ala Ser Ile Ile Lys
            580                 585                 590

Pro Gln Asn Thr Tyr Cys Val Arg Arg Tyr Ala Val Val Gln Lys Ala
            595                 600                 605

Ala His Gly His Val Arg Lys Gly Gly Gly Gly Gly Cys Val Pro
            610                 615                 620

Ala Ala Glu His Arg Leu Arg Glu Glu Ile Leu Ala Lys Phe Leu His
625                 630                 635                 640

Trp Leu Met Ser Val Tyr Val Val Glu Leu Leu Arg Ser Phe Phe Tyr
            645                 650                 655

Val Thr Glu Thr Thr Phe Gln Lys Asn Arg Leu Phe Phe Tyr Arg Lys
            660                 665                 670

Ser Val Trp Ser Lys Leu Gln Ser Ile Gly Ile Arg Gln His Leu Lys
            675                 680                 685

Arg Val Gln Gly Gly Gly Gly Gly Ala Gly Val Cys Ala Arg Glu
            690                 695                 700

Lys Pro Gln Gly Ser Val Ala Ala Pro Glu Glu Asp Thr Asp Pro
705                 710                 715                 720

Arg Arg Leu Val Gln Leu Leu Arg Gln His Ser Ser Pro Trp Gln Val
            725                 730                 735

Tyr Gly Phe Val Arg Ala Cys Leu Arg Arg Leu Val Pro Pro Gly Leu
            740                 745                 750

Trp Gly Ser Arg His Asn Glu Arg Arg Phe Leu Arg Asn Thr Lys Lys
            755                 760                 765

Phe Ile Ser Leu Gly Lys His Ala Lys Leu Ser Leu Gln Glu Leu Thr
            770                 775                 780

Trp Lys Met Ser Val Arg Gly Cys Ala Trp Leu Arg Arg Ser Pro Gly
785                 790                 795                 800

Val Gly Gly Gly Gly Gly Pro Cys Pro Pro Val Tyr Ala Glu Thr
            805                 810                 815
```

Lys His Phe Leu Tyr Ser Ser Gly Asp Lys Glu Gln Leu Arg Pro Ser
            820                 825                 830

Phe Leu Leu Ser Ser Leu Arg Pro Ser Leu Thr Gly Ala Arg Arg Leu
            835                 840                 845

Val Glu Thr Ile Phe Leu Gly Ser Arg Pro Trp Met Pro Gly Thr Pro
850                 855                 860

Arg Arg Leu Pro Arg Leu Pro Gln Arg Tyr Trp Gln Met Arg Pro Leu
865                 870                 875                 880

Phe Leu Glu Leu Leu Gly Asn His Ala Gln Cys Pro Tyr Gly Val Leu
                885                 890                 895

Leu Lys Thr His Cys Pro Leu Arg Ala Ala Val Thr Gly Gly Gly Gly
            900                 905                 910

Gly Gly Ser Trp Ala His Pro Gly Arg Thr Arg Gly Pro Ser Asp Arg
            915                 920                 925

Gly Phe Cys Val Val Ser Pro Ala Arg Pro Ala Glu Glu Ala Thr Ser
            930                 935                 940

Leu Glu Gly Ala Leu Ser Gly Thr Arg Gly Gly Gly Gly Gly Gly Trp
945                 950                 955                 960

Asn His Ser Val Arg Glu Ala Gly Val Pro Leu Gly Leu Pro Ala Pro
                965                 970                 975

Gly Ala Arg Arg Arg Gly Gly Ser Ala Ser Arg Ser Leu Pro Leu Pro
            980                 985                 990

Lys Arg Pro Arg Arg Gly Ala Gly Gly Gly Gly Gly Phe Thr Thr
            995                1000                1005

Ser Val Arg Ser Tyr Leu Pro Asn Thr Val Thr Asp Ala Leu Arg
   1010                 1015                 1020

Gly Ser Gly Ala Trp Gly Leu Leu Leu Arg Arg Val Gly Asp Asp
   1025                 1030                 1035

Val Leu Val His Leu Leu Ala Arg Cys Ala Leu Phe Val Leu Val
   1040                 1045                 1050

Ala Pro Ser Cys Ala Tyr Gln Val Cys Gly Pro Pro Leu Tyr Gln
   1055                 1060                 1065

Leu Gly Ala Ala Gly Gly Gly Gly Gly Leu Ala Thr Phe Val
   1070                 1075                 1080

Arg Arg Leu Gly Pro Gln Gly Trp Arg Leu Val Gln Arg Gly Asp
   1085                 1090                 1095

Pro Ala Ala Phe Arg Ala Leu Val Ala Gln Cys Leu Val Cys Val
   1100                 1105                 1110

Pro Trp Asp Ala Arg Pro Pro Ala Ala Pro Ser Phe Arg Gln
   1115                 1120                 1125

Val Ser Cys Leu Lys Glu Leu Val Ala Arg Val Leu Gln Arg Leu
   1130                 1135                 1140

Cys Glu Arg Gly Ala Lys Asn Val Leu Ala Phe Gly Phe Ala Leu
   1145                 1150                 1155

Leu Asp Gly Ala Arg Gly Gly Gly Gly Gly Gly Gly Lys Pro
   1160                 1165                 1170

Ile Pro Asn Pro Leu Leu Gly Leu Asp Ser Thr
   1175                 1180

<210> SEQ ID NO 51
<211> LENGTH: 86
<212> TYPE: PRT
<213> ORGANISM: Homo sapiens

<400> SEQUENCE: 51

Leu Ala Thr Phe Val Arg Arg Leu Gly Pro Gln Gly Trp Arg Leu Val
1               5                   10                  15

Gln Arg Gly Asp Pro Ala Ala Phe Arg Ala Leu Val Ala Gln Cys Leu
            20                  25                  30

Val Cys Val Pro Trp Asp Ala Arg Pro Pro Ala Ala Pro Ser Phe
        35                  40                  45

Arg Gln Val Ser Cys Leu Lys Glu Leu Val Ala Arg Val Leu Gln Arg
    50                  55                  60

Leu Cys Glu Arg Gly Ala Lys Asn Val Leu Ala Phe Gly Phe Ala Leu
65                  70                  75                  80

Leu Asp Gly Ala Arg Gly
                85

<210> SEQ ID NO 52
<211> LENGTH: 67
<212> TYPE: PRT
<213> ORGANISM: Homo sapiens

<400> SEQUENCE: 52

Phe Thr Thr Ser Val Arg Ser Tyr Leu Pro Asn Thr Val Thr Asp Ala
1               5                   10                  15

Leu Arg Gly Ser Gly Ala Trp Gly Leu Leu Arg Arg Val Gly Asp
            20                  25                  30

Asp Val Leu Val His Leu Leu Ala Arg Cys Ala Leu Phe Val Leu Val
        35                  40                  45

Ala Pro Ser Cys Ala Tyr Gln Val Cys Gly Pro Pro Leu Tyr Gln Leu
    50                  55                  60

Gly Ala Ala
65

<210> SEQ ID NO 53
<211> LENGTH: 40
<212> TYPE: PRT
<213> ORGANISM: Homo sapiens

<400> SEQUENCE: 53

Trp Asn His Ser Val Arg Glu Ala Gly Val Pro Leu Gly Leu Pro Ala
1               5                   10                  15

Pro Gly Ala Arg Arg Arg Gly Gly Ser Ala Ser Arg Ser Leu Pro Leu
            20                  25                  30

Pro Lys Arg Pro Arg Arg Gly Ala
            35                  40

<210> SEQ ID NO 54
<211> LENGTH: 39
<212> TYPE: PRT
<213> ORGANISM: Homo sapiens

<400> SEQUENCE: 54

Ser Trp Ala His Pro Gly Arg Thr Arg Gly Pro Ser Asp Arg Gly Phe
1               5                   10                  15

Cys Val Val Ser Pro Ala Arg Pro Ala Glu Glu Ala Thr Ser Leu Glu
            20                  25                  30

Gly Ala Leu Ser Gly Thr Arg
                35

```
<210> SEQ ID NO 55
<211> LENGTH: 101
<212> TYPE: PRT
<213> ORGANISM: Homo sapiens

<400> SEQUENCE: 55

Pro Cys Pro Pro Val Tyr Ala Glu Thr Lys His Phe Leu Tyr Ser Ser
1               5                   10                  15

Gly Asp Lys Glu Gln Leu Arg Pro Ser Phe Leu Leu Ser Ser Leu Arg
            20                  25                  30

Pro Ser Leu Thr Gly Ala Arg Arg Leu Val Glu Thr Ile Phe Leu Gly
        35                  40                  45

Ser Arg Pro Trp Met Pro Gly Thr Pro Arg Arg Leu Pro Arg Leu Pro
    50                  55                  60

Gln Arg Tyr Trp Gln Met Arg Pro Leu Phe Leu Glu Leu Leu Gly Asn
65                  70                  75                  80

His Ala Gln Cys Pro Tyr Gly Val Leu Leu Lys Thr His Cys Pro Leu
                85                  90                  95

Arg Ala Ala Val Thr
            100

<210> SEQ ID NO 56
<211> LENGTH: 104
<212> TYPE: PRT
<213> ORGANISM: Homo sapiens

<400> SEQUENCE: 56

Ala Gly Val Cys Ala Arg Glu Lys Pro Gln Gly Ser Val Ala Ala Pro
1               5                   10                  15

Glu Glu Glu Asp Thr Asp Pro Arg Arg Leu Val Gln Leu Leu Arg Gln
            20                  25                  30

His Ser Ser Pro Trp Gln Val Tyr Gly Phe Val Arg Ala Cys Leu Arg
        35                  40                  45

Arg Leu Val Pro Pro Gly Leu Trp Gly Ser Arg His Asn Glu Arg Arg
    50                  55                  60

Phe Leu Arg Asn Thr Lys Lys Phe Ile Ser Leu Gly Lys His Ala Lys
65                  70                  75                  80

Leu Ser Leu Gln Glu Leu Thr Trp Lys Met Ser Val Arg Gly Cys Ala
                85                  90                  95

Trp Leu Arg Arg Ser Pro Gly Val
            100

<210> SEQ ID NO 57
<211> LENGTH: 70
<212> TYPE: PRT
<213> ORGANISM: Homo sapiens

<400> SEQUENCE: 57

Cys Val Pro Ala Ala Glu His Arg Leu Arg Glu Glu Ile Leu Ala Lys
1               5                   10                  15

Phe Leu His Trp Leu Met Ser Val Tyr Val Val Glu Leu Leu Arg Ser
            20                  25                  30

Phe Phe Tyr Val Thr Glu Thr Thr Phe Gln Lys Asn Arg Leu Phe Phe
        35                  40                  45

Tyr Arg Lys Ser Val Trp Ser Lys Leu Gln Ser Ile Gly Ile Arg Gln
    50                  55                  60

His Leu Lys Arg Val Gln
65                  70
```

<210> SEQ ID NO 58
<211> LENGTH: 159
<212> TYPE: PRT
<213> ORGANISM: Homo sapiens

<400> SEQUENCE: 58

```
Arg Glu Leu Ser Glu Ala Glu Val Arg Gln His Arg Glu Ala Arg Pro
1               5                   10                  15

Ala Leu Leu Thr Ser Arg Leu Arg Phe Ile Pro Lys Pro Asp Gly Leu
            20                  25                  30

Arg Pro Ile Val Asn Met Asp Tyr Val Val Gly Ala Arg Thr Phe Arg
        35                  40                  45

Arg Glu Lys Arg Ala Glu Arg Leu Thr Ser Arg Val Lys Ala Leu Phe
    50                  55                  60

Ser Val Leu Asn Tyr Glu Arg Ala Arg Arg Pro Gly Leu Leu Gly Ala
65                  70                  75                  80

Ser Val Leu Gly Leu Asp Asp Ile His Arg Ala Trp Arg Thr Phe Val
                85                  90                  95

Leu Arg Val Arg Ala Gln Asp Pro Pro Glu Leu Tyr Phe Val Lys
            100                 105                 110

Val Asp Val Thr Gly Ala Tyr Asp Thr Ile Pro Gln Asp Arg Leu Thr
        115                 120                 125

Glu Val Ile Ala Ser Ile Ile Lys Pro Gln Asn Thr Tyr Cys Val Arg
    130                 135                 140

Arg Tyr Ala Val Val Gln Lys Ala Ala His Gly His Val Arg Lys
145                 150                 155
```

<210> SEQ ID NO 59
<211> LENGTH: 192
<212> TYPE: PRT
<213> ORGANISM: Homo sapiens

<400> SEQUENCE: 59

```
Lys Ser His Val Ser Thr Leu Thr Asp Leu Gln Pro Tyr Met Arg Gln
1               5                   10                  15

Phe Val Ala His Leu Gln Glu Thr Ser Pro Leu Arg Asp Ala Val Val
            20                  25                  30

Ile Glu Gln Ser Ser Ser Leu Asn Glu Ala Ser Ser Gly Leu Phe Asp
        35                  40                  45

Val Phe Leu Arg Phe Met Cys His His Ala Val Arg Ile Arg Gly Lys
    50                  55                  60

Ser Tyr Val Gln Cys Gln Gly Ile Pro Gln Gly Ser Ile Leu Ser Thr
65                  70                  75                  80

Leu Leu Cys Ser Leu Cys Tyr Gly Asp Met Glu Asn Lys Leu Phe Ala
                85                  90                  95

Gly Ile Arg Arg Asp Gly Leu Leu Leu Arg Leu Phe Leu Leu Val Thr
            100                 105                 110

Pro His Leu Thr His Ala Lys Thr Phe Leu Arg Thr Leu Val Arg Gly
        115                 120                 125

Val Pro Glu Tyr Gly Cys Val Val Asn Leu Arg Lys Thr Val Val Asn
    130                 135                 140

Phe Pro Val Glu Asp Glu Ala Leu Gly Gly Thr Ala Phe Val Gln Met
145                 150                 155                 160

Pro Ala His Gly Leu Phe Pro Trp Cys Gly Leu Leu Leu Asp Thr Arg
                165                 170                 175
```

```
Thr Leu Glu Val Gln Ser Asp Tyr Ser Ser Tyr Ala Arg Thr Ser Ile
            180                 185                 190

<210> SEQ ID NO 60
<211> LENGTH: 172
<212> TYPE: PRT
<213> ORGANISM: Homo sapiens

<400> SEQUENCE: 60

Asn Arg Gly Phe Lys Ala Gly Arg Asn Met Arg Arg Lys Leu Phe Gly
1               5                   10                  15

Val Leu Arg Leu Lys Cys His Ser Leu Phe Leu Asp Leu Gln Val Asn
            20                  25                  30

Ser Leu Gln Thr Val Cys Thr Asn Ile Tyr Lys Ile Leu Leu Leu Gln
        35                  40                  45

Ala Tyr Arg Phe His Ala Cys Val Leu Gln Leu Pro Phe His Gln Gln
    50                  55                  60

Val Trp Lys Asn Pro Thr Phe Phe Leu Arg Val Ile Ser Asp Thr Ala
65                  70                  75                  80

Ser Leu Cys Tyr Ser Ile Leu Lys Ala Lys Asn Ala Gly Met Ser Leu
                85                  90                  95

Gly Ala Lys Gly Ala Ala Gly Pro Leu Pro Ser Glu Ala Val Gln Trp
            100                 105                 110

Leu Cys His Gln Ala Phe Leu Leu Lys Leu Thr Arg His Arg Val Thr
        115                 120                 125

Tyr Val Pro Leu Leu Gly Ser Leu Arg Thr Ala Gln Thr Gln Leu Ser
    130                 135                 140

Arg Lys Leu Pro Gly Thr Thr Leu Thr Ala Leu Glu Ala Ala Ala Asn
145                 150                 155                 160

Pro Ala Leu Pro Ser Asp Phe Lys Thr Ile Leu Asp
                165                 170

<210> SEQ ID NO 61
<211> LENGTH: 35
<212> TYPE: PRT
<213> ORGANISM: Homo sapiens

<400> SEQUENCE: 61

Arg Arg Leu Gly Pro Gln Gly Trp Arg Leu Val Gln Arg Gly Asp Pro
1               5                   10                  15

Ala Ala Phe Arg Ala Leu Val Ala Gln Cys Leu Val Cys Val Pro Trp
            20                  25                  30

Asp Ala Arg
        35

<210> SEQ ID NO 62
<211> LENGTH: 15
<212> TYPE: PRT
<213> ORGANISM: Homo sapiens

<400> SEQUENCE: 62

Val Ser Cys Leu Lys Glu Leu Val Ala Arg Val Leu Gln Arg Leu
1               5                   10                  15

<210> SEQ ID NO 63
<211> LENGTH: 9
<212> TYPE: PRT
<213> ORGANISM: Homo sapiens
```

```
<400> SEQUENCE: 63

Val Leu Ala Phe Gly Phe Ala Leu Leu
1               5

<210> SEQ ID NO 64
<211> LENGTH: 57
<212> TYPE: PRT
<213> ORGANISM: Homo sapiens

<400> SEQUENCE: 64

Arg Ser Tyr Leu Pro Asn Thr Val Thr Asp Ala Leu Arg Gly Ser Gly
1               5                   10                  15

Ala Trp Gly Leu Leu Arg Arg Val Gly Asp Val Leu Val His
            20                  25                  30

Leu Leu Ala Arg Cys Ala Leu Phe Val Leu Val Ala Pro Ser Cys Ala
        35                  40                  45

Tyr Gln Val Cys Gly Pro Pro Leu Tyr
    50                  55

<210> SEQ ID NO 65
<211> LENGTH: 9
<212> TYPE: PRT
<213> ORGANISM: Homo sapiens

<400> SEQUENCE: 65

Arg Glu Ala Gly Val Pro Leu Gly Leu
1               5

<210> SEQ ID NO 66
<211> LENGTH: 16
<212> TYPE: PRT
<213> ORGANISM: Homo sapiens

<400> SEQUENCE: 66

Arg Arg Arg Gly Gly Ser Ala Ser Arg Ser Leu Pro Leu Pro Lys Arg
1               5                   10                  15

<210> SEQ ID NO 67
<211> LENGTH: 29
<212> TYPE: PRT
<213> ORGANISM: Homo sapiens

<400> SEQUENCE: 67

Gly Arg Thr Arg Gly Pro Ser Asp Arg Gly Phe Cys Val Val Ser Pro
1               5                   10                  15

Ala Arg Pro Ala Glu Glu Ala Thr Ser Leu Glu Gly Ala
            20                  25

<210> SEQ ID NO 68
<211> LENGTH: 30
<212> TYPE: PRT
<213> ORGANISM: Homo sapiens

<400> SEQUENCE: 68

Tyr Ala Glu Thr Lys His Phe Leu Tyr Ser Ser Gly Asp Lys Glu Gln
1               5                   10                  15

Leu Arg Pro Ser Phe Leu Leu Ser Ser Leu Arg Pro Ser Leu
            20                  25                  30

<210> SEQ ID NO 69
<211> LENGTH: 14
<212> TYPE: PRT
```

<213> ORGANISM: Homo sapiens

<400> SEQUENCE: 69

Ala Arg Arg Leu Val Glu Thr Ile Phe Leu Gly Ser Arg Pro
1               5                   10

<210> SEQ ID NO 70
<211> LENGTH: 28
<212> TYPE: PRT
<213> ORGANISM: Homo sapiens

<400> SEQUENCE: 70

Arg Arg Leu Pro Arg Leu Pro Gln Arg Tyr Trp Gln Met Arg Pro Leu
1               5                   10                  15

Phe Leu Glu Leu Leu Gly Asn His Ala Gln Cys Pro
            20                  25

<210> SEQ ID NO 71
<211> LENGTH: 9
<212> TYPE: PRT
<213> ORGANISM: Homo sapiens

<400> SEQUENCE: 71

Val Leu Leu Lys Thr His Cys Pro Leu
1               5

<210> SEQ ID NO 72
<211> LENGTH: 9
<212> TYPE: PRT
<213> ORGANISM: Homo sapiens

<400> SEQUENCE: 72

Arg Glu Lys Pro Gln Gly Ser Val Ala
1               5

<210> SEQ ID NO 73
<211> LENGTH: 14
<212> TYPE: PRT
<213> ORGANISM: Homo sapiens

<400> SEQUENCE: 73

Glu Glu Asp Thr Asp Pro Arg Arg Leu Val Gln Leu Leu Arg
1               5                   10

<210> SEQ ID NO 74
<211> LENGTH: 20
<212> TYPE: PRT
<213> ORGANISM: Homo sapiens

<400> SEQUENCE: 74

Val Tyr Gly Phe Val Arg Ala Cys Leu Arg Arg Leu Val Pro Pro Gly
1               5                   10                  15

Leu Trp Gly Ser
            20

<210> SEQ ID NO 75
<211> LENGTH: 9
<212> TYPE: PRT
<213> ORGANISM: Homo sapiens

<400> SEQUENCE: 75

Arg Arg Phe Leu Arg Asn Thr Lys Lys
1               5

```
<210> SEQ ID NO 76
<211> LENGTH: 9
<212> TYPE: PRT
<213> ORGANISM: Homo sapiens

<400> SEQUENCE: 76

His Ala Lys Leu Ser Leu Gln Glu Leu
1               5

<210> SEQ ID NO 77
<211> LENGTH: 9
<212> TYPE: PRT
<213> ORGANISM: Homo sapiens

<400> SEQUENCE: 77

Ser Val Arg Gly Cys Ala Trp Leu Arg
1               5

<210> SEQ ID NO 78
<211> LENGTH: 28
<212> TYPE: PRT
<213> ORGANISM: Homo sapiens

<400> SEQUENCE: 78

Glu His Arg Leu Arg Glu Ile Leu Ala Lys Phe Leu His Trp Leu
1               5                   10                  15

Met Ser Val Tyr Val Val Glu Leu Leu Arg Ser Phe
            20                  25

<210> SEQ ID NO 79
<211> LENGTH: 9
<212> TYPE: PRT
<213> ORGANISM: Homo sapiens

<400> SEQUENCE: 79

Glu Thr Thr Phe Gln Lys Asn Arg Leu
1               5

<210> SEQ ID NO 80
<211> LENGTH: 15
<212> TYPE: PRT
<213> ORGANISM: Homo sapiens

<400> SEQUENCE: 80

Lys Ser Val Trp Ser Lys Leu Gln Ser Ile Gly Ile Arg Gln His
1               5                   10                  15

<210> SEQ ID NO 81
<211> LENGTH: 23
<212> TYPE: PRT
<213> ORGANISM: Homo sapiens

<400> SEQUENCE: 81

Ala Glu Val Arg Gln His Arg Glu Ala Arg Pro Ala Leu Leu Thr Ser
1               5                   10                  15

Arg Leu Arg Phe Ile Pro Lys
            20

<210> SEQ ID NO 82
<211> LENGTH: 25
<212> TYPE: PRT
<213> ORGANISM: Homo sapiens
```

<400> SEQUENCE: 82

Asp Tyr Val Val Gly Ala Arg Thr Phe Arg Arg Glu Lys Arg Ala Glu
1               5                   10                  15

Arg Leu Thr Ser Arg Val Lys Ala Leu
            20                  25

<210> SEQ ID NO 83
<211> LENGTH: 17
<212> TYPE: PRT
<213> ORGANISM: Homo sapiens

<400> SEQUENCE: 83

Tyr Glu Arg Ala Arg Arg Pro Gly Leu Leu Gly Ala Ser Val Leu Gly
1               5                   10                  15

Leu

<210> SEQ ID NO 84
<211> LENGTH: 50
<212> TYPE: PRT
<213> ORGANISM: Homo sapiens

<400> SEQUENCE: 84

His Arg Ala Trp Arg Thr Phe Val Leu Arg Val Arg Ala Gln Asp Pro
1               5                   10                  15

Pro Pro Glu Leu Tyr Phe Val Lys Val Asp Val Thr Gly Ala Tyr Asp
            20                  25                  30

Thr Ile Pro Gln Asp Arg Leu Thr Glu Val Ile Ala Ser Ile Ile Lys
        35                  40                  45

Pro Gln
    50

<210> SEQ ID NO 85
<211> LENGTH: 15
<212> TYPE: PRT
<213> ORGANISM: Homo sapiens

<400> SEQUENCE: 85

Thr Tyr Cys Val Arg Arg Tyr Ala Val Val Gln Lys Ala Ala His
1               5                   10                  15

<210> SEQ ID NO 86
<211> LENGTH: 16
<212> TYPE: PRT
<213> ORGANISM: Homo sapiens

<400> SEQUENCE: 86

Thr Leu Thr Asp Leu Gln Pro Tyr Met Arg Gln Phe Val Ala His Leu
1               5                   10                  15

<210> SEQ ID NO 87
<211> LENGTH: 28
<212> TYPE: PRT
<213> ORGANISM: Homo sapiens

<400> SEQUENCE: 87

Ser Pro Leu Arg Asp Ala Val Val Ile Glu Gln Ser Ser Ser Leu Asn
1               5                   10                  15

Glu Ala Ser Ser Gly Leu Phe Asp Val Phe Leu Arg
            20                  25

-continued

<210> SEQ ID NO 88
<211> LENGTH: 9
<212> TYPE: PRT
<213> ORGANISM: Homo sapiens

<400> SEQUENCE: 88

Ala Val Arg Ile Arg Gly Lys Ser Tyr
1               5

<210> SEQ ID NO 89
<211> LENGTH: 18
<212> TYPE: PRT
<213> ORGANISM: Homo sapiens

<400> SEQUENCE: 89

Ile Leu Ser Thr Leu Leu Cys Ser Leu Cys Tyr Gly Asp Met Glu Asn
1               5                   10                  15

Lys Leu

<210> SEQ ID NO 90
<211> LENGTH: 48
<212> TYPE: PRT
<213> ORGANISM: Homo sapiens

<400> SEQUENCE: 90

Ile Arg Arg Asp Gly Leu Leu Arg Leu Phe Leu Leu Val Thr Pro
1               5                   10                  15

His Leu Thr His Ala Lys Thr Phe Leu Arg Thr Leu Val Arg Gly Val
            20                  25                  30

Pro Glu Tyr Gly Cys Val Val Asn Leu Arg Lys Thr Val Val Asn Phe
        35                  40                  45

<210> SEQ ID NO 91
<211> LENGTH: 39
<212> TYPE: PRT
<213> ORGANISM: Homo sapiens

<400> SEQUENCE: 91

Asp Glu Ala Leu Gly Gly Thr Ala Phe Val Gln Met Pro Ala His Gly
1               5                   10                  15

Leu Phe Pro Trp Cys Gly Leu Leu Leu Asp Thr Arg Thr Leu Glu Val
            20                  25                  30

Gln Ser Asp Tyr Ser Ser Tyr
            35

<210> SEQ ID NO 92
<211> LENGTH: 31
<212> TYPE: PRT
<213> ORGANISM: Homo sapiens

<400> SEQUENCE: 92

Ala Gly Arg Asn Met Arg Arg Lys Leu Phe Gly Val Leu Arg Leu Lys
1               5                   10                  15

Cys His Ser Leu Phe Leu Asp Leu Gln Val Asn Ser Leu Gln Thr
            20                  25                  30

<210> SEQ ID NO 93
<211> LENGTH: 25
<212> TYPE: PRT
<213> ORGANISM: Homo sapiens

```
<400> SEQUENCE: 93

Ile Tyr Lys Ile Leu Leu Leu Gln Ala Tyr Arg Phe His Ala Cys Val
1               5                   10                  15

Leu Gln Leu Pro Phe His Gln Gln Val
            20                  25

<210> SEQ ID NO 94
<211> LENGTH: 28
<212> TYPE: PRT
<213> ORGANISM: Homo sapiens

<400> SEQUENCE: 94

Asn Pro Thr Phe Phe Leu Arg Val Ile Ser Asp Thr Ala Ser Leu Cys
1               5                   10                  15

Tyr Ser Ile Leu Lys Ala Lys Asn Ala Gly Met Ser
            20                  25

<210> SEQ ID NO 95
<211> LENGTH: 9
<212> TYPE: PRT
<213> ORGANISM: Homo sapiens

<400> SEQUENCE: 95

Gly Ala Lys Gly Ala Ala Gly Pro Leu
1               5

<210> SEQ ID NO 96
<211> LENGTH: 41
<212> TYPE: PRT
<213> ORGANISM: Homo sapiens

<400> SEQUENCE: 96

Trp Leu Cys His Gln Ala Phe Leu Leu Lys Leu Thr Arg His Arg Val
1               5                   10                  15

Thr Tyr Val Pro Leu Leu Gly Ser Leu Arg Thr Ala Gln Thr Gln Leu
            20                  25                  30

Ser Arg Lys Leu Pro Gly Thr Thr Leu
        35                  40

<210> SEQ ID NO 97
<211> LENGTH: 17
<212> TYPE: PRT
<213> ORGANISM: Homo sapiens

<400> SEQUENCE: 97

Leu Glu Ala Ala Ala Asn Pro Ala Leu Pro Ser Asp Phe Lys Thr Ile
1               5                   10                  15

Leu

<210> SEQ ID NO 98
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Gly Gly Gly
1
```

```
<210> SEQ ID NO 99
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Gly Gly Gly Gly Gly
1               5

<210> SEQ ID NO 100
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(6)
<223> OTHER INFORMATION: This sequence may encompass 4-6 residues

<400> SEQUENCE: 100

Gly Gly Gly Gly Gly Gly
1               5

<210> SEQ ID NO 101
<211> LENGTH: 23
<212> TYPE: PRT
<213> ORGANISM: Homo sapiens

<400> SEQUENCE: 101

Ile Arg Arg Asp Gly Leu Leu Leu Arg Leu Val Asp Asp Phe Leu Leu
1               5                   10                  15

Val Thr Pro His Leu Thr His
            20
```